US012646340B2

(12) United States Patent
Wang et al.

(10) Patent No.: US 12,646,340 B2
(45) Date of Patent: Jun. 2, 2026

(54) MULTI-SCALE SPATIAL TRANSCRIPTOMICS ANALYSIS

(71) Applicants: The Broad Institute, Inc., Cambridge, MA (US); Massachusetts Institute of Technology, Cambridge, MA (US); President and Fellows of Harvard College, Cambridge, MA (US)

(72) Inventors: Xiao Wang, Cambridge, MA (US); Jia Liu, Cambridge, MA (US); Yichun He, Cambridge, MA (US)

(73) Assignees: THE BROAD INSTITUTE, INC., Cambridge, MA (US); MASSACHUSETTS INSTITUTE OF TECHNOLOGY, Cambridge, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 312 days.

(21) Appl. No.: 18/277,950

(22) PCT Filed: Feb. 18, 2022

(86) PCT No.: PCT/US2022/017016
§ 371 (c)(1),
(2) Date: Aug. 18, 2023

(87) PCT Pub. No.: WO2022/178274
PCT Pub. Date: Aug. 25, 2022

(65) Prior Publication Data
US 2024/0144704 A1 May 2, 2024

Related U.S. Application Data

(60) Provisional application No. 63/151,374, filed on Feb. 19, 2021.

(51) Int. Cl.
*G06V 10/26* (2022.01)
*G06V 10/44* (2022.01)
(Continued)

(52) U.S. Cl.
CPC .............. *G06V 20/69* (2022.01); *G06V 10/44* (2022.01); *G16H 20/00* (2018.01); *G06V 2201/03* (2022.01)

(58) Field of Classification Search
CPC .... G06V 20/69; G06V 10/44; G06V 2201/03; G06V 10/26; G06V 10/762; G16H 20/00
See application file for complete search history.

(56) References Cited

U.S. PATENT DOCUMENTS 3,687,808 A 8/1972 Merigan, Jr. et al.
4,849,336 A 7/1989 Miyoshi et al.
(Continued)

FOREIGN PATENT DOCUMENTS

EP 2 270 205 A2 1/2011
EP 2 794 928 B1 2/2019
(Continued)

OTHER PUBLICATIONS

Qian, Xiaoyan, et al. "Probabilistic cell typing enables fine mapping of closely related cell types in situ." Nature methods 17.1 (2020): 101-106. (Year: 2020).*
(Continued)

*Primary Examiner* — Andrew M Moyer
*Assistant Examiner* — Dylan John Mendez Muniz
(74) *Attorney, Agent, or Firm* — FOLEY & LARDNER LLP; Sunit Talapatra

(57) ABSTRACT

The present disclosure provides methods for identifying cells in an image. An apparatus for identifying cells in an image is also provided by the present disclosure. Further provided herein is a non-transitory computer-readable stor-
(Continued)

age medium for performing the methods disclosed herein. Methods of diagnosing a disease or disorder and of treating a disease or disorder in a subject using the methods disclosed are also provided herein.

19 Claims, 95 Drawing Sheets

(51) Int. Cl.
  *G06V 10/762*  (2022.01)
  *G06V 20/69*  (2022.01)
  *G16H 20/00*  (2018.01)

(56) References Cited

U.S. PATENT DOCUMENTS

| | | | |
|---|---|---|---|
| 4,945,050 A | | 7/1990 | Sanford et al. |
| 4,946,778 A | | 8/1990 | Ladner et al. |
| 5,036,006 A | | 7/1991 | Sanford et al. |
| 5,067,805 A | | 11/1991 | Corle et al. |
| 5,091,519 A | | 2/1992 | Morrison et al. |
| 5,100,792 A | | 3/1992 | Sanford et al. |
| 5,135,855 A | | 8/1992 | Moss et al. |
| 5,173,414 A | | 12/1992 | Lebkowski et al. |
| 5,179,022 A | | 1/1993 | Sanford et al. |
| 5,344,757 A | | 9/1994 | Holtke et al. |
| 5,354,657 A | * | 10/1994 | Holtke ................. C12Q 1/6804 |
| | | | 435/6.12 |
| 5,371,015 A | | 12/1994 | Sanford et al. |
| 5,399,346 A | | 3/1995 | Anderson et al. |
| 5,478,744 A | | 12/1995 | Sanford et al. |
| 5,489,677 A | | 2/1996 | Sanghvi et al. |
| 5,535,052 A | | 7/1996 | Jorgens |
| 5,538,871 A | | 7/1996 | Nuovo et al. |
| 5,539,082 A | | 7/1996 | Nielsen et al. |
| 5,602,240 A | | 2/1997 | De Mesmaeker et al. |
| 5,612,818 A | | 3/1997 | Kumagai et al. |
| 5,619,371 A | | 4/1997 | Pontius |
| 5,688,648 A | | 11/1997 | Mathies et al. |
| 5,702,888 A | | 12/1997 | Joachim-Holtke et al. |
| 5,714,331 A | | 2/1998 | Buchardt et al. |
| 5,719,262 A | | 2/1998 | Buchardt et al. |
| 5,831,005 A | | 11/1998 | Zuckerman et al. |
| 6,054,274 A | | 4/2000 | Sampson et al. |
| 6,094,300 A | | 7/2000 | Kashima et al. |
| 6,235,502 B1 | | 5/2001 | Weissman et al. |
| 6,291,187 B1 | | 9/2001 | Kingsmore et al. |
| 6,323,009 B1 | | 11/2001 | Lasken et al. |
| 6,344,329 B1 | | 2/2002 | Lizardi |
| 6,368,801 B1 | | 4/2002 | Faruqi |
| 6,558,928 B1 | | 5/2003 | Landegren |
| 7,335,898 B2 | | 2/2008 | Donders et al. |
| 7,479,630 B2 | | 1/2009 | Bandura et al. |
| 8,497,069 B2 | | 7/2013 | Hutchison, III et al. |
| 9,175,095 B2 | | 11/2015 | Deisseroth et al. |
| 9,279,973 B2 | | 3/2016 | Takaya |
| 9,359,449 B2 | | 6/2016 | Deisseroth et al. |
| 9,376,717 B2 | | 6/2016 | Gao et al. |
| 9,423,601 B2 | | 8/2016 | Toda et al. |
| 9,458,208 B2 | | 10/2016 | Deisseroth et al. |
| 9,791,409 B2 | | 10/2017 | Gordon et al. |
| 10,138,509 B2 | | 11/2018 | Church et al. |
| 10,227,639 B2 | | 3/2019 | Levner et al. |
| 10,266,888 B2 | | 4/2019 | Daugharthy et al. |
| 10,323,272 B1 | | 6/2019 | Rabbani et al. |
| 10,364,457 B2 | | 7/2019 | Wassie et al. |
| 10,590,484 B2 | | 3/2020 | Korlach et al. |
| RE47,983 E | | 5/2020 | Gao et al. |
| 10,787,701 B2 | | 9/2020 | Chee |
| 10,829,814 B2 | | 11/2020 | Fan et al. |
| 11,008,608 B2 | | 5/2021 | Samusik et al. |
| 11,085,072 B2 | | 8/2021 | Church et al. |
| 11,098,303 B2 | | 8/2021 | Zhuang et al. |
| 11,111,521 B2 | | 9/2021 | Church et al. |
| 11,187,581 B2 | | 11/2021 | Kokota et al. |
| 11,299,770 B2 | | 4/2022 | Samusik et al. |
| 11,377,689 B2 | | 7/2022 | Beechem et al. |
| 11,408,094 B2 | | 8/2022 | Fu et al. |
| 11,447,807 B2 | | 9/2022 | Church et al. |
| RE49,304 E | | 11/2022 | Gao et al. |
| 11,566,276 B2 | | 1/2023 | Church et al. |
| 11,649,485 B2 | | 5/2023 | Yin et al. |
| 11,656,447 B2 | | 5/2023 | Tsia et al. |
| 12,060,603 B2 | | 8/2024 | Bava |
| 12,157,124 B2 | | 12/2024 | Cox et al. |
| 12,188,085 B2 | | 1/2025 | Bava |
| 12,359,253 B2 | | 7/2025 | Wang et al. |
| 2005/0112639 A1 | | 5/2005 | Wang et al. |
| 2005/0239184 A1 | | 10/2005 | Ohara et al. |
| 2006/0141501 A1 | | 6/2006 | Friend et al. |
| 2008/0124735 A1 | | 5/2008 | Schuster et al. |
| 2009/0011943 A1 | | 1/2009 | Drmanac et al. |
| 2009/0093403 A1 | | 4/2009 | Zhang et al. |
| 2009/0262183 A1 | | 10/2009 | Hayashi et al. |
| 2010/0055733 A1 | | 3/2010 | Lutolf et al. |
| 2010/0120129 A1 | | 5/2010 | Amshey et al. |
| 2012/0003657 A1 | | 1/2012 | Myllykangas et al. |
| 2013/0045872 A1 | | 2/2013 | Zhou et al. |
| 2013/0178372 A1 | | 7/2013 | Geiss et al. |
| 2013/0266512 A1 | | 10/2013 | Fox et al. |
| 2014/0162892 A1 | | 6/2014 | Mir |
| 2014/0170654 A1 | | 6/2014 | Landegren et al. |
| 2015/0144490 A1 | | 5/2015 | Deisseroth et al. |
| 2016/0080632 A1 | | 3/2016 | Iwase et al. |
| 2016/0169923 A1 | | 6/2016 | Holmes et al. |
| 2016/0252715 A1 | | 9/2016 | Nakano et al. |
| 2016/0258003 A1 | | 9/2016 | Celedon et al. |
| 2017/0068086 A1 | | 3/2017 | Tomer et al. |
| 2017/0145510 A1 | | 5/2017 | Oliphant et al. |
| 2017/0211133 A1 | | 7/2017 | Landegren et al. |
| 2018/0119219 A1 | | 5/2018 | Chen et al. |
| 2018/0208975 A1 | | 7/2018 | Peterson et al. |
| 2018/0216161 A1 | | 8/2018 | Chen et al. |
| 2018/0267283 A1 | | 9/2018 | Matsumoto |
| 2018/0340221 A1 | | 11/2018 | Davis et al. |
| 2019/0002971 A1 | | 1/2019 | Koslover et al. |
| 2019/0055594 A1 | | 2/2019 | Samusik et al. |
| 2019/0085383 A1 | | 3/2019 | Church et al. |
| 2019/0154679 A1 | | 5/2019 | Doyle et al. |
| 2019/0179127 A1 | | 6/2019 | Mertz et al. |
| 2020/0199667 A1 | | 6/2020 | Erickstad et al. |
| 2020/0277663 A1 | | 9/2020 | Iyer et al. |
| 2021/0130810 A1 | | 5/2021 | Schwartz et al. |
| 2021/0164039 A1 | | 6/2021 | Wang et al. |
| 2021/0238662 A1 | | 8/2021 | Bava et al. |
| 2021/0238665 A1 | | 8/2021 | Samusik et al. |
| 2021/0238674 A1 | | 8/2021 | Bava |
| 2021/0262018 A1 | | 8/2021 | Bava et al. |
| 2021/0340621 A1 | | 11/2021 | Daugharthy et al. |
| 2021/0388424 A1 | | 12/2021 | Bava |
| 2022/0015638 A1 | | 1/2022 | Zeng et al. |
| 2022/0016624 A1 | | 1/2022 | Daugharthy et al. |
| 2022/0083832 A1 | | 3/2022 | Shah |
| 2022/0084628 A1 | | 3/2022 | Shah |
| 2022/0251642 A1 | | 8/2022 | Church et al. |
| 2022/0290228 A1 | | 9/2022 | Hauling et al. |
| 2022/0316004 A1 | | 10/2022 | Miller et al. |
| 2022/0364160 A1 | | 11/2022 | Nolan et al. |
| 2022/0372570 A1 | | 11/2022 | Costa |
| 2022/0380838 A1 | | 12/2022 | Kåœhnemund et al. |
| 2022/0403458 A1 | | 12/2022 | Bava |
| 2023/0012607 A1 | | 1/2023 | Kåœhnemund et al. |
| 2023/0013775 A1 | | 1/2023 | Chen et al. |
| 2023/0026886 A1 | | 1/2023 | Chen |
| 2023/0034039 A1 | | 2/2023 | Shahjamali |
| 2023/0037182 A1 | | 2/2023 | Bava et al. |
| 2023/0061542 A1 | | 3/2023 | Kåœhnemund |
| 2023/0077364 A1 | | 3/2023 | Patterson et al. |
| 2023/0081232 A1 | | 3/2023 | Weisenfeld et al. |
| 2023/0109070 A1 | | 4/2023 | Richman et al. |
| 2023/0115903 A1 | | 4/2023 | Hernåndez Neuta et al. |
| 2023/0126825 A1 | | 4/2023 | Nagendran et al. |
| 2023/0143569 A1 | | 5/2023 | Iyer et al. |

(56) References Cited

U.S. PATENT DOCUMENTS

| | | |
|---|---|---|
| 2023/0227894 A1 | 7/2023 | Nilsson et al. |
| 2023/0238078 A1 | 7/2023 | Gonzalez Lozano et al. |
| 2023/0242974 A1 | 8/2023 | Costa et al. |
| 2023/0279480 A1 | 9/2023 | Kãœhnemund |
| 2023/0314327 A1 | 10/2023 | Hoffman |
| 2023/0314328 A1 | 10/2023 | Costa |
| 2023/0323437 A1 | 10/2023 | Chen et al. |
| 2023/0324421 A1 | 10/2023 | Zhang et al. |
| 2023/0351619 A1 | 11/2023 | Tentori et al. |
| 2024/0019353 A1 | 1/2024 | Wang et al. |
| 2024/0033743 A1 | 2/2024 | Tentori et al. |
| 2024/0132938 A1 | 4/2024 | Kãœhnemund |
| 2024/0150816 A1 | 5/2024 | Feng et al. |
| 2024/0151937 A1 | 5/2024 | Hoffman |
| 2024/0167081 A1 | 5/2024 | Bava et al. |
| 2024/0167956 A1 | 5/2024 | Hoffman et al. |
| 2024/0168273 A1 | 5/2024 | Monkowski et al. |
| 2024/0171723 A1 | 5/2024 | Shutov et al. |
| 2024/0171833 A1 | 5/2024 | Hoffman et al. |
| 2024/0177348 A1 | 5/2024 | Shutov et al. |
| 2024/0209346 A1 | 6/2024 | Shastry |
| 2024/0233415 A1 | 7/2024 | Hoffman |
| 2024/0254553 A1 | 8/2024 | Deisseroth et al. |
| 2024/0254554 A1 | 8/2024 | Deisseroth et al. |
| 2024/0257912 A1 | 8/2024 | Deisseroth et al. |
| 2024/0263228 A1 | 8/2024 | Deisseroth et al. |
| 2024/0305314 A1 | 9/2024 | Hoffman et al. |
| 2024/0369471 A1 | 11/2024 | Hoffman et al. |
| 2024/0428880 A1 | 12/2024 | Marks et al. |
| 2025/0012786 A1 | 1/2025 | Skrynnyk et al. |
| 2025/0052979 A1 | 2/2025 | Miller et al. |
| 2025/0061732 A1 | 2/2025 | Li et al. |
| 2025/0305036 A1 | 10/2025 | Fu et al. |

FOREIGN PATENT DOCUMENTS

| | | |
|---|---|---|
| EP | 2 971 184 B1 | 4/2019 |
| EP | 3 578 666 A1 | 12/2019 |
| EP | 4 045 887 A1 | 8/2022 |
| EP | 4 108 782 B1 | 6/2023 |
| EP | 4 513 431 A2 | 2/2025 |
| JP | 2005-511058 A | 4/2005 |
| JP | 2017-207481 A | 11/2017 |
| KR | 20080091125 A | 10/2008 |
| KR | 20140068264 A | 6/2014 |
| WO | WO-99/14226 A2 | 3/1999 |
| WO | WO-01/61037 A1 | 8/2001 |
| WO | WO-2005/033340 A2 | 4/2005 |
| WO | WO-2005/042759 A2 | 5/2005 |
| WO | WO 2010/062775 A2 | 6/2010 |
| WO | WO-2012/005595 A2 | 1/2012 |
| WO | WO-2012/110899 A2 | 8/2012 |
| WO | WO-2012/160083 A1 | 11/2012 |
| WO | WO-2013/173774 A2 | 11/2013 |
| WO | WO-2014/030066 A2 | 2/2014 |
| WO | WO-2015/200139 A1 | 12/2015 |
| WO | WO-2017/019481 A1 | 2/2017 |
| WO | WO-2017/096248 A1 | 6/2017 |
| WO | WO-2017/147483 A1 | 8/2017 |
| WO | WO-2018/033528 A1 | 2/2018 |
| WO | WO-2018/136856 A1 | 7/2018 |
| WO | WO-2018/175779 A1 | 9/2018 |
| WO | WO-2019/016048 A1 | 1/2019 |
| WO | WO 2019/199579 A1 | 10/2019 |
| WO | WO-2019/222284 A1 | 11/2019 |
| WO | WO 2020/148769 A1 | 7/2020 |
| WO | WO 2020/160044 A1 | 8/2020 |
| WO | WO-2020/176788 A1 | 9/2020 |
| WO | WO-2020/214885 A1 | 10/2020 |
| WO | WO-2020/240025 A1 | 12/2020 |
| WO | WO-2021/076770 A1 | 4/2021 |
| WO | WO-2022/178274 A1 | 8/2022 |
| WO | WO-2022/236011 A1 | 11/2022 |
| WO | WO-2022/246269 A1 | 11/2022 |
| WO | WO-2022/246279 A1 | 11/2022 |
| WO | WO-2022/251586 A1 | 12/2022 |
| WO | WO-2022/261255 A1 | 12/2022 |
| WO | WO-2022/261481 A2 | 12/2022 |
| WO | WO-2024/103007 A1 | 5/2024 |
| WO | WO-2025/014828 A1 | 1/2025 |
| WO | WO-2025/189030 A1 | 9/2025 |

OTHER PUBLICATIONS

Zeng, Hongkui, and Joshua R. Sanes. "Neuronal cell-type classification: challenges, opportunities and the path forward." Nature Reviews Neuroscience 18.9 (2017): 530-546. (Year: 2017).*

Mount, Natalie M., et al. "Cell-based therapy technology classifications and translational challenges." Philosophical Transactions of the Royal Society B: Biological Sciences 370.1680 (2015): 20150017. (Year: 2015).*

Vickovic, Sanja, et al. "High-definition spatial transcriptomics for in situ tissue profiling." Nature methods 16.10 (2019): 987-990. (Year: 2019).*

Lowe, Rohan, et al. "Transcriptomics technologies." PLoS computational biology 13.5 (2017): e1005457. (Year: 2017).*

International Search Report and Written Opinion for Application No. PCT/US2022/028012, mailed Aug. 17, 2022.

International Preliminary Report on Patentability for Application No. PCT/US2022/028012, mailed Nov. 16, 2023.

International Search Report and Written Opinion for Application No. PCT/US2021/05682, mailed Feb. 10, 2022.

International Preliminary Report on Patentability for Application No. PCT/US2021/05682, mailed May 11, 2023.

International Search Report and Written Opinion for Application No. PCT/US2022/035271, mailed Oct. 11, 2022.

International Preliminary Report on Patentability for Application No. PCT/US2022/035271, mailed Jan. 11, 2024.

International Search Report and Written Opinion for Application No. PCT/US2022/017016, mailed May 24, 2022.

International Preliminary Report on Patentability for Application No. PCT/US2022/017016, mailed Aug. 31, 2023.

Invitation to Pay Additional Fees for Application No. PCT/US2022/031275, mailed Sep. 8, 2022.

International Search Report and Written Opinion for Application No. PCT/US2022/031275, mailed Oct. 31, 2022.

International Preliminary Report on Patentability for Application No. PCT/US2022/031275, mailed Dec. 7, 2023.

International Search Report and Written Opinion for Application No. PCT/US2022/039895, mailed Nov. 17, 2022.

International Preliminary Report on Patentability for Application No. PCT/US2022/039895, mailed Feb. 22, 2024.

Abbott et al., A nanoelectrode array for obtaining intracellular recordings from thousands of connected neurons. Nat Biomed Eng. Feb. 2020;4(2):232-241. doi: 10.1038/s41551-019-0455-7. Epub Sep. 23, 2019.

Abdelaal et al., SpaGE: spatial gene enhancement using scRNA-seq. Nucleic Acids Res. Oct. 9, 2020;48(18):e107. doi: 10.1093/nar/gkaa740.

Achim et al., High-throughput spatial mapping of single-cell RNA-seq data to tissue of origin. Nat Biotechnol. May 2015;33(5):503-9. doi: 10.1038/nbt.3209. Epub Apr. 13, 2015.

Akbalik et al., Visualization of newly synthesized neuronal RNA in vitro and in vivo using click-chemistry. RNA Biol. Jan. 2, 2017;14(1):20-28. doi: 10.1080/15476286.2016.1251541. Epub Nov. 1, 2016.

Alfaro et al., The emerging landscape of single-molecule protein sequencing technologies. Nat Methods. Jun. 2021;18(6):604-617. doi: 10.1038/s41592-021-01143-1. Epub Jun. 7, 2021.

Arganda-Carreras et al., Trainable Weka Segmentation: a machine learning tool for microscopy pixel classification. Bioinformatics. Aug. 1, 2017;33(15):2424-2426. doi: 10.1093/bioinformatics/btx180.

Asakura et al., Improvement of acquisition and analysis methods in multi-electrode array experiments with iPS cell-derived cardiomyocytes. J Pharmacol Toxicol Methods. Sep.-Oct. 2015;75:17-26. doi: 10.1016/j.vascn.2015.04.002. Epub Apr. 22, 2015.

(56) References Cited

OTHER PUBLICATIONS

Asp et al., Spatially Resolved Transcriptomes-Next Generation Tools for Tissue Exploration. Bioessays. Oct. 2020;42(10):e1900221. doi: 10.1002/bies.201900221. Epub May 4, 2020.

Axelrod et al., starfish: scalable pipelines for image-based transcriptomics. Journal of Open Source Software. 2021; 6(61): 2440. https://doi.org/10.21105/joss.02440.

Blondel et al., Fast unfolding of communities in large networks. arXiv. Oct. 2008; 2008: 1-12. DOI 10.1088/1742-5468/2008/10/P10008.

Bolanos-Burgos et al., Thiamine Deficiency Increases Intrinsic Excitability of Mouse Cerebellar Purkinje Cells. Cerebellum. Apr. 2021;20(2):186-202. doi: 10.1007/s12311-020-01202-x. Epub Oct. 24, 2020.

Braselmann et al., Illuminating RNA Biology: Tools for Imaging RNA in Live Mammalian Cells. Cell Chem Biol. Aug. 20, 2020;27(8):891-903. doi: 10.1016/j.chembiol.2020.06.010. Epub Jul. 7, 2020.

Burke et al., A Fluorescence in Situ Hybridization Method to Quantify mRNA Translation by Visualizing Ribosome-mRNA Interactions in Single Cells. ACS Cent Sci. May 24, 2017;3(5):425-433. doi: 10.1021/acscentsci.7b00048. Epub May 3, 2017.

Buxbaum et al., In the right place at the right time: Visualizing and understanding mRNA localization. Nat Rev Mol Cell Biol. Author manuscript; available in PMC Jun. 29, 2015. Published in final edited form as: Nat Rev Mol Cell Biol. Feb. 2015; 16(2): 95-109. Published online Dec. 30, 2014. doi: 10.1038/nrm3918.

Cadwell et al., Electrophysiological, transcriptomic and morphologic profiling of single neurons using Patch-seq. Nat Biotechnol. Feb. 2016;34(2):199-203. doi: 10.1038/nbt.3445. Epub Dec. 21, 2015.

Cao et al., Sci-fate characterizes the dynamics of gene expression in single cells. Nat Biotechnol. Author manuscript; available in PMC Oct. 13, 2020. Published in final edited form as: Nat Biotechnol. Aug. 2020; 38(8): 980-988. Published online Apr. 13, 2020. doi: 10.1038/s41587-020-0480-9.

Cao et al., The single-cell transcriptional landscape of mammalian organogenesis. Nature. Feb. 2019;566(7745):496-502. doi: 10.1038/s41586-019-0969-x. Epub Feb. 20, 2019.

Chatterjee et al., Nontoxic, double-deletion-mutant rabies viral vectors for retrograde targeting of projection neurons. Nat Neurosci. Apr. 2018;21(4):638-646. doi: 10.1038/s41593-018-0091-7. Epub Mar. 5, 2018.

Chen et al., Spatial Transcriptomics and In Situ Sequencing to Study Alzheimer's Disease. Cell. Aug. 20, 2020;182(4):976-991.e19. doi: 10.1016/j.cell.2020.06.038. Epub Jul. 22, 2020.

Chen et al., Spatially resolved, highly multiplexed RNA profiling in single cells. Science. Apr. 24, 2015;348(6233):aaa6090. doi: 10.1126/science.aaa6090. Epub Apr. 9, 2015.

Codeluppi et al., Spatial organization of the somatosensory cortex revealed by osmFISH. Nat Methods. Nov. 2018;15(11):932-935. doi: 10.1038/s41592-018-0175-z. Epub Oct. 30, 2018.

Coelho et al., Nuclear segmentation in microscope cell images: a hand-segmented dataset and comparison of algorithms. Proc IEEE Int Symp Biomed Imaging. 2009:5193098:518-521. doi: 10.1109/ISBI.2009.5193098.

Crosetto et al., Spatially resolved transcriptomics and beyond. Nat Rev Genet. Jan. 2015;16(1):57-66. doi: 10.1038/nrg3832. Epub Dec. 2, 2014.

Cui et al., Single-Cell Transcriptome Analysis Maps the Developmental Track of the Human Heart. Cell Rep. Feb. 12, 2019;26(7):1934-1950.e5. doi: 10.1016/j.celrep.2019.01.079.

Dixit et al., Perturb-Seq: Dissecting Molecular Circuits with Scalable Single-Cell RNA Profiling of Pooled Genetic Screens. Cell. Dec. 15, 2016;167(7):1853-1866.e17. doi: 10.1016/j.cell.2016.11.038.

Djebali et al., Landscape of transcription in human cells. Nature. Sep. 6, 2012;489(7414):101-8. doi: 10.1038/nature11233.

Dominissini et al., The topology of the human and mouse m6A RNA methylomes revealed by m6A-seq. Nature. Apr. 29, 2012;485(7397):201-6. doi: 10.1038/nature11112.

Eng et al., Transcriptome-scale super-resolved imaging in tissues by RNA seqFISH. Nature. Apr. 2019;568(7751):235-239. doi: 10.1038/s41586-019-1049-y. Epub Mar. 25, 2019.

Fazal et al., Atlas of Subcellular RNA Localization Revealed by APEX-Seq. Cell. Jul. 11, 2019;178(2):473-490.e26. doi: 10.1016/j.cell.2019.05.027. Epub Jun. 20, 2019.

Feiner et al., Engineered hybrid cardiac patches with multifunctional electronics for online monitoring and regulation of tissue function. Nat Mater. Jun. 2016;15(6):679-85. doi: 10.1038/nmat4590. Epub Mar. 14, 2016.

Franti et al., K-means properties on six clustering benchmark datasets. Applied Intelligence. Dec. 2018; 48(2): 4743-4759. DOI:10.1007/s10489-018-1238-7.

Friedman et al., Diverse Brain Myeloid Expression Profiles Reveal Distinct Microglial Activation States and Aspects of Alzheimer's Disease Not Evident in Mouse Models. Cell Rep. Jan. 16, 2018;22(3):832-847. doi: 10.1016/j.celrep.2017.12.066.

Friedman et al., Single-Cell Transcriptomic Analysis of Cardiac Differentiation from Human PSCs Reveals HOPX-Dependent Cardiomyocyte Maturation. Cell Stem Cell. Oct. 4, 2018;23(4):586-598.e8. doi: 10.1016/j.stem.2018.09.009.

Fu et al., Stable long-term chronic brain mapping at the single-neuron level. Nat Methods. Oct. 2016;13(10):875-82. doi: 10.1038/nmeth.3969. Epub Aug. 29, 2016.

Fuzik et al., Integration of electrophysiological recordings with single-cell RNA-seq data identifies neuronal subtypes. Nat Biotechnol. Feb. 2016;34(2):175-183. doi: 10.1038/nbt.3443. Epub Dec. 21, 2015.

Gao et al., Intracellular neuronal recording in awake nonhuman primates. Nature Protoc. Nov. 2020;15(11):3615-3631. doi: 10.1038/s41596-020-0388-3. Epub Oct. 12, 2020.

Gao, ClusterMap—Compare multiple Single cell RNA-seq profiling. May 22, 2018. 57 pages. Retrieved from the Internet: https://xgaoo.github.io/ClusterMap/ClusterMap.html. [last accessed: Jul. 12, 2023].

Goddard et al., UCSF ChimeraX: Meeting modern challenges in visualization and analysis. Protein Sci. Jan. 2018;27(1):14-25. doi: 10.1002/pro.3235. Epub Sep. 6, 2017.

Goddard et al., Visualizing density maps with UCSF Chimera. J Struct Biol. Jan. 2007;157(1):281-7. doi: 10.1016/j.jsb.2006.06.010. Epub Jul. 15, 2006.

Goltsev et al., Deep profiling of mouse splenic architecture with CODEX multiplexed imaging. Cell. Aug. 9, 2018;174(4):968-981.e15. doi: 10.1016/j.cell.2018.07.010. Epub Aug. 2, 2018.

Han et al., Mapping the Mouse Cell Atlas by Microwell-Seq. Cell. Feb. 22, 2018;172(5):1091-1107.e17. doi: 10.1016/j.cell.2018.02.001.

Hao et al., Integrated analysis of multimodal single-cell data. Cell. Jun. 24, 2021;184(13):3573-3587.e29. doi: 10.1016/j.cell.2021.04.048. Epub May 31, 2021.

He et al., ClusterMap: multi-scale clustering analysis of spatial gene expression. Nat Commun. Oct. 8, 2021;12(1):5909. doi: 10.1038/s41467-021-26044-x.

He et al., Integrating spatial gene expression and breast tumor morphology via deep learning. Nat Biomed Eng. Aug. 2020;4(8):827-834. doi: 10.1038/s41551-020-0578-x. Epub Jun. 22, 2020.

Heideman et al., Gauss and the history of the fast Fourier transform. IEEE ASSP Magazine. Oct. 1994; 1(4): 14-21. 10.1109/MASSP.1984.1162257.

Hendriks et al., NASC-seq monitors RNA synthesis in single cells. Nat Commun. Jul. 17, 2019;10(1):3138. doi: 10.1038/s41467-019-11028-9.

Hernandez-Ochoa et al., Voltage clamp methods for the study of membrane currents and SR Ca(2+) release in adult skeletal muscle fibres. Prog Biophys Mol Biol. Apr. 2012; 108(3):98-118. doi: 10.1016/j.pbiomolbio.2012.01.001. Epub Jan. 26, 2012.

Higham et al., Linear Algebra. Chapter 9 in: MATLAB Guide. 3rd Edition. Siam, Eds. 2016. pp. 135-158.

Hunter, Matplotlib: a 2D graphics environment. Comput Sci Eng. May-Jun. 2007; 9(3): 90-95. DOI: 10.1109/MCSE.2007.55.

(56)     References Cited

OTHER PUBLICATIONS

Ingolia et al., Genome-wide analysis in vivo of translation with nucleotide resolution using ribosome profiling. Science. Apr. 10, 2009;324(5924):218-23. doi: 10.1126/science.1168978. Epub Feb. 12, 2009.

Ingolia, Ribosome Footprint Profiling of Translation throughout the Genome. Cell. Mar. 24, 2016;165(1):22-33. doi: 10.1016/j.cell.2016.02.066.

Jan et al., Principles of ER cotranslational translocation revealed by proximity-specific ribosome profiling. Science. Author manuscript; available in PMC Jan. 6, 2015. Published in final edited form as: Science. Nov. 7, 2014; 346(6210): 1257521. Published online Nov. 6, 2014. doi: 10.1126/science.1257521.

Jao et al., Exploring RNA transcription and turnover in vivo by using click chemistry. Proc Natl Acad Sci U S A. Oct. 14, 2008;105(41):15779-84. doi: 10.1073/pnas.0808480105. Epub Oct. 7, 2008.

Jonkhout et al., The RNA modification landscape in human disease. RNA. Dec. 2017;23(12):1754-1769. doi: 10.1261/rna.063503.117. Epub Aug. 30, 2017.

Jun et al., Fully integrated silicon probes for high-density recording of neural activity. Nature. Nov. 8, 2017;551(7679):232-236. doi: 10.1038/nature24636.

Katz et al., Mapping translation "hot-spots" in live cells by tracking single molecules of mRNA and ribosomes. Elife. Jan. 13, 2016:5:e10415. doi: 10.7554/eLife.10415.

Ke et al., In situ sequencing for RNA analysis in preserved tissue and cells. Nat Methods. Sep. 2013;10(9):857-60. doi: 10.1038/nmeth.2563. Epub Jul. 14, 2013.

Keller et al., Visualizing whole-brain activity and development at the single-cell level using light-sheet microscopy. Neuron. Feb. 4, 2015;85(3):462-83. doi: 10.1016/j.neuron.2014.12.039.

Kishi et al., SABER amplifies FISH: enhanced multiplexed imaging of RNA and DNA in cells and tissues. Nat Methods. Jun. 2019;16(6):533-544. doi: 10.1038/s41592-019-0404-0. Epub May 20, 2019.

Kodandaramaiah et al., Automated whole-cell patch-clamp electrophysiology of neurons in vivo. Nat Methods. Jun. 2012;9(6):585-7. doi: 10.1038/nmeth.1993. Epub May 6, 2012.

Koh et al., Quantitative FastFUCCI assay defines cell cycle dynamics at single-cell level. J Cell Sci. Jan. 15, 2017;130(2):512-520. doi: 10.1242/jcs.195164. Epub Nov. 25, 2016.

Koos et al., Analysis of protein interactions in situ by proximity ligation assays. Curr Top Microbiol Immunol. 2014;377:111-26. doi: 10.1007/82_2013_334.

Lau et al., Single-nucleus transcriptome analysis reveals dysregulation of angiogenic endothelial cells and neuroprotective glia in Alzheimer's disease. Proc Natl Acad Sci U S A. Oct. 13, 2020;117(41):25800-25809. doi: 10.1073/pnas.2008762117. Epub Sep. 28, 2020.

Lee et al., Fluorescent in situ sequencing (FISSEQ) of RNA for gene expression profiling in intact cells and tissues. Nat Protoc. Mar. 2015;10(3):442-58. doi: 10.1038/nprot.2014.191. Epub Feb. 12, 2015.

Lee et al., Highly multiplexed subcellular RNA sequencing in situ. Science. Mar. 21, 2014;343(6177):1360-3. doi: 10.1126/science.1250212. Epub Feb. 27, 2014.

Lein et al., The promise of spatial transcriptomics for neuroscience in the era of molecular cell typing. Science. Oct. 6, 2017;358(6359):64-69. doi: 10.1126/science.aan6827.

Li et al., Cyborg Organoids: Implantation of Nanoelectronics via Organogenesis for Tissue-Wide Electrophysiology. Nano Lett. Aug. 14, 2019;19(8):5781-5789. doi: 10.1021/acs.nanolett.9b02512. Epub Aug. 2, 2019.

Li et al., Epitranscriptome sequencing technologies: decoding RNA modifications. Nat Methods. Dec. 29, 2016;14(1):23-31. doi: 10.1038/nmeth.4110.

Liu et al., Intrinsically stretchable electrode array enabled in vivo electrophysiological mapping of atrial fibrillation at cellular reso-lution. Proc Natl Acad Sci U S A. Jun. 30, 2020;117(26):14769-14778. doi: 10.1073/pnas.2000207117. Epub Jun. 15, 2020.

Liu et al., Multifunctional three-dimensional macroporous nanoelectronic networks for smart materials. Proc Natl Acad Sci U S A. Apr. 23, 2013;110(17):6694-9. doi: 10.1073/pnas.1305209110. Epub Apr. 8, 2013.

Liu et al., Probing N6-methyladenosine RNA modification status at single nucleotide resolution in mRNA and long non-coding RNA. RNA. Dec. 2013;19(12):1848-56. doi: 10.1261/rna.041178.113. Epub Oct. 18, 2013.

Liu et al., Syringe-injectable electronics. Nat Nanotechnol. Jul. 2015;10(7):629-636. doi: 10.1038/nnano.2015.115. Epub Jun. 8, 2015.

Machiraju et al., Current methods for the maturation of induced pluripotent stem cell-derived cardiomyocytes. World J Stem Cells. Jan. 26, 2019;11(1):33-43. doi: 10.4252/wjsc.v11.i1.33.

MacQueen, Some methods for classification and analysis of multivariate observations. Berkeley Symp on Math Statist and Prob. 1967; 5.1: 281-297.

Mathys et al., Single-cell transcriptomic analysis of Alzheimer's disease. Nature. Author manuscript; available in PMC Dec. 1, 2019. Published in final edited form as: Nature. Jun. 2019; 570(7761): 332-337. Published online May 1, 2019. doi: 10.1038/s41586-019-1195-2.

McCabe et al., Automated quantitative analysis (AQUA) of in situ protein expression, antibody concentration, and prognosis. J Natl Cancer Inst. Dec. 21, 2005;97(24):1808-15. doi: 10.1093/jnci/dji427.

McInnes et al., UMAP: Uniform Manifold Approximation and Projection. Journal of Open Source Software. Sep. 2, 2018; 3(29): 861. https://doi.org/10.21105/joss.00861.

McInnes et al., UMAP: Uniform Manifold Approximation and Projection for Dimension Reduction. ArXiv. Sep. 21, 2020; 1-63. https://arxiv.org/pdf/1802.03426.pdf [last accessed Nov. 6, 2023].

McKinney, Data structures for statistical computing in Python. Proc of the 9th Python in Science Conference. Jan. 2010; 56-61. DOI:10.25080/Majora-92bf1922-00a.

Moen et al., Deep learning for cellular image analysis. Nat Methods. Dec. 2019;16(12):1233-1246. doi: 10.1038/s41592-019-0403-1. Epub May 27, 2019.

Moffitt et al., Molecular, spatial, and functional single-cell profiling of the hypothalamic preoptic region. Science. Nov. 16, 2018;362(6416):eaau5324. doi: 10.1126/science.aau5324. Epub Nov. 1, 2018.

Nitzan et al., Gene expression cartography. Nature. Dec. 2019;576(7785):132-137. doi: 10.1038/s41586-019-1773-3. Epub Nov. 20, 2019.

No Author Listed, Starfish: Open-Source Image Based Transcriptomics and Proteomics Tools. 2018. http://github.com/spacetx/starfish [Online; accessed Feb. 1, 2023].

Oliphant, Guide to NumPy. 1st Edition. Trelgol Publishing USA, Eds. 2006, 378 pages.

Park et al., Segmentation-free inference of cell types from in situ transcriptomics data. Nat Commun. Jun. 10, 2021;12(1):3545. doi: 10.1038/s41467-021-23807-4.

Pedregosa et al., Scikit-learn: machine learning in Python. J Machine Learn Res. Oct. 2011; 12: 2825-2830.

Perez et al., Python: an ecosystem for scientific computing. Comput Sci Eng. May 2011; 13(2): 13-21. DOI:10.1109/MCSE.2010.119.

Perkel, Starfish enterprise: finding RNA patterns in single cells. Nature. Aug. 2019;572(7770):549-551. doi: 10.1038/d41586-019-02477-9.

Petukhov et al., Bayesian segmentation of spatially resolved transcriptomics data. bioRxiv. Oct. 6, 2020. 34 pages. doi: https://doi.org/10.1101/2020.10.05.326777.

Qian et al., Probabilistic cell typing enables fine mapping of closely related cell types in situ. Nat Methods. Jan. 2020;17(1):101-106. doi: 10.1038/s41592-019-0631-4. Epub Nov. 18, 2019.

Qiu et al., Mapping transcriptomic vector fields of single cells. Cell. Feb. 17, 2022;185(4):690-711.e45. doi: 10.1016/j.cell.2021.12.045. Epub Feb. 1, 2022.

Qiu et al., Massively parallel and time-resolved RNA sequencing in single cells with scNT-seq. Nat Methods. Author manuscript; avail-

(56)                    References Cited

OTHER PUBLICATIONS able in PMC May 7, 2021. Published in final edited form as: Nat Methods. Oct. 2020; 17(10): 991-1001. Published online Aug. 31, 2020. doi: 10.1038/s41592-020-0935-4.

Qu et al., Layer-Enriched Tissue Dissection of the Mouse Placenta in Late Gestation. In: The Guide to Investigation of Mouse Pregnancy. Academic Press, Eds. 2014; 529-535. DOI:10.1016/B978-0-12-394445-0.00044-8.

Rabani et al., Metabolic labeling of RNA uncovers principles of RNA production and degradation dynamics in mammalian cells. Nat Biotechnol. Author manuscript; available in PMC Nov. 1, 2011. Published in final edited form as: Nat Biotechnol. May 2011; 29(5): 436-442. Published online Apr. 24, 2011. doi: 10.1038/nbt.1861.

Rodriguez et al., Clustering by fast search and find of density peaks. Science. Jun. 27, 2014;344(6191):1492-6. doi: 10.1126/science. 1242072.

Rokach et al., Clustering Methods. Chapter 15 in: Data Mining and Knowledge Discovery Handbook. 2005; 321-352.

Rosenberg et al., Single-cell profiling of the developing mouse brain and spinal cord with split-pool barcoding. Science. Apr. 13, 2018;360(6385):176-182. doi:10.1126/science.aam8999. Epub Mar. 15, 2018.

Roundtree et al., Dynamic RNA Modifications in Gene Expression Regulation. Cell. Jun. 15, 2017;169(7):1187-1200. doi: 10.1016/j. cell.2017.05.045.

Rueden et al., ImageJ2: ImageJ for the next generation of scientific image data. BMC Bioinformatics. Nov. 29, 2017;18(1):529. doi: 10.1186/s12859-017-1934-z.

Sakaue-Sawano et al., Visualizing spatiotemporal dynamics of multicellular cell-cycle progression. Cell. Feb. 8, 2008;132(3):487-98. doi: 10.1016/j.cell.2007.12.033.

Schlegel et al., Charged pore-lining residues are required for normal channel kinetics in the eukaryotic mechanosensitive ion channel MSL1. Channels. (Austin). Dec. 2020;14(1):310-325. doi: 10.1080/19336950.2020.1818509.

Schmidt et al., Cell detection with star-convex polygons. Medical Image Computing and Computer Assisted Intervention Conference (MICCAI). Lecture Notes in Computer Science book series. Sep. 26, 2018;11071: 265-273.

Schwanhausser et al., Global quantification of mammalian gene expression control. Nature. May 19, 2011;473(7347):337-42. doi: 10.1038/nature10098.

Shah et al., In Situ Transcription Profiling of Single Cells Reveals Spatial Organization of Cells in the Mouse Hippocampus. Neuron. Oct. 19, 2016;92(2):342-357. doi: 10.1016/j.neuron.2016.10.001.

Shah et al., seqFISH accurately detects transcripts in single cells and reveals robust spatial organization in the hippocampus. Neuron. May 17, 2017;94(4):752-758.e1. doi: 10.1016/j.neuron.2017.05. 008.

Stahl et al., Visualization and analysis of gene expression in tissue sections by spatial transcriptomics. Science. Jul. 1, 2016;353(6294):78-82. doi: 10.1126/science.aaf2403.

Stark et al., RNA sequencing: the teenage years. Nat Rev Genet. Nov. 2019;20(11):631-656. doi: 10.1038/s41576-019-0150-2. Epub Jul. 24, 2019.

Stickels et al., Highly sensitive spatial transcriptomics at near-cellular resolution with Slide-seqV2. Nat Biotechnol. Author manuscript; available in PMC Nov. 21, 2021. Published in final edited form as: Nat Biotechnol. Mar. 2021; 39(3): 313-319. Published online Dec. 7, 2020. doi: 10.1038/s41587-020-0739-1.

Strell et al., Placing RNA in context and space—methods for spatially resolved transcriptomics. FEBS J. Apr. 2019;286(8):1468-1481. doi: 10.1111/febs.14435. Epub Mar. 31, 2018.

Stuart et al., Comprehensive integration of single-cell data. Cell. Jun. 13, 2019;177(7):1888-1902.e21. doi: 10.1016/j.cell.2019.05. 031. Epub Jun. 6, 2019.

Stuart et al., Integrative single-cell analysis. Nat Rev Genet. May 2019;20(5):257-272. doi: 10.1038/s41576-019-0093-7.

Thomas et al., A review on cell detection and segmentation in microscopic images. 2017 International Conference on Circuit, Power and Computing Technologies (ICCPCT). Date of Conference: Apr. 20-21, 2017. 5 pages. 10.1109/ICCPCT.2017.8074189.

Tian et al., Macroporous nanowire nanoelectronic scaffolds for synthetic tissues. Nat Mater. Nov. 2012;11(11):986-94. doi: 10.1038/nmat3404. Epub Aug. 26, 2012.

Tirosh et al., Dissecting the multicellular ecosystem of metastatic melanoma by single-cell RNA-seq. Science. Author manuscript; available in PMC Jul. 14, 2016. Published in final edited form as: Science. Apr. 8, 2016; 352(6282): 189-196. doi: 10.1126/science. aad0501.

Toga et al., Towards multimodal atlases of the human brain. Nat Rev Neurosci. Dec. 2006;7(12):952-66. doi: 10.1038/nrn2012.

Traag et al., From Louvain to Leiden: guaranteeing well-connected communities. Sci Rep. Mar. 26, 2019;9(1):5233. doi: 10.1038/s41598-019-41695-z.

Van Den Berge et al., Trajectory-based differential expression analysis for single-cell sequencing data. Nat Commun. Mar. 5, 2020;11(1):1201. doi: 10.1038/s41467-020-14766-3.

Van Der Walt et al., scikit-image: image processing in Python. Peer J. Jun. 19, 2014:2:e453. doi: 10.7717/peerj.453. eCollection 2014.

Van't Sant et al., In vivo 5-ethynyluridine (EU) labelling detects reduced transcription in Purkinje cell degeneration mouse mutants, but can itself induce neurodegeneration. Acta Neuropathol Commun. May 21, 2021;9(1):94. doi: 10.1186/s40478-021-01200-y.

Viventi et al., Flexible, foldable, actively multiplexed, high-density electrode array for mapping brain activity in vivo. Nat Neurosci. Nov. 13, 2011;14(12):1599-605. doi: 10.1038/nn.2973.

Wang et al., N6-methyladenosine modulates messenger RNA translation Efficiency. Cell. Jun. 4, 2015;161(6):1388-99. doi: 10.1016/j.cell.2015.05.014.

Wang et al., N6-methyladenosine-dependent regulation of messenger RNA stability. Nature. Author manuscript; available in PMC Jul. 2, 2014. Published in final edited form as: Nature. Jan. 2, 2014; 505(7481): 117-120. Published online Nov. 27, 2013. doi: 10.1038/nature12730.

Wang et al., Spatial organization of the transcriptome in individual neurons. bioRxiv. Dec. 7, 2020; 1-45. doi: https://doi.org/10.1101/2020.12.07.414060.

Wang et al., Three-dimensional intact-tissue sequencing of single-cell transcriptional states. Science. Jul. 27, 2018;361(6400):eaat5691. doi: 10.1126/science.aat5691. Epub Jun. 21, 2018.

Weibrecht et al., Visualising individual sequence-specific protein-DNA interactions in situ. N Biotechnol. Jun. 15, 2012;29(5):589-98. doi: 10.1016/j.nbt.2011.08.002. Epub Aug. 31, 2011.

Widagdo et al., The m6A-epitranscriptomic signature in neurobiology: from neurodevelopment to brain plasticity. J Neurochem. Oct. 2018;147(2):137-152. doi: 10.1111/jnc.14481. Epub Aug. 1, 2018.

Wolf et al., SCANPY: large-scale single-cell gene expression data analysis. Genome Biol. Feb. 6, 2018;19(1):15. doi: 10.1186/s13059-017-1382-0.

Xia et al., Spatial transcriptome profiling by MERFISH reveals subcellular RNA compartmentalization and cell cycle-dependent gene expression. Proc Natl Acad Sci U S A. Sep. 24, 2019;116(39):19490-19499. doi: 10.1073/pnas.1912459116. Epub Sep. 9, 2019.

Zechel et al., Topographical transcriptome mapping of the mouse medial ganglionic eminence by spatially resolved RNA-seq. Genome Biol. 2014;15(10):486. doi: 10.1186/s13059-014-0486-z.

Zhou et al., Encoding Method of Single-cell Spatial Transcriptomics Sequencing. Int J Biol Sci. 2020; 16(14): 2663-2674. Published online Jul. 30, 2020. doi: 10.7150/ijbs.43887.

Zhou et al., Human and mouse single nucleus transcriptomics reveal TREM2-dependent and TREM2-independent cellular responses in Alzheimer's disease. Nat Med. Author manuscript; available in PMC Jul. 13, 2020. Published in final edited form as: Nat Med. Jan. 2020; 26(1): 131-142. Published online Jan. 13, 2020. doi: 10.1038/s41591-019-0695-9.

Zhu et al., Single-cell multimodal omics: the power of many. Nat Methods. Jan. 2020;17(1):11-14. doi: 10.1038/s41592-019-0691-5.

Virtanen et al., "SciPy 1.0: Fundamental Algorithms for Scientific Computing in Python," Nature Methods, 2020, vol. 17, (pp. 261-272).

(56)            References Cited

OTHER PUBLICATIONS

Alpert, N.M. et al., "The principal axes transformation—a method for image registration," Journal of nuclear Medicine: official publication, Society of Nuclear Medicine, 1990, vol. 31, No. 10 (pp. 1717-1722).

Avey, et al., "Single-cell RNA-seq uncovers a robust transcriptional response to morphine by glia," Cell Reports, Sep. 2018, vol. 24, No. 13 (pp. 3619-3629, e1-e4).

Bagasra, Omar, "Protocols for the in situ PCR-amplification and detection of mRNA and DNA sequences," Nature Protocols, Nov. 2007, vol. 2, No. 11 (pp. 2782-2795).

Baner, et al., "Signal amplification of padlock probes by rolling circle replication," Nucleic Acids Research, Nov. 1998, vol. 26, No. 22 (pp. 5073-5078).

Braasch, et al., "Novel antisense and peptide nucleic acid strategies for controlling gene expression," Biochemistry, Mar. 2002, vol. 41, No. 14 (pp. 4503-4510).

Buchwalow, et al., "Immunohistochemistry: Basics and Methods," Springer-Verlag Berlin Heidelberg, 2010, vol. 4, No. 13 (pp. 109-127).

Chen, et al., "Efficient in situ barcode sequencing using padlock probe-based BaristaSeq," Nucleic Acids Research, Feb. 2018, vol. 46, No. 4 (10 pages).

Chen, et al., "High-Throughput Mapping of Long-Range Neuronal Projection Using In Situ Sequencing," Oct. 2019, Cell, vol. 179, No. 3 (pp. 772-786).

Chen, et al., "Nanoscale Imaging of RNA with Expansion Microscopy," Nature Methods, Jul. 2016, vol. 13 (pp. 679-684).

Cheng, et al., "Sequencing-free whole-genome spatial transcriptomics at single-molecule resolution," Cell, Nov. 2025, vol. 188, No. 24 (pp. 6953-6970).

Clausson, et al., "Compaction of rolling circle amplification products increases signal integrity and signal-to-noise ratio," Scientific Reports, Jul. 2015, vol. 5, No. 12317 (pp. 1-10).

Data Portal: Allen Mouse Brain Atlas Data Portal 2004; [retrieved on Oct. 3, 2025], Available at URL:https://mouse.brain-map.org/ (pp. 1-2).

Deng, et al., "DNA-Sequence-Encoded Rolling Circle Amplicon for Single-Cell RNA Imaging," Chem, Jun. 2018, vol. 4, No. 6 (pp. 1373-1386).

El-Nachef, et al., "High-resolution 3D fluorescent imaging of intact tissues," International Journal of Cardiology and Cardiovascular Diseases, 2021, vol. 1, No. 1 (pp. 1-14).

Englisch, et al., "Chemically Modified Oligonucleotides as Probes and Inhibitors," Angewandte Chemie, International Edition, Jun. 1991, vol. 30, No. 6 (pp. 613-629).

Fang, et al., "Three-dimensional single-cell transcriptome imaging of thick tissues," Elife, Dec. 2024, vol. 12, RP90029 (pp. 1-18).

Faruqi, et al., "High-throughput genotyping of single nucleotide polymorphisms with rolling circle amplification," BMC Genomics, Aug. 2001, vol. 2, No. 4 (pp. 1-10).

Ferkowicz, et al., "Large-scale, three-dimensional tissue cytometry of the human kidney: a complete and accessible pipeline," Laboratory Investigation, Jan. 2021, vol. 101, No. 5 (pp. 661-676).

Fredriksson et al., "Protein detection using proximity-dependent DNA ligation assays," Nature Biotechnology, May 2002, vol. 20 (pp. 473-477).

Gandin, et al., "Deep-tissue spatial omics: imaging whole-embryo transcriptomics and subcellular structures at high spatial resolution," bioRxiv, Dec. 2024, https://doi.org/10.1101/2024.05.17. 594641 (137 pages).

Guenthner, et al., "Permanent genetic access to transiently active neurons via TRAP: targeted recombination in active populations," Neuron, Jun. 2013, vol. 78, No. 5 (pp. 773-784).

Hrvatin, et al., "Single-cell analysis of experience-dependent transcriptomic states in the mouse visual cortex," Nature Neuroscience, 2018, vol. 21, No. 1 (pp. 120-129).

International Preliminary Report on Patentability for Appl. Ser. No. PCT/US2017/019443 dated Sep. 7, 2018 (8 pages).

International Preliminary Report on Patentability for Appl. Ser. No. PCT/US2019/025835 dated Oct. 22, 2020 (8 pages).

International Preliminary Report on Patentability for Appl. Ser. No. PCT/US2020/055800 dated Apr. 28, 2022 (8 pages).

International Preliminary Report on Patentability for Appl. Ser. No. PCT/US2022/030232 dated Nov. 30, 2023 (11 pages).

International Preliminary Report on Patentability for Appl. Ser. No. PCT/US2022/030321 dated Nov. 30, 2023 (7 pages).

International Preliminary Report on Patentability for Appl. Ser. No. PCT/US2022/030363 dated Nov. 30, 2023 (7 pages).

International Search Report and Written Opinion for Appl. Ser. No. PCT/US2017/019443 dated May 19, 2017 (10 pages).

International Search Report and Written Opinion for Appl. Ser. No. PCT/US2020/055800 dated Feb. 22, 2021 (10 pages).

International Search Report and Written Opinion for Appl. Ser. No. PCT/US2022/030232 dated Oct. 26, 2022 (15 pages).

International Search Report and Written Opinion for Appl. Ser. No. PCT/US2022/030321 dated Oct. 6, 2022 (9 pages).

International Search Report and Written Opinion for Appl. Ser. No. PCT/US2022/030363 dated Sep. 1, 2022 (9 pages).

International Search Report and Written Opinion for Appl. Ser. No. PCT/US2022/030370 dated Sep. 1, 2022 (9 pages).

International Search Report and Written Opinion for Appl. Ser. No. PCT/US2022/030374 dated Sep. 1, 2022 (9 pages).

International Search Report and Written Opinion for Appl. Ser. No. PCT/US2024/060469 dated May 7, 2025 (16 pages).

International Search Report and Written Opinion for Appl. Ser. No. PCT/US2025/018783 dated Jun. 27, 2025 (10 pages).

International Search Report and Written Opinion for Appl. Ser. No. PCT/US2025/030656 dated Aug. 7, 2025 (15 pages).

International Search Report and Written Opinion for Appl. Ser. PCT/US2024/036943 dated Oct. 18, 2024 (14 pages).

International Search Report for Appl. Ser. No. PCT/US2019/025835 dated Jul. 1, 2019 (3 pages).

Jerby-Arnon et al., "A Cancer Cell Program Promotes T Cell Exclusion and Resistance to Checkpoint Blockade," Cell, Nov. 1, 2018, vol. 175, No. 4 (pp. 984-997).

Ji, et al., "Multimodal Analysis of Composition and Spatial Architecture in Human Squamous Cell Carcinoma," Cell, Jul. 2020, vol. 182, No. 6 (pp. 1661-1662).

Joost, et al., "The molecular anatomy of mouse skin during hair growth and rest," Cell Stem Cell, Mar. 2020, vol. 26, No. 3 (pp. 441-457).

JP Office Action for JP Appl. Ser. No. 2024-088875 dated Nov. 28, 2025 (5 pages).

Klein, et al., "elastix: a toolbox for intensity-based medical image registration," IEEE transactions on medical imaging, Published Online Nov. 17, 2009, vol. 29, No. 1 (pp. 196-205).

Korsunsky et al., "Fast, sensitive and accurate integration of single-cell data with Harmony," Nature Methods, Dec. 2019, vol. 16, No. 12 (pp. 1289-1296).

Larsson, et al., "In situ detection and genotyping of individual mRNA molecules," Nature Methods, May 2010, vol. 7, No. 5 (pp. 395-397).

Li, et al., "High-dimensional cell-level analysis of tissues with Ce3D multiplex volume imaging," Nature Protocols, Apr. 2019, vol. 14, No. 6 (pp. 1708-1733).

Lizardi et al. "Mutation detection and single-molecule counting using isothermal rolling-circle amplification," Nature Genetics, Jul. 1998, vol. 19 (pp. 225-232).

Lubeck, et al., "Single-cell systems biology by super-resolution imaging and combinatorial labeling," Nature Methods, Jun. 2012, vol. 9, No. 7 (pp. 743-748).

Maintz, et al., "A survey of medical Image Registration," Medical Image Analysis, Mar. 1998, vol. 2, No. 1 (pp. 1-36).

Mondal, et al., "Highly multiplexed single-cell in situ RNA and DNA analysis with bioorthogonal cleavable fluorescent oligonucleotides," Chemical Science, Feb. 2018, vol. 9, No. 11 (pp. 2909-2917).

Nawy, Tal., "In situ sequencing," Nature Methods, Jan. 2014, vol. 11, No. 1 (p. 29).

(56)                References Cited

OTHER PUBLICATIONS

Nejad, et al., "Interstrand DNA cross-links derived from reaction of a 2-aminopurine residue with an abasic site," ACS Chemical Biology, Jun. 2019, vol. 14, No. 7 (pp. 1481-1489).

Norris, et al., "Whole Tissue Imaging of Cellular Boundaries at Sub-Micron Resolutions for Automatic Cell Segmentation: Applications in Epithelial Bending of Ectodermai Appendages," bioRxiv, Oct. 2024 (pp. 1-18).

Ornatsky, et al., "Highly multiparametric analysis by mass cytometry," Journal of Immunological Methods, Sep. 2010, vol. 361 Nos. 1-2 (pp. 1-20).

Player, et al., "Single-copy gene detection using branched DNA (bDNA) in situ hybridization," The Journal of Histochemistry and Cytochemistry, May 2001, vol. 49, No. 5 (pp. 603-612).

Robles-Remacho, et al., "Spatial Transcriptomics: Emerging Technologies in Tissue Gene Expression Profiling," Analytical Chemistry, Oct. 2023, vol. 95, No. 42 (pp. 15450-15460).

Rosales, et al., "The design of reversible hydrogels to capture extracellular matrix dynamics," Nature Reviews Materials, Feb. 2016, vol. 1 No. 15012 (pp. 1-15).

Sakaguchi, et al., "Bright multicolor labeling of neuronal circuits with fluorescent proteins and chemical tags," Elife, Nov. 2018, vol. 7 (pp. 1-28).

Samusik et al., "Automated mapping of phenotype space with single-cell data," Nature Methods, Jun. 2016, vol. 13, No. 6 (pp. 493-496).

Sanz, et al., "Cell-type-specific isolation of ribosome-associated mRNA from complex tissues," Proceedings of the National Academy of Sciences, USA, Aug. 2009, vol. 106, No. 33 (pp. 13939-13944).

Scheffer, et al. "A connectome and analysis of the adult Drosophila central brain," elife, Sep.-Oct. 2020, No. 57443 (pp. 1-83).

Schweitzer, et al. "Multiplexed protein profiling on microarrays by rolling-circle amplification," Nature Biotechnology, Apr. 2002, vol. 20 (pp. 359-365).

Schweitzer, et al., "Immunoassays with rolling circle DNA amplification: A versatile platform for ultrasensitive antigen detection," Proceedings of the National Academy of Sciences, USA, Aug. 29, 2000, vol. 97, No. 18 (pp. 10113-10119).

Shah, et al., "Single-molecule RNA detection at depth by hybridization chain reaction and tissue hydrogel embedding and clearing," Development, 2016, vol. 143, No. 15 (pp. 2862-2867).

Shkrob, et al., "Far-red fluorescent proteins evolved from a blue chromoprotein from Actinia equina," The Biochemical Journal, Dec. 2005, vol. 392, No. 3 (pp. 649-654).

Soderberg, et al., "Direct observation of individual endogenous protein complexes in situ by proximity ligation," Nature Methods, Oct. 2006, vol. 3, No. 12 (pp. 995-1000).

Stevens, et al., "Furan-modified oligonucleotides for fast, high-yielding and site-selective DNA inter-strand cross-linking with non-modified complements," Nucleic Acids Research, Jan. 2009, vol. 37, No. 5 (pp. 1555-1565).

Sui, et al., "Scalable Spatial Single-cell Transcriptomics and Translatomics in 3d Thick Tissue Blocks," Biorxiv : the Preprint Server for Biology, Aug. 2024 (pp. 1-37).

Sui, et al., "Scalable spatial single-cell transcriptomics and translatomics in 3D thick tissue blocks," Nature Methods, Nov. 2025, vol. 22 (pp. 2574-2584).

Tainaka, et al., "Whole-body imaging with single-cell resolution by tissue decolorization," Cell, Nov. 2014, vol. 159, No. 4 (pp. 911-924).

Takko, et al., "ShapeMetrics: A userfriendly pipeline for 3D cell segmentation and spatial tissue analysis," Developmental Biology, Jun. 2020, vol. 462, No. 1 (7-19).

Tam, et al., "Engineering cellular microenvironments with photo- and enzymatically responsive hydrogels: toward biomimetic 3D cell culture models," Accounts of Chemical Research, Mar. 2017 vol. 50, No. 4 (pp. 703-713).

Taranda, et al., "Combined whole-organ imaging at single-cell resolution and immunohistochemical analysis of prostate cancer and its liver and brain metastases," Cell Reports, Nov. 2021, vol. 37, No. 7, 110027 (pp. 1-14).

Tasic, et al., "Shared and distinct transcriptomic cell types across neocortical areas," Nature, Oct. 2018, vol. 563, No. 7729 (pp. 72-78).

Tomer, et al., "Advanced Clarity for rapid and high-resolution imaging of intact tissues," Nature Protocols, Jun. 2014, vol. 9 (pp. 1682-1697).

US Final Office Action for U.S. Appl. No. 19/230,050 dated Dec. 17, 2025 (8 pages).

US Non-Final Office Action for U.S. Appl. No. 17/768,996 dated Aug. 22, 2025 (pages).

US Non-Final Office Action for U.S. Appl. No. 19/230,050 dated Sep. 4, 2025 (14 pages).

US Non-Final Office Action for U.S. Appl. No. 19/236,720 dated Aug. 7, 2025 (pages).

US Non-Final Restriction Requirement for U.S. Appl. No. 19/270,278 dated Sep. 11, 2025 (8 pages).

US Notice of Allowance for Appl. U.S. Appl. No. 19/270,264 dated Sep. 8, 2025 (9 pages).

US Office Non-Final Office Action for U.S. Appl. No. 19/236,732 dated Aug. 8, 2025 (32 pages).

Wang, et al. Supplemental Information: "Three-dimensional intact-tissue sequencing of single-cell transcriptional states," Science, Jun. 2018, vol. 361, No. 6400 (pp. 1-39).

Wang, et al., "EASI-FISH for thick tissue defines lateral hypothalamus spatio-molecular organization," Cell, Dec. 2021, vol. 184, No. 26 (pp. 6361-6377, e1-e24).

Weibrecht, et al., "In situ detection of individual mRNA molecules and protein complexes or post-translational modifications using padlock probes combined with the in situ proximity ligation assay," Nature protocols, Jan. 2013, vol. 8, No. 2 (pp. 355-372).

West, et al., "Polymeric Biomaterials with Degradation Sites for Proteases Involved in Cell Migration," Macromolecules, 1999 vol. 32, No. 1 (pp. 241-244).

Wetmur, James G., "DNA probes: applications of the principles of nucleic acid hybridization," Critical Reviews in Biochemistry and Molecular Biology, 1991, vol. 26, Nos. 3-4 (pp. 227-259).

Xu, et al., "Enhanced FIB-SEM systems for large-volume 3D imaging,"elife, May 2017 6, e25916 (pp. 1-36).

Yang, et al., "Single-cell phenotyping within transparent intact tissue through whole-body clearing," Cell, Aug. 2014, vol. 158, No. 4 (pp. 945-958).

Yapp, et al., "Highly Multiplexed 3D Profiling of Cell States and Immune Niches in Human Tumours," bioRxiv, Apr. 2025, bioRxiv: [Preprint]. Apr. 11, 2025:2023.11.10.566670. doi: 10.1101/2023.11. 10.566670 (pp. 1-53).

Yoshimura, et al., "A New Approach for Reversible RNA Photocrosslinking Reaction: Application to Sequence-Specific RNA Selection," ChemBioChem, Jun. 2009, vol. 10, No. 9 (pp. 1473-1476).

Yoshimura, et al., "Ultrafast reversible photo-cross-linking reaction: toward in situ DNA manipulation," Organic letters, Jun. 2008, vol. 10, No. 15 (pp. 3227-3230).

Zeisel et al., Brain Strcuture: "Cell Types in The Mouse Cortex and Hippocampus Revealed by Single-cell RNA-seq," Science, Mar. 6, 2015, vol. 347, No. 6226 (pp. 1138-1142).

Zhang, et al., "Detection of nucleic acids with a novel stem-loop primer rolling circle amplification technique," Biotechniques, Feb. 2018, vol. 64, No. 2 (pp. 69-80).

Zhang, et al., "Proximity-dependent Assay for Specific RNA-protein Interactions in Intact Cells," RNA, 2016, vol. 22, No. 11 (pp. 1785-1792).

Zhong, et al., "Visualization of oligonucleotide probes and point mutations in interphase nuclei and DNA fibers using rolling circle DNA amplification," Proceedings of the National Academy of Sciences, USA, Mar. 2001, vol. 98, No. 7 (pp. 3940-3945).

* cited by examiner

Raw fluorescent signals

Raw fluorescent and DAPI signals

Clusters / cells

UMAP

Cell type map

⊚ 0: Trophoblast Giant -1        ⊚ 6: Endothelia
⊚ 1: Trophoblast Giant -2        ⊚ 7: Trophoblast Giant -3
⊚ 2: Glandular Trophoblast -1 ⊚ 8: Stromal
⊚ 3: Spongiotrophoblast -1      ⊚ 9: Glandular Trophoblast -2
⊚ 4: Spongiotrophoblast -2      ⊚ 10: NK
⊚ 5: Maternal Decidua -1        ⊚ 11: Maternal Decidua -2

100 μm

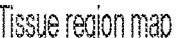
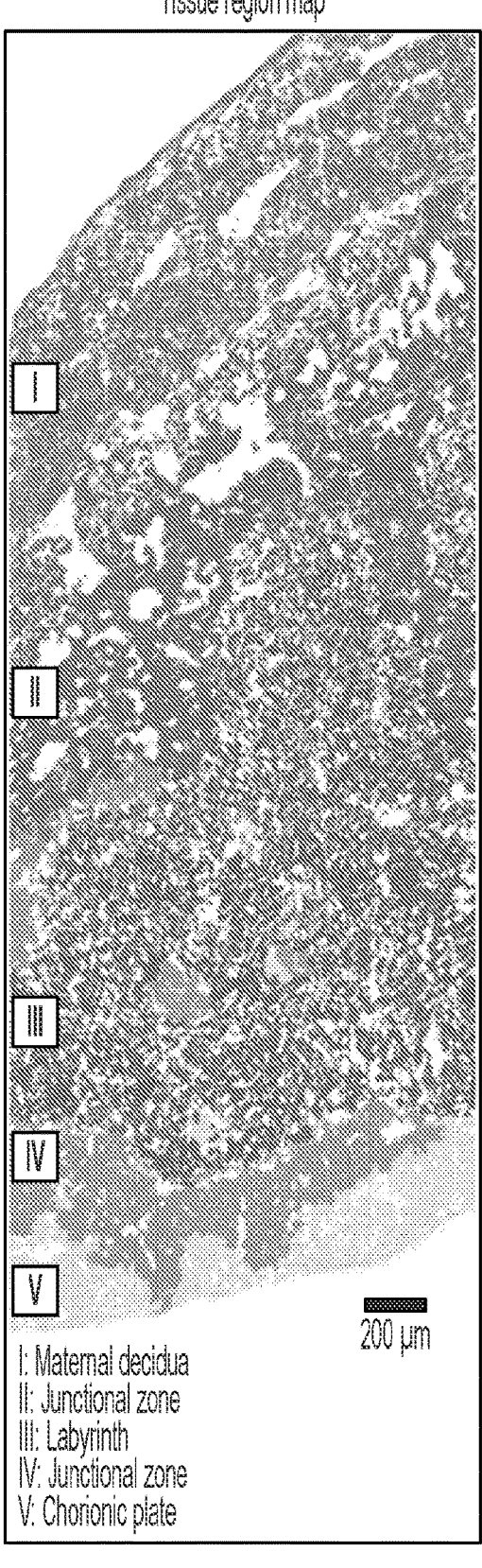
I: Maternal decidua
II: Junctional zone
III: Labyrinth
IV: Junctional zone
V: Chorionic plate
FIG. 3G Niche type I Niche type II Niche type III Py Cpne5
Py L2/3
Py L4
Py L5
Py kcnip2
Py other
I Inhibl. Pthlh
Inhib. Vip
Inhib. other
II Choroid plexus
Ependymal
III Astro Mfge8
Astro Gfap
IV Oligo
OPC
V

PVM
VI

Pericytes
Endothelial
Endothelial 1
VII

Cell type map

Average compositional number of cells in first tier of neighbors per cell type

| | eL2/3 | eL4 | eL5 | eL6 | PV | Sst | Vip | Others | Astro | Oligo-A | Oligo-B |
|---|---|---|---|---|---|---|---|---|---|---|---|
| eL2/3 | 6.4 | 4.3 | 0.57 | 1.1 | 0.48 | 0.51 | 0.11 | 0.43 | 0.56 | 0.25 | 0.45 |
| eL4 | 5.0 | 5.5 | 0.78 | 1.3 | 0.52 | 0.46 | 0.14 | 0.4 | 0.43 | 0.23 | 0.49 |
| eL5 | 0.93 | 1.1 | 4 | 4.9 | 0.73 | 0.82 | 0.24 | 0.49 | 0.64 | 0.50 | 0.87 |
| eL6 | 0.9 | 0.88 | 2.5 | 7.2 | 0.51 | 0.51 | 0.1 | 0.49 | 0.62 | 0.62 | 0.74 |
| PV | 2.6 | 2.4 | 2.4 | 3.3 | 1.01 | 0.99 | 0.16 | 0.4 | 0.73 | 0.46 | 0.66 |
| Sst | 2.3 | 1.8 | 2.3 | 2.9 | 0.85 | 1.2 | 0.21 | 0.49 | 1.5 | 0.64 | 1.1 |
| Vip | 2.2 | 2.3 | 2.9 | 2.5 | 0.59 | 0.91 | 0.43 | 0.44 | 0.92 | 0.4 | 1.1 |
| Others-In | 2.8 | 2.2 | 2.0 | 3.9 | 0.49 | 0.7 | 0.15 | 0.68 | 1.2 | 1.1 | 1.5 |
| Astro | 1.8 | 1.2 | 1.3 | 2.4 | 0.45 | 1 | 0.15 | 0.6 | 2.7 | 1.5 | 1.7 |
| Oligo-A | 0.53 | 0.44 | 0.66 | 1.6 | 0.19 | 0.3 | 0.044 | 0.36 | 1.0 | 7 | 2.8 |
| Oligo-B | 1.1 | 1.0 | 1.3 | 2.2 | 0.3 | 0.57 | 0.14 | 0.54 | 1.3 | 3.2 | 3.4 |

FIG. 6K

0: Astro Mfge8　11: PVM
1: Oligo　12: Endothelial 1
2: Py L2/3　13: Choroid plexus
3: Oligo-1　14: Astro -1
4: Endothelial　15: Ependymal
5: Inhib. Vip　16: Py L6
6: Pericytes　17: Py L4
7: OPC　18: Py kcnip2
8: Py Cpne5　19: Py other
9: Inhib. 1　20: inhibi. Pthlh
10: Astro Gfap　21: Oligo - 2
　　22: Py L5

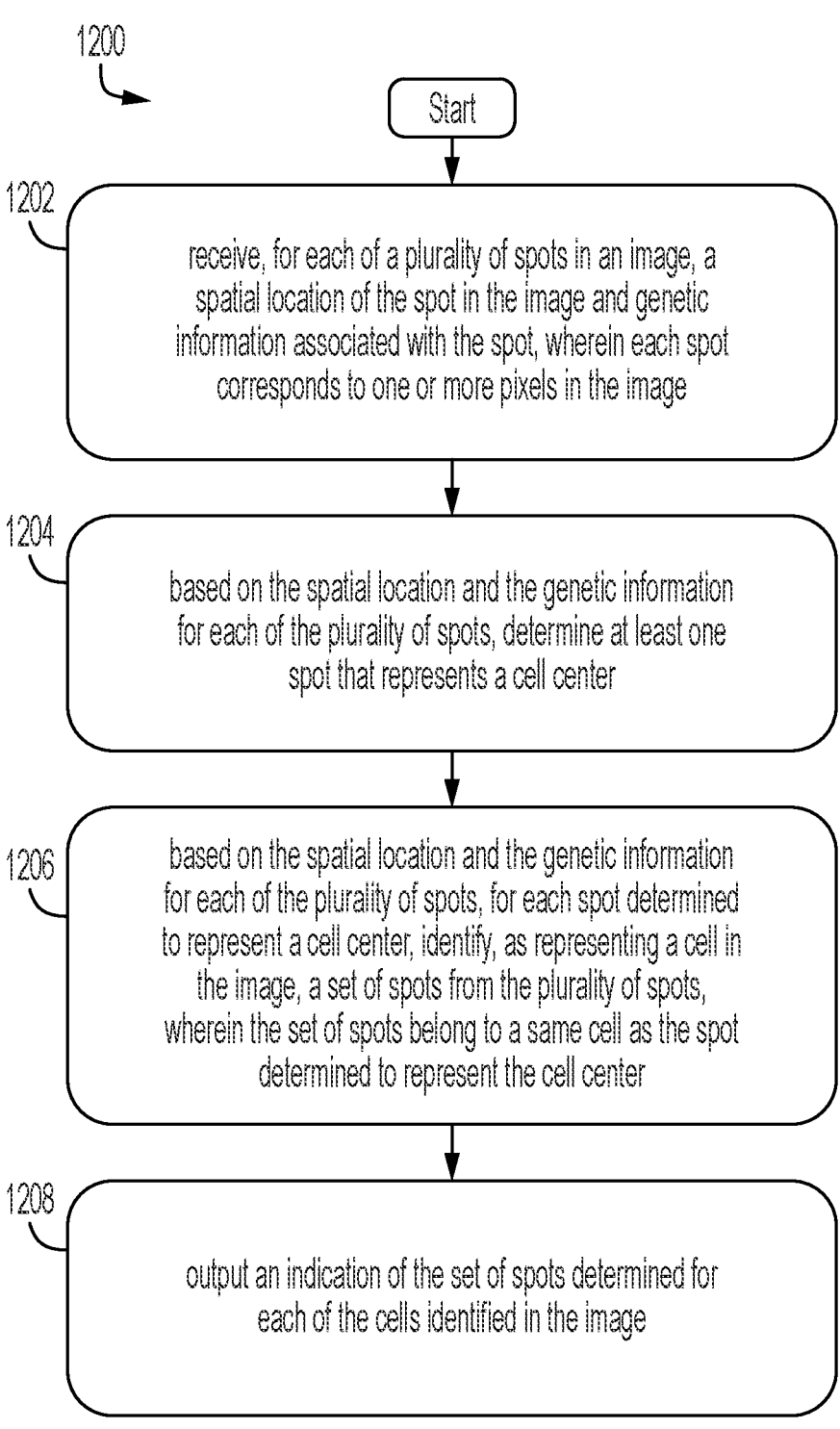

1200

Start

1202 receive, for each of a plurality of spots in an image, a spatial location of the spot in the image and genetic information associated with the spot, wherein each spot corresponds to one or more pixels in the image

1204 based on the spatial location and the genetic information for each of the plurality of spots, determine at least one spot that represents a cell center

1206 based on the spatial location and the genetic information for each of the plurality of spots, for each spot determined to represent a cell center, identify, as representing a cell in the image, a set of spots from the plurality of spots, wherein the set of spots belong to a same cell as the spot determined to represent the cell center

1208 output an indication of the set of spots determined for each of the cells identified in the image

FIG. 12

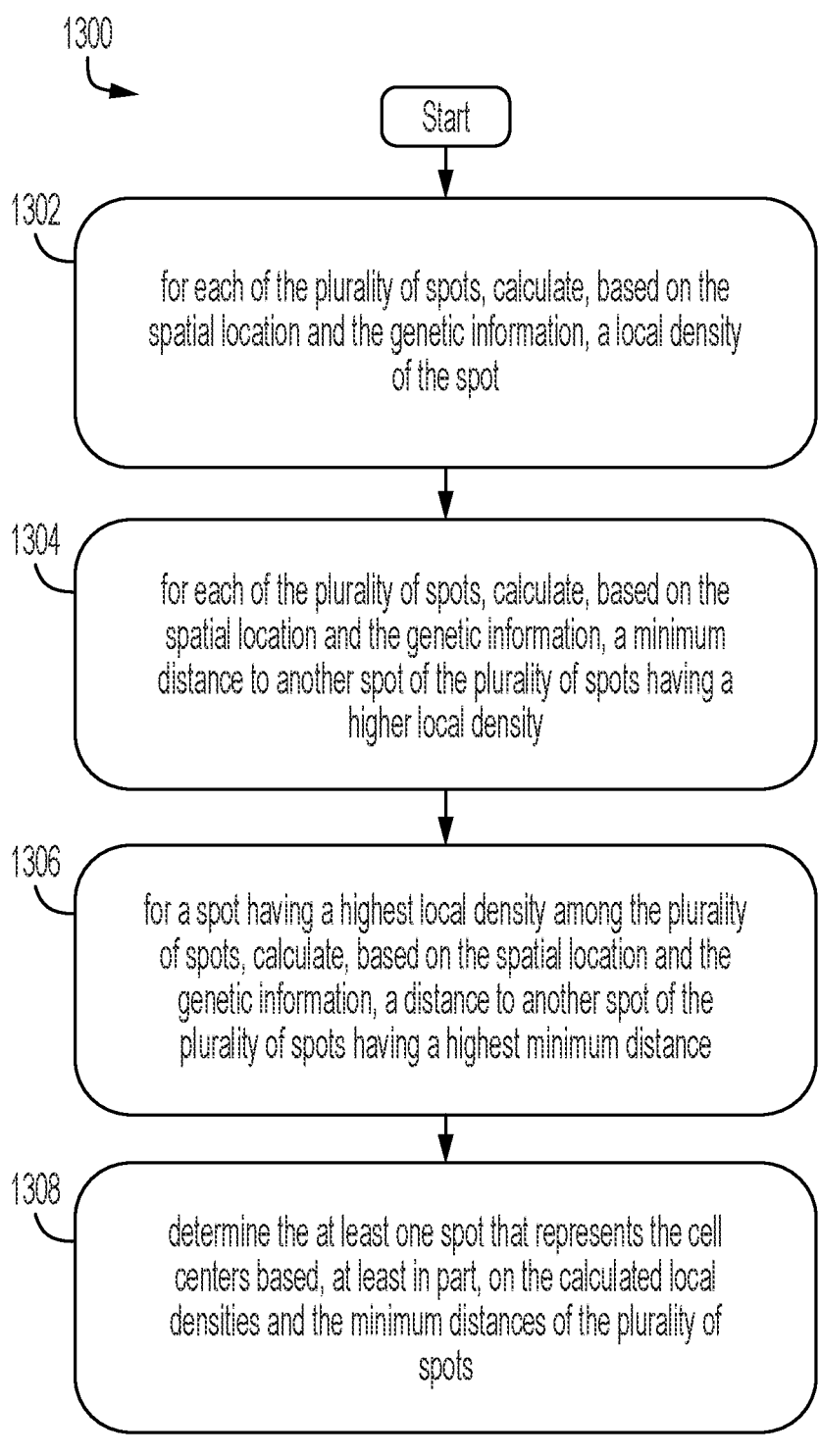

1300

1302

Start for each of the plurality of spots, calculate, based on the spatial location and the genetic information, a local density of the spot

1304 for each of the plurality of spots, calculate, based on the spatial location and the genetic information, a minimum distance to another spot of the plurality of spots having a higher local density

1306 for a spot having a highest local density among the plurality of spots, calculate, based on the spatial location and the genetic information, a distance to another spot of the plurality of spots having a highest minimum distance

1308 determine the at least one spot that represents the cell centers based, at least in part, on the calculated local densities and the minimum distances of the plurality of spots

FIG. 13

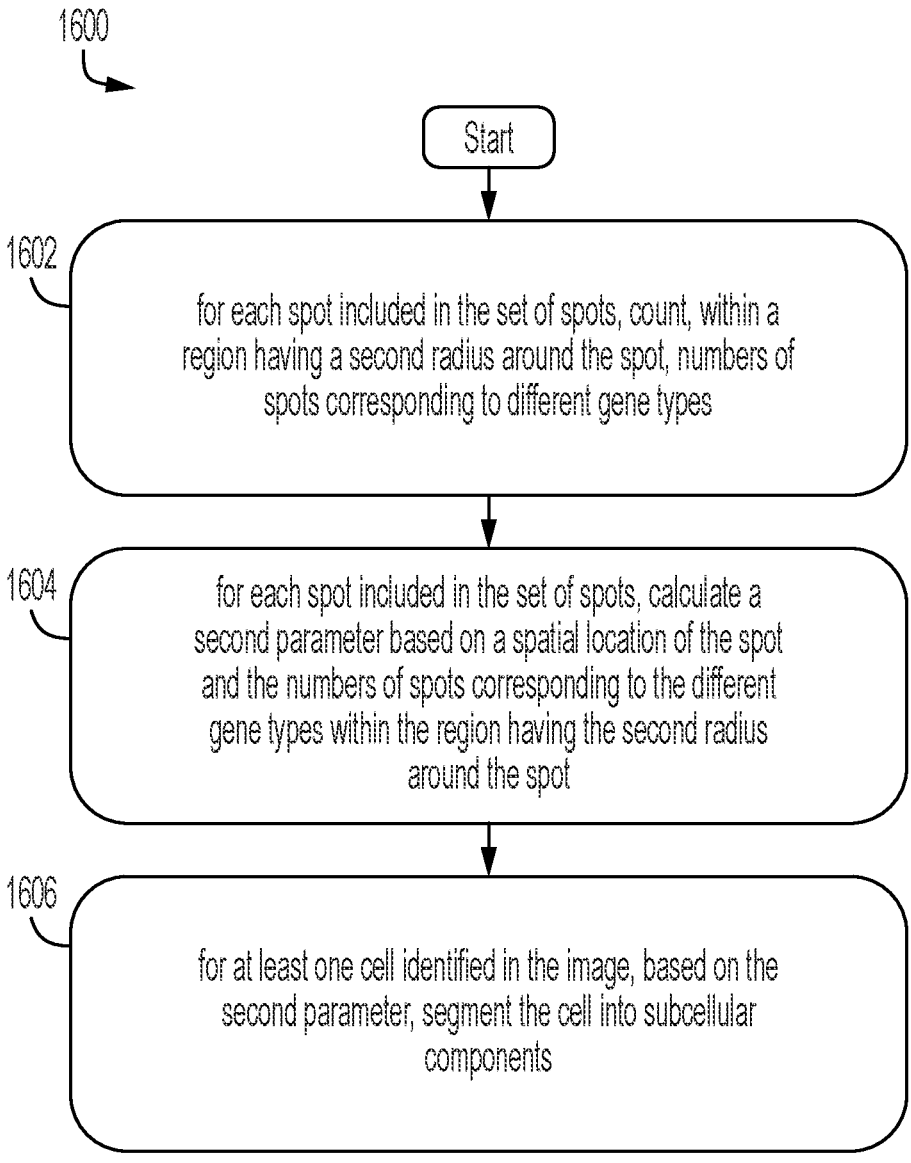

1600

Start

1602 for each spot included in the set of spots, count, within a region having a second radius around the spot, numbers of spots corresponding to different gene types

1604 for each spot included in the set of spots, calculate a second parameter based on a spatial location of the spot and the numbers of spots corresponding to the different gene types within the region having the second radius around the spot

1606 for at least one cell identified in the image, based on the second parameter, segment the cell into subcellular components

FIG. 16

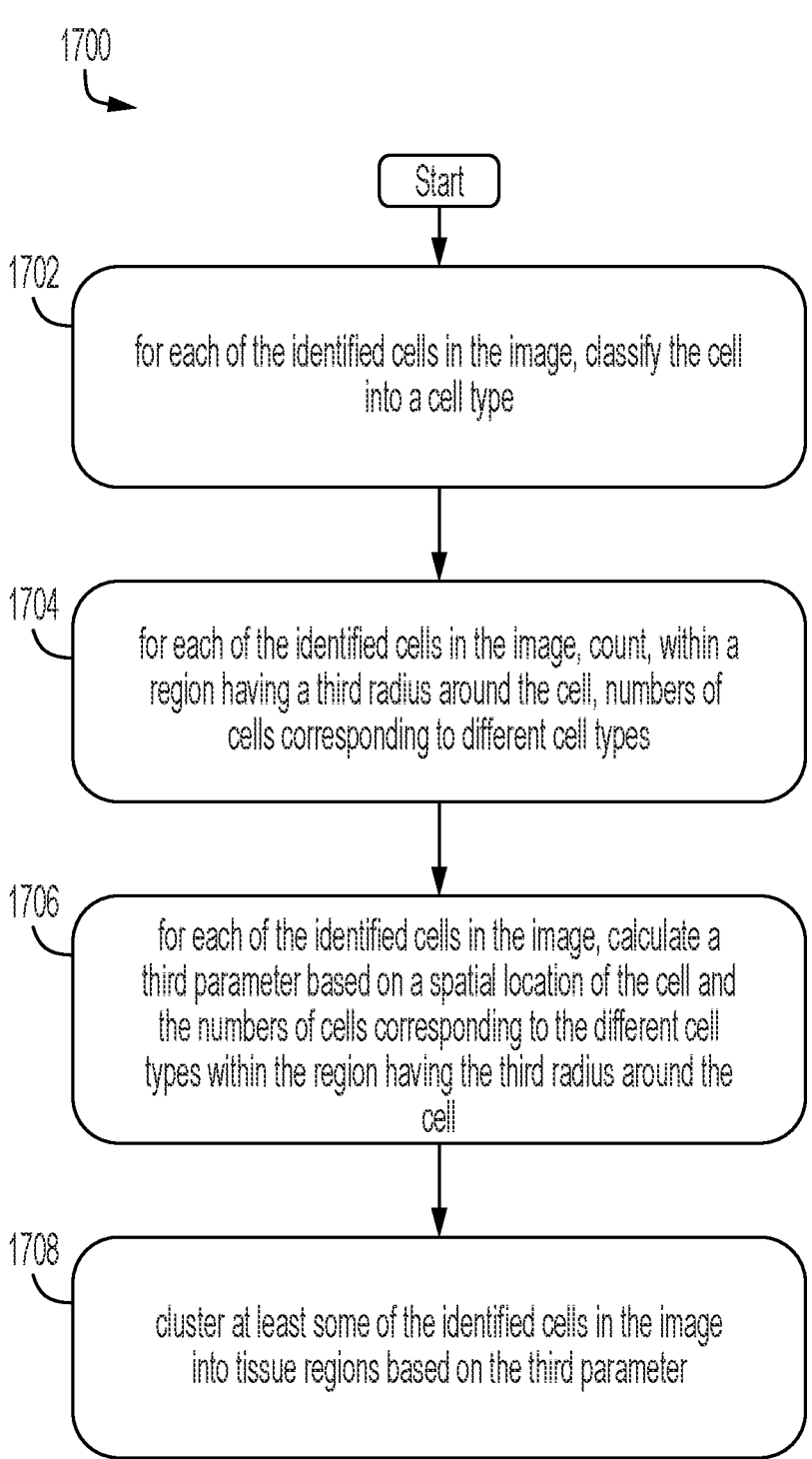

1700

Start

1702 for each of the identified cells in the image, classify the cell into a cell type

1704 for each of the identified cells in the image, count, within a region having a third radius around the cell, numbers of cells corresponding to different cell types

1706 for each of the identified cells in the image, calculate a third parameter based on a spatial location of the cell and the numbers of cells corresponding to the different cell types within the region having the third radius around the cell

1708 cluster at least some of the identified cells in the image into tissue regions based on the third parameter

FIG. 17

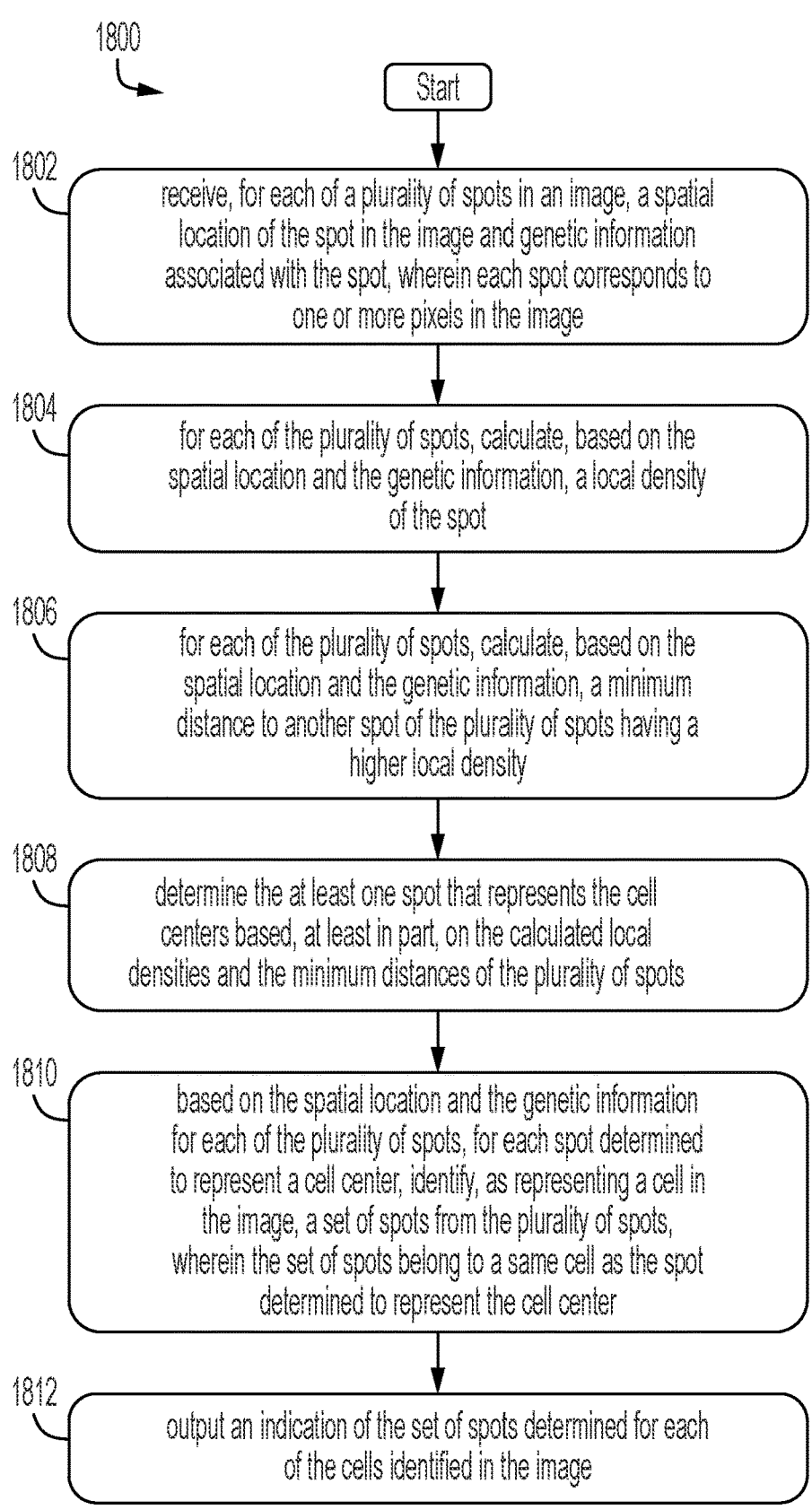

1800

Start

1802 — receive, for each of a plurality of spots in an image, a spatial location of the spot in the image and genetic information associated with the spot, wherein each spot corresponds to one or more pixels in the image 1804 — for each of the plurality of spots, calculate, based on the spatial location and the genetic information, a local density of the spot 1806 — for each of the plurality of spots, calculate, based on the spatial location and the genetic information, a minimum distance to another spot of the plurality of spots having a higher local density 1808 — determine the at least one spot that represents the cell centers based, at least in part, on the calculated local densities and the minimum distances of the plurality of spots 1810 — based on the spatial location and the genetic information for each of the plurality of spots, for each spot determined to represent a cell center, identify, as representing a cell in the image, a set of spots from the plurality of spots, wherein the set of spots belong to a same cell as the spot determined to represent the cell center 1812 — output an indication of the set of spots determined for each of the cells identified in the image

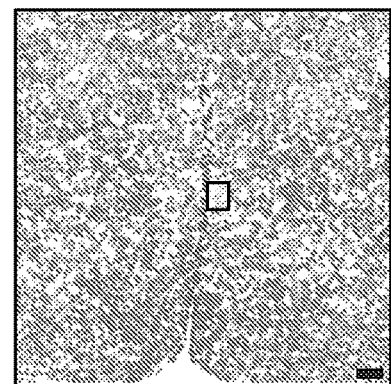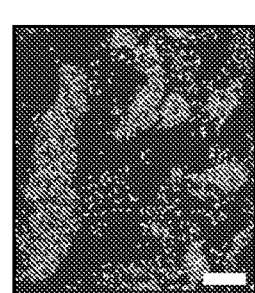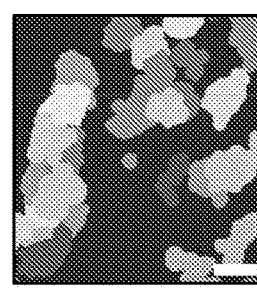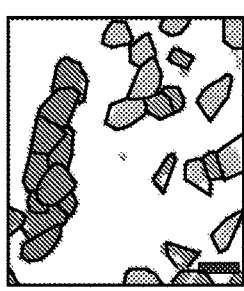
○Inhibitory ○Excitatory ○Mature OD○Immature OD ○Astrocyte ○Microglia
○Ependymal ○Endothelial ○Mural
FIG. 21C Cell segmentation map

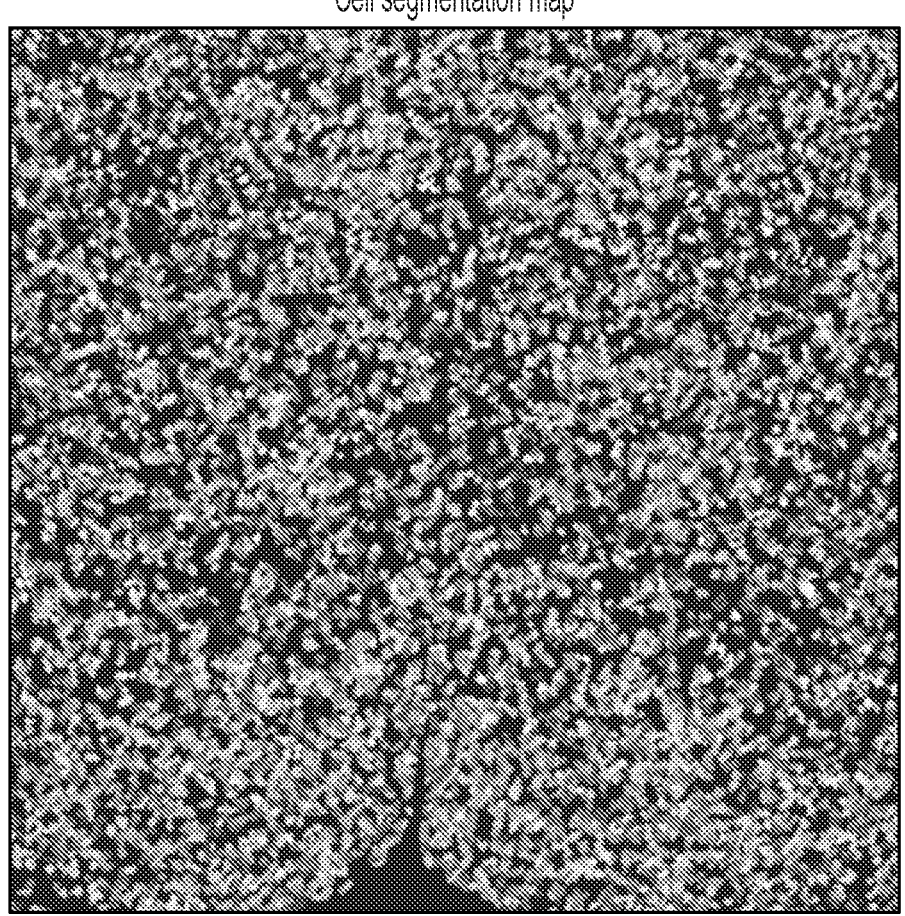
FIG. 26D

Cell map by ClusterMap

○1: Axo-axonic  ○4: CGE IVY    ○7: Cck Cxcl 14+     ○10: Hippo   ○11: IS1   ○14: Ivy        ○17: O-Bi       ○20: PC other  ●Uncalled
○2: Basket      ●5: CGE NGF    ○8: Cck Vip Cxcl 14- ○11: IS1     ○12: IS2   ○15: MGE        ○18: OLM        ○21: Radiatum retrohip
○3: Bistratified ○6: Cck Calb1/Slc17a8 ○9: Cxcl14 NGC ○13: IS3 ○16: Nonneuron ○19: PC CA1  ○22: Trilaminar

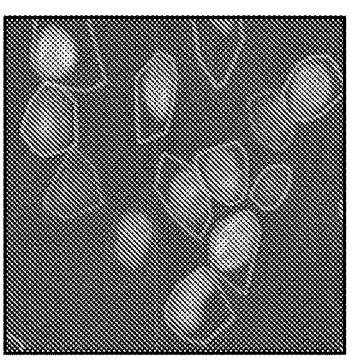
FIG. 28N
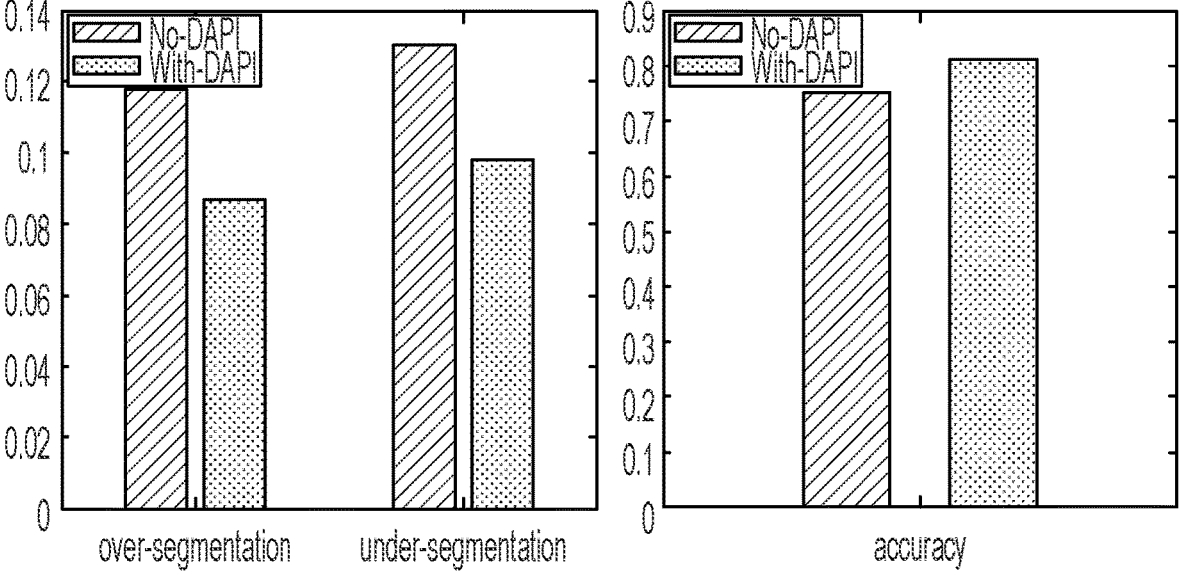
FIG. 28O
FIG. 28P

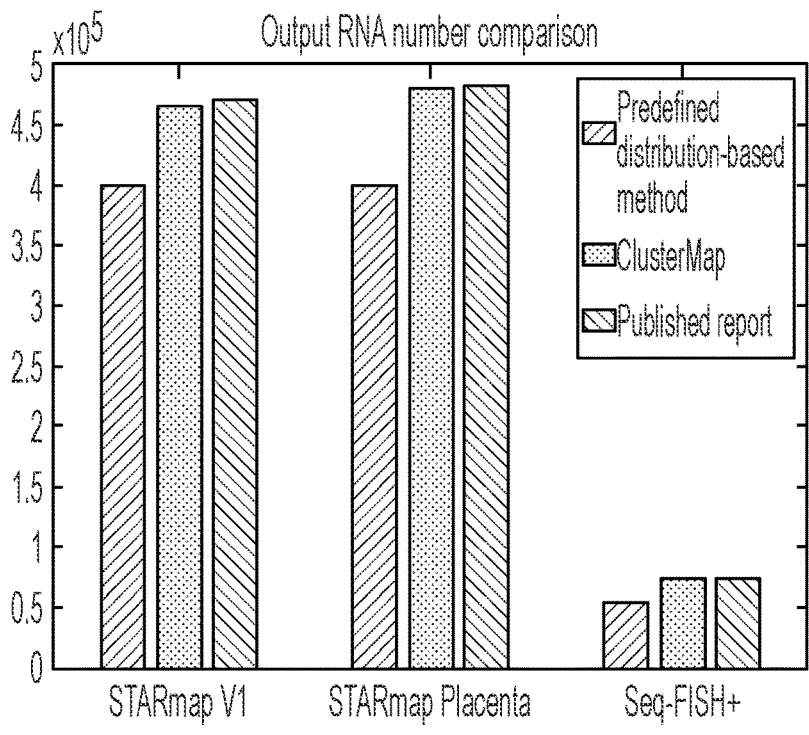
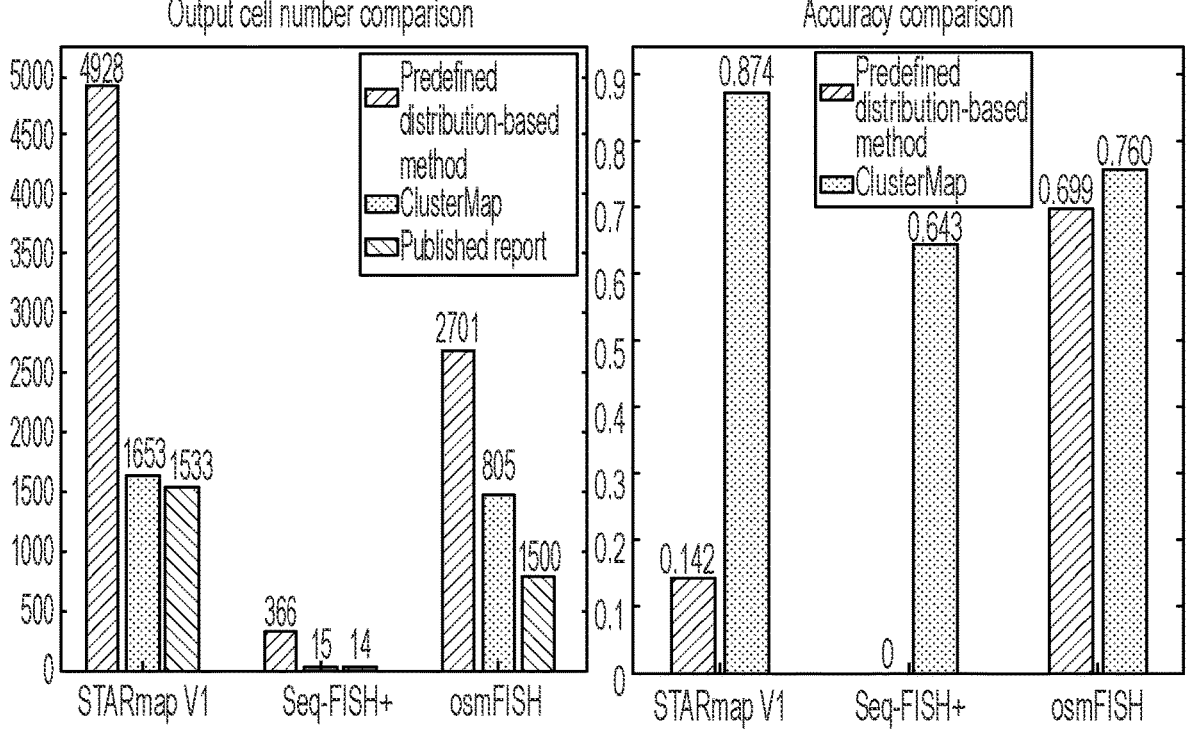
FIG. 29D

MULTI-SCALE SPATIAL TRANSCRIPTOMICS ANALYSIS

RELATED APPLICATIONS

This application is a national stage filing under 35 U.S.C. § 371 of International PCT Application PCT/US2022/017016, filed on Feb. 18, 2022, which claims priority under 35 U.S.C. § 119 (e) to U.S. Provisional Application, U.S. Ser. No. 63/151,374, filed on Feb. 19, 2021, each of which is incorporated herein by reference.

GOVERNMENT SUPPORT

This invention was made with government support under Grant No. MH123948 awarded by the National Institutes of Health and Grant No. 2038603 awarded by the National Science Foundation. The government has certain rights in the invention.

BACKGROUND OF THE INVENTION

Quantifying RNAs in their spatial context is crucial to understanding gene expression and regulation in complex tissues. Tissue functions arise from the orchestrated interactions of multiple cell types, which are shaped by differential gene expression in three-dimensional (3D) space. To chart the spatial heterogeneity of gene expression in cells and tissues, a myriad of image-based in situ transcriptomics methods (e.g., STARmap, FISSEQ, pciSeq, MERFISH, seqFISH, osmFISH, etc.) have been developed[1-8], providing an atlas of subcellular RNA localization in intact tissues. In situ transcriptomic methods generate spatially resolved RNA profiles in intact tissues; however, it has proven challenging to directly extract low-dimensional representations of biological patterns from high-dimensional spatial transcriptomic data.

One of the main challenges is achieving precise and automated cell segmentation that accurately assigns RNAs into individual cells for single-cell analysis. The most common cell segmentation strategy is labelling cell nuclei or cell bodies by fluorescent staining[9-11] (e.g., DAPI, Nissl, WGA, etc.) and then segmenting the continuous fluorescent signals by conventional or machine learning (ML)-based methods[12]. However, conventional methods, such as distance-transformed watershed[13], require manual curation to achieve optimal segmentation results. On the other hand, while ML-based methods[14,15] can automatically detect the targets (cells) in fluorescent stainings, they still require manually annotated datasets for model training. A unified computational framework for integrative analysis of in situ transcriptomic data is needed to address these challenges.

SUMMARY OF THE INVENTION

Disclosed herein is an unsupervised and annotation-free framework, termed ClusterMap, which incorporates physical proximity and gene identity of RNAs, formulates the task as a point pattern analysis problem, and defines biologically meaningful structures and groups (e.g., cells, and organelles within cells). Specifically, ClusterMap can precisely cluster RNAs into cells, as well as subcellular structures, cell bodies, and tissue regions in both two- and three-dimensional space and consistently perform on diverse tissue types, including brain, placenta, gut, and cardiac tissues. ClusterMap is broadly applicable to a variety of in situ transcriptomic measurements to uncover gene expression patterns, cell-cell interactions, and tissue organization principles from high-dimensional transcriptomic images. ClusterMap is also useful in the diagnosis and treatment of disease (e.g., Alzheimer's disease, cancer).

Here, instead of using fluorescent staining, patterns of spatially resolved RNAs that intrinsically encode high-dimensional gene expression information were utilized for subcellular and cellular segmentation, followed by cell-type mapping. To leverage the spatial heterogeneity of RNA-defined cell types, the same strategy was applied to cluster discrete cells into tissue regions. It was demonstrated that this computational framework (ClusterMap) can identify subcellular structures, cells, and tissue regions in a way that bypasses auxiliary cell staining, hyperparameter tuning, and manual labeling (FIG. 1).

In one aspect, the present disclosure provides methods of identifying cells in an image comprising the steps of:

receiving, for each of a plurality of spots in the image, a spatial location of the spot in the image and genetic information associated with the spot, wherein each spot corresponds to one or more pixels in the image;

based on the spatial location and the genetic information for each of the plurality of spots:

determining at least one spot that represents a cell center; and for each spot determined to represent a cell center, identifying, as representing a cell in the image, a set of spots from the plurality of spots, wherein the set of spots belong to a same cell as the spot determined to represent the cell center; and outputting an indication of the set of spots determined for each of the cells identified in the image.

In some embodiments, determining one spot that represents a cell center comprises: for each of the plurality of spots:

calculating, based on the spatial location and the genetic information, a local density of the spot;

calculating, based on the spatial location and the genetic information, a minimum distance to another spot of the plurality of spots having a higher local density; and determining the at least one spot that represents the cell centers based, at least in part, on the calculated local densities and the minimum distances of the plurality of spots.

In another aspect, the present disclosure provides an apparatus comprising:

at least one computer processor; and at least one non-transitory computer-readable storage medium encoded with a plurality of instructions that, when executed by at least one computer processor, perform a method of identifying cells in an image, the method comprising:

receiving, for each of a plurality of spots in the image, a spatial location of the spot in the image and genetic information associated with the spot, wherein each spot corresponds to one or more pixels in the image;

based on the spatial location and the genetic information for each of the plurality of spots:

determining at least one spot that represents a cell center; and for each spot determined to represent a cell center, identifying, as representing a cell in the image, a set of spots from the plurality of spots, wherein the set of spots belong to a same cell as the spot determined to represent the cell center; and outputting an indication of the set of spots determined for each of the cells identified in the image.

Another aspect of the present disclosure provides at least one non-transitory computer-readable storage medium encoded with a plurality of instructions that, when executed at least one computer processor, perform a method of identifying cells in an image, the method comprising:

receiving, for each of a plurality of spots in the image, a spatial location of the spot in the image and genetic information associated with the spot, wherein each spot corresponds to one or more pixels in the image;

based on the spatial location and the genetic information for each of the plurality of spots:

determining at least one spot that represents a cell center; and for each spot determined to represent a cell center, identifying, as representing a cell in the image, a set of spots from the plurality of spots, wherein the set of spots belong to a same cell as the spot determined to represent the cell center; and outputting an indication of the set of spots determined for each of the cells identified in the image.

In another aspect, the present disclosure provides methods of diagnosing a disease or disorder in a subject using the methods or systems disclosed herein. Such a method comprises the steps of:

performing the any of the methods of identifying cells in an image disclosed herein, wherein the image is an image of a sample provided by a subject;

classifying each cell identified in the image into a cell type; and determining, based on the cell type of each cell identified in the image, whether the subject has or is at risk of having the disease or disorder. Determining whether the subject has or is at risk of having the disease or disorder may be accomplished by various methods, for example, by determining the ratio of various cell types relative to one another in the sample and comparing the ratios to other samples from cancer patients and healthy subjects, as is described further herein in the detailed description of certain embodiments.

Another aspect of the present disclosure provides methods of treating a disease or disorder in a subject in need thereof using the methods disclosed herein. Such a method comprises the steps of:

performing the any of the methods of identifying cells in an image disclosed herein, wherein the image is an image of a sample provided by a subject;

classifying each cell identified in the image into a cell type;

determining, based on the cell type of each cell identified in the image, whether the subject has or is at risk of having the disease or disorder; and administering a therapy capable of treating the disease or disorder to the subject.

Diagnosis and treatment of any disease or disorder is contemplated by the present disclosure. In some embodiments, the disease or disorder is selected from the group consisting of genetic diseases, proliferative diseases, inflammatory diseases, autoimmune diseases, liver diseases, pulmonary diseases, hematological diseases, psychiatric diseases, cardiovascular diseases, gastrointestinal diseases, musculoskeletal diseases, genitourinary diseases, and neurological diseases. In certain embodiments, the disease is cancer. In certain embodiments, the disease is a neurodegenerative disease (e.g., Alzheimer's disease).

It should be appreciated that the foregoing concepts, and the additional concepts discussed below, may be arranged in any suitable combination, as the present disclosure is not limited in this respect. Further, other advantages and novel features of the present disclosure will become apparent from the following detailed description of various non-limiting embodiments when considered in conjunction with the accompanying drawings.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein.

FIG. 1A provides an overview of the ClusterMap method. The input is a matrix that contains both spatial and transcript information of mRNA molecules sequenced by in situ transcriptomic methods[1-8]. ClusterMap clusters mRNA spots, identifies cells, and profiles them into different cell types as output. FIG. 1B provides a workflow of the ClusterMap method. I, The physical and neighborhood gene composition (NGC) coordinates of mRNA spots are extracted for each spot (e.g., S1, S2, and S3), and projected to physical and NGC spaces, respectively, which are then computationally integrated. II, A density peak clustering (DPC) algorithm[18] is used to cluster mRNA in the P-NGC space. III, Each spot is assigned to one cluster, representing one cell. IV, Cell types are identified by gene expression profiling in each cell. FIG. 1C shows representative ClusterMap analysis on STARmap mouse V1 1020-gene dataset[6]. Corresponds to (I)-(IV) in FIG. 1B. FIG. 1D provides a representative ClusterMap cell segmentation analysis on different samples. I, Human HeLa cell in 2D. The white dashed lines highlight the nucleus boundary identified by the subcellular mRNA distribution from ClusterMap (upper) and DAPI staining (bottom) from the same cell. II, Comparison of ClusterMap (upper) and marker-seeded watershed (bottom) segmentation in mouse visual cortex cells. III, Mouse cerebellum in 2D, 4,050 cells. IV, Mouse ileum in 2D, 5,550 cells. V, Mouse visual cortex in 3D, 2,251 cells. Width: 309 μm, height: 582 μm, depth: 100 μm.

FIG. 2A provides a workflow of the ClusterMap method that integrates DAPI signals for spatial clustering. FIG. 2B provides a cell (segmentation) map generated by ClusterMap of the STARmap mouse V1 1020-gene dataset[6], which includes 1,447 identified cells. mRNA molecules are shaded by their cell attributes. FIG. 2C provides a cell-type map of the STARmap mouse V1 1020-gene dataset[6]. The cell type names and shading shown in the legend provided are from Reference (6). The number of cells in each cell type is as follows: eL2/3-A, 208; eL2/3-B, 42; eL4, 149; eL5, 118; eL6, 155; Pv, 37; Vip, 27; Sst, 40; Others-In, 18; Astro, 121; Endo, 134; SMC, 62; Micro, 150; Oligo-A, 164; Oligo-B, 12. The bottom panels in FIG. 2B and FIG. 2C provide zoomed-in views from the rectangular highlighted regions in the upper panels. FIG. 2D provides a tissue region map of the STARmap mouse V1 1020-gene dataset[6]. The tissue regions are segmented and cells in the same layer are shown in the same shade of gray. From top to bottom, the tissue region map shows: L1 to L6, the six neocortical layers; cc, corpus callosum; HPC, hippocampus. FIG. 2E provides bar plots of the composition of 16 cell types across 7 layers.

Values are normalized in each row. The shading corresponds to the cell type legend in FIG. 2C.

Figure 3A:
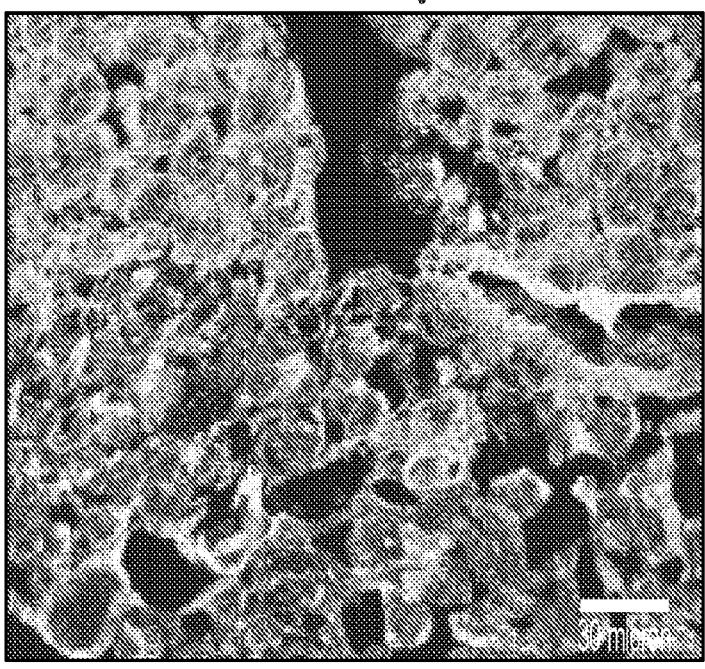
Figure 3B:
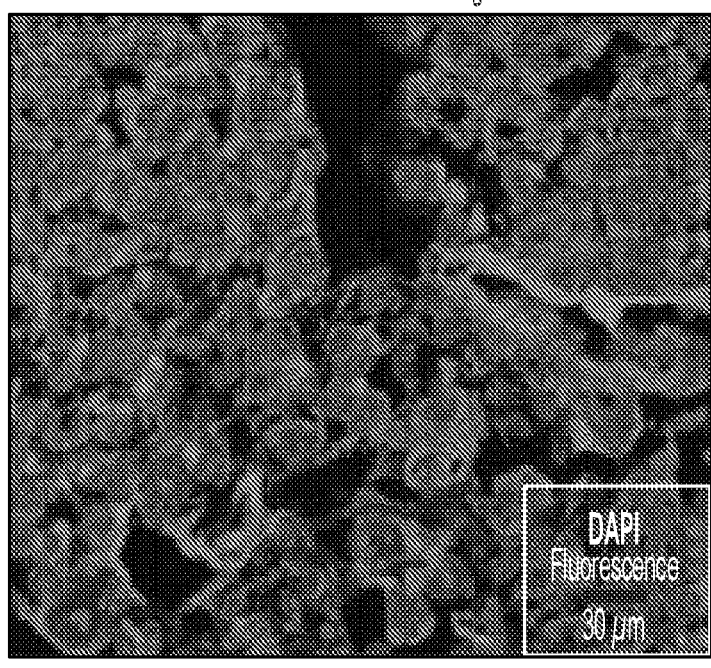
Figure 3C:
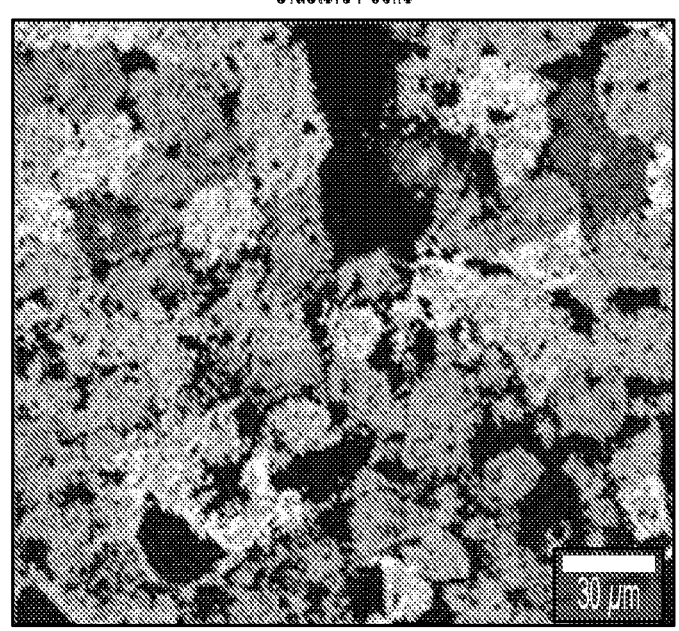
Figure 3D:
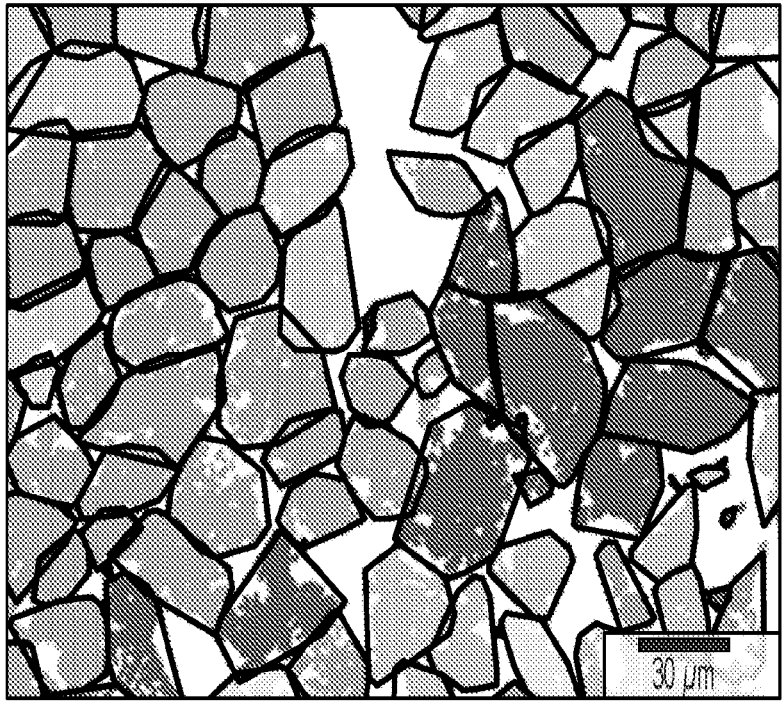
Figure 3E:
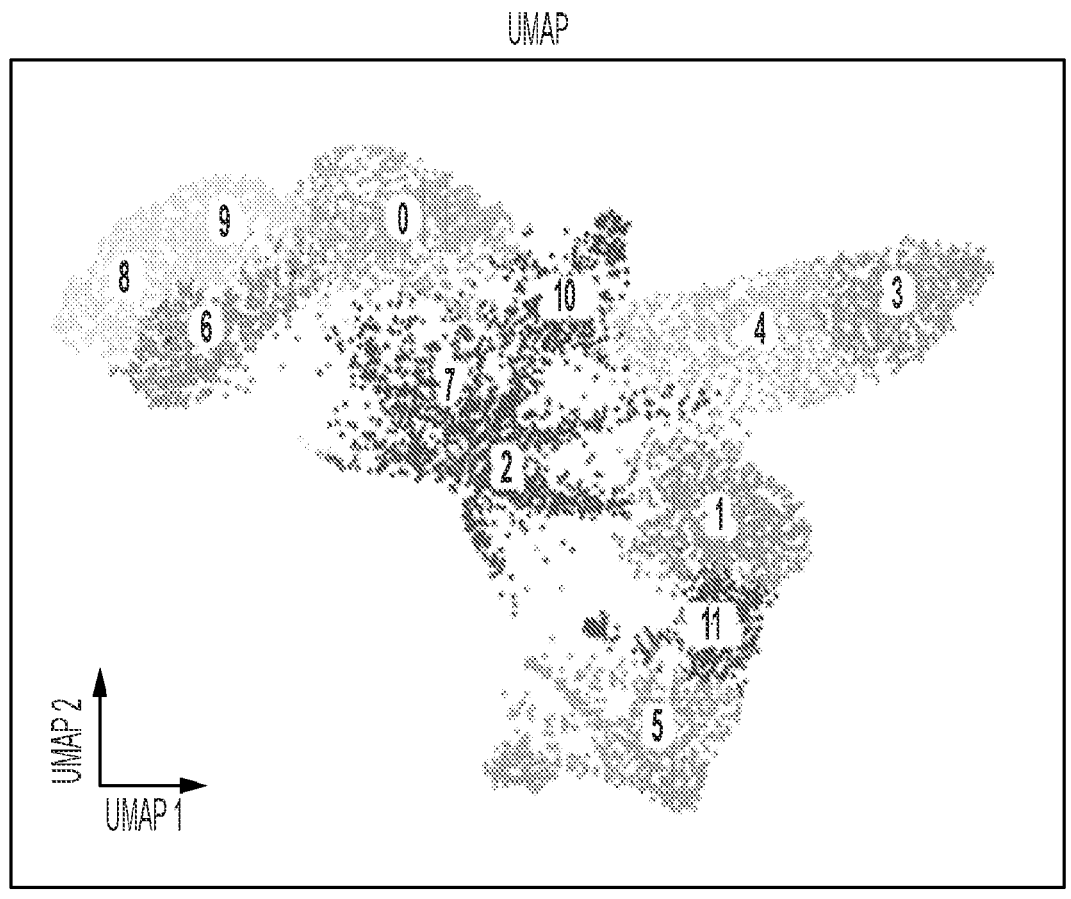
Figure 3F:
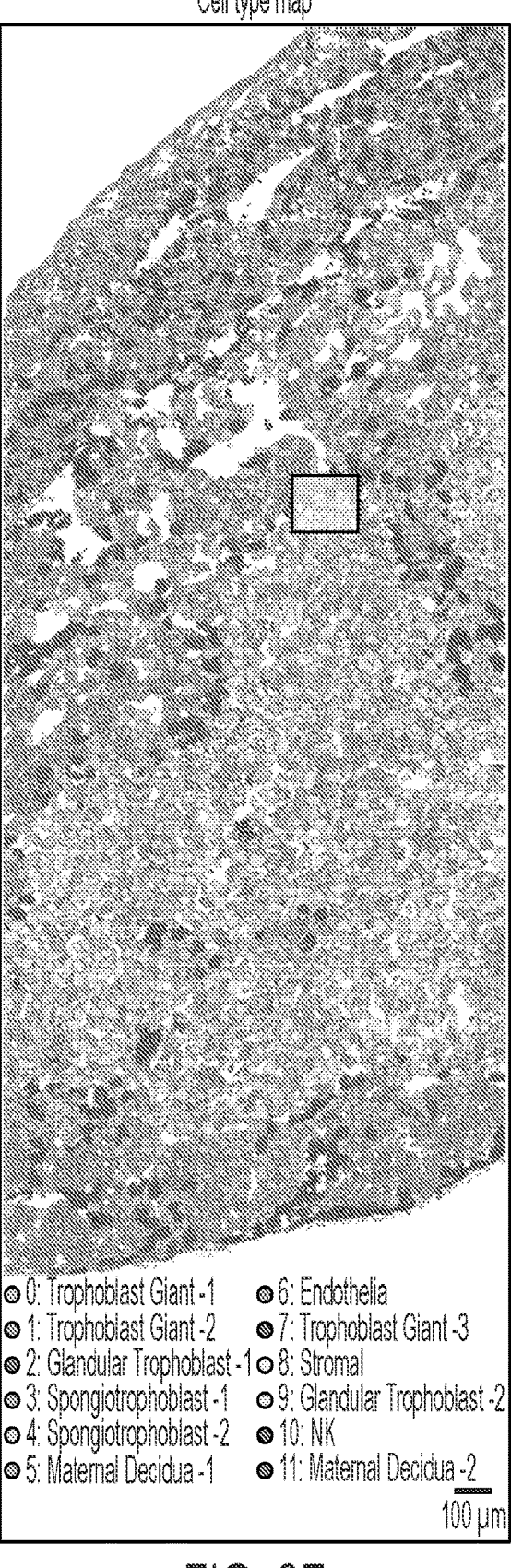
Figure 3H:
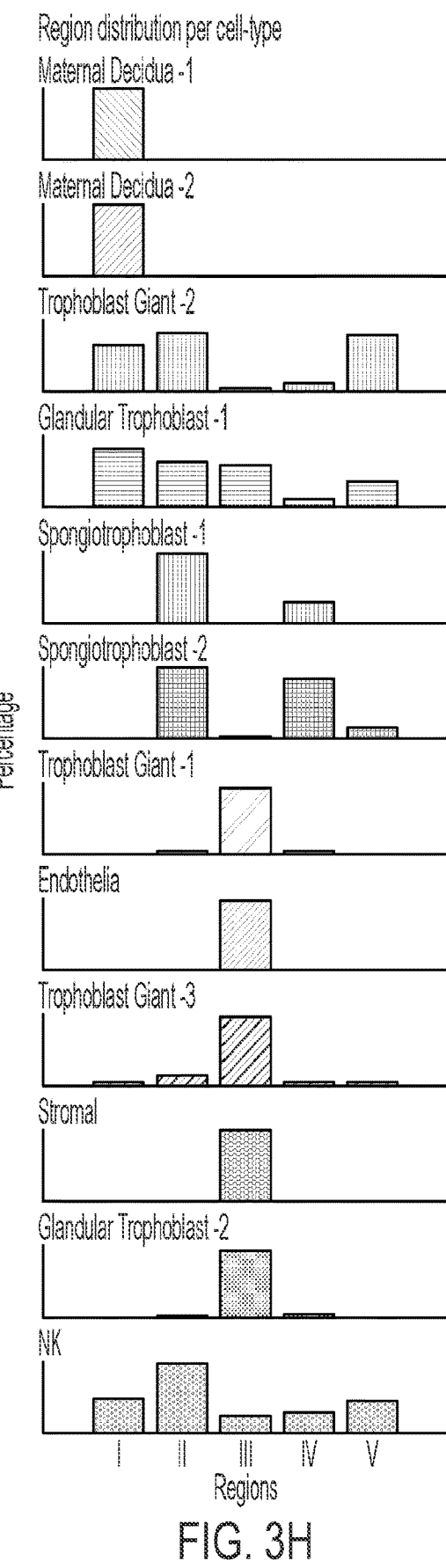

FIGS. 3A-3H show the use of ClusterMap to generate cell-type and tissue-region maps in mouse placenta. FIG. 3A shows raw fluorescent signals for a part in the STARmap mouse placenta 903-gene dataset[6]. Four-channel images in the first sequencing round are overlapped in grayscale to show the mRNA distribution. FIG. 3B provides a composite image by overlapping FIG. 3A in light gray and DAPI signals in dark gray. The image shows the distribution of mRNA relative to cell nuclei. A majority of mRNA molecules distributed outside the cell nucleus, resulting in holes in the cell center. FIGS. 3C-3D show that ClusterMap generates a cell map (FIG. 3C) and cell type map (FIG. 3D) of FIG. 3A. FIGS. 3A-3D provide the zoomed-in view from the highlighted rectangle in FIG. 3F, the original dataset. FIG. 3E provides a uniform manifold approximation plot (UMAP) that shows clustering of 11 groups across 7,224 cells in the original placental dataset. FIG. 3F shows spatial organization of the cell types in the placental tissue section. The number of cells in each type is as follows: 0: Trophoblast Giant-1 (TG-1), 947; 1: Endothelial/Stromal (E/S), 924; 2: Trophoblast Giant-2 (TG-2), 921; 3: Maternal Decidua-1 (MD-1), 851; 4: Glandular Trophoblast-1 (GT-1), 706; 5: Spongiotrophoblast-1 (ST-1), 696; 6: Spongiotrophoblast-2 (ST-2), 680; 7: Trophoblast Giant-3 (TG-3), 550; 8: Glandular Trophoblast-2 (GT-2), 420; 9: NK, 392; 10: Maternal Decidua-2 (MD-2), 137. FIG. 3G provides the spatial tissue region map of FIG. 3F. FIG. 3H provides bar plots of the composition of 11 cell types across 7 regions. Values are normalized in each row. Cell types in FIGS. 3F and 3H are color-coded as in FIG. 3E.

Figures 4A, 4B, 4C, 4D:
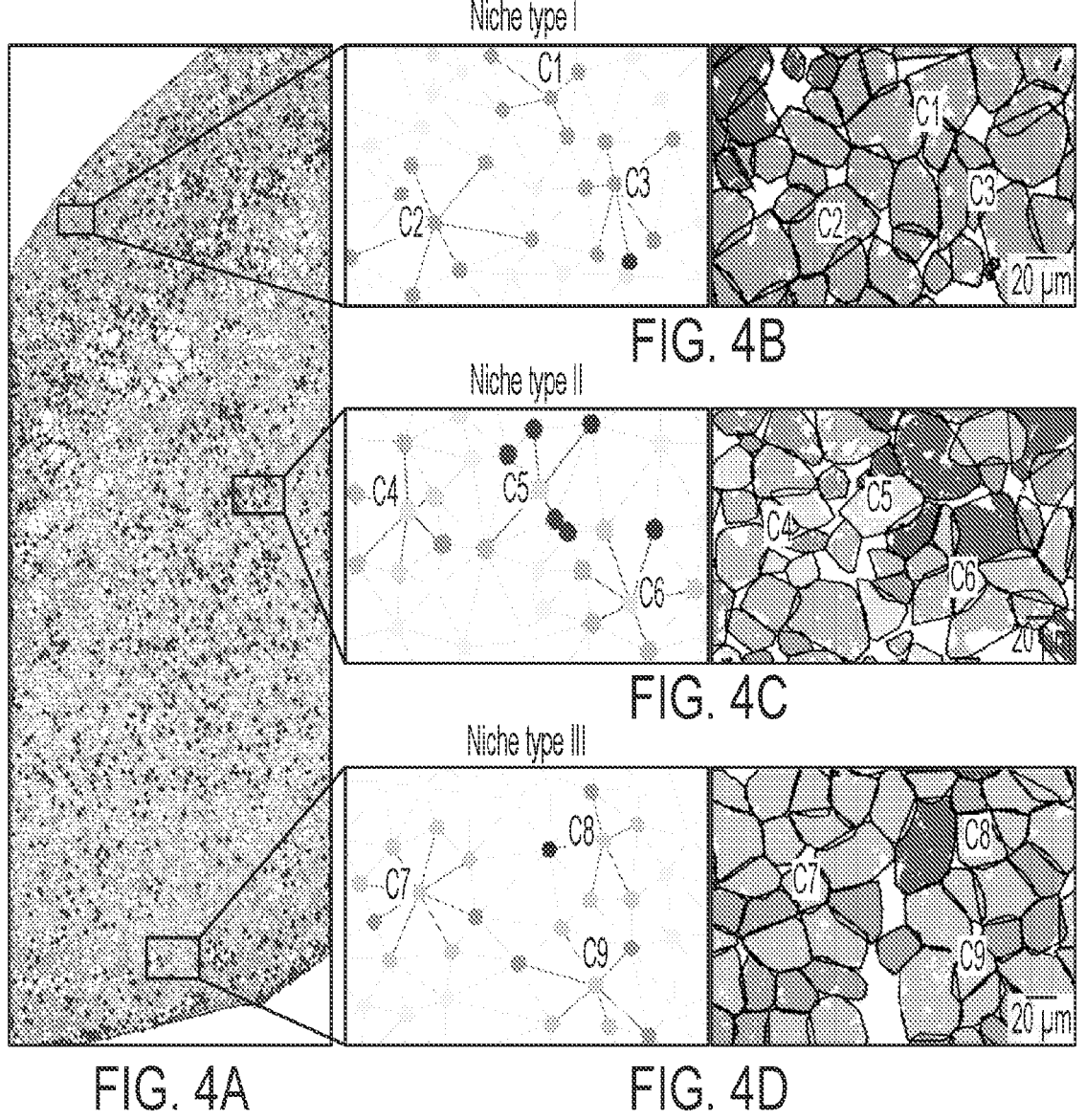
Figure 4E:
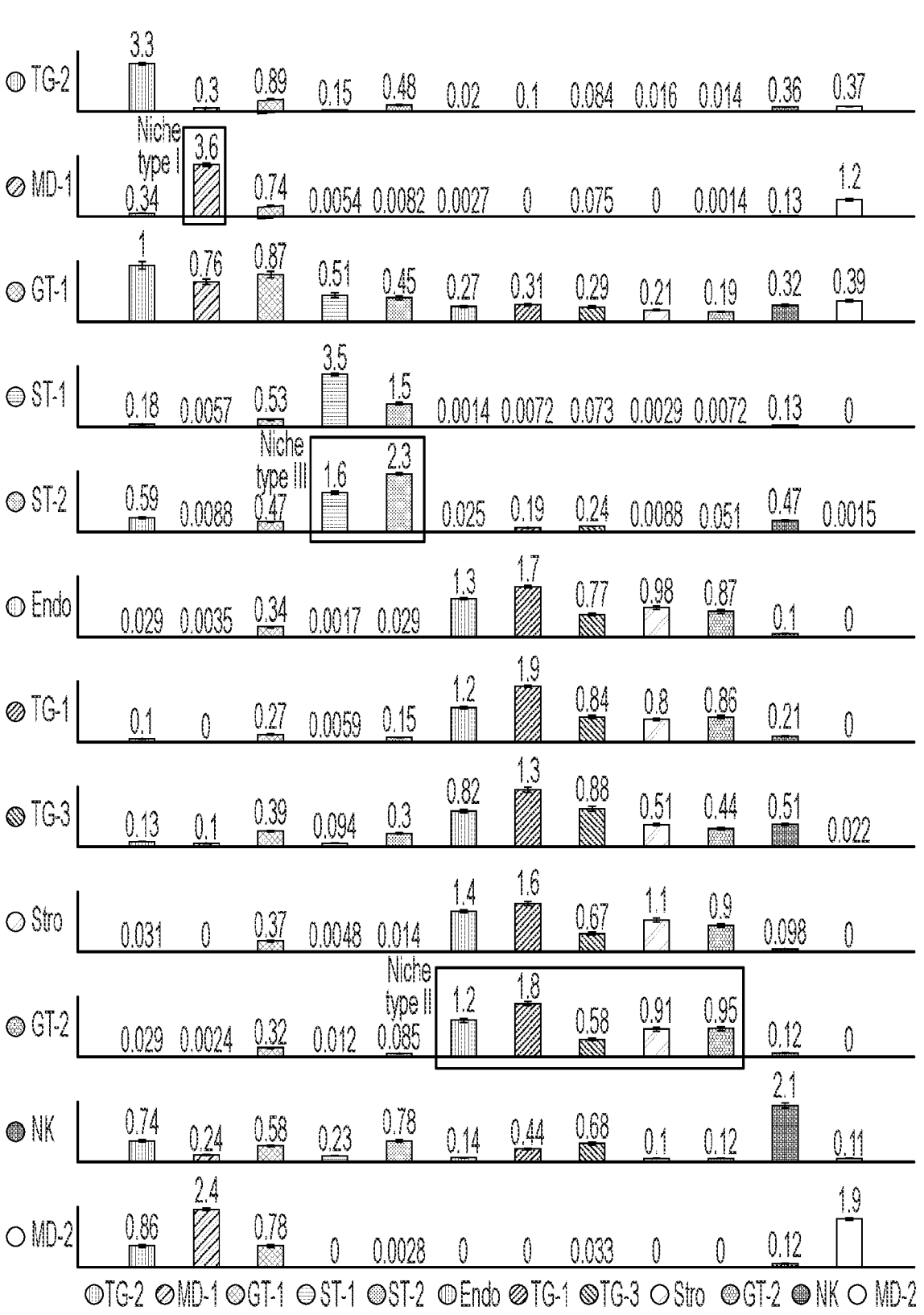

FIGS. 4A-4E show that ClusterMap reveals cell-cell interactions in the placenta. FIG. 4A provides a mesh graph generated by Delaunay triangulation of cells shown in the STARmap mouse placenta 903-gene that reveals cell-cell interactions. Each cell is represented by a spot shaded according to its corresponding cell type. Physically neighboring cells are connected via edges. FIGS. 4B-4D provide a zoomed-in view of the top, middle, and bottom square in FIG. 4A. The intercellular connection is centered on three MD-1 type (C1, C2, C3), GT-2 type (C4, C5, C6), and ST-2 (C7, C8, C9) type cells, respectively, with their first tier of neighboring cells highlighted. Left: schematic; right: cell map. FIG. 4E provides bar plots of the average number of cells per cell-type among the first-tier neighbors, revealing clear patterns of cell-type specific cell-cell communication. Cells in Interaction Type I, II, and III show selective association with cell types highlighted in the corresponding bounding box. The cell types on the axes are denoted by initials.

Figures 5A, 5B:
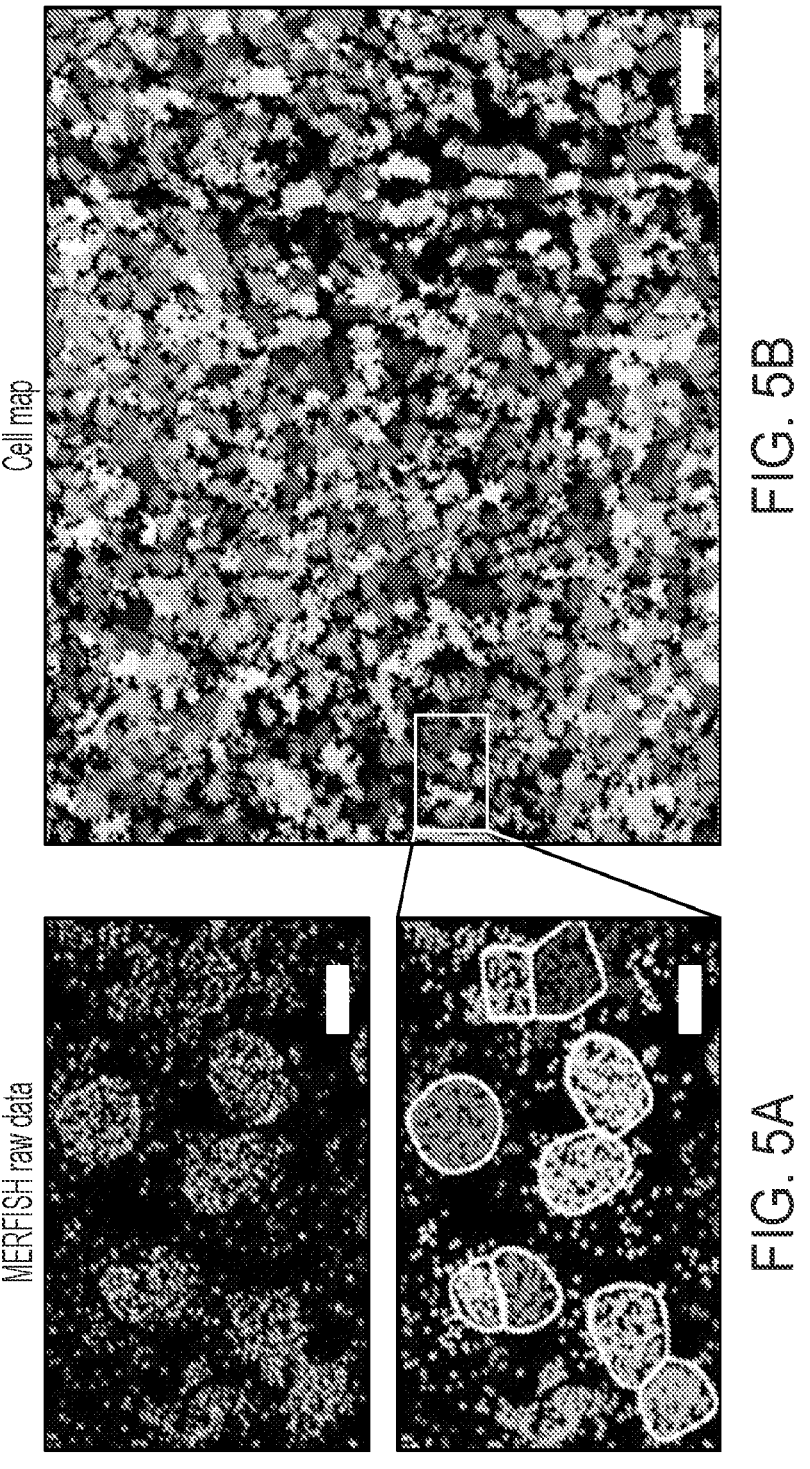
Figure 5C:
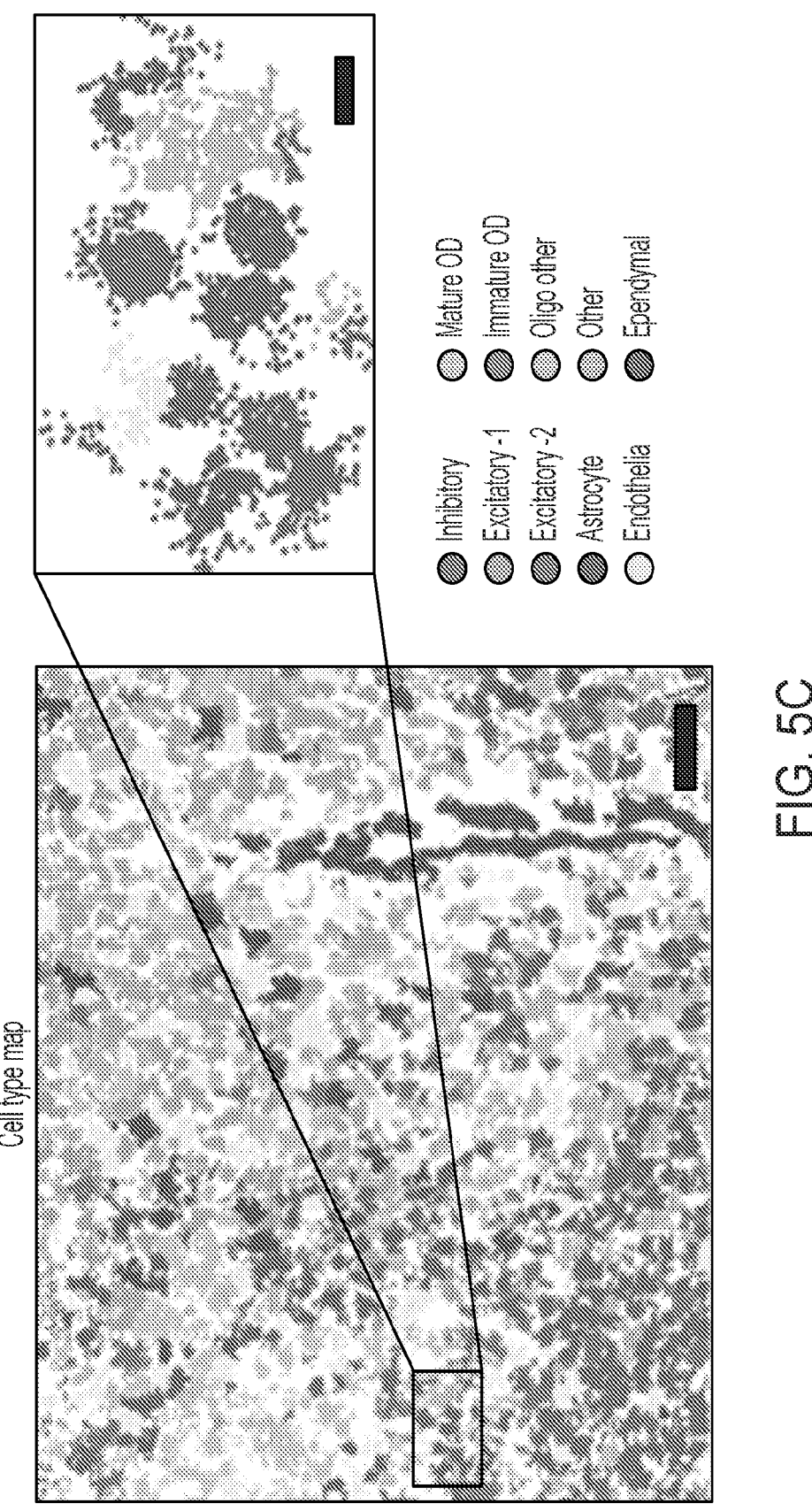
Figures 5D, 5E, 5F:
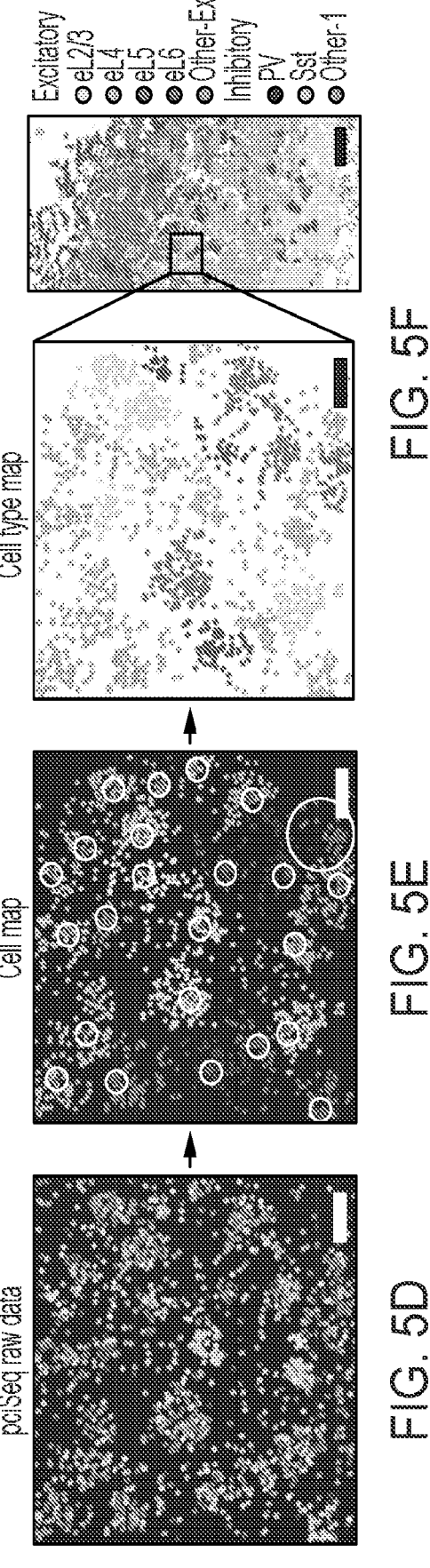
Figure 5G:
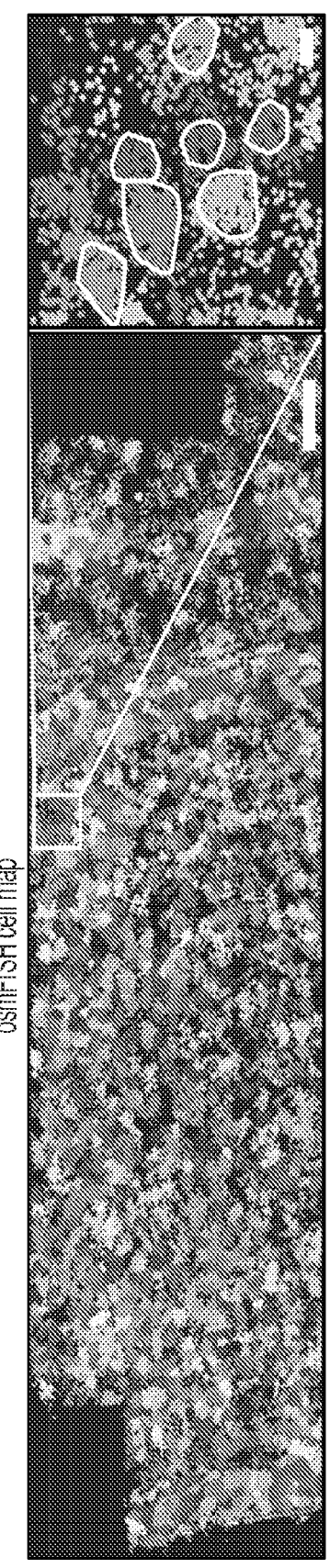
Figure 5H:
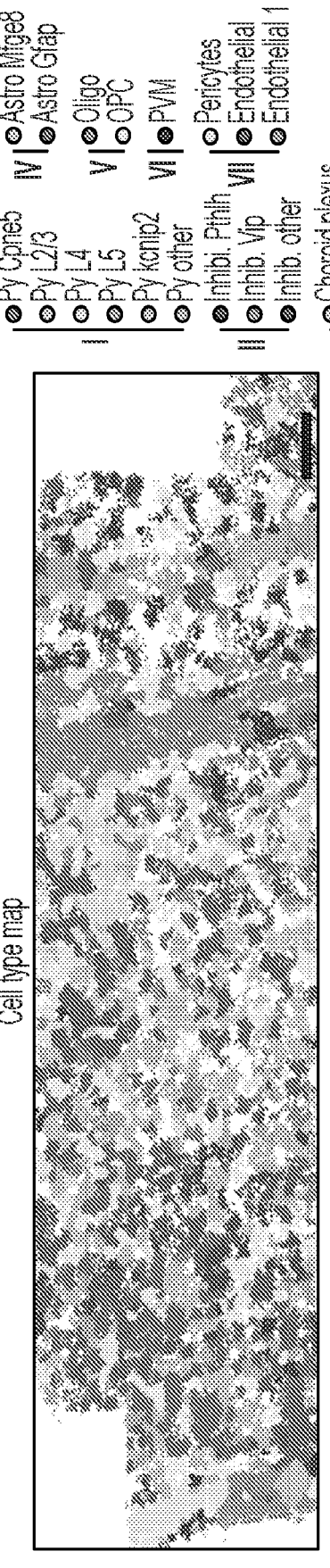

FIGS. 5A-5H show ClusterMap across various protocols. FIG. 5A provides raw spatial transcriptomics data from the MERFISH dataset[3] (zoomed-in view corresponding to the highlighted rectangle in FIG. 5B). Different shading represent different gene types. Scale bar: 10 μm. FIG. 5B shows that ClusterMap generates the cell map of a selected area in MERFISH mouse POA dataset[3], including 3,113 cells. Scale bar: 100 μm. Lower left: zoomed-in view of the highlighted square, the cell map of FIG. 5A. Scale bar: 10 μm. White convex hulls are based on previous cell segmentation[3]. FIG. 5C shows the spatial organization of cell types in FIG. 5B. Scale bar: 100 μm. Upper right: zoomed in view of the highlighted rectangle, the cell type map of FIG. 5A. FIG. 5D provides raw spatial transcriptomics data from the pciSeq mouse isocortex dataset[4]. FIG. 5E shows that ClusterMap generates the cell map of FIG. 5D. Circled points: the density peak of cells. Scale bar for FIGS. 5D-5E: 5 μm. FIG. 5F provides the cell-type map in FIG. 5E. Left: scale bar: 5 μm. Right: the spatial cell type map of the selected area in the pciSeq mouse isocortex dataset4. Scale bar: 100 μm. FIG. 5G provides the cell map of a part of the osmFISH mouse SSp dataset[5], including 1,962 cells. Scale bar: 100 μm. Left: zoomed-in view of the highlighted rectangle. White convex hulls are based on previously reported cell segmentation[5]. Scale bar: 10 μm. FIG. 5H shows the spatial organization of cell types in FIG. 5G. Seven main types including I: Excitatory neurons; II: Inhibitory neurons; III: Ventricle; IV: Astro.; V: Oligodendrocytes; VI: Immune; VII: Vasculature[5].

Figure 6A:
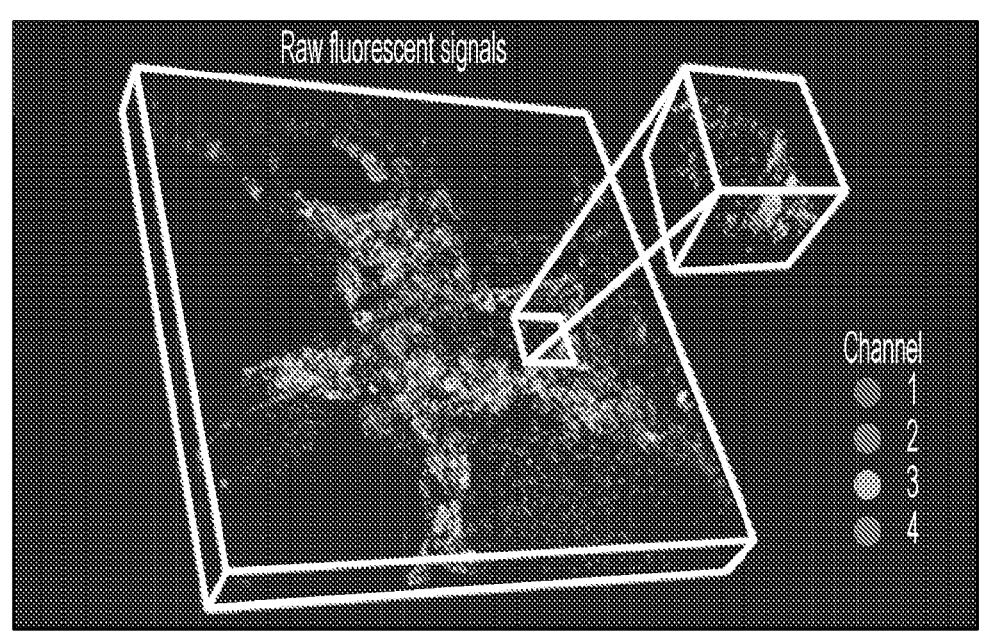
Figure 6B:
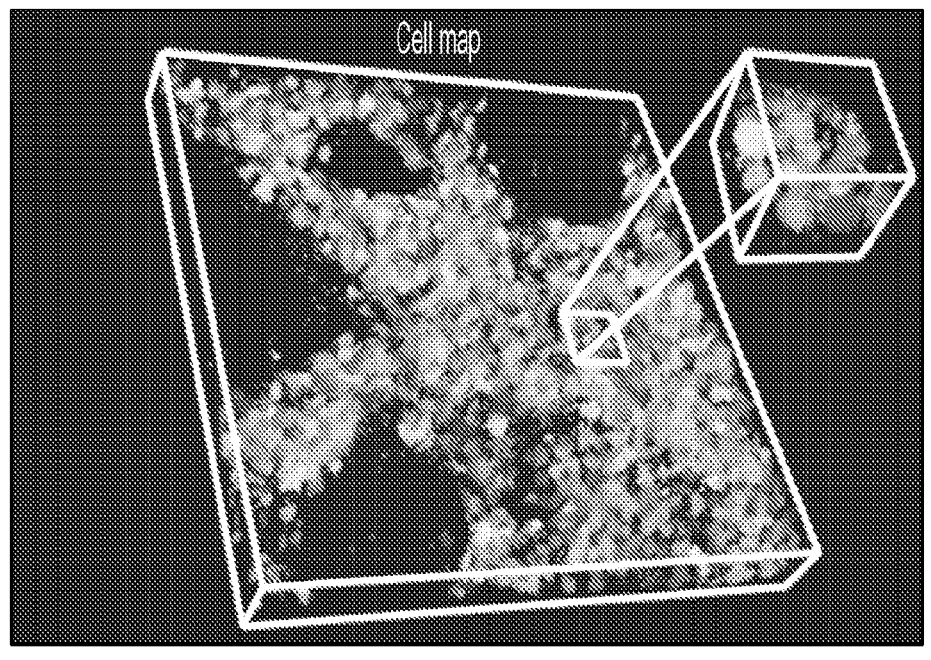
Figure 6C:
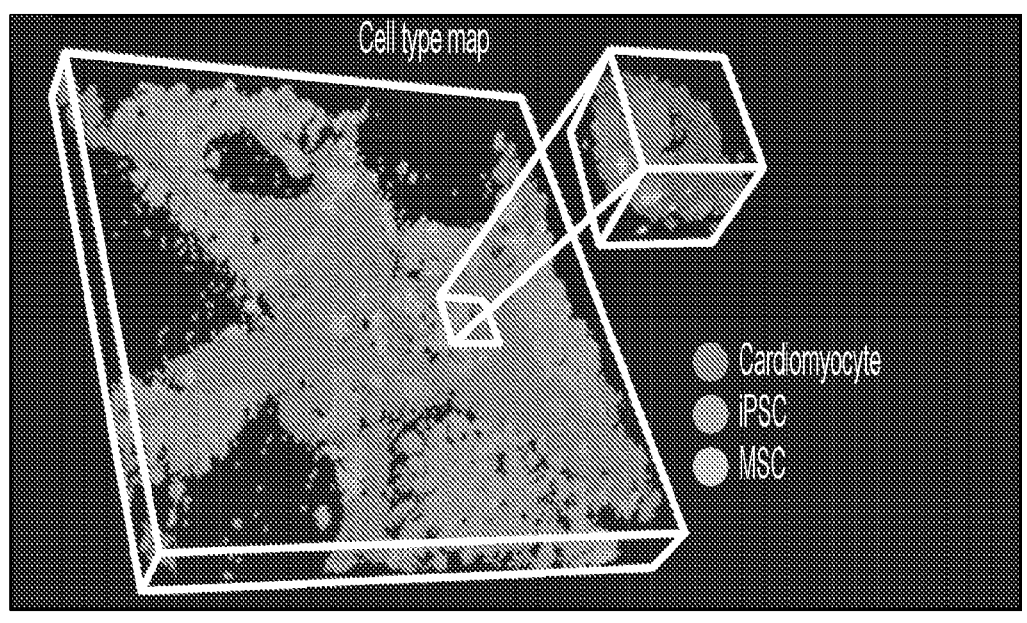
Figure 6D:
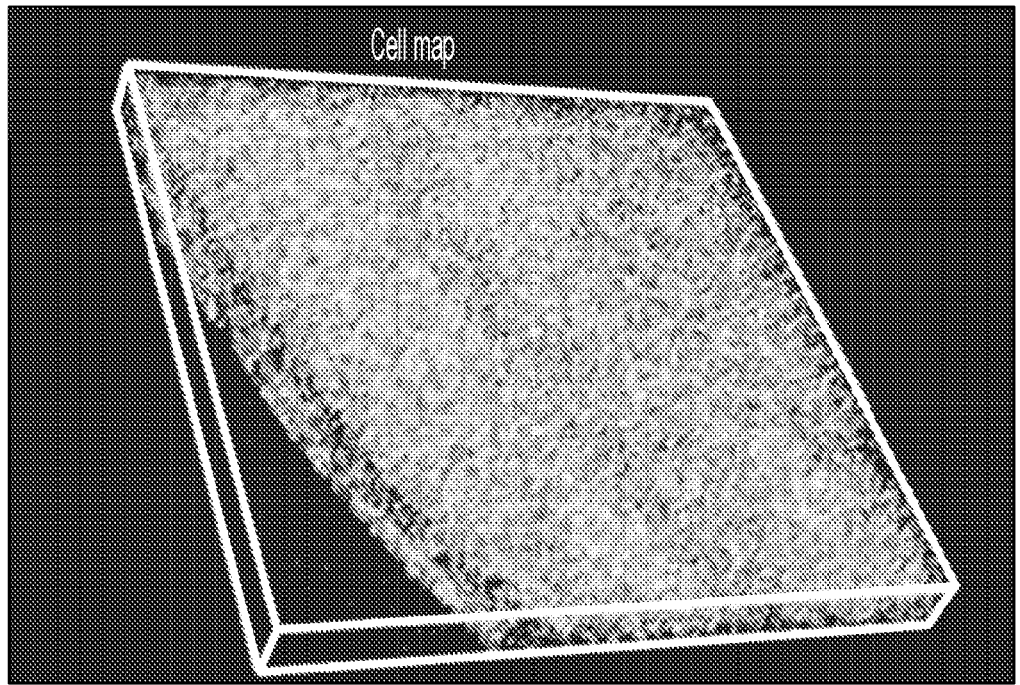
Figure 6E:
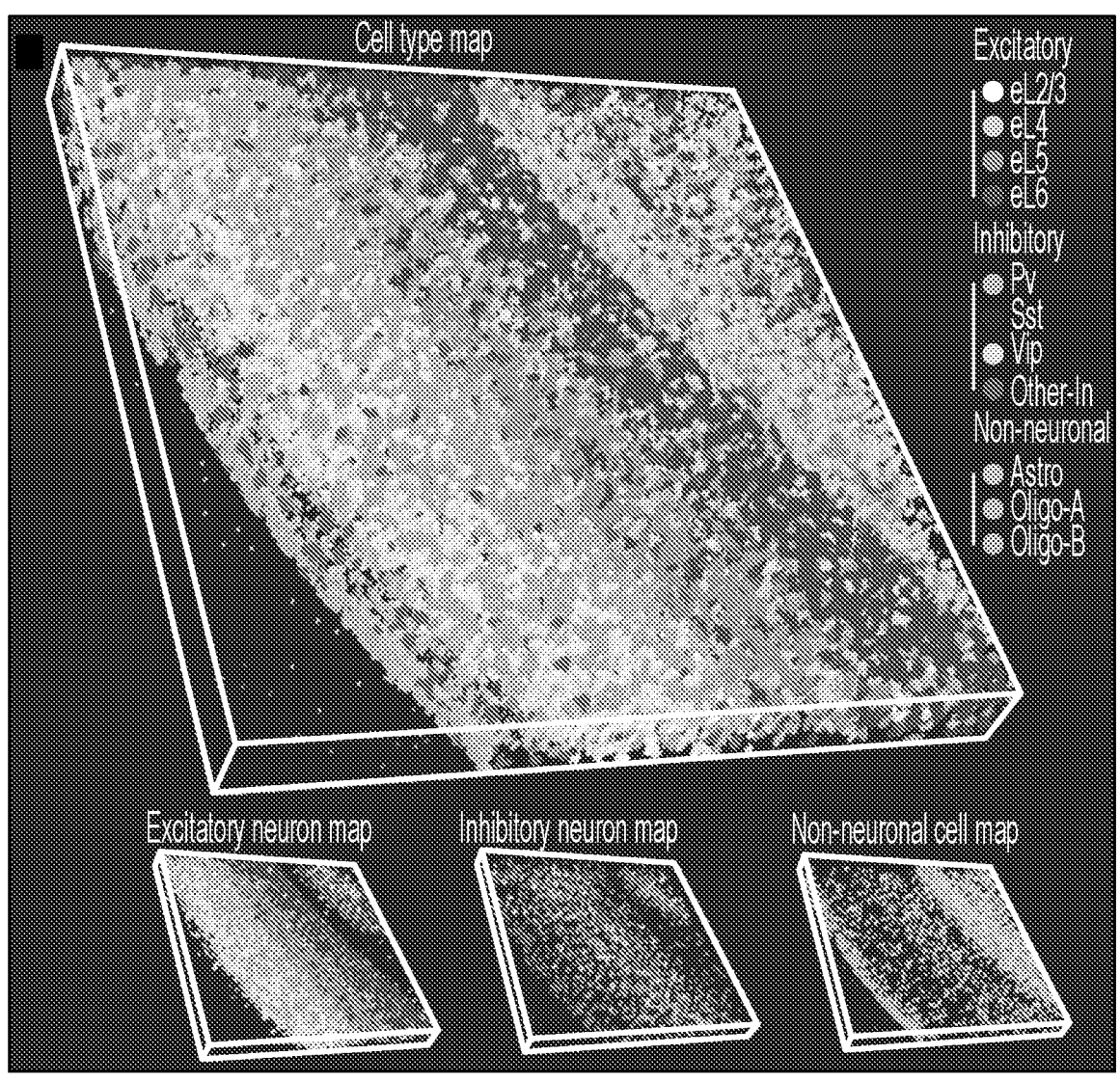
Figure 6F:
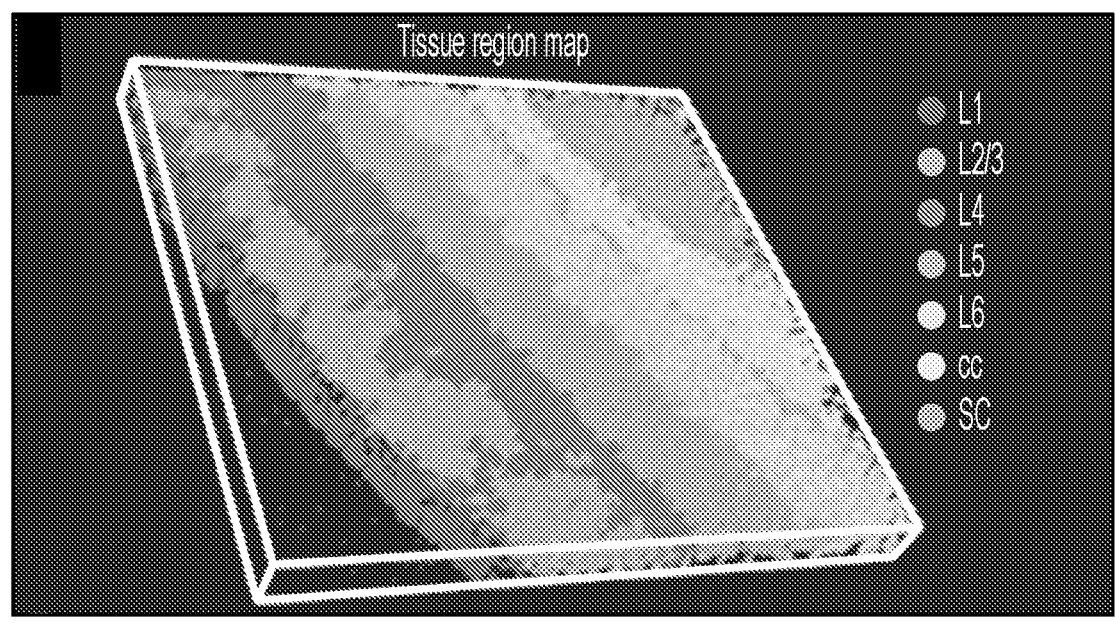
Figure 6G:
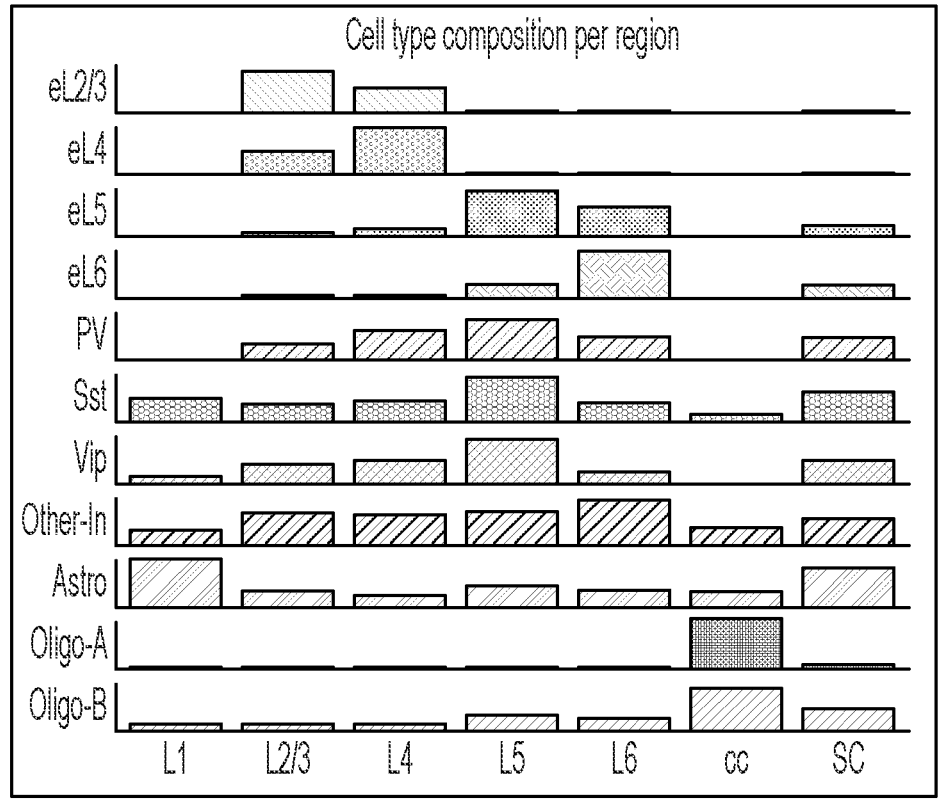
Figure 6H:
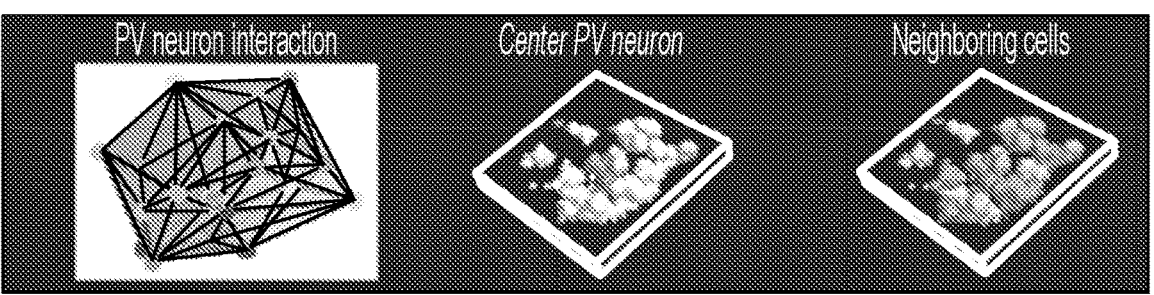
Figure 6I:
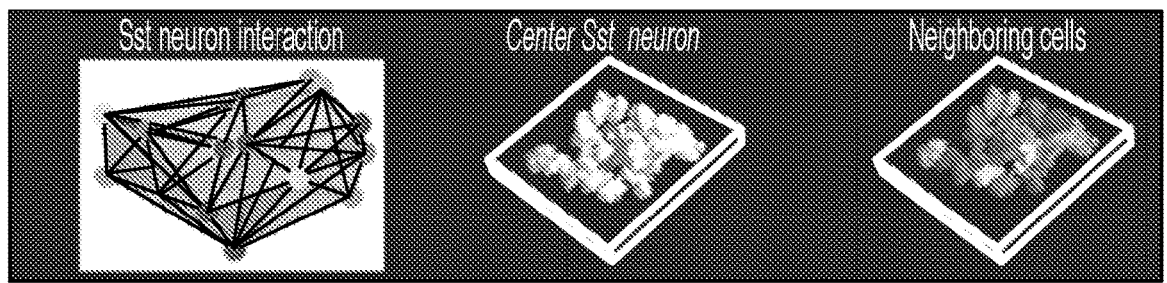
Figure 6J:
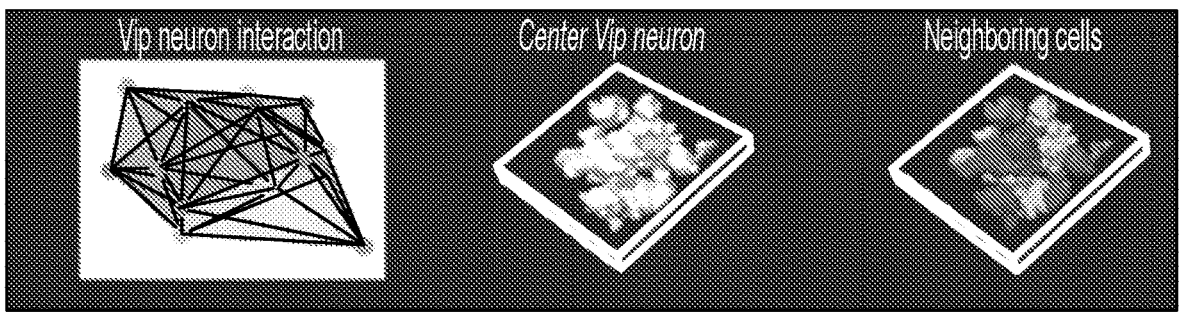

FIGS. 6A-6K show that ClusterMap enables 3D in situ transcriptomics analysis. FIG. 6A shows raw fluorescent signals of 3D STARmap cardiac organoid 8-gene dataset. Width: 465 μm, height: 465 μm, depth: 97 μm. FIGS. 6B-6C show that ClusterMap generates a 3D cell map (FIG. 6B) and cell-type map (FIG. 6C) of FIG. 6A, which includes 1,519 cells. Insets in FIGS. 6A-6C show zoomed-in views of the highlighted regions. FIG. 6D shows that ClusterMap generates a volumetric cell map of 3D STARmap mouse V1 28-gene dataset[6], showing 24,590 cells. Width: 1545 μm, height: 1545 μm, depth: 100 μm. FIG. 6E shows that the 3D cell type maps of (FIG. 6D) show spatial cell type distribution. FIG. 6F shows the 3D tissue region map of FIG. 6E. SC, subcortical. FIG. 6G provides bar plots of the composition of 11 cell types across 7 layers. FIGS. 6H-6J provide an example of cellular communication at a Pv, Sst, or Vip neuron, respectively. Left: schematics of 3D Delaunay triangulation of the Pv, Sst, or Vip neuron (highlighted in a white circle) and its first tier of neighboring cells. Middle: 3D spatial cell distribution of the first panel with the first tier of neighboring cells shown in white. Right: 3D spatial cell distribution of the first panel. Width 184 μm, height 194 μm, depth 100 μm. FIG. 6K provides bar plots of average composition of cell types around each cell type. Patterns of self-association in the minority inhibitory neurons are highlighted in the bounding box. Cell types in FIGS. 6G-6K are shaded as in FIG. 6E.

Figure 7A:
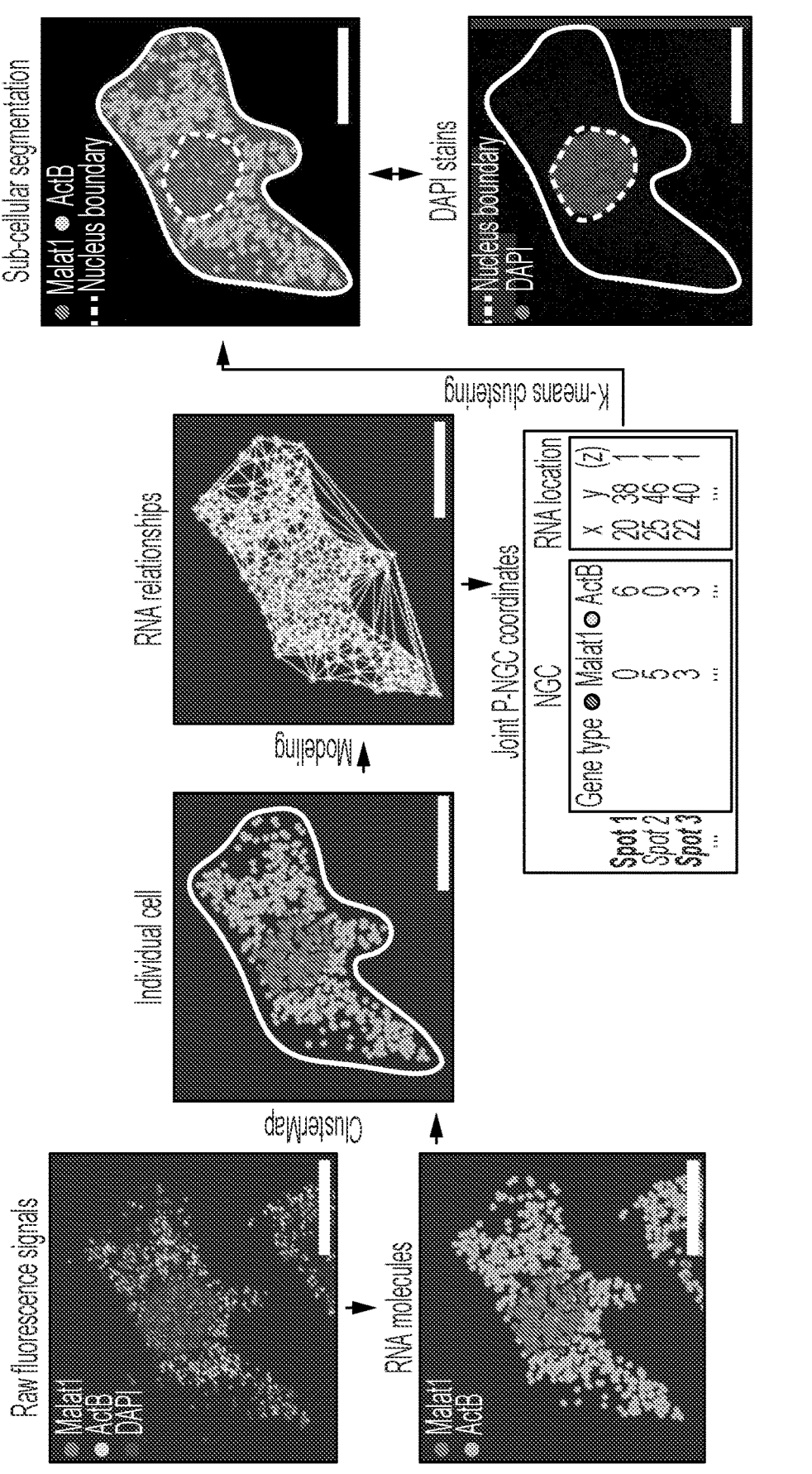
Figure 7B:
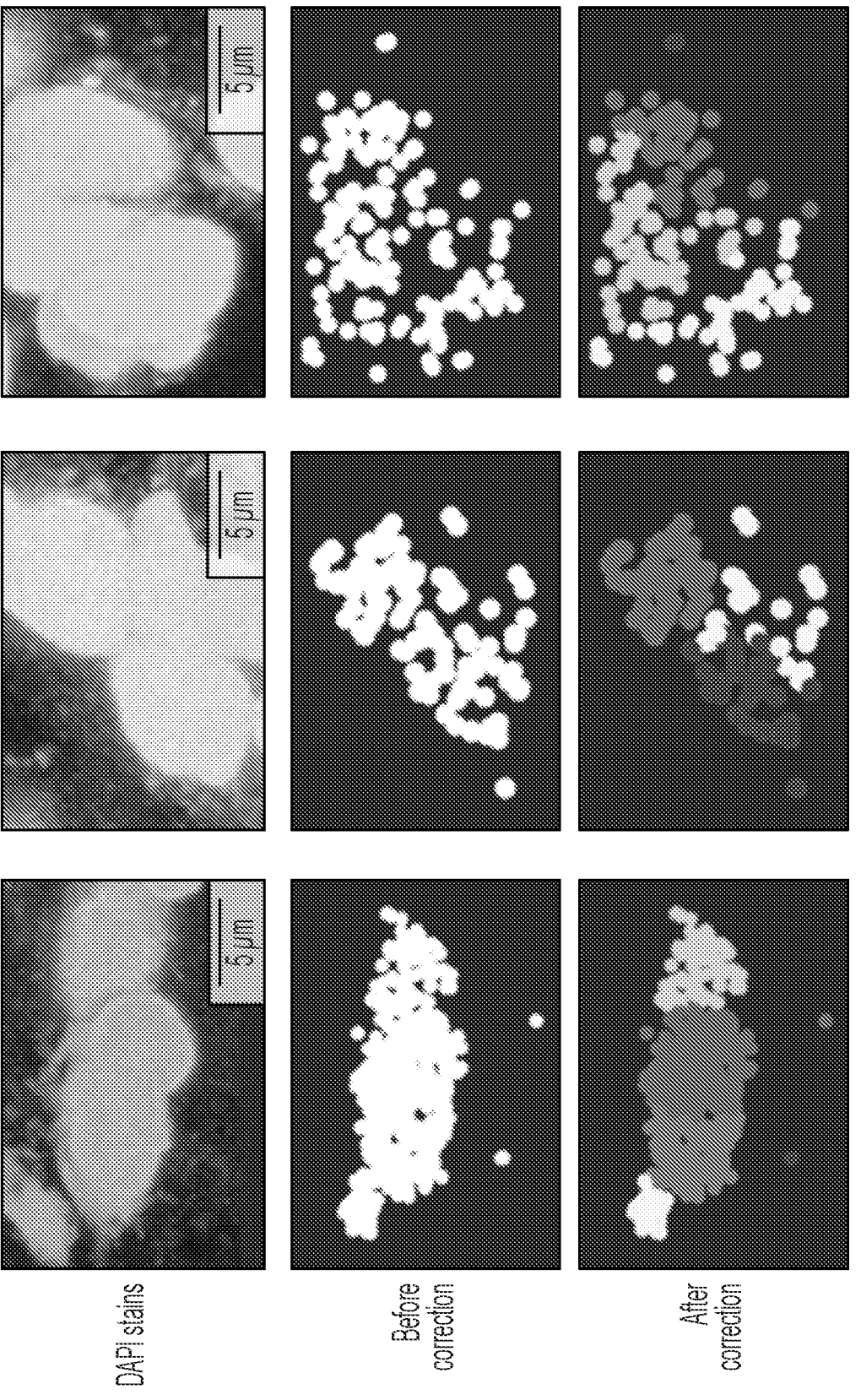
Figure 7C:
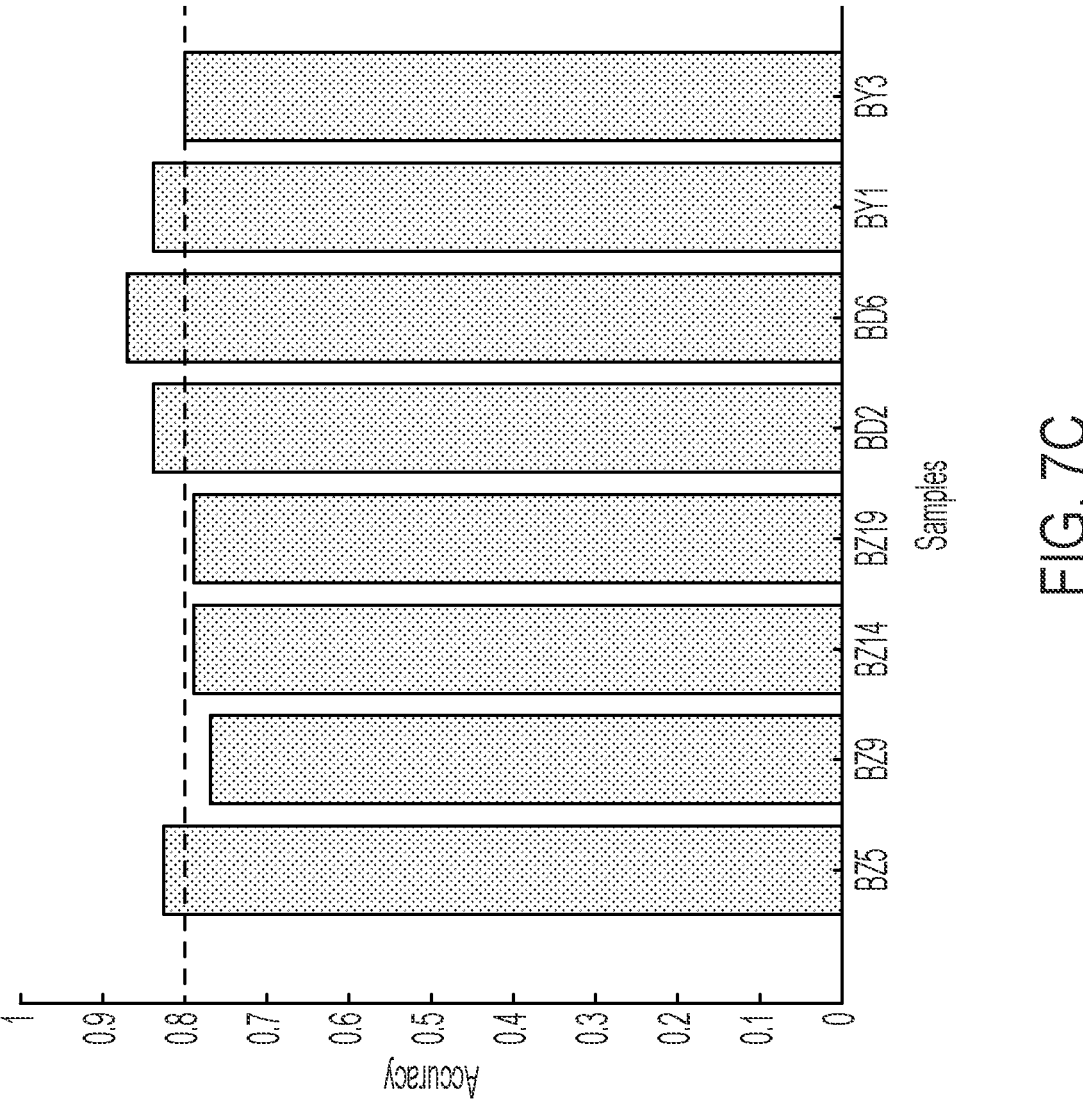
Figure 7D:
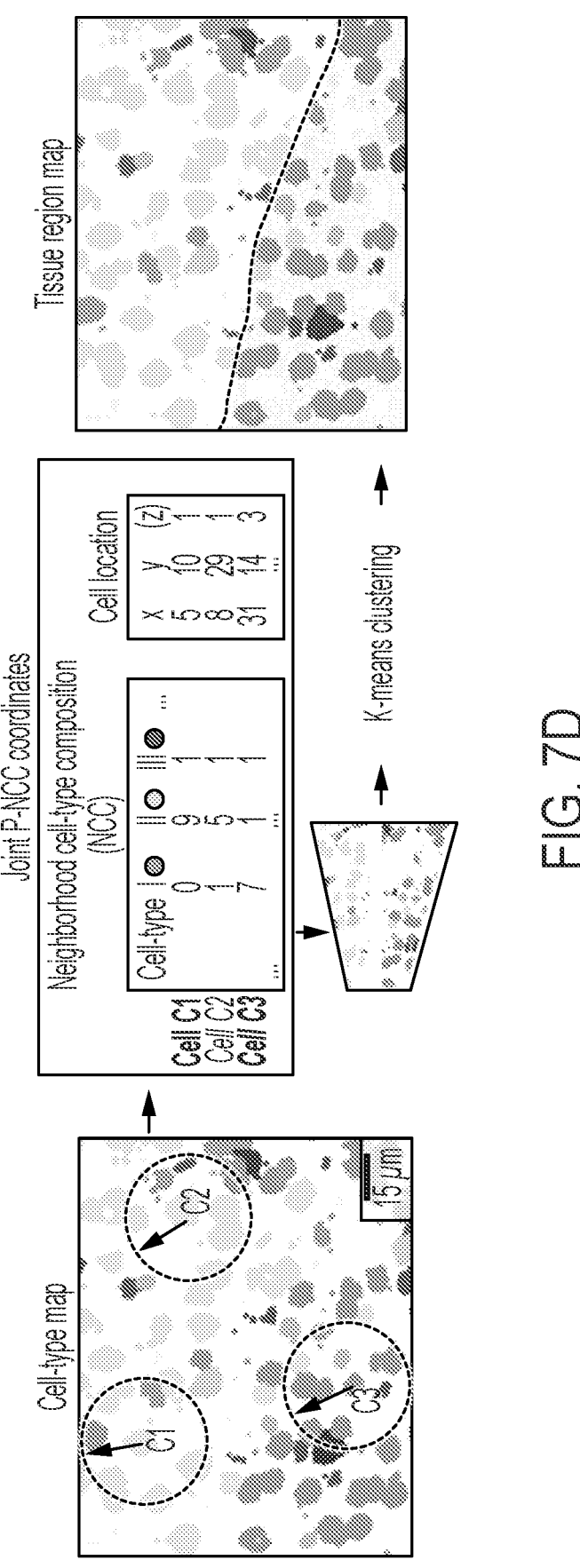

FIGS. 7A-7D shows sub-cellular analysis, validation of the cell identification method, and tissue region analysis. FIG. 7A shows the sub-cellular analysis process for the fourth panel IV in FIG. 1D by ClusterMap. A three channel composite image (showing Malat1, ActB, and DAPI shaded according to the legend provided) shows raw fluorescent signals. After preprocessing, mRNA molecules with specific genes are located. ClusterMap first performs cellular resolution and identifies individual cells. Then a mesh graph that models the relationship between mRNA spots in the cell is generated to compute the NGC coordinates and K-means clustering separate spots into two regions using joint physical and NGC coordinates. Finally, a convex hull was constructed from the nucleus spots, denoting the nucleus boundary. The pattern of ClusterMap-constructed nucleus boundary compared with the DAPI stains. Scale bar: 20 μm. FIG. 7B provides examples of cell identification correction using information from NGC space during ClusterMap procedures in FIG. 2A. Upper: DAPI stains showing the cell nuclei. Middle: Cell clustering results using only information in the physical space. Closely overlapping cells are not separated. Lower: With information from NGC space, the under-clustered cells are separated. FIG. 7C shows the accuracy of cell identification results on eight STARmap datasets compared with corresponding expert-annotated labels. BZS, BZ9, BZ14, BZ19: four STARmap 166-gene sets in mouse medial prefrontal cortex (mPFC); BD2, BD6:

two STARmap 160-gene sets in mouse V1. BY1, BY3: two STARmap 1020-gene sets in mouse V1. The horizontal line is at 80% accuracy. FIG. 7D shows construction of tissue regions by ClusterMap after cell-typing. First, the neighborhood cell-type composition (NCC) of each cell is computed by considering a sliding window over the cell-type map. Then both the NCC and physical locations of cells are combined for K-means clustering. Cells with highly correlated neighboring cell-type composition and close spatial distances are merged into a single tissue region signature.

Figure 8A:
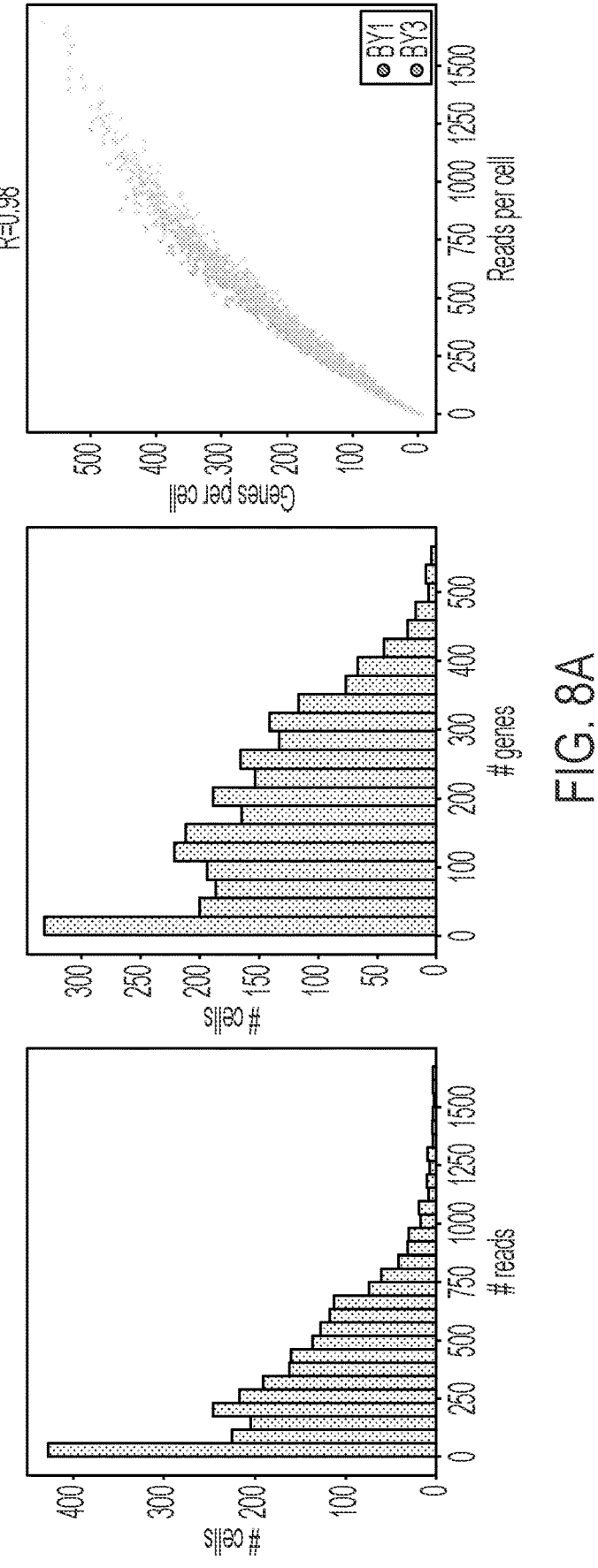
Figure 8B:
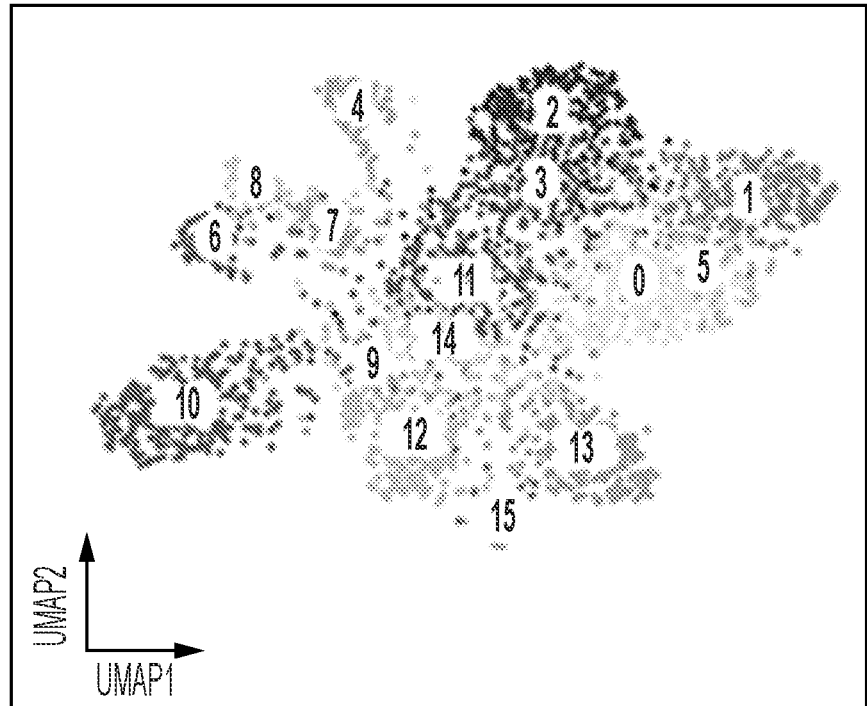
Figure 8C:
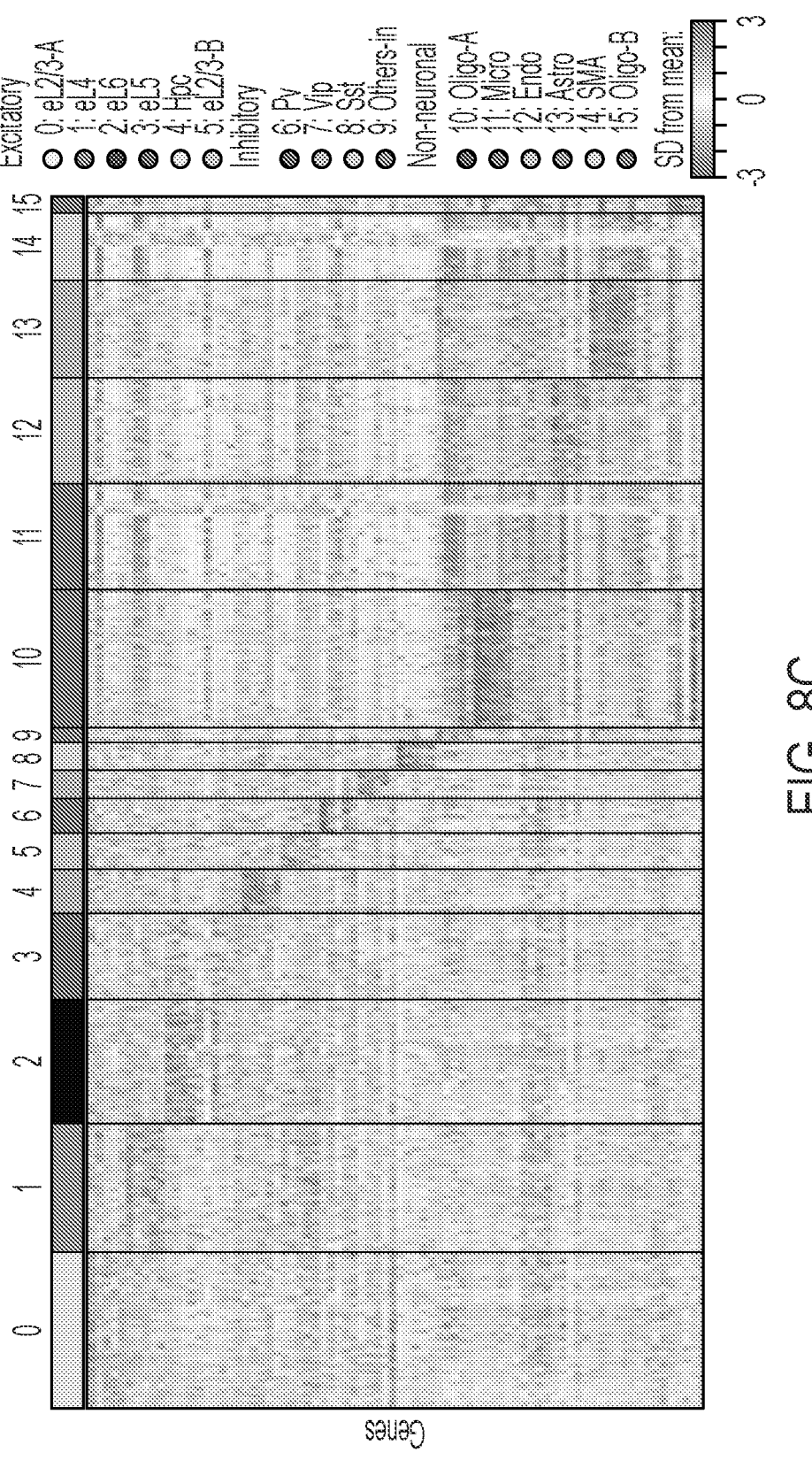
Figure 8D:
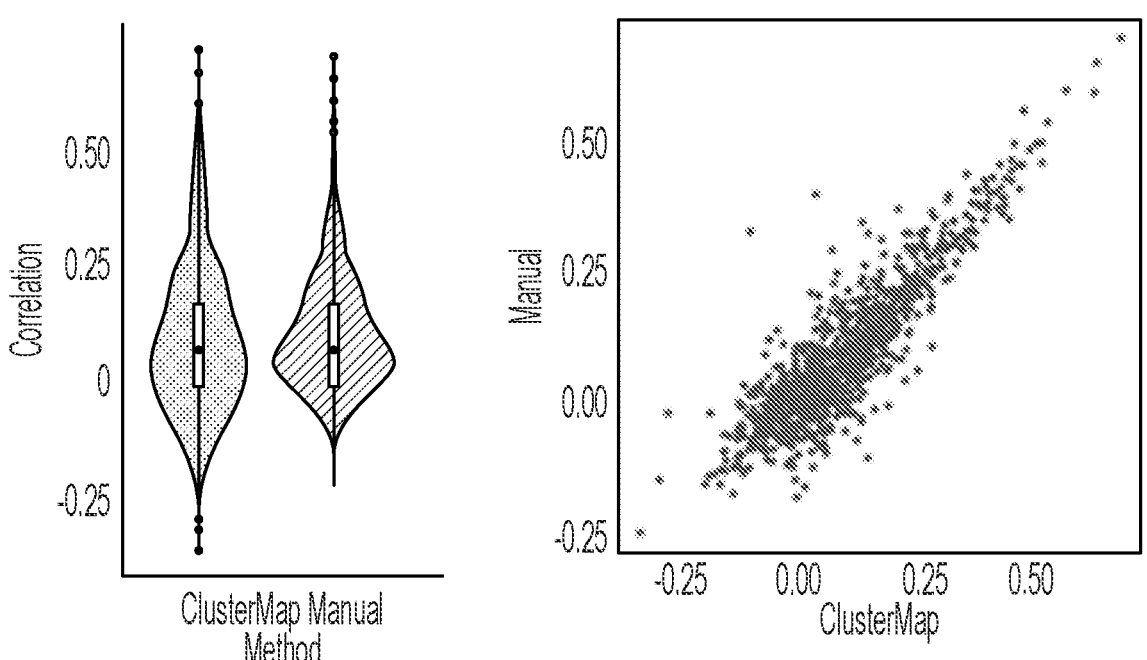
Figure 8E:
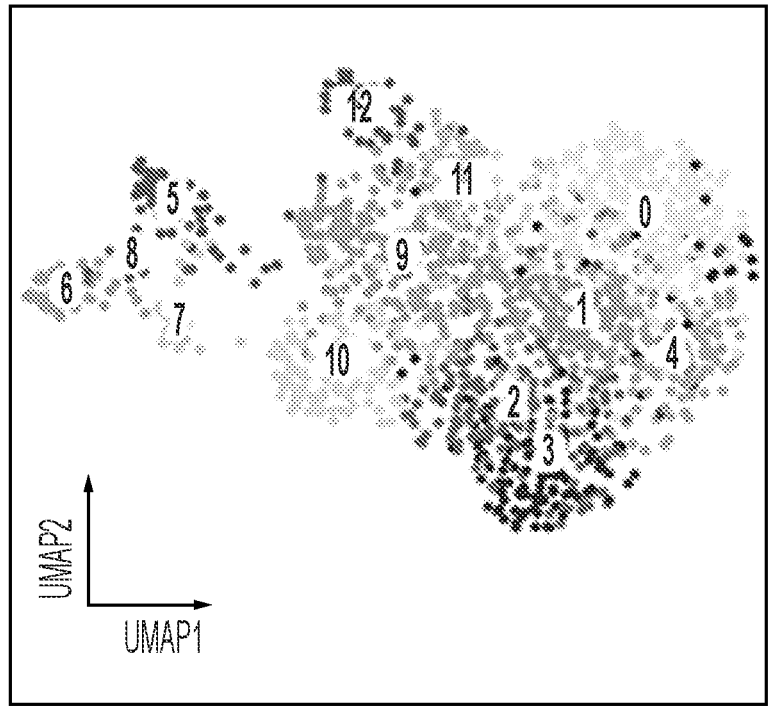
Figure 8F:
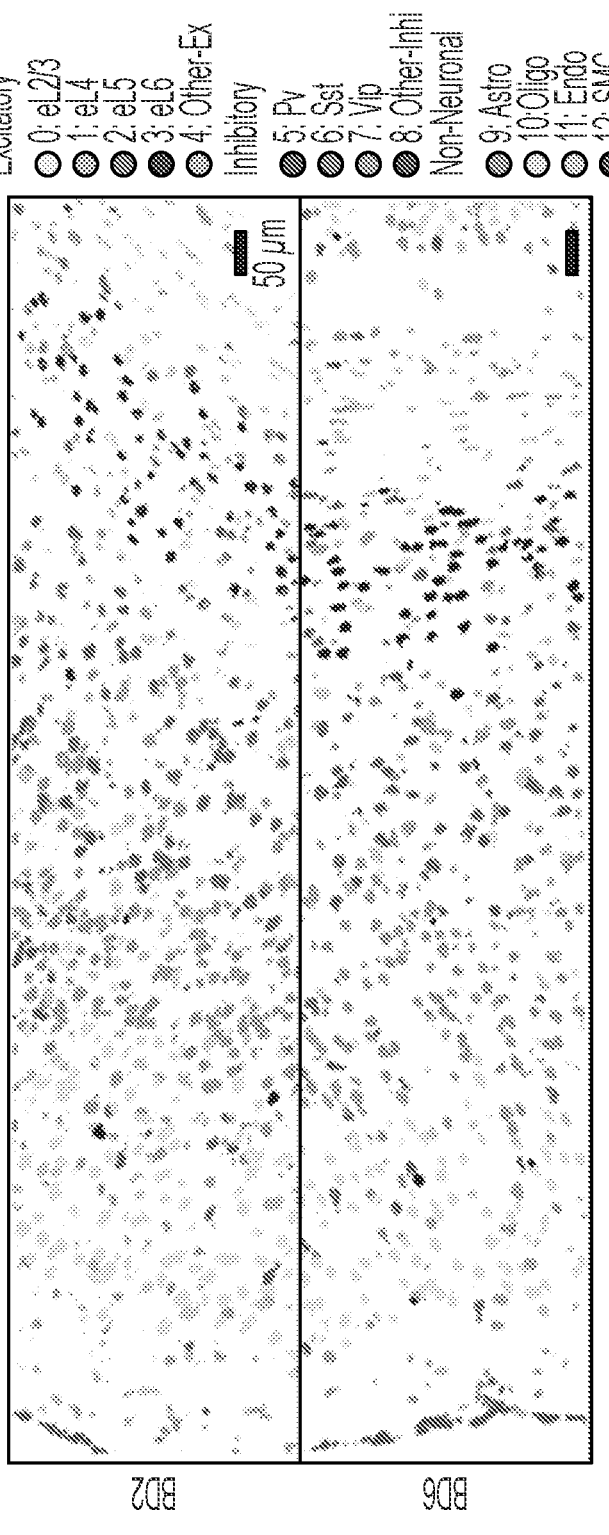
Figure 8G:
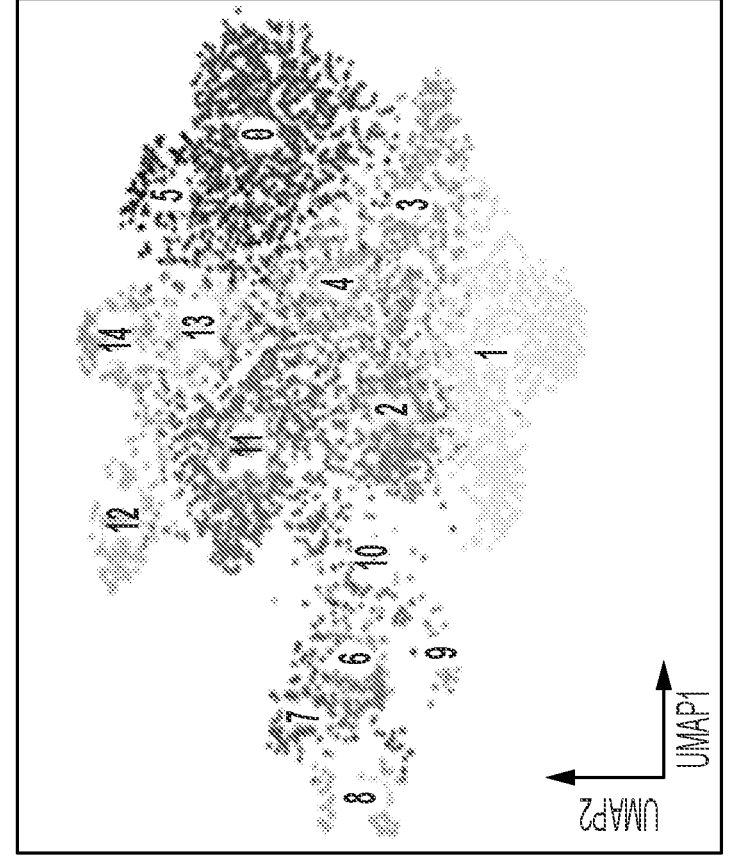
Figure 8H:
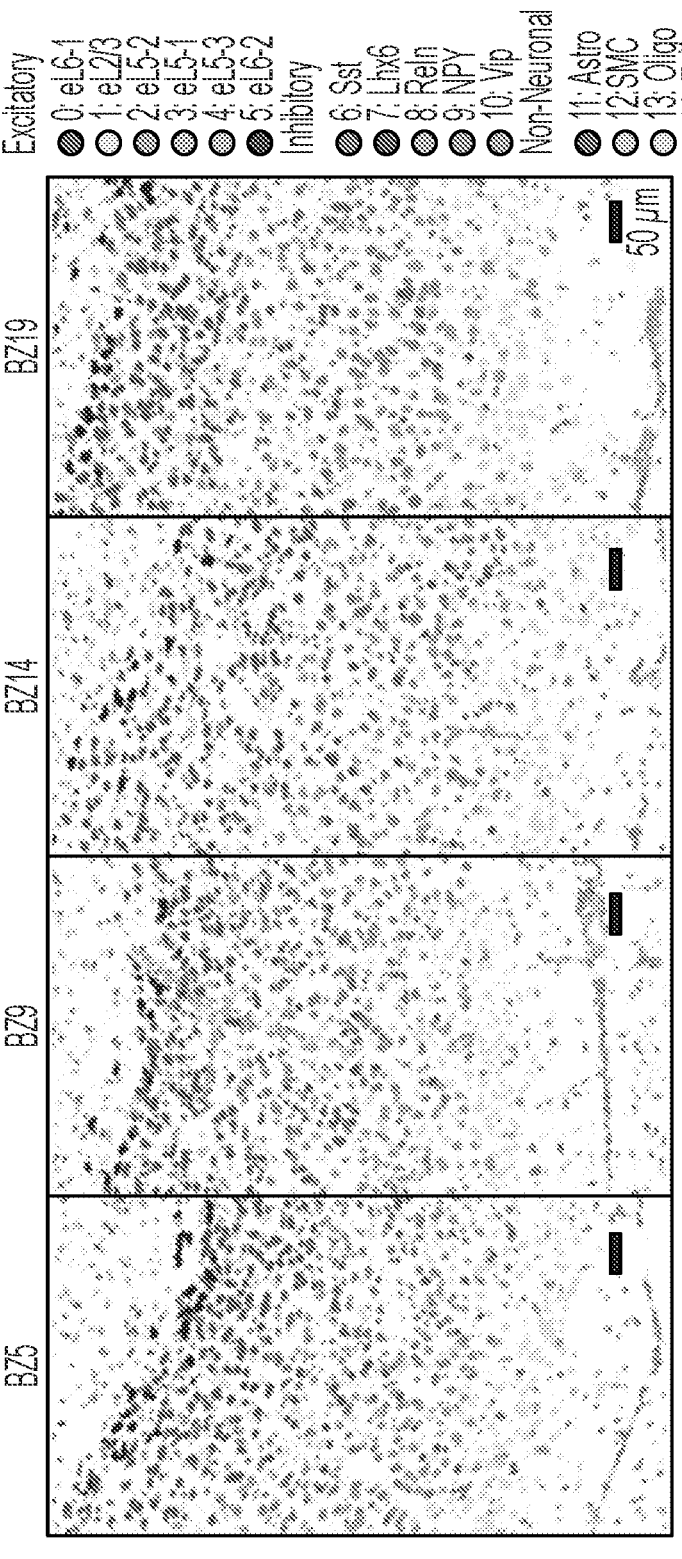

FIGS. 8A-8H show the identification of cell types in mouse V1 datasets. FIG. 8A provides statistics of ClusterMap identified cells in STARmap mouse V1 1020-gene (two replicates: BY1 and BY3). Left: Histogram of detected reads (DNA amplicons) per cell. Middle: Histogram of genes per cell. Right: Correlation plot between genes per cell and reads per cell. FIGS. 8B-8C show UMAP and heatmap visualization of all excitatory, inhibitory and non-neuronal cell types in BY1 and BY3. FIG. 8D provides correlation plots after integration with scRNA-seq atlas. Left: Violin plots of Pearson correlation between gene expression in scRNA-seq atlas and ClusterMap or manual. Right: Correlation plot between integration results of ClusterMap manual annotation. FIGS. 8E and 8G show UMAP visualization of all excitatory, inhibitory and non-neuronal cell types in STARmap 160-gene datasets in mouse V1 (two replicates: BD2, BD6 (FIG. 8E)), and STARmap 166-gene datasets in mPFC (four replicates, BZ5, BZ9, BZ14, BZ19 (FIG. 8H)). FIGS. 8F and 8H show a spatial organization map of cell types in BD2 and BD6 (FIG. 8E), and in BZ5, BZ9, BZ14, and BZ19 (FIG. 8H).

Figure 9A:
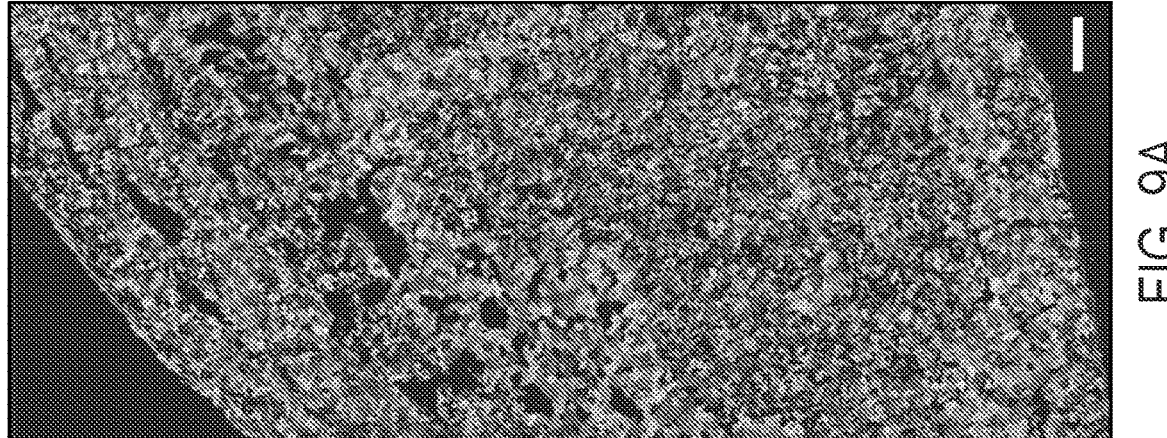
Figure 9B:
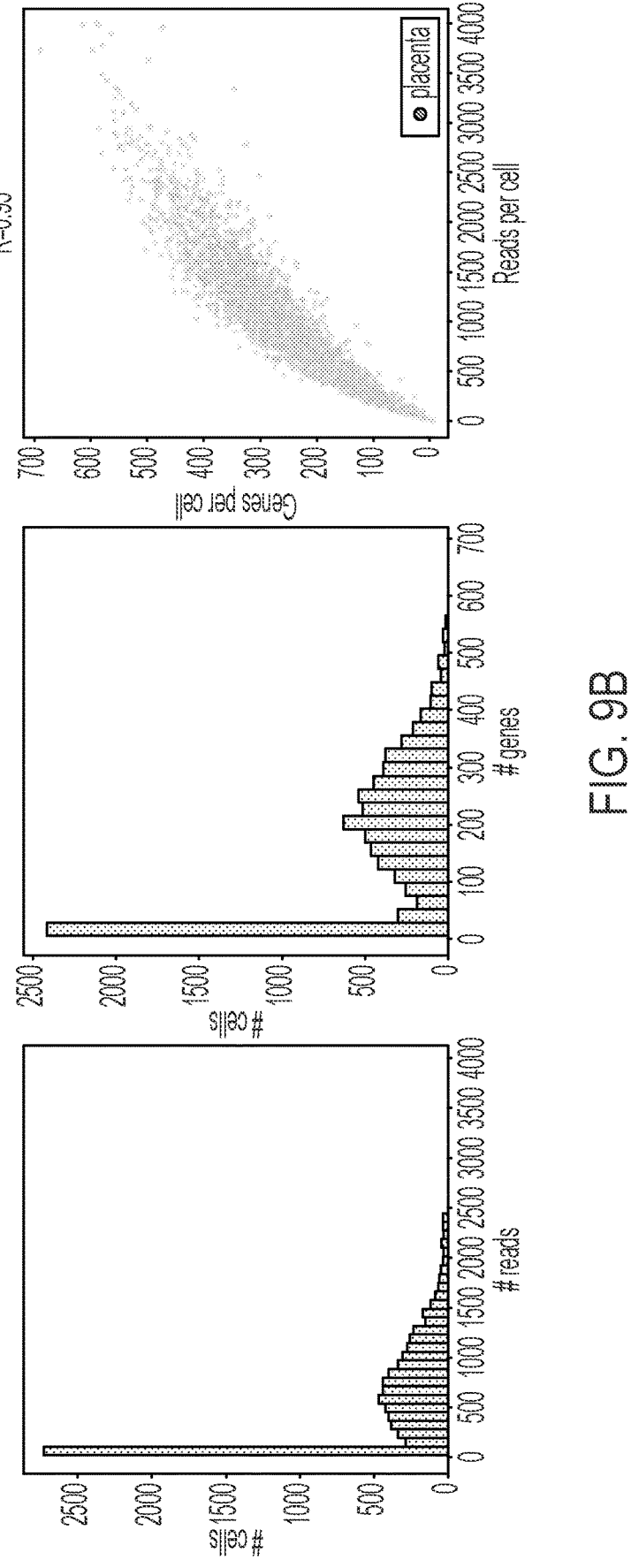
Figure 9C:
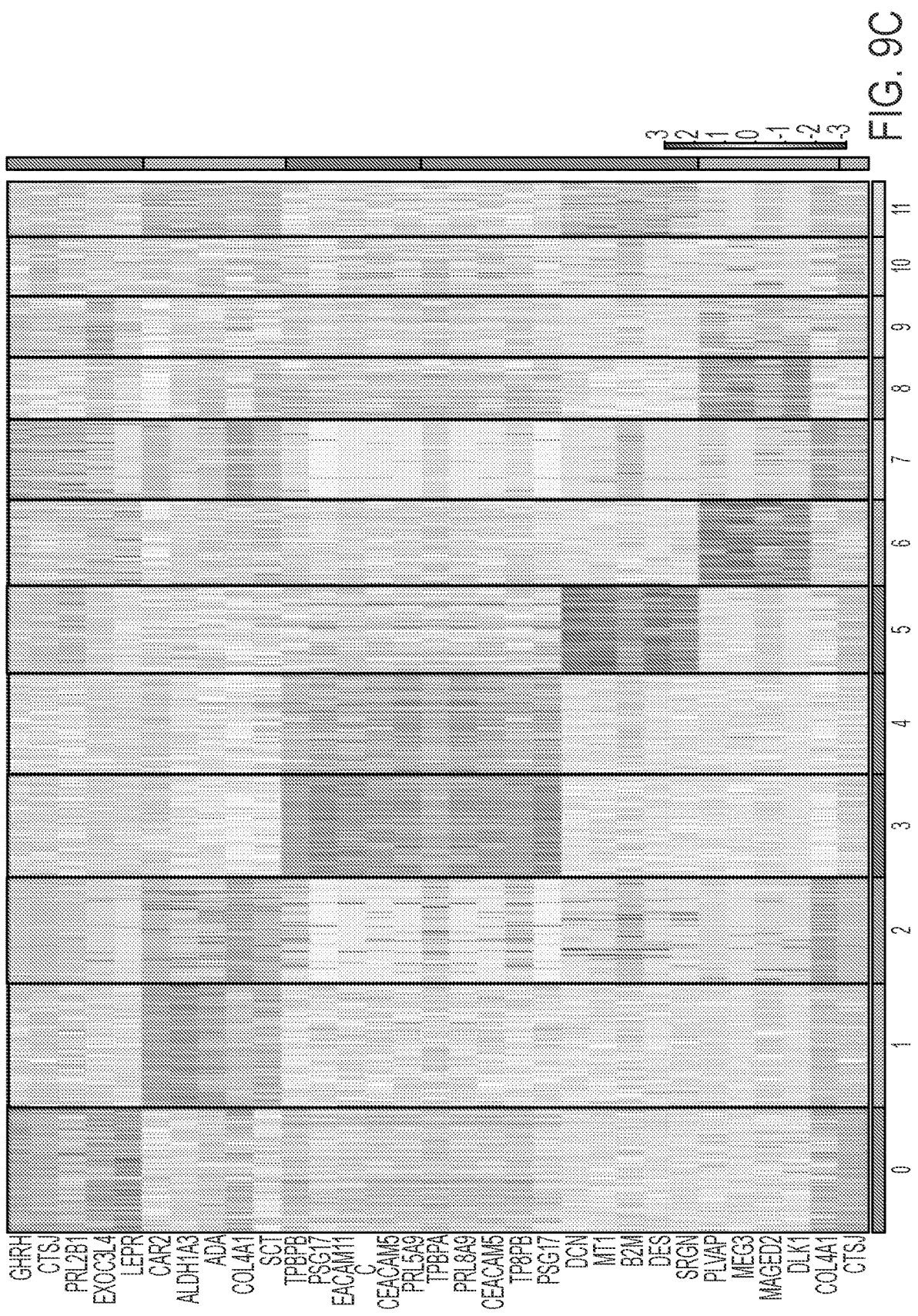
Figure 9C:
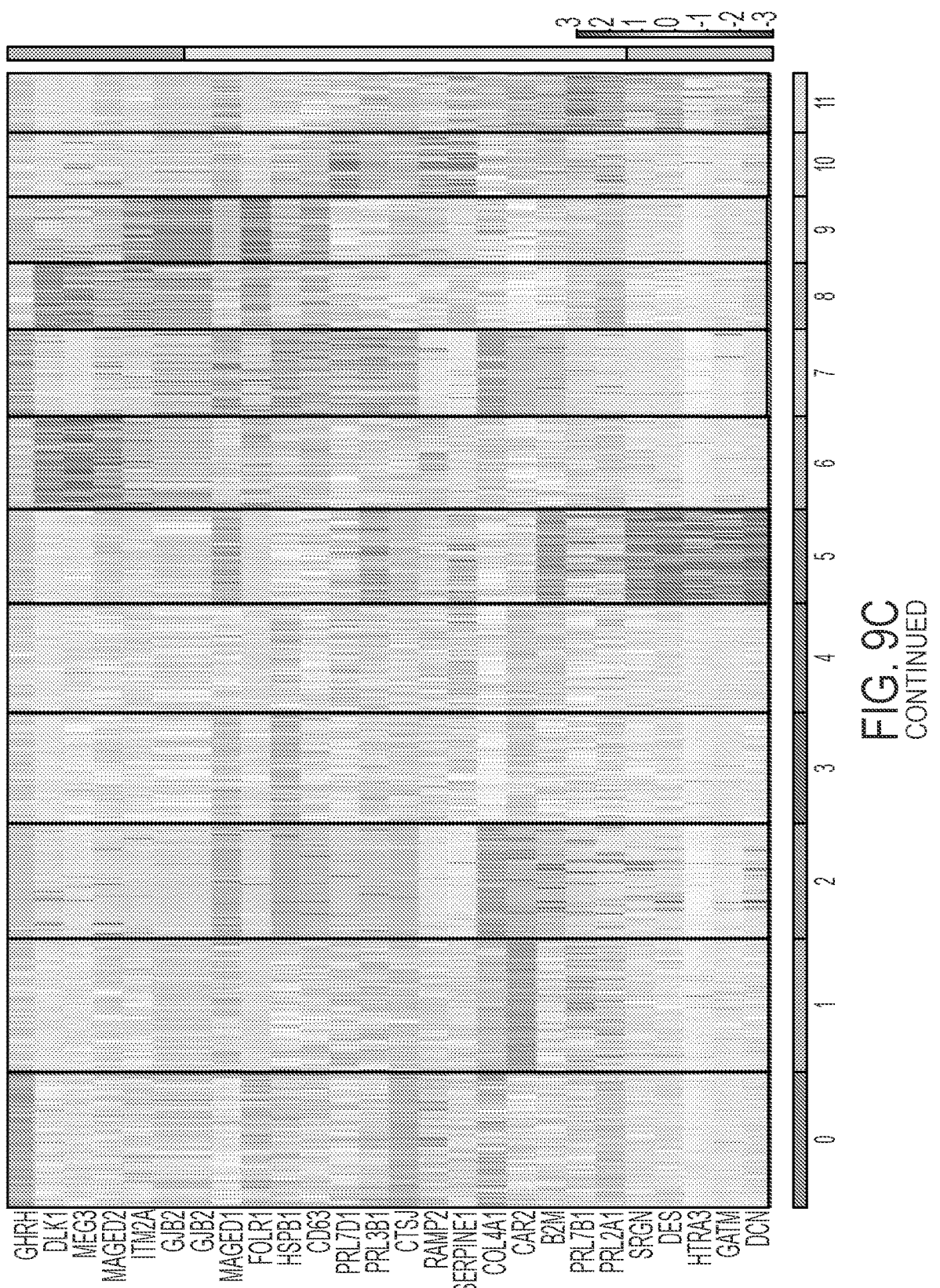
Figure 9D:
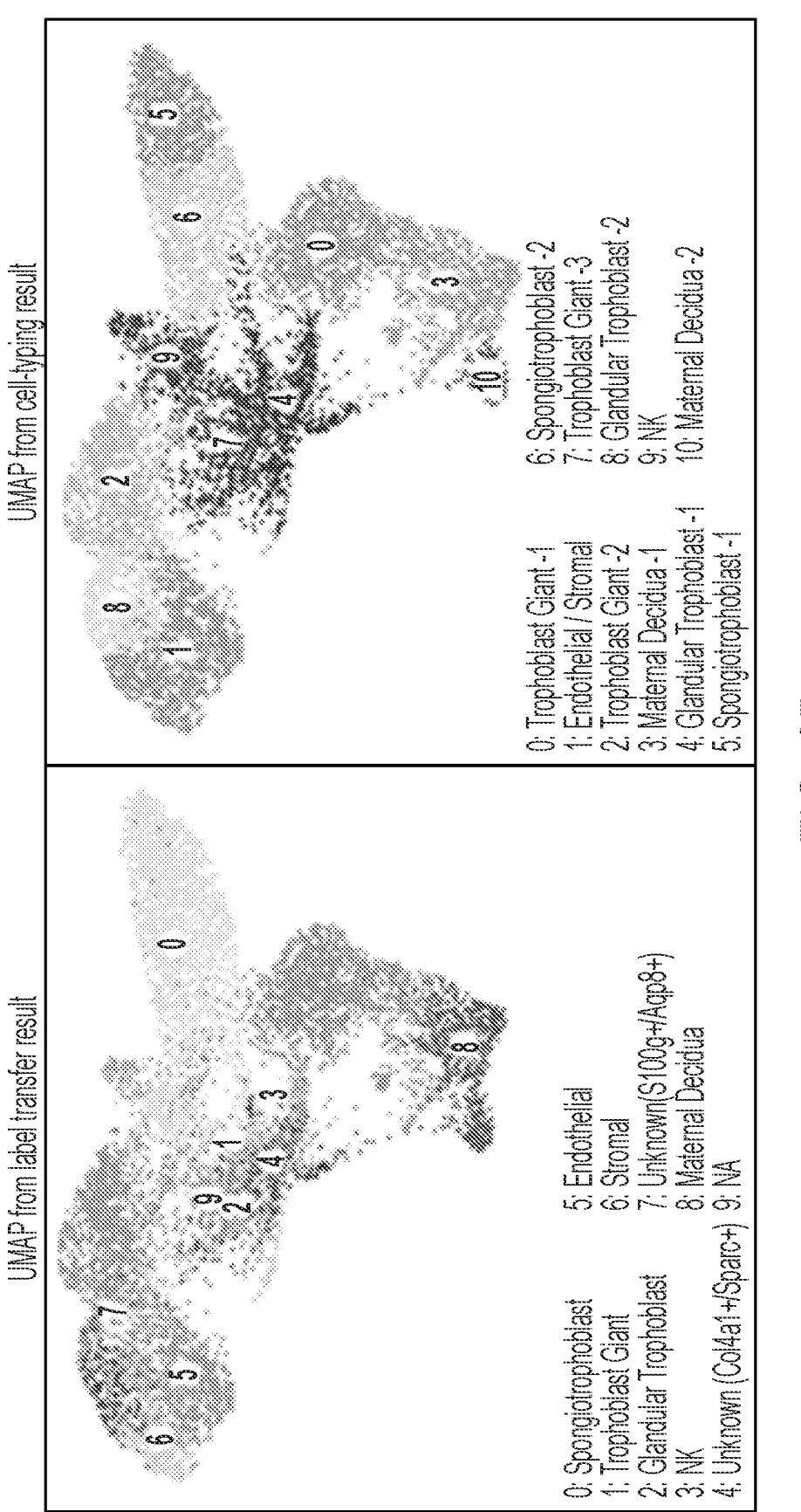

FIGS. 9A-9D provide analyses of the placental dataset. FIG. 9A shows that ClusterMap generates the cell map of the STARmap mouse placenta 903-gene dataset, including 7,224 cells. Scale bar: 100 μm. FIG. 9B provides statistics of ClusterMap identified placental cells as shown in FIG. 9A. Left: Histogram of detected reads (DNA amplicons) per cell. Middle: Histogram of genes per cell. Right: Correlation plot between genes per cell and reads per cell. FIG. 9C shows heatmap visualization of 11 cell types. Names are in the right panel of FIG. 9D. FIG. 9D provides UMAP from label transfer results with scRNA-seq, compared with UMAP of the Louvain clustering in ClusterMap.

Figure 10A:
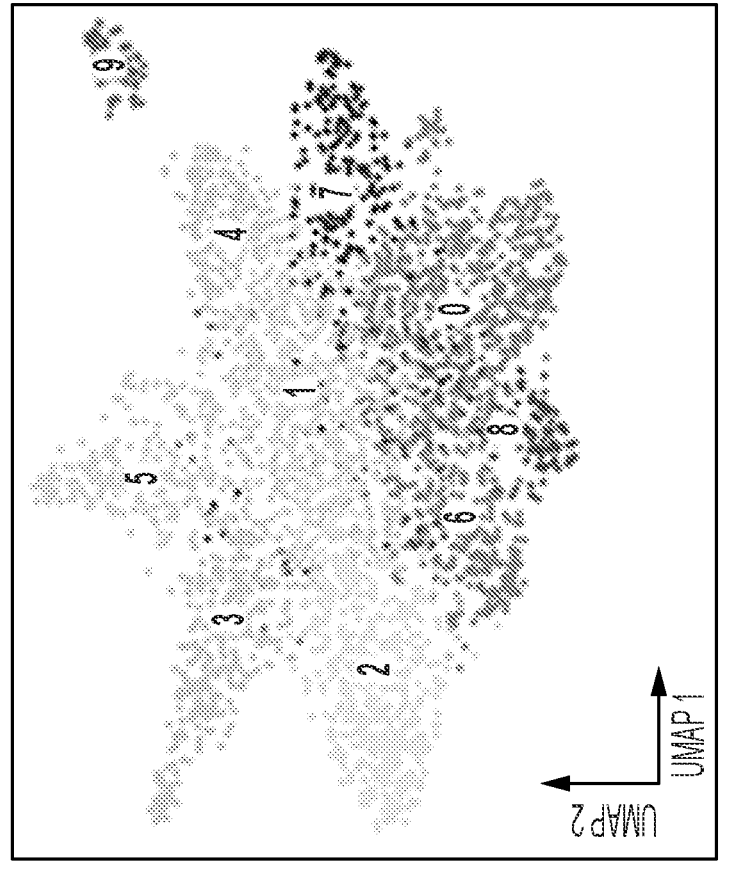
Figure 10B:
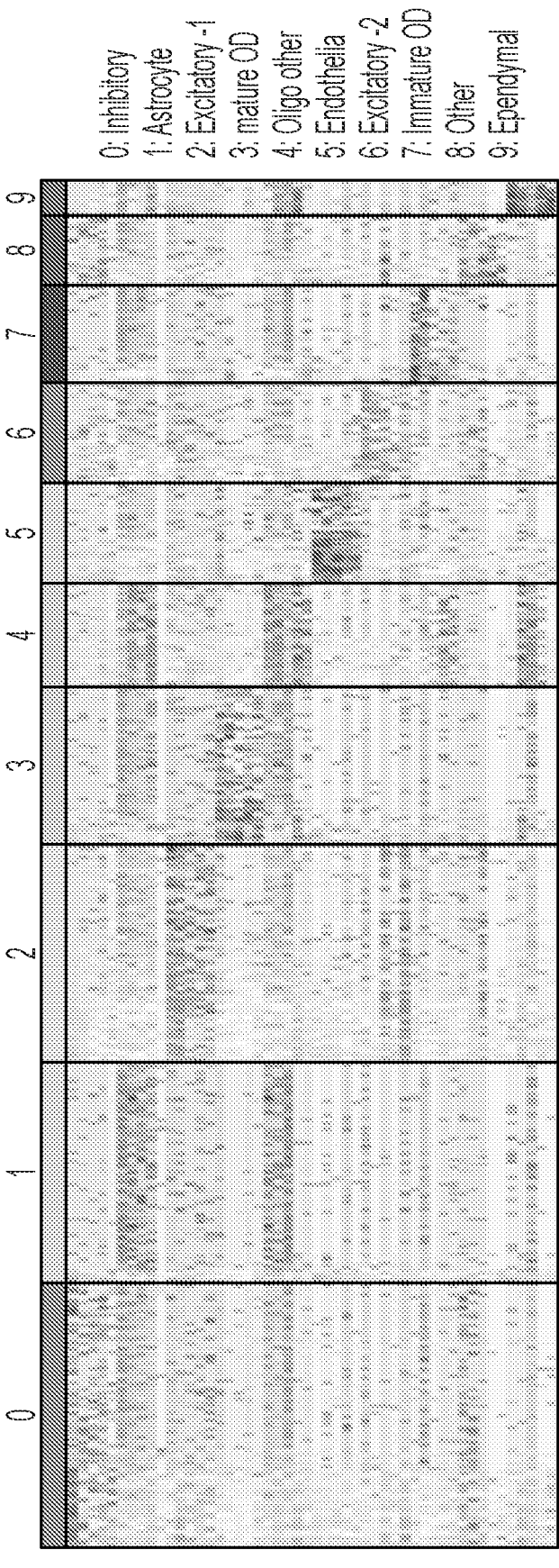
Figure 10C:
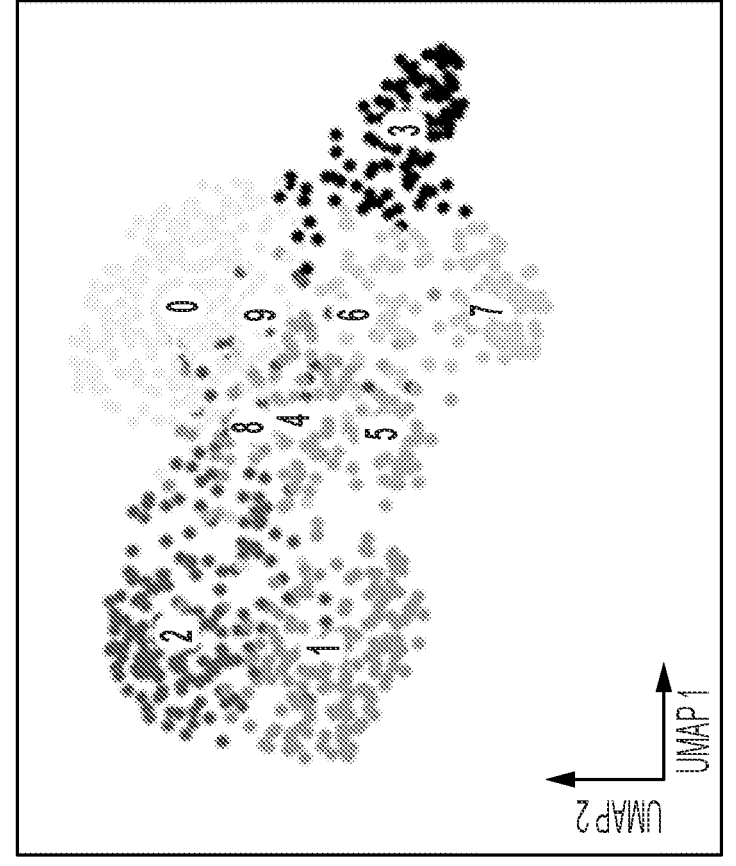
Figure 10D:
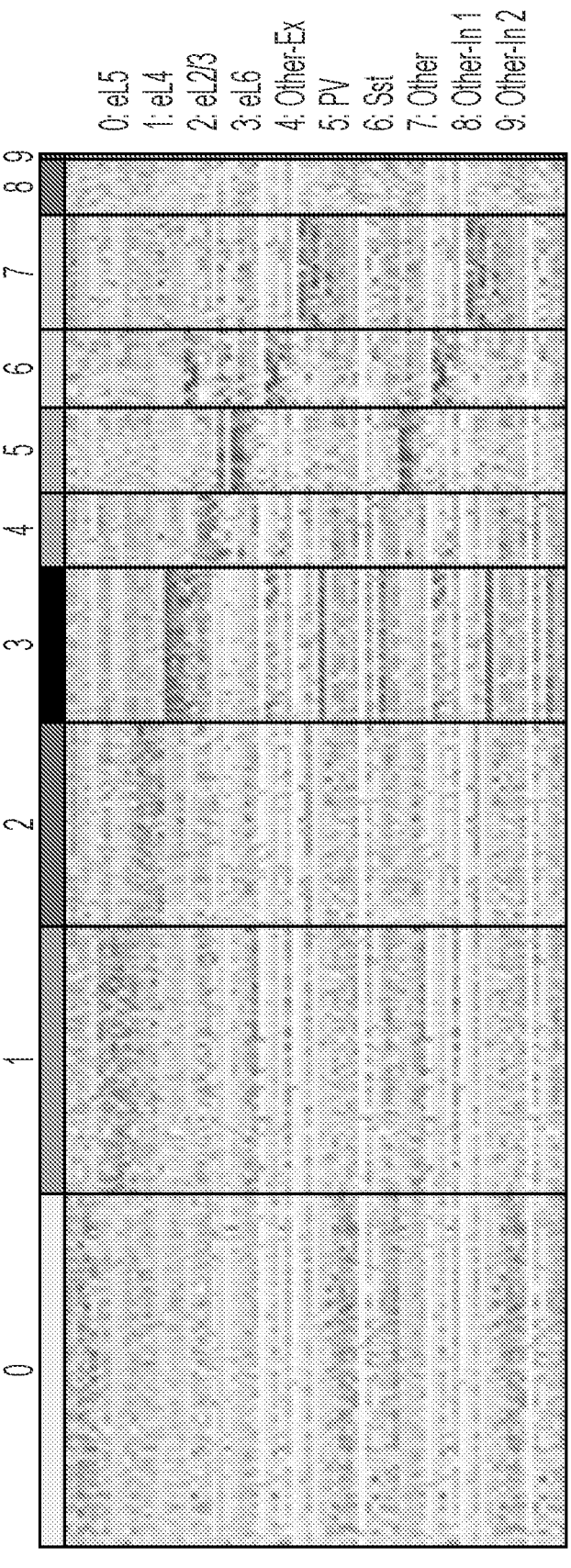
Figure 10E:
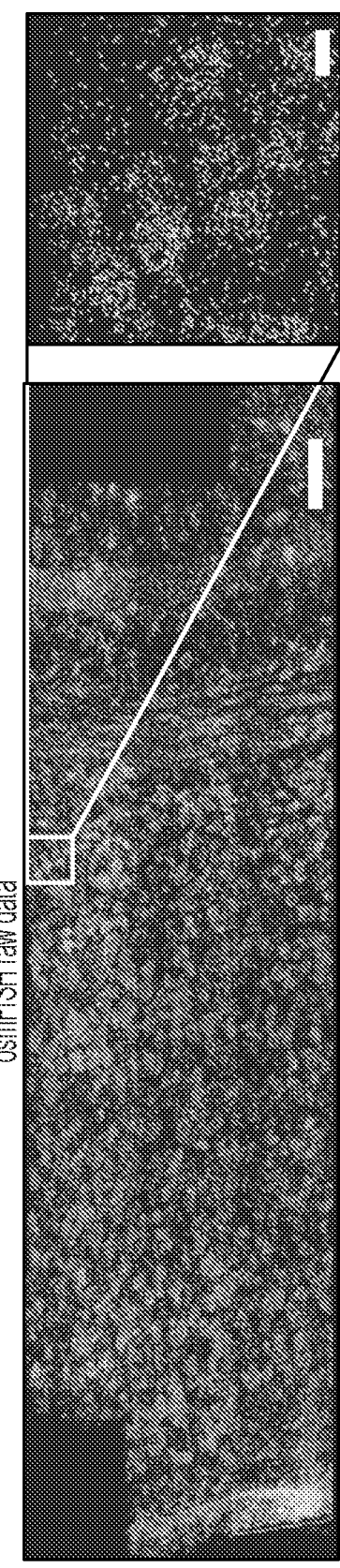
Figure 10F:
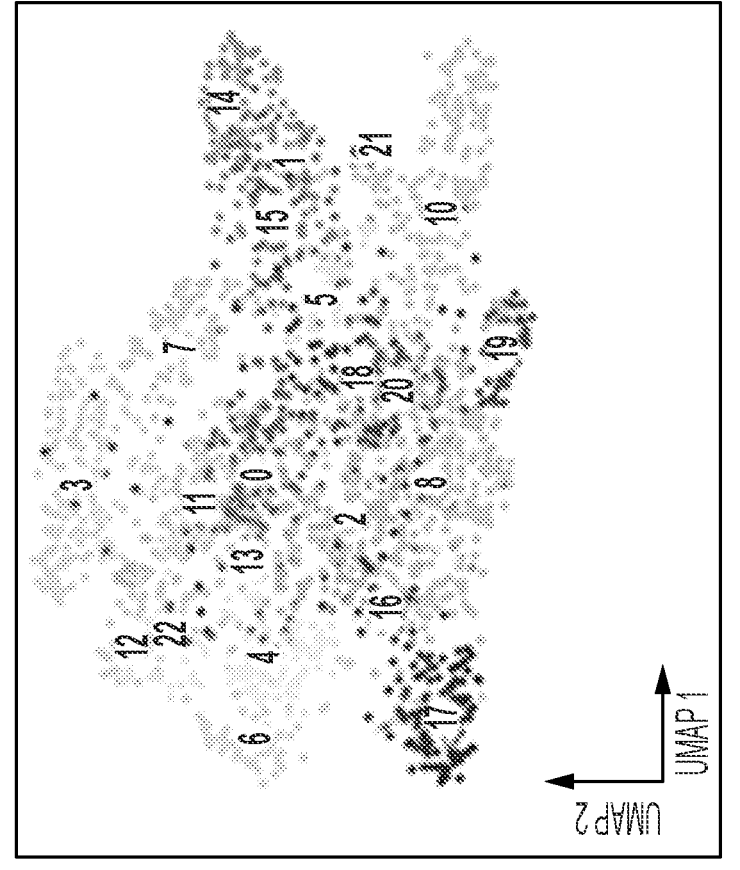
Figure 10G:
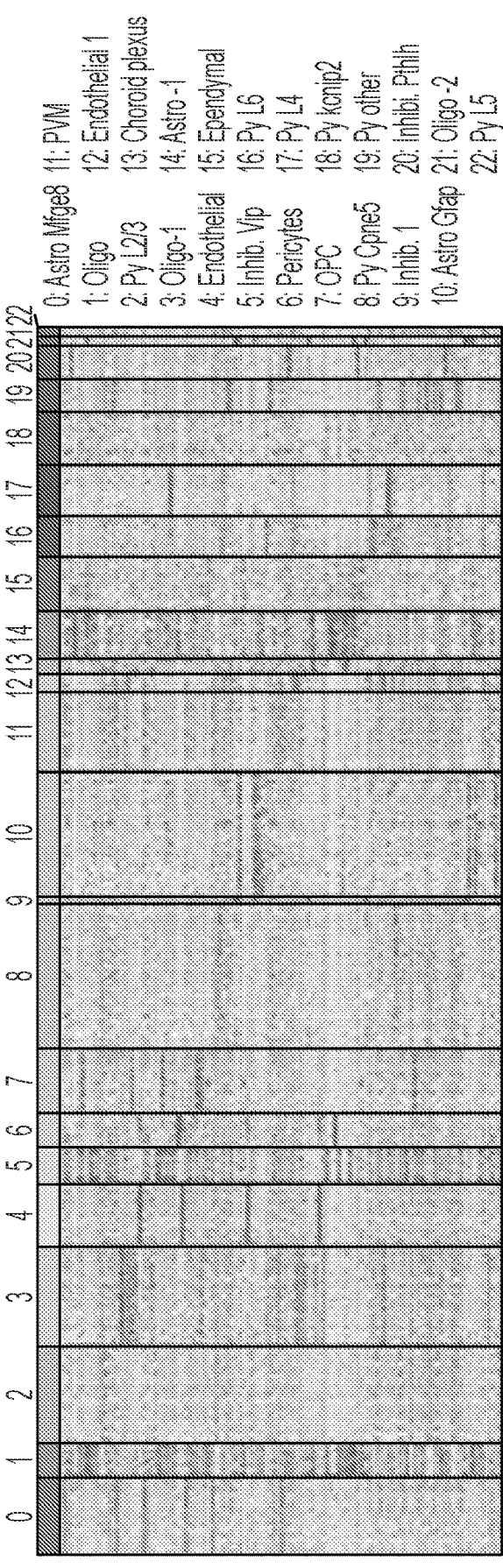

FIGS. 10A-10G provide analyses in datasets across various protocols. FIGS. 10A-10B provide UMAP and heatmap visualization of ten cell types in the selected area from the MERFISH mouse POA dataset. FIGS. 10C-10D provide UMAP and heatmap visualization of ten cell types in the selected area from the pciSeq mouse isocortex dataset. FIG. 10E shows raw spatial transcriptomics data of the selected area from the osmFISH mouse SSp dataset. Scale bar: 100 μm. Left: zoomed in view of the highlighted square. Scale bar: 10 μm. FIGS. 10F-10G provide UMAP and heatmap visualization of seven main types and 22 subtypes of FIG. 10E.

Figure 11A:
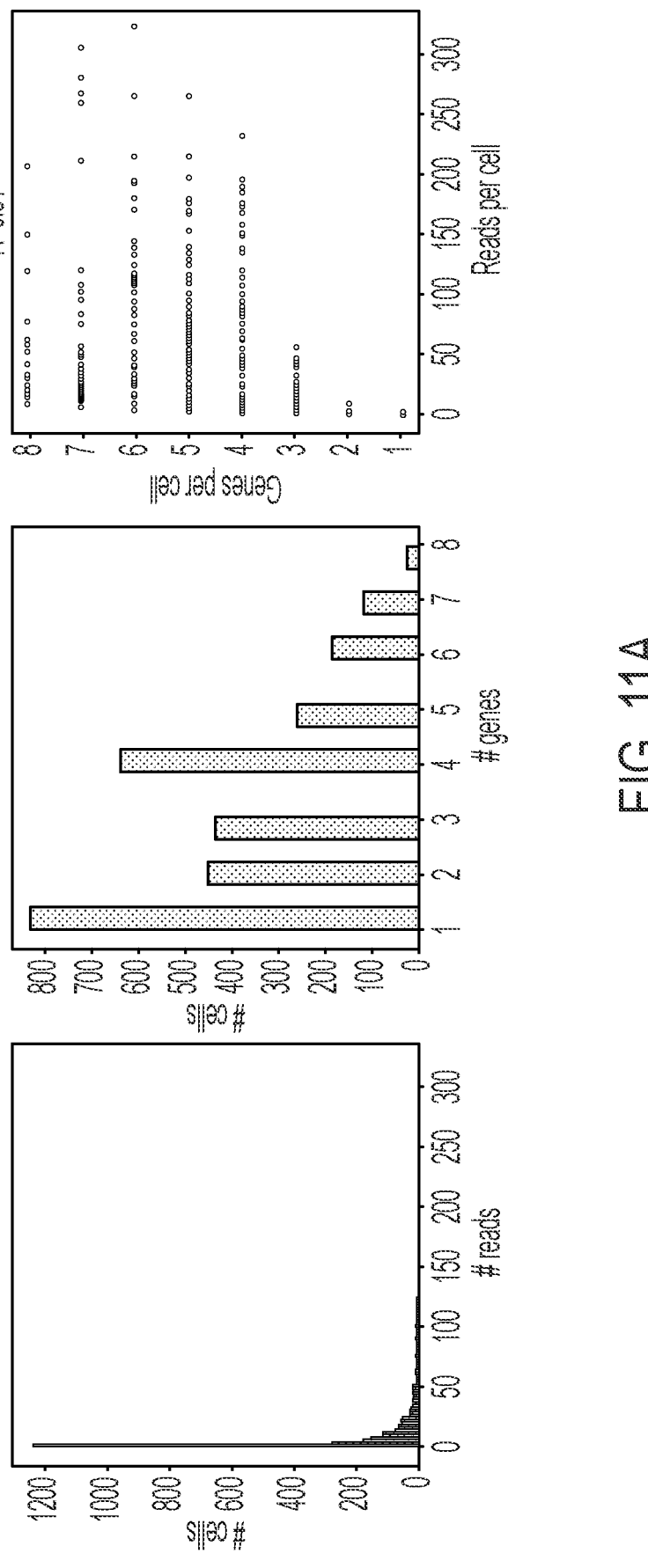
Figure 11B:
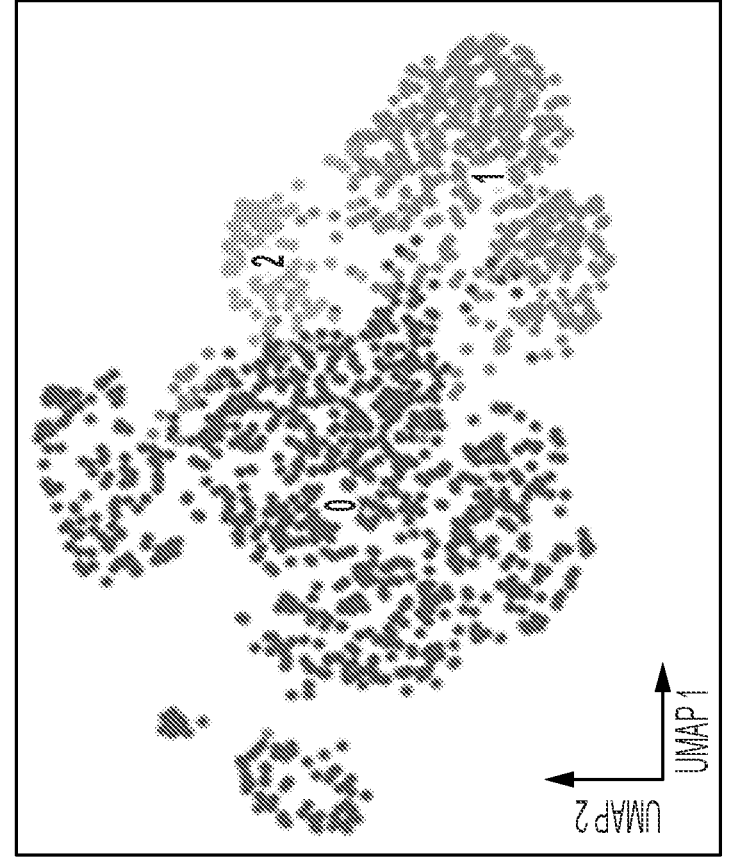
Figure 11C:
Figure 11D:
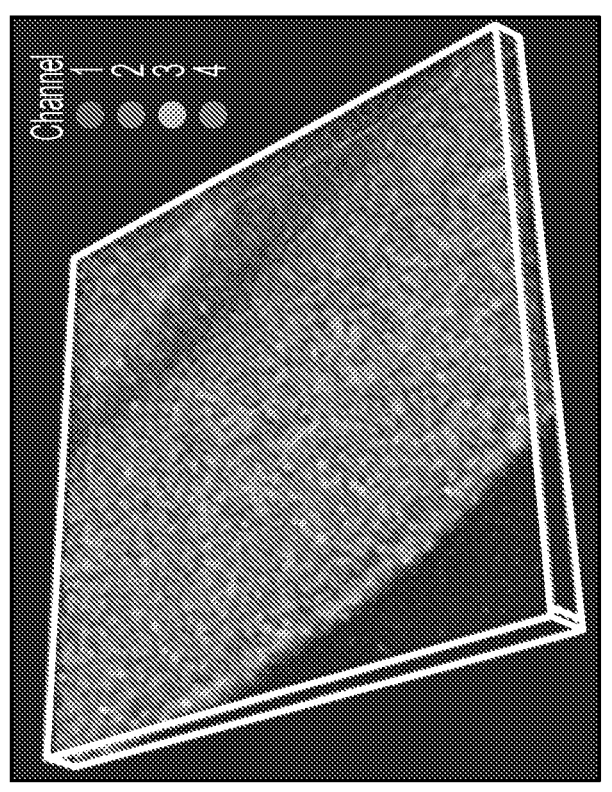
Figure 11E:
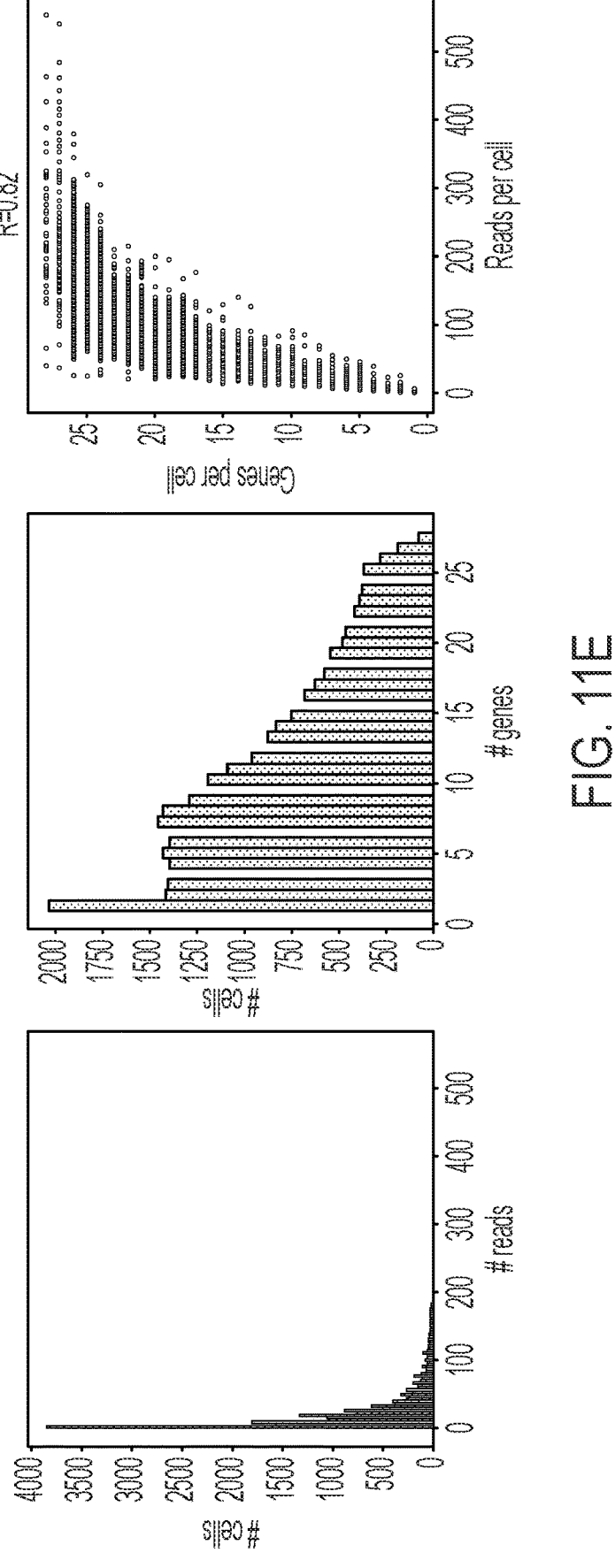
Figure 11F:
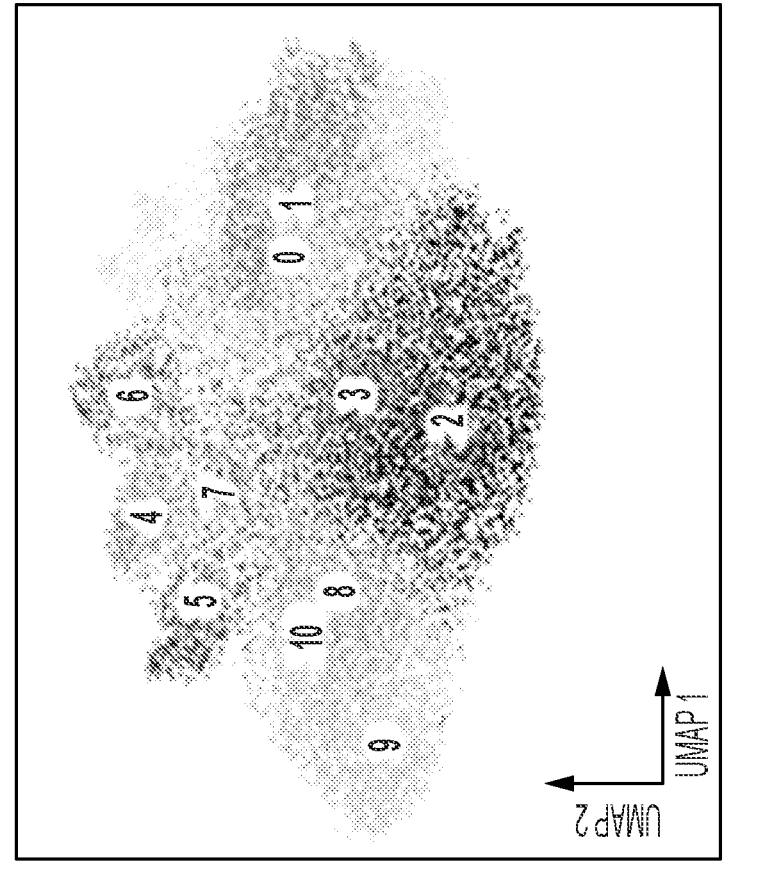
Figure 11G:
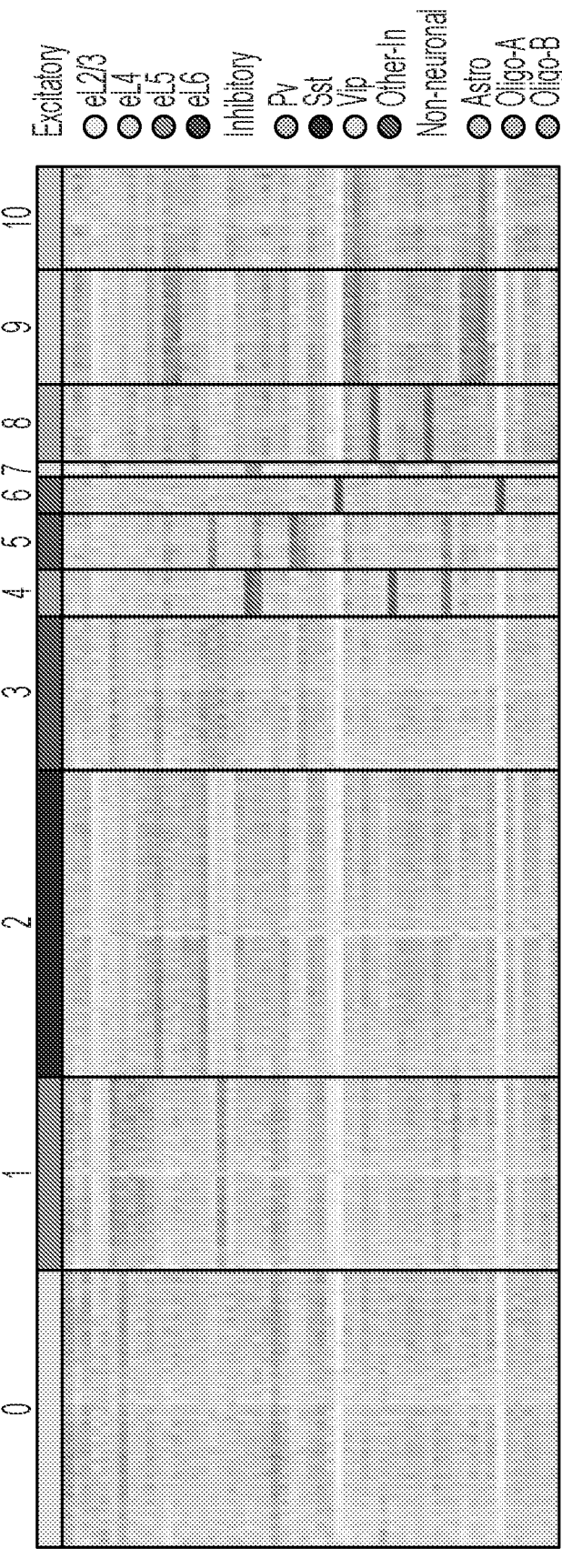

FIGS. 11A-11G provide analyses in the 3D datasets. FIG. 11A provides statistics of ClusterMap identified cells in the 3D STARmap cardiac organoid 8-gene dataset. Left: Histogram of detected reads (DNA amplicons) per cell. Middle: Histogram of genes per cell. Right: Correlation plot between genes per cell and reads per cell. FIGS. 11B-11C provide UMAP and heatmap visualization of three cell types in the STARmap cardiac organoid 8-gene dataset. The number of cells in each cell type is as follows: cardiomyocytes, 929; induced pluripotent stem cells (iPSCs), 489; mesenchymal stem cells (MSCs), 101. FIG. 11D provides a 3D four-channel composite raw fluorescent image of the first sequencing round that shows spatial arrangement of mRNA molecules in the STARmap mouse V1 28-gene dataset. FIG. 11E provides statistics of ClusterMap identified cells in FIG. 11D. Left: Histogram of detected reads (DNA amplicons) per cell. Middle: Histogram of genes per cell. Right: Correlation plot between genes per cell and reads per cell. FIGS. 11F-11G provide UMAP and heatmap visualization of three cell types of FIG. 11D.

FIGS. 12-19 are flow diagrams of various embodiments of methods related to identifying cells in an image.

FIG. 12 is a flow diagram of one embodiment of a method related to identifying cells in an image.

FIG. 13 is a flow diagram of one embodiment of a method related to determining cell centers.

Figure 14:
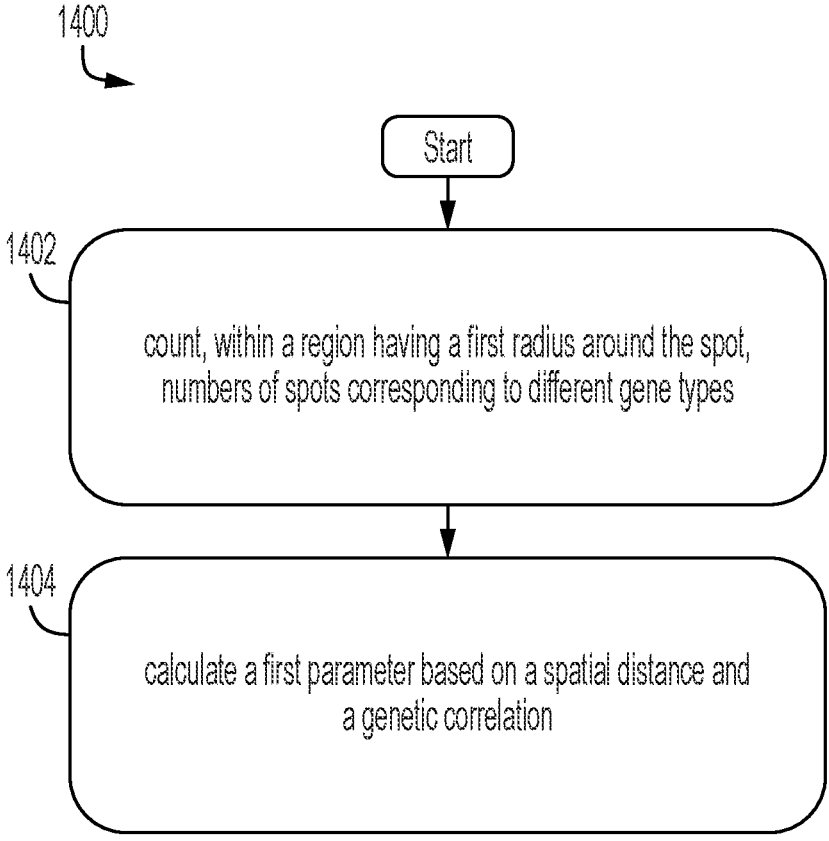

FIG. 14 is a flow diagram of one embodiment of a method related to calculating local density and minimum distance of spots.

Figure 15:
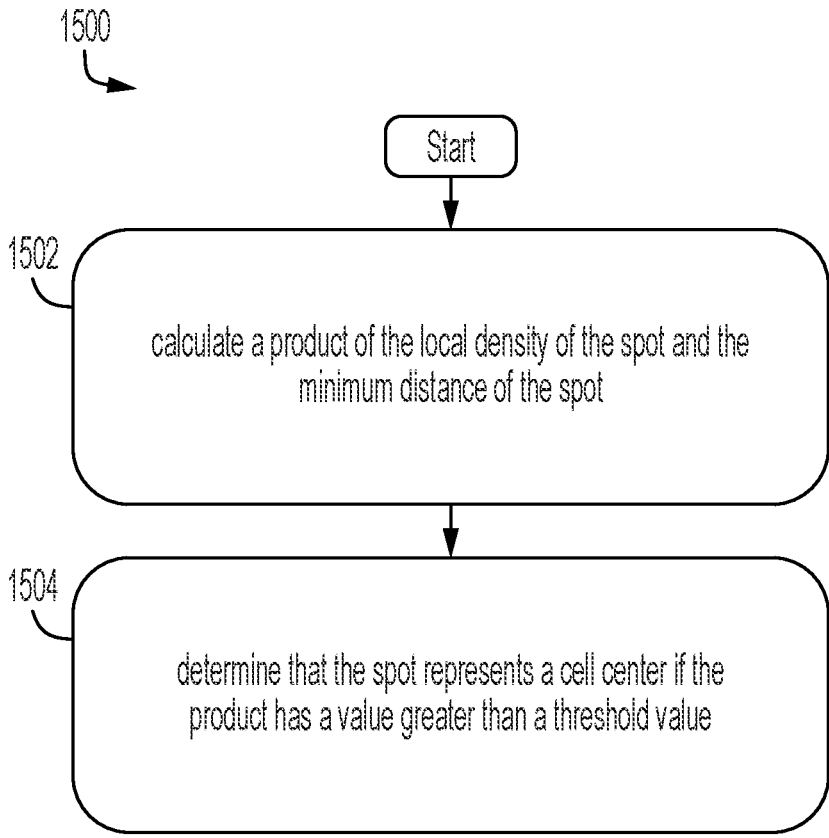

FIG. 15 is a flow diagram of one embodiment of a method related to determining cell centers.

FIG. 16 is a flow diagram of one embodiment of a method related to segmenting cells into subcellular components.

FIG. 17 is a flow diagram of one embodiment of a method related to clustering cells into tissue regions.

FIG. 18 is a flow diagram of one embodiment of a method related to identifying cells in an image.

Figure 19:
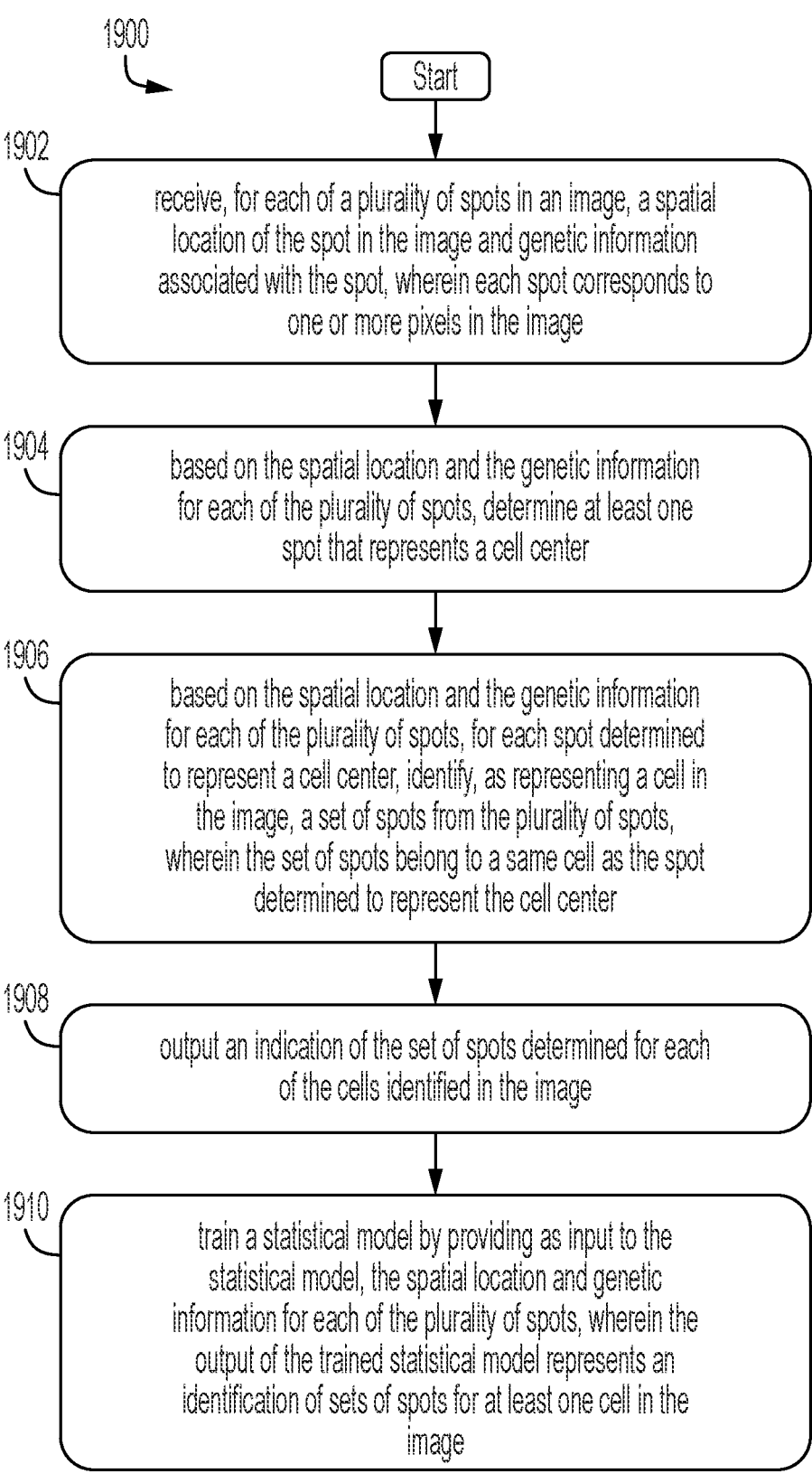

FIG. 19 is a flow diagram of one embodiment of a method related to training a statistical model to identify cells in an image.

Figure 20:
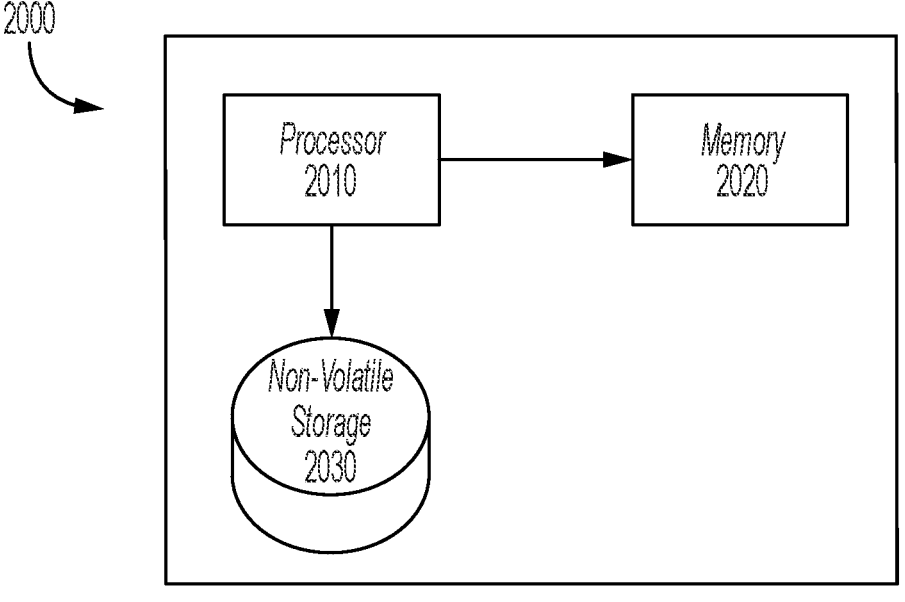

FIG. 20 is a block diagram of a computer system on which various functions or methods may be implemented.

Figure 21A:
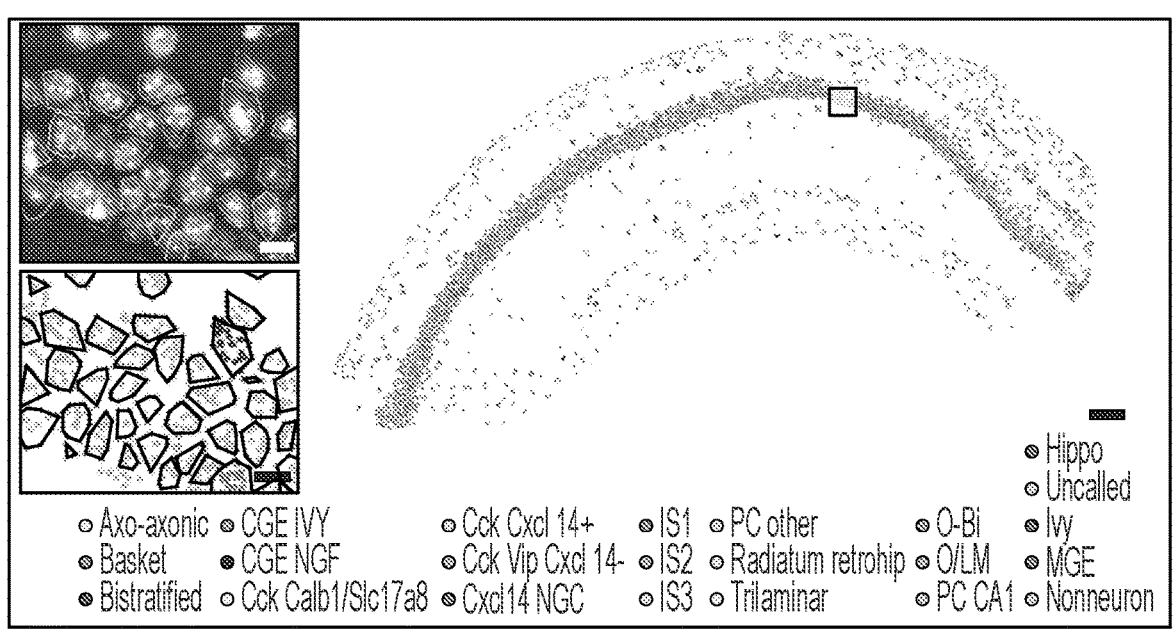
Figure 21B:
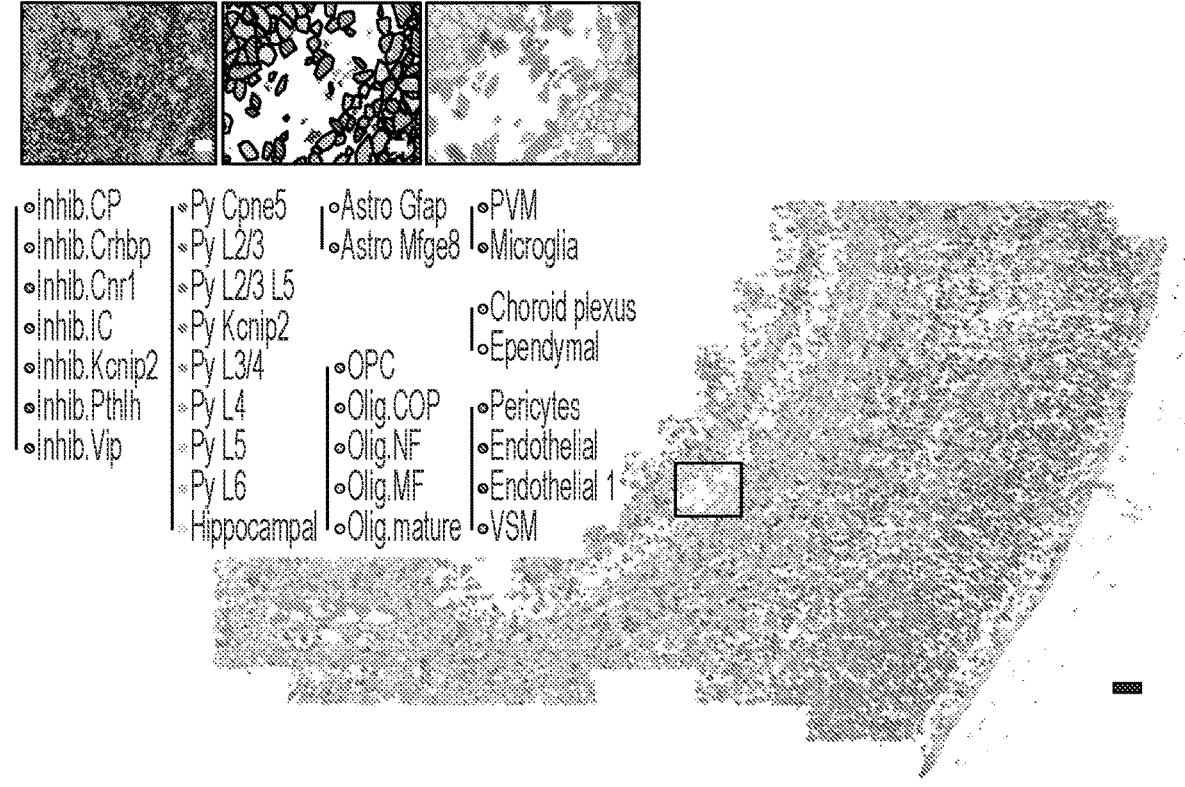

FIGS. 21A-21C show ClusterMap across different spatial transcriptomics methods. FIG. 21A shows a cell type map of the pciSeq (ISS data) section 4-3 left CA1 dataset[4]. Scale bar: 200 μm. Insets from top to bottom: convex hull of ClusterMap-identified cells overlapped with the DAPI image and zoomed-in cell type map in the black box highlighted region. Scale bar: 10 μm. FIG. 21B shows a cell type map of whole osmFISH mouse SSp datasets[5]. Scale bar: 100 μm. Insets from left to right: raw spatial transcriptomics data, and corresponding cell segmentation map and cell type map of the box highlighted region. Scale bar: 10 μm. FIG. 21C shows the 2D cell type map of whole MERFISH mouse POA datasets[3]. Scale bar: 200 μm. Insets from left to right: 2D raw spatial transcriptomics data, and corresponding cell segmentation map and cell type map of the highlighted region. Scale bar: 10 μm.

Figure 22:
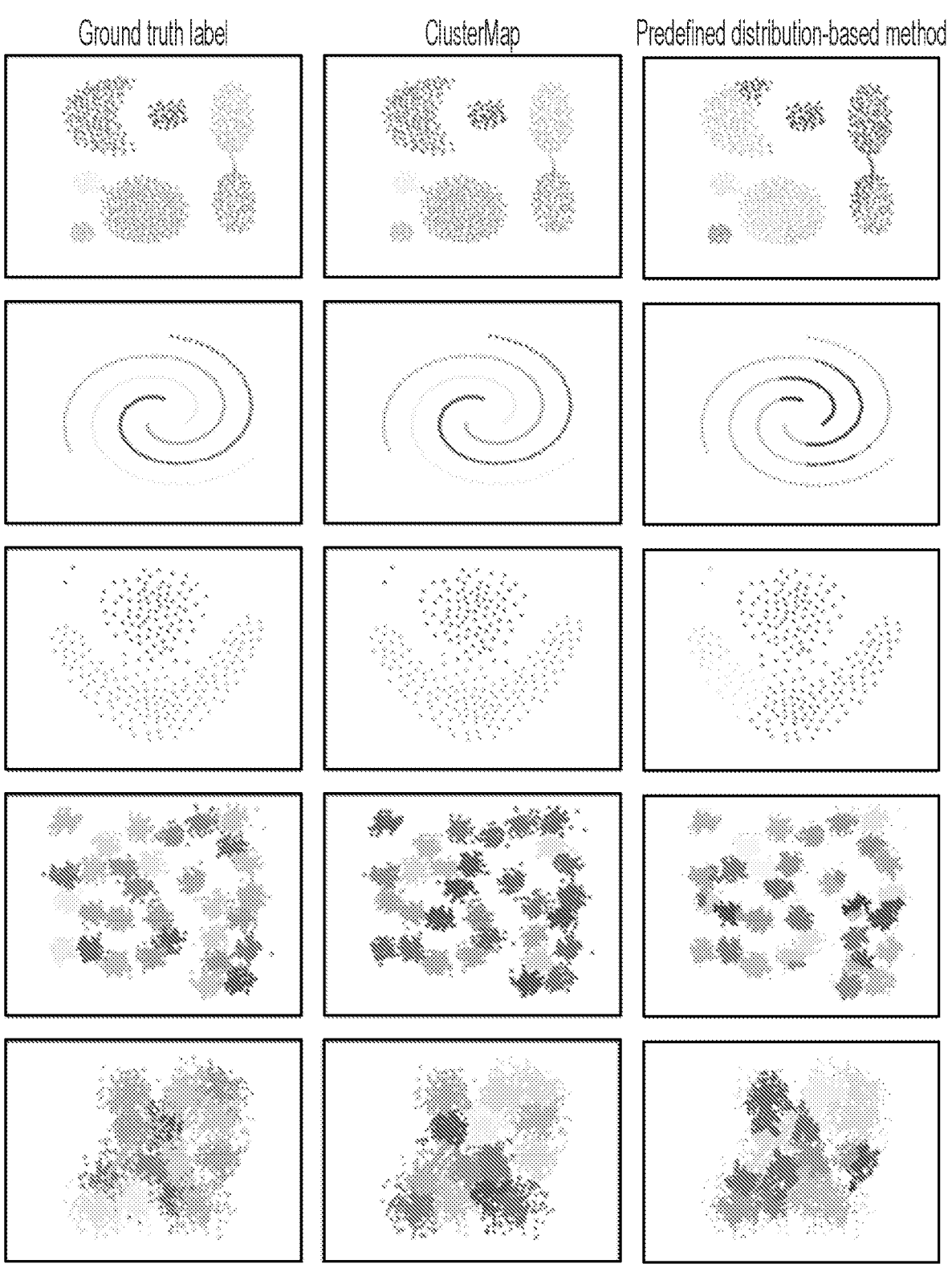

FIG. 22 shows a performance comparison of ClusterMap and a predefined distribution-based method in simulated data. Different shading represents different segmentation results. Note that the gene identity of each spot is randomly assigned from 1 to 5 as pseudo gene type. Left: ground truth; Middle: ClusterMap results; Right: results using predefined distribution-based method[43].

Figure 23:
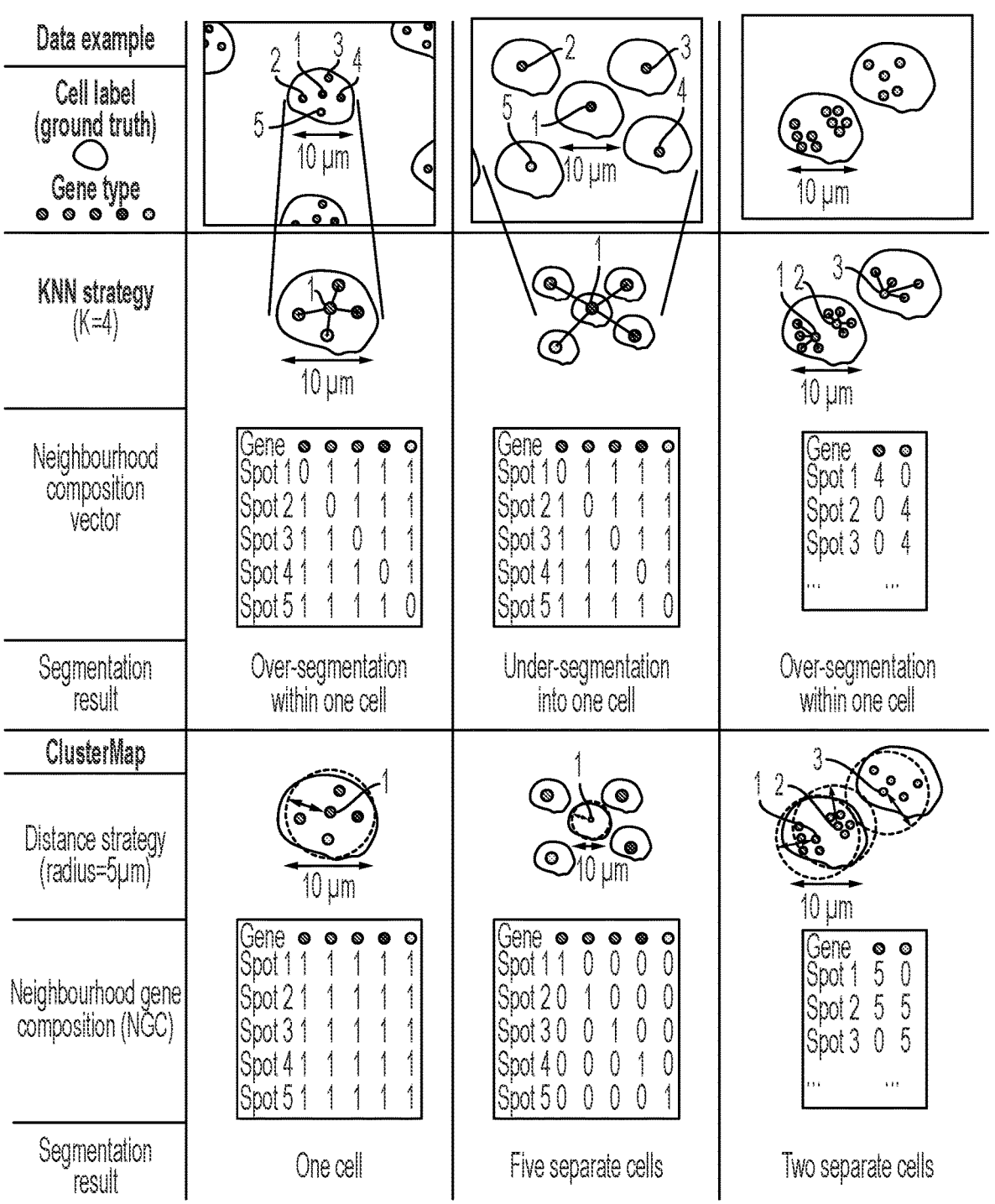

FIG. 23 shows a comparison of RNA sampling approaches between ClusterMap using absolute physical distance with other methods[43] using k-nearest neighbours (kNN) in simulated data. Three examples of RNAs with various local density are shown, demonstrating that ClusterMap preserves local physical density information, while kNN does not consider the physical density of RNAs.

Figures 24A, 24B:
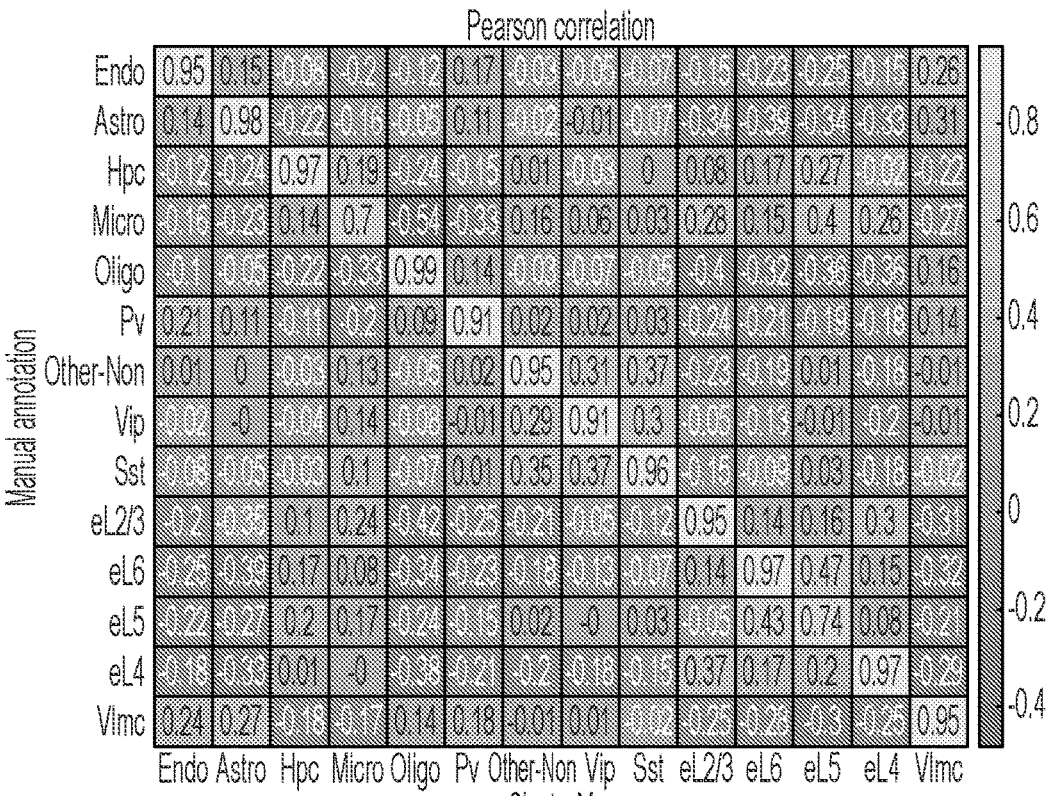

FIGS. 24A-24F show a cell-type correlation matrices comparison of ClusterMap-based and manually-segmented cell types. FIGS. 24A-24B show a comparison on STARmap mouse V1 1020-gene datasets. Heat maps of Pearson correlation (FIG. 24A) and $-\log$(p-value) (FIG. 24B) for null hypothesis testing. The p value is based on a t statistic that has $n-2$ degrees of freedom and 95% confidence interval.

Figure 24C:
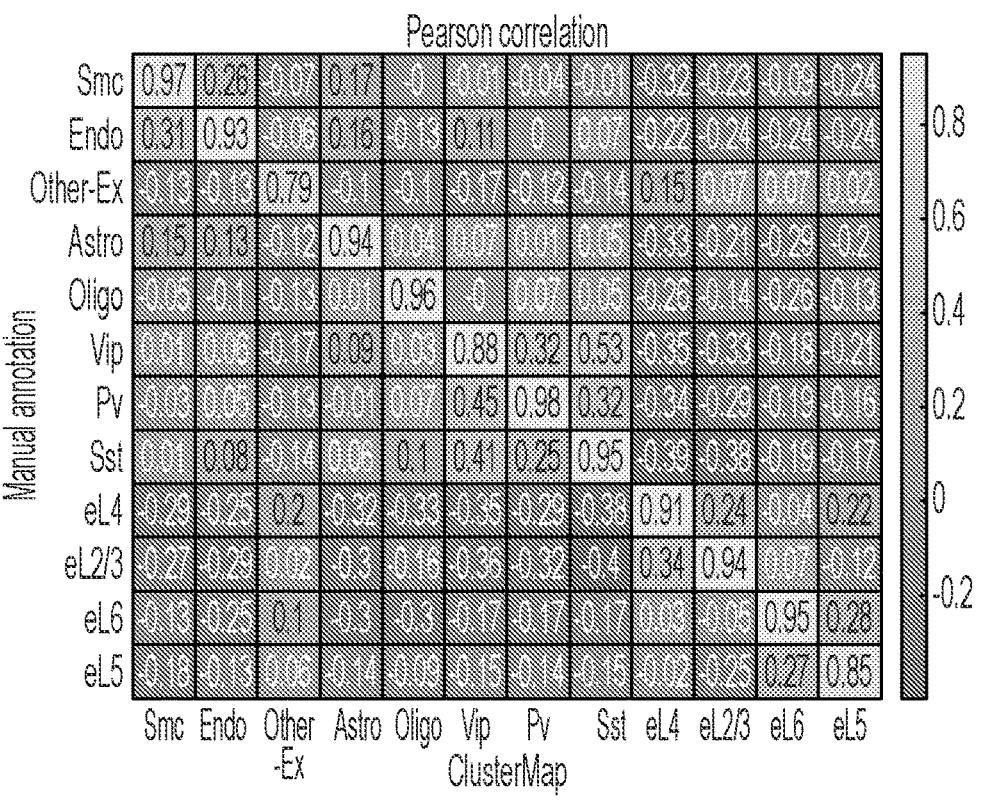
Figure 24D:
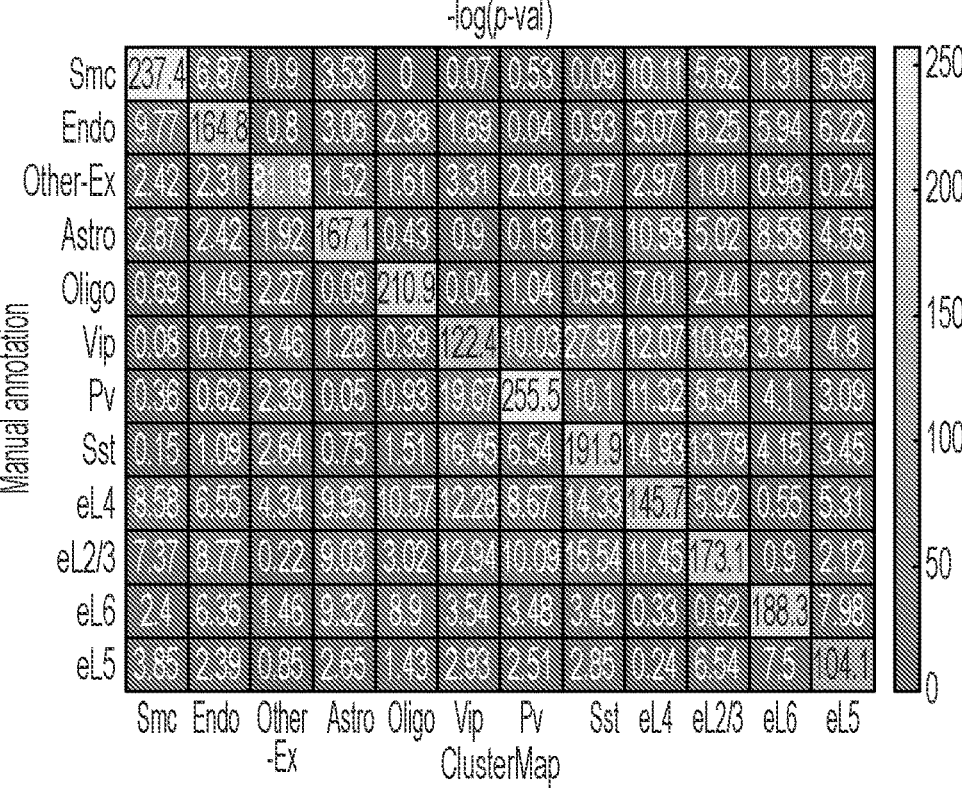
Figure 24E:
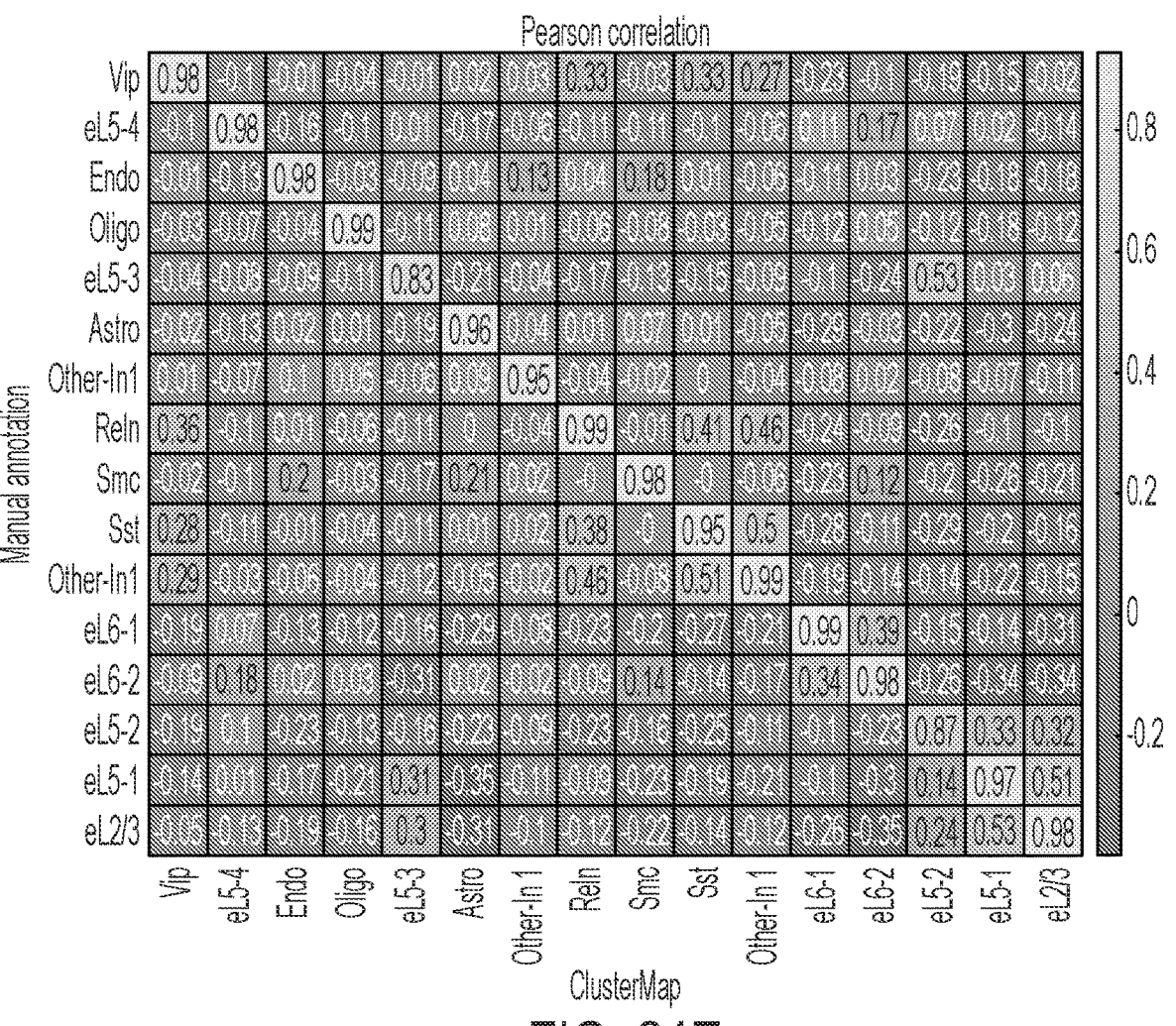
Figure 24F:
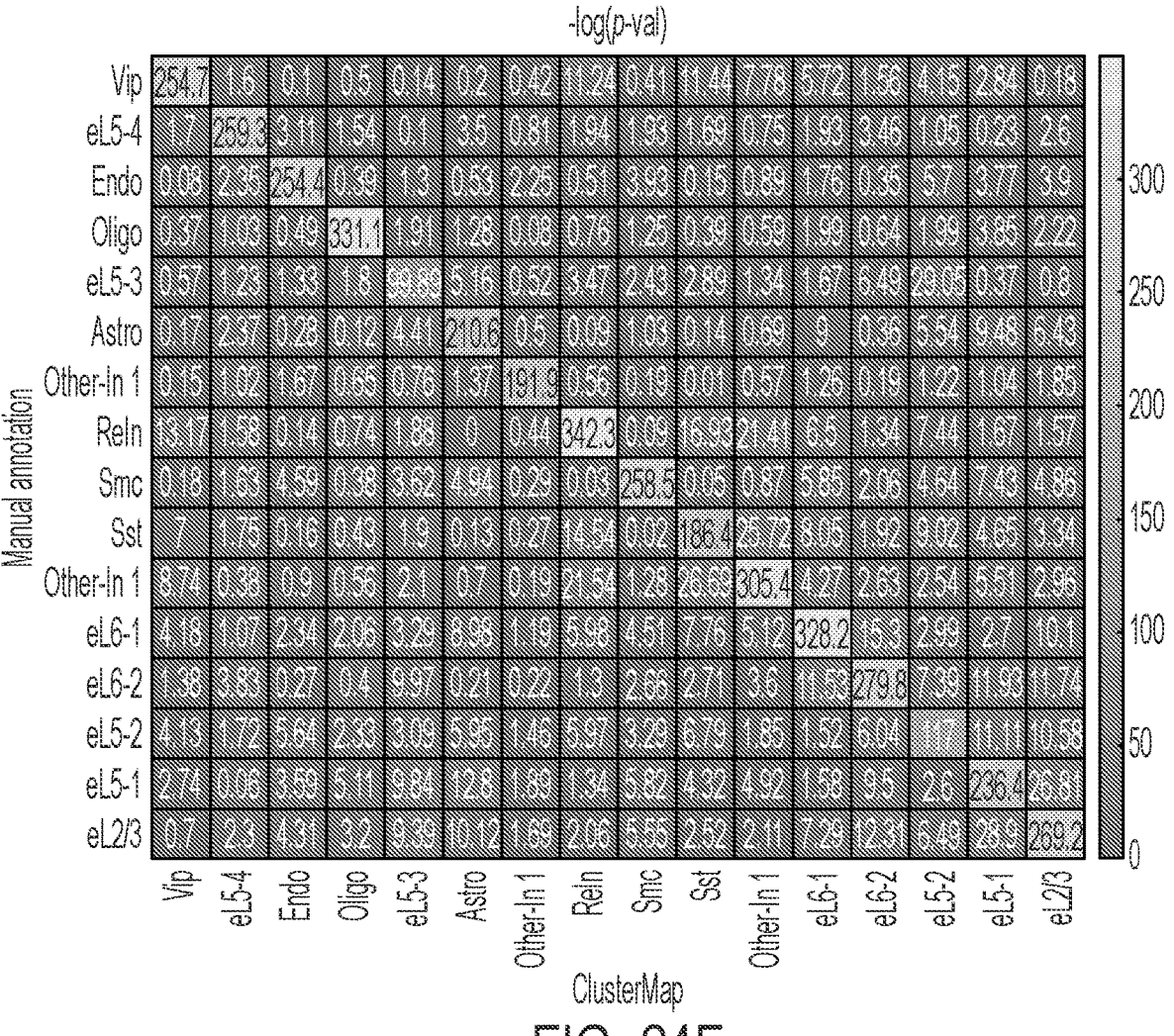

The single-cell gene expression profiles from ClusterMap with manual annotation are compared. FIGS. 24C-24D show a comparison on STARmap mouse V1 160-gene datasets. Heat maps of correlation (FIG. 24C) and −log(p-value) (FIG. 24D) comparing the single-cell gene expression profiles from ClusterMap with manual annotation are provided. FIGS. 24E-24F show a comparison on STARmap mouse mPFC 166-gene datasets. Heat maps of correlation (FIG. 24E) and −log(p-value) (FIG. 24F) comparing the single-cell gene expression profiles from ClusterMap with manual annotation are provided. Horizontal: ClusterMap; vertical: manual annotation.

Figure 25A:
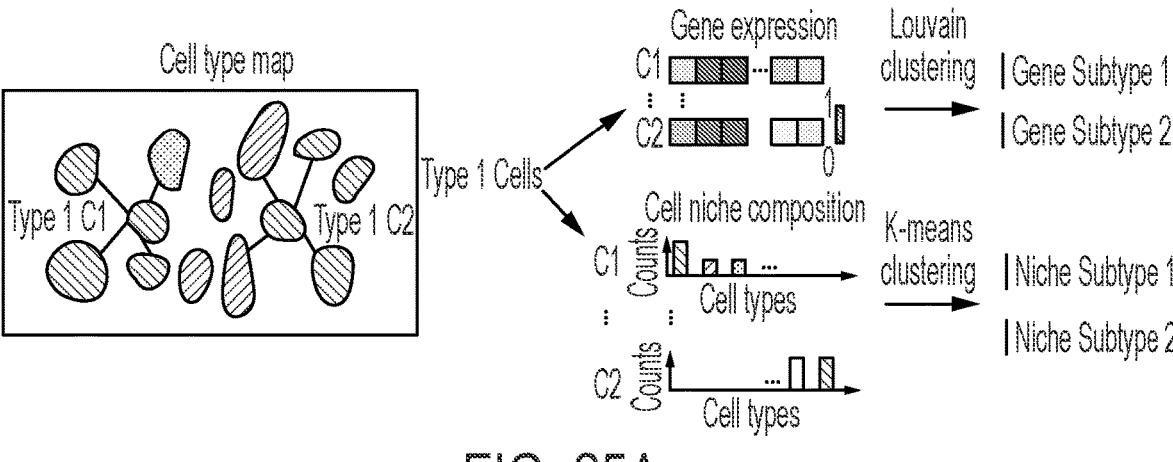
Figure 25B:
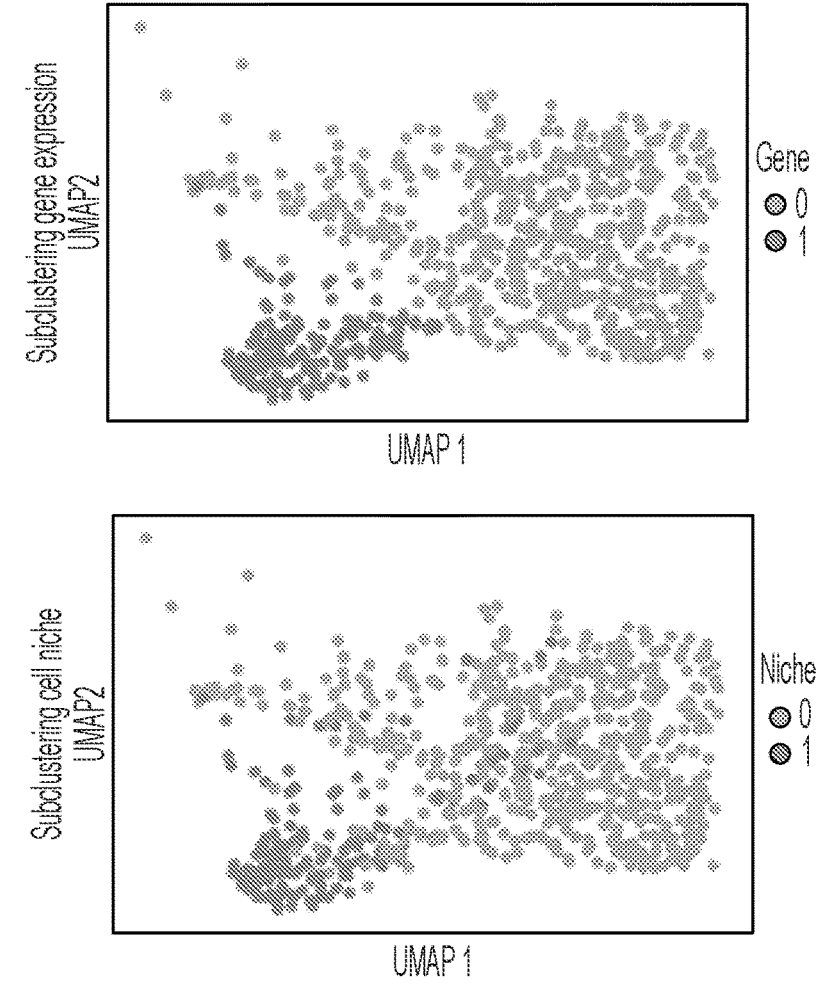
Figure 25C:
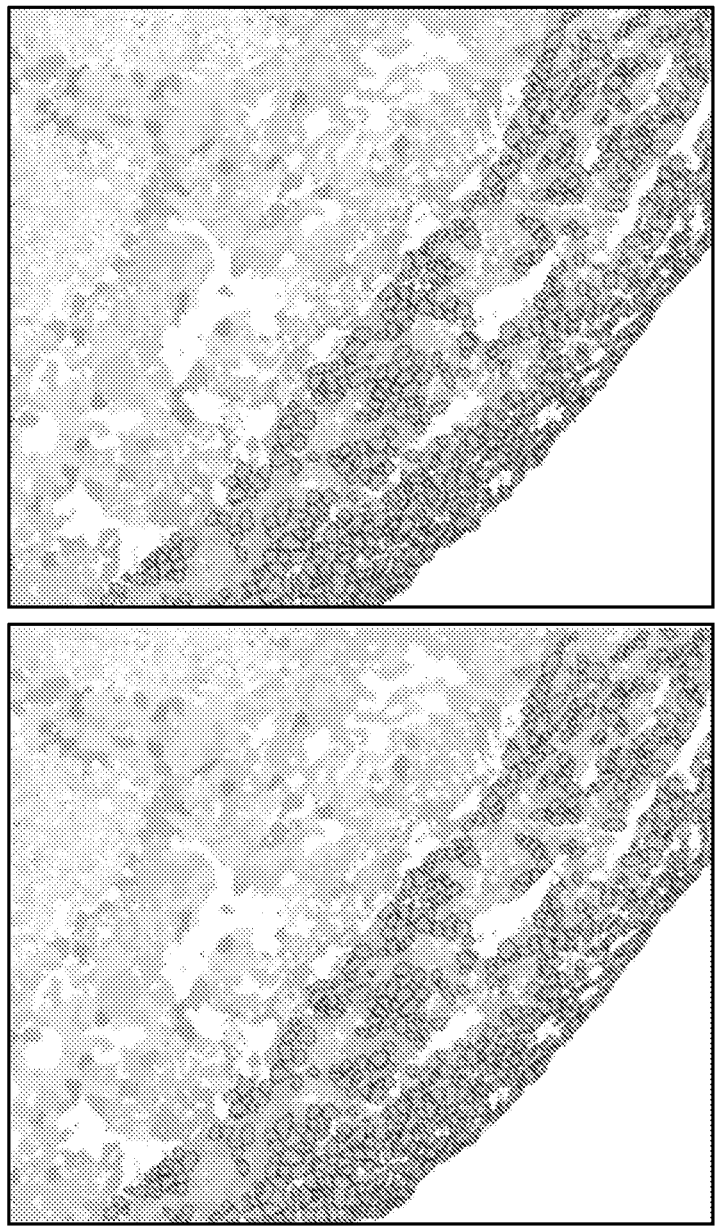
Figure 25D:
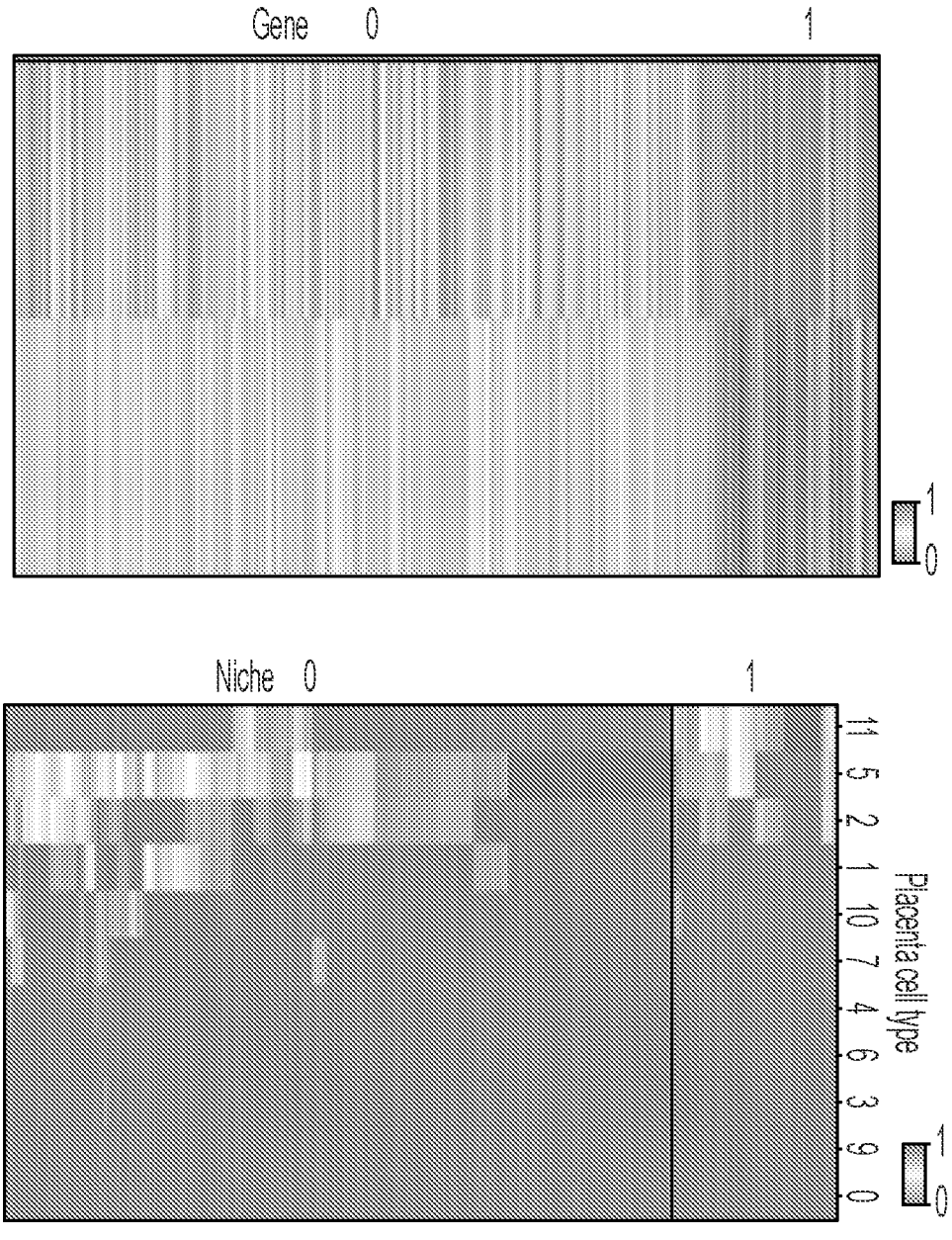

FIGS. 25A-25D show sub-clustering within one cell type using cell niche compositions in STARmap mouse placenta 903-gene dataset. FIG. 25A shows a schematic indicating how cells in one cell type are sub-clustered based on either gene expression (Louvain clustering[22]) or the cell niche compositions (K-means clustering[44]). FIG. 25B shows a UMAP of gene expression sub-clustering (top) or cell niche composition sub-clustering (bottom) in Maternal Decidua-1 (MD-1). FIG. 25C shows spatial subtype maps using gene expression (top) or cell niche composition (bottom) in MD-1. FIG. 25D shows a heatmap of sub-clustering using gene expression (top) or cell niche composition sub-clustering (bottom) in MD-1. Gene markers in the top heatmaps of gene expression sub-clustering are 0: GPNMB, 1: CXCL14. Row names in the bottom heatmaps of cell niche composition sub-clustering are cell types in numbers annotated in FIGS. 3A-3H.

Figure 26A:
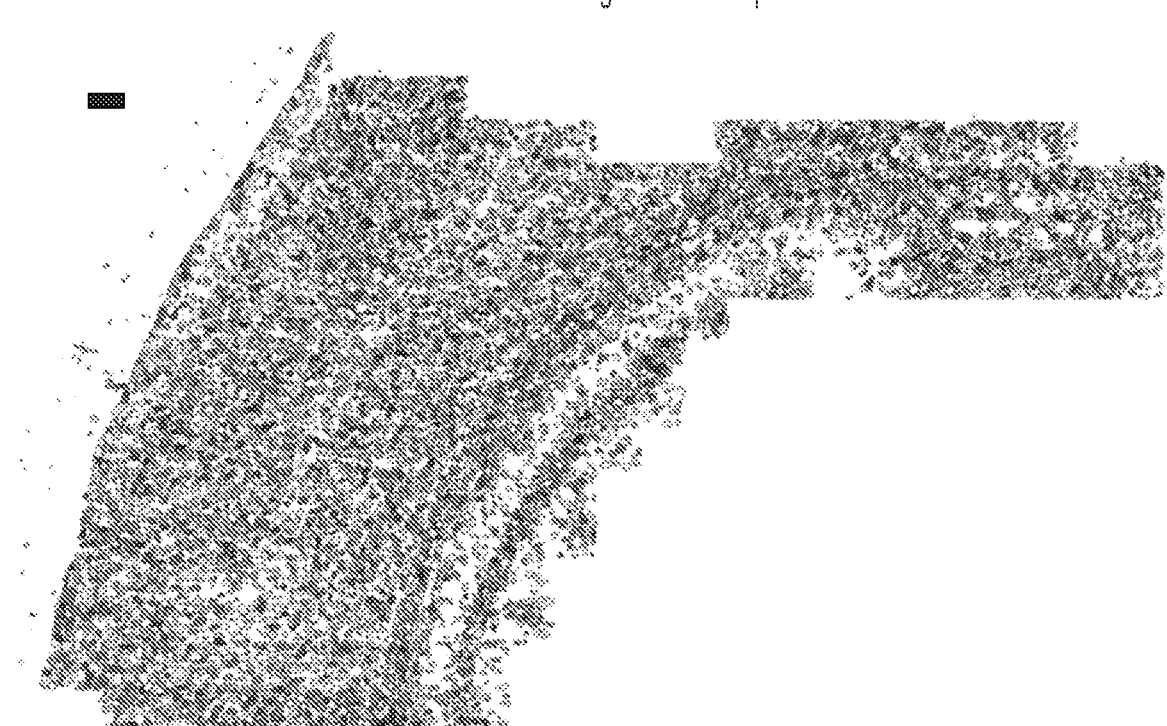
Figure 26B:
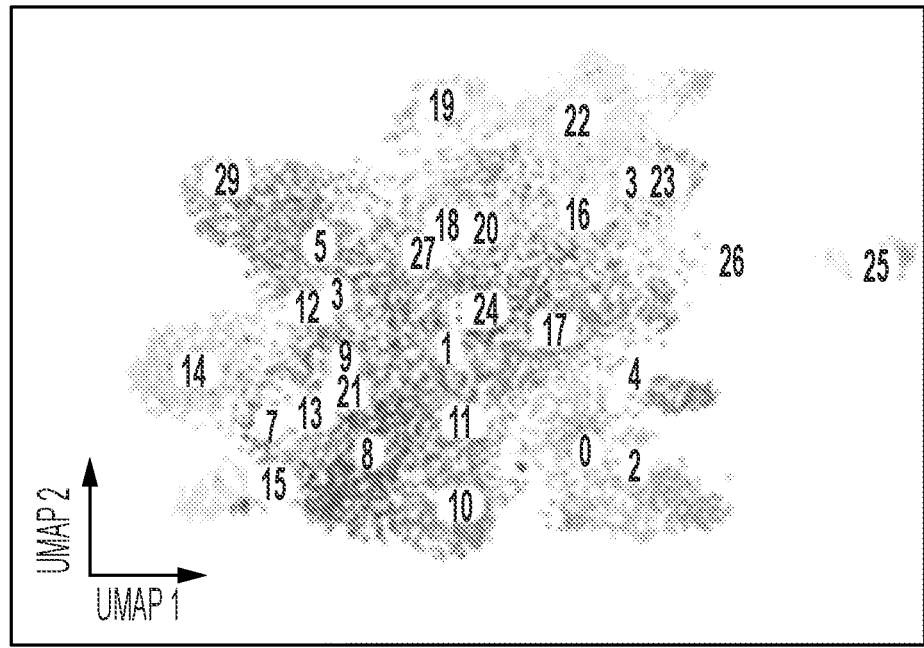
Figure 26C:
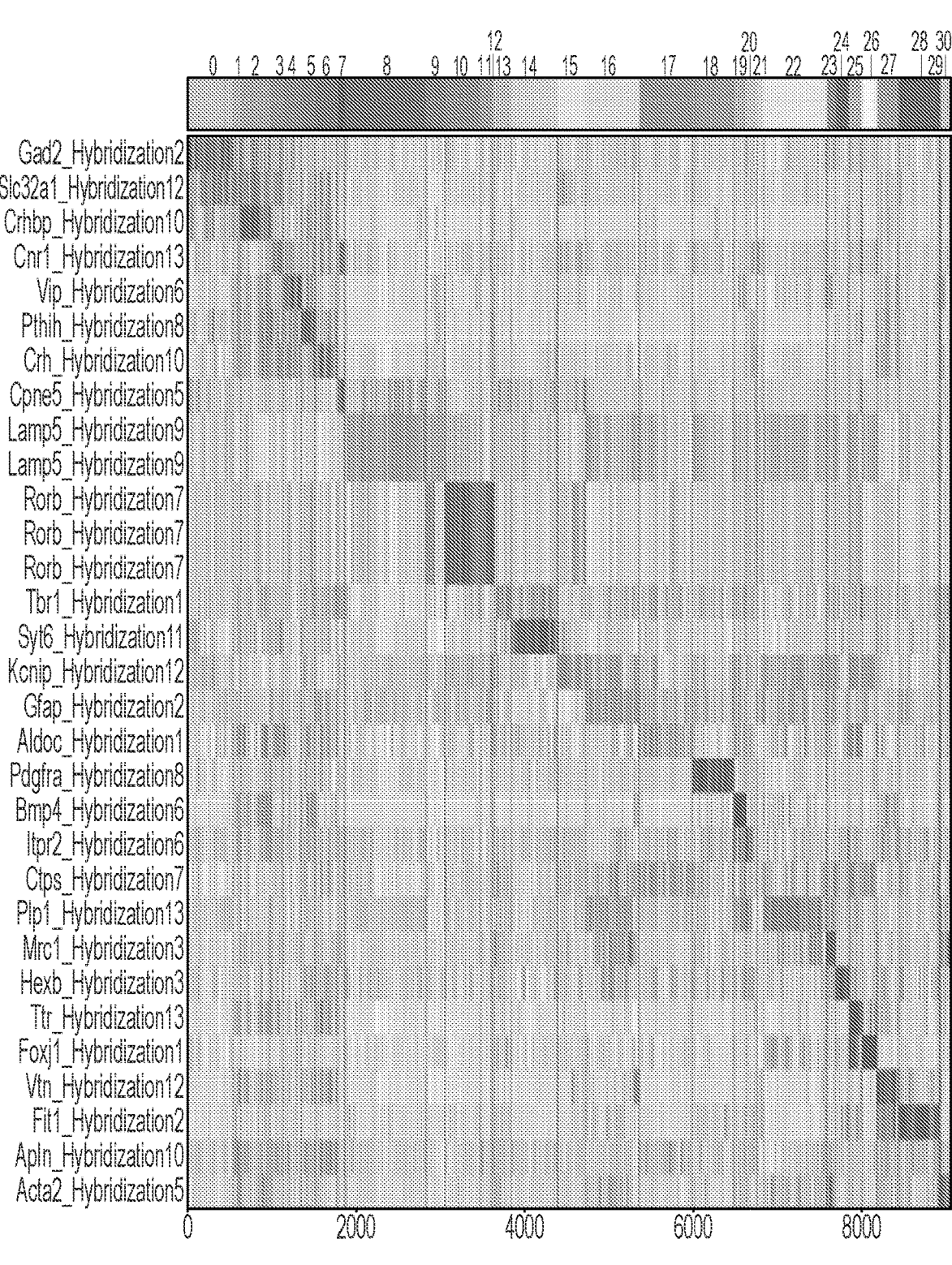
Figure 26E:
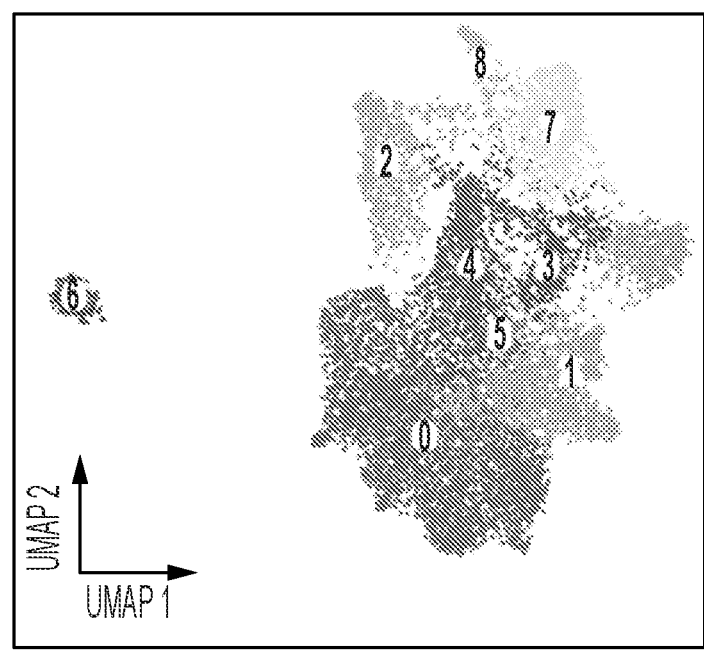
Figure 26F:
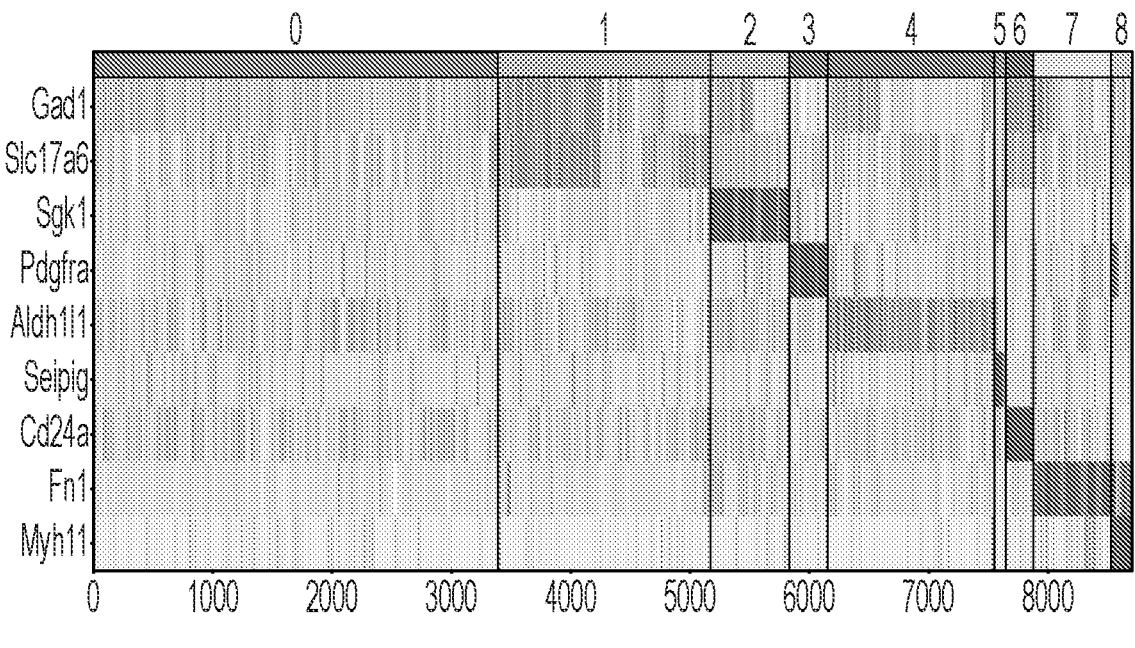

FIGS. 26A-26F show ClusterMap analyses across different experimental methods. FIG. 26A shows a cell segmentation map of whole osmFISH mouse somatosensory cortex (SSp) datasets. Scale bar: 100 μm. FIGS. 26B-26C show UMAP and heatmap visualization of 31 cell types in osmFISH datasets. FIG. 26D shows a 2D cell segmentation map of whole MERFISH mouse preoptic area (POA) datasets. Scale bar: 200 μm. FIGS. 26E-26F show UMAP and heatmap visualization of 9 cell types in MERFISH datasets. The number of cells increased from 6,471 to 8,538 for osmFISH, from 2,620 to 2,924 for pciSeq, and from 6,977 to 10,320 for MERFISH. The number of reads increased from 1,248,106 to 1,690,328 for osmFISH, from 31,246 to 31,750 for pciSeq, from 1,927,913 to 3,065,171 for MERFISH.

Figure 27A:
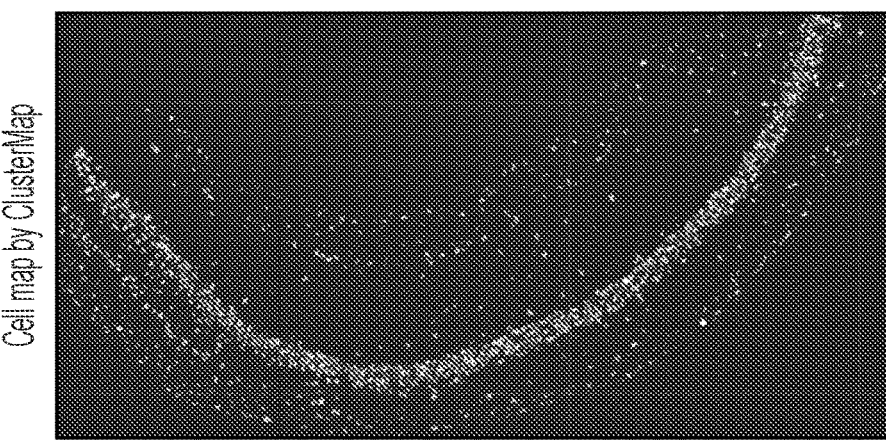
Figure 27B:
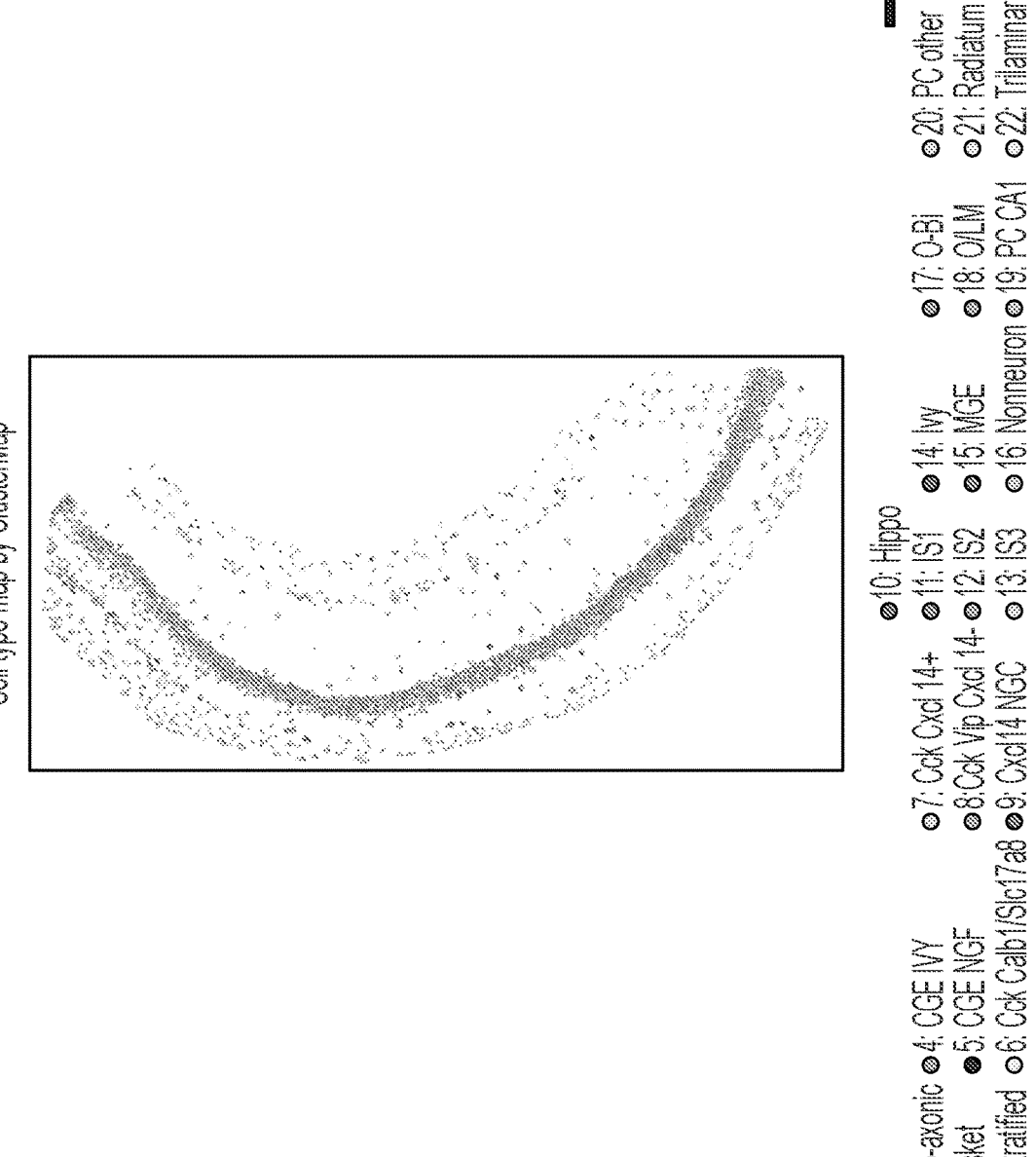
Figure 27C:
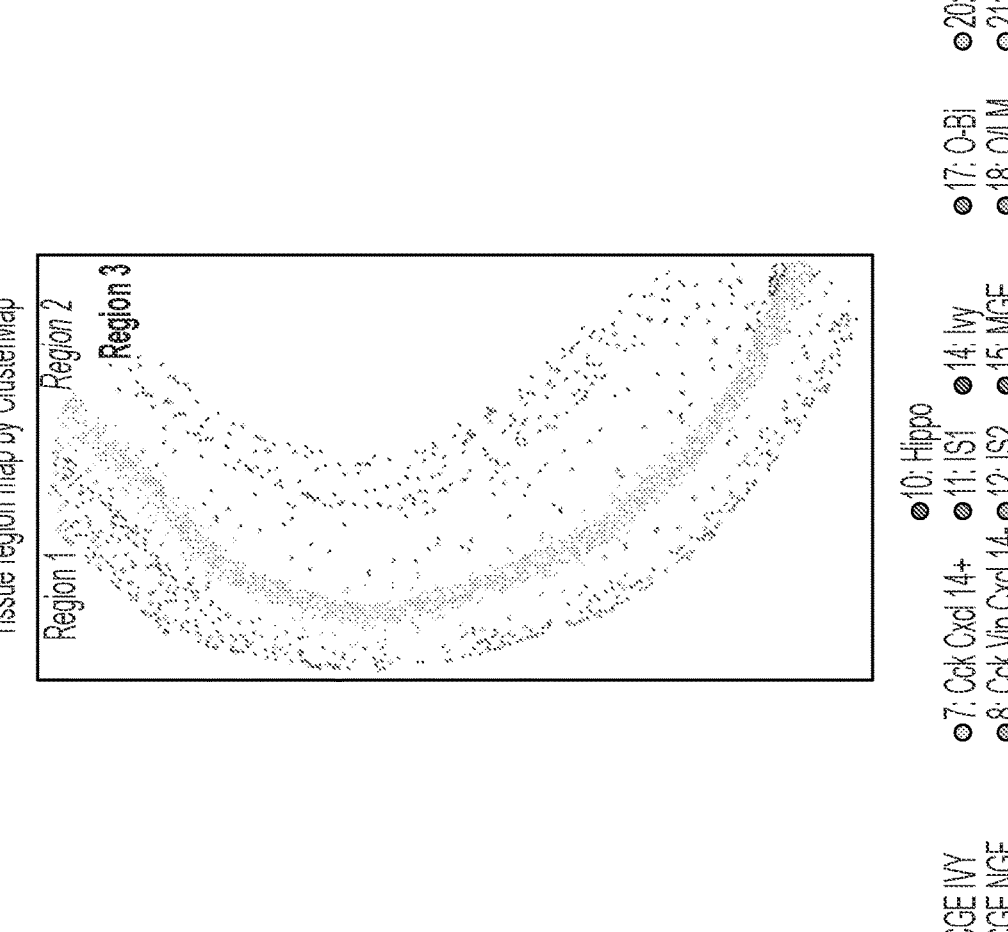
Figure 27D:
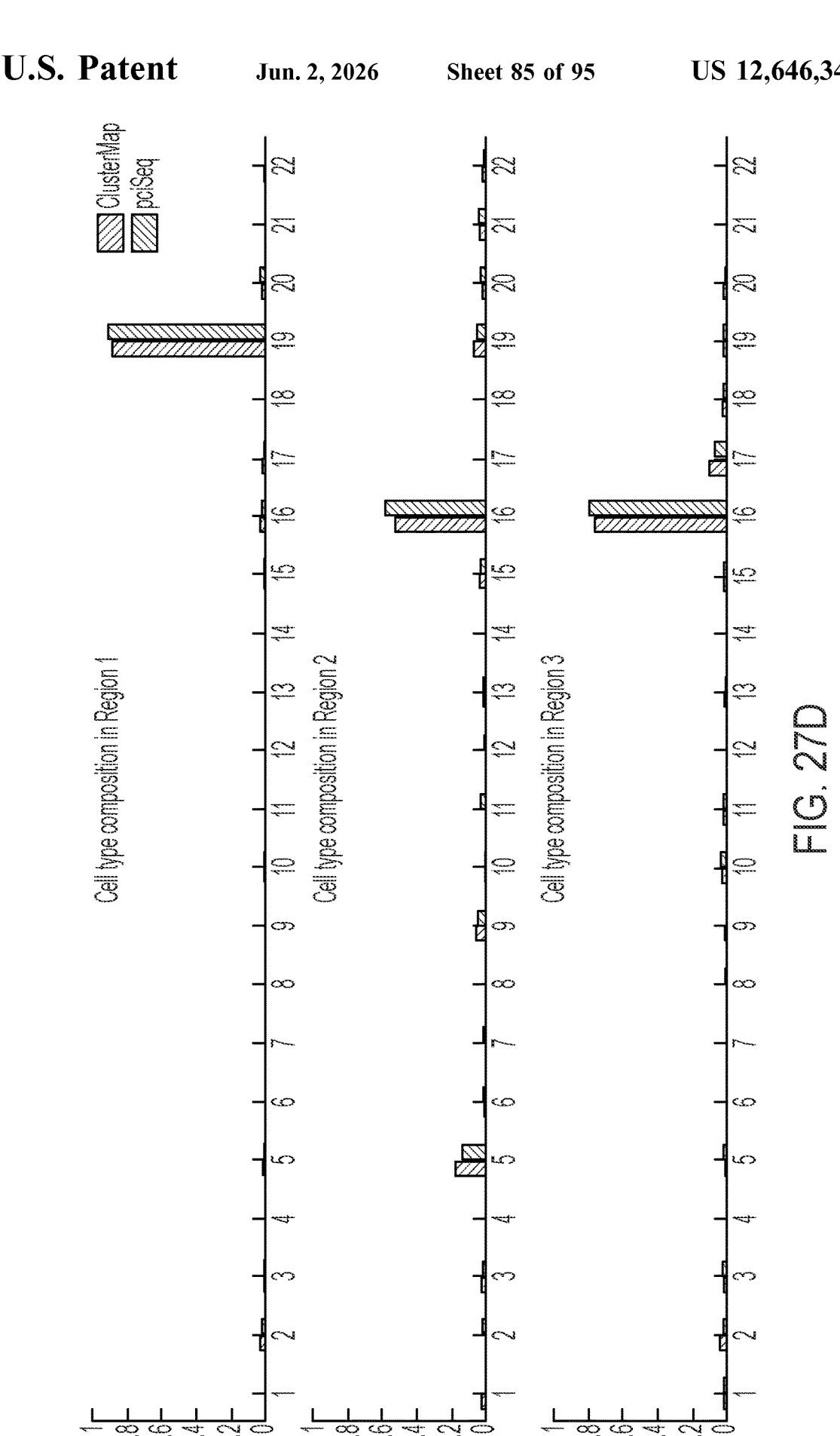

FIGS. 27A-27D show ClusterMap analyses of ISS data. FIG. 27A provides a cell segmentation map showing cell segmentation results by ClusterMap. Each cell mask is shaded according to the legend provided. FIG. 27B provides a cell type map showing the cell type calling results. Corresponding cell type categories are shaded according to the legend provided. FIG. 27C provides a tissue region map showing the laminar structure of the hippocampus. Scale bar: 200 μm. FIG. 27D shows a side-by-side comparison of cell type compositions in each tissue region from ClusterMap and pciSeq of the ISS data.

Figure 28A:
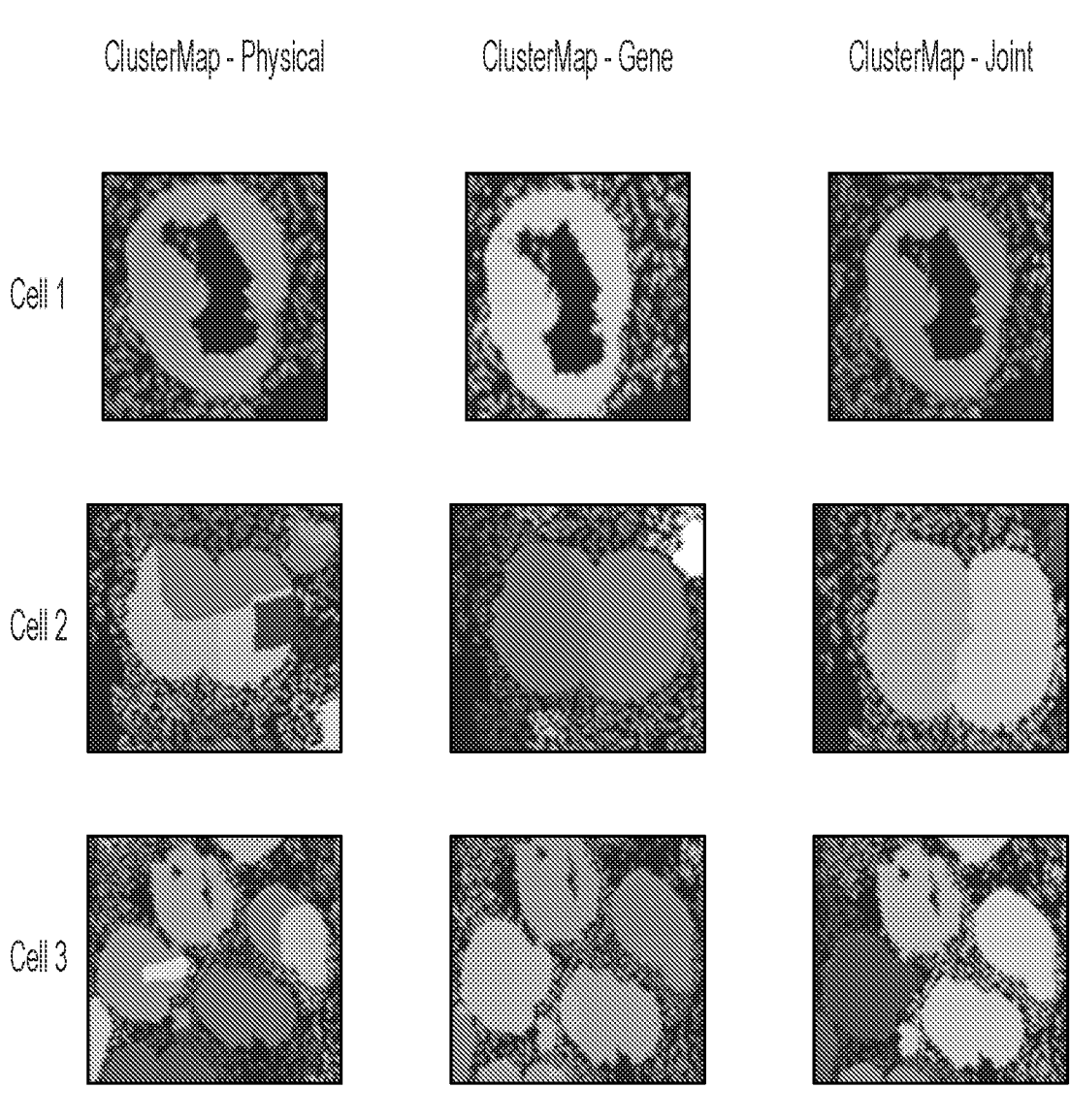
Figure 28B:
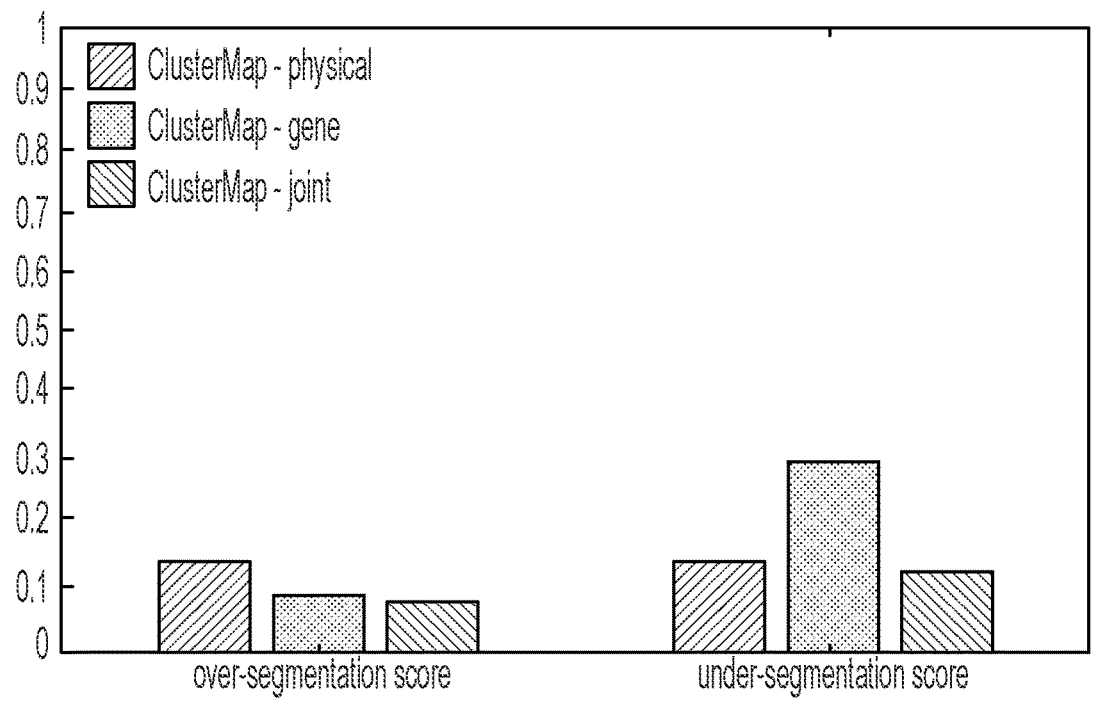
Figure 28C:
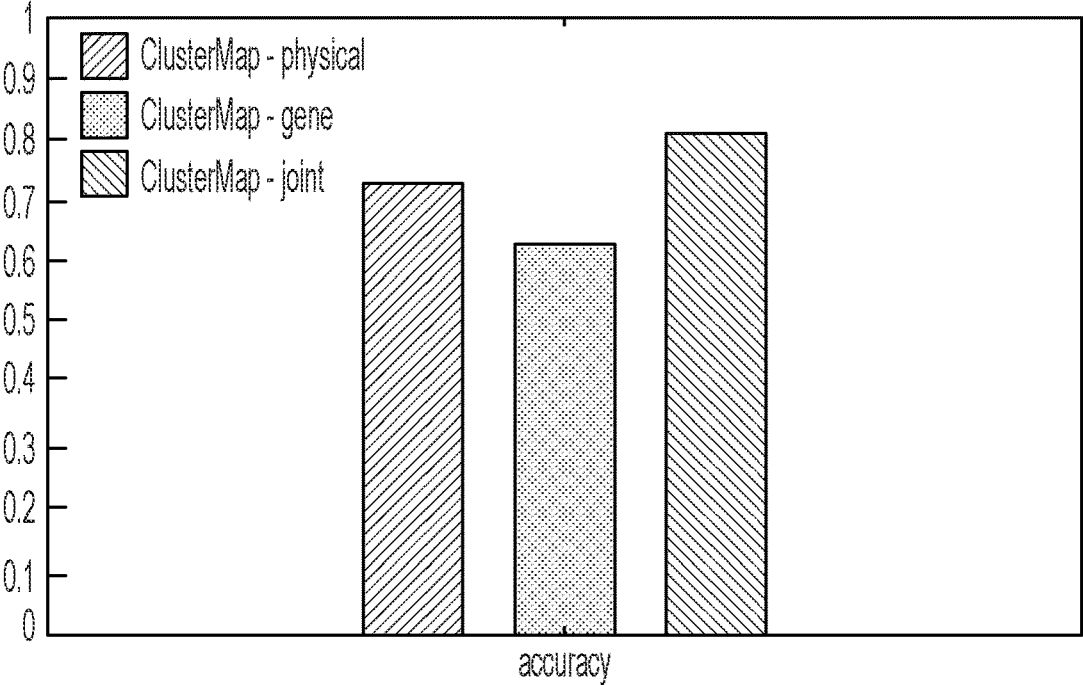
Figure 28D:
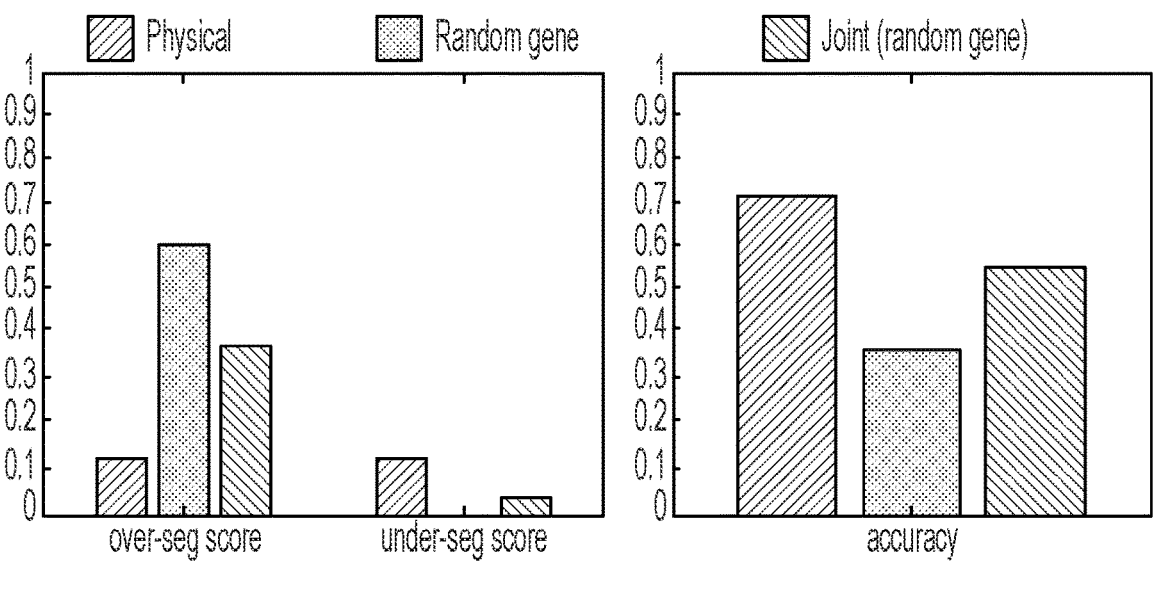
Figure 28E:
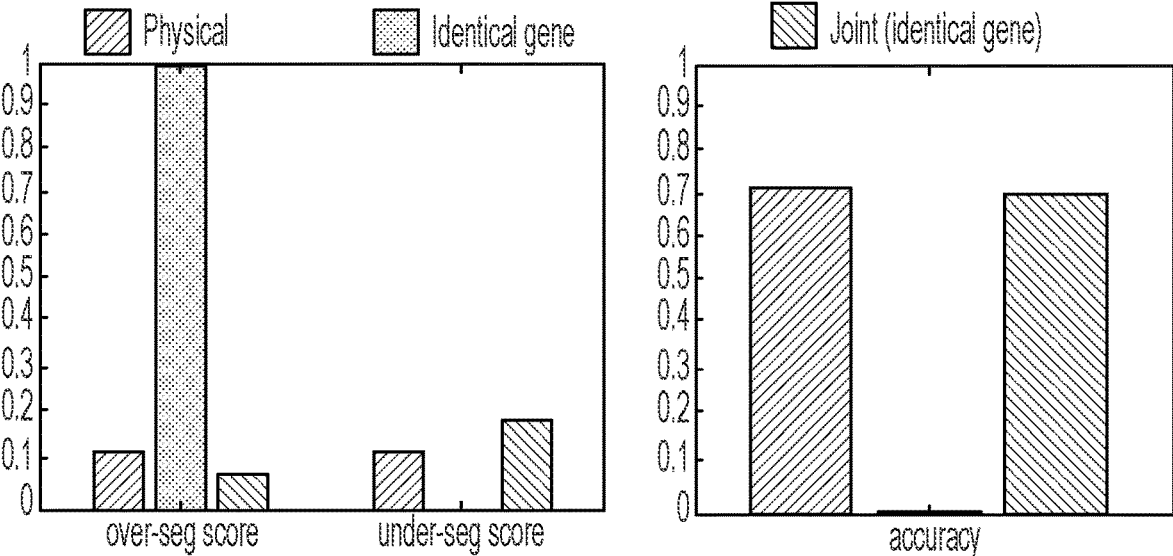
Figure 28F:
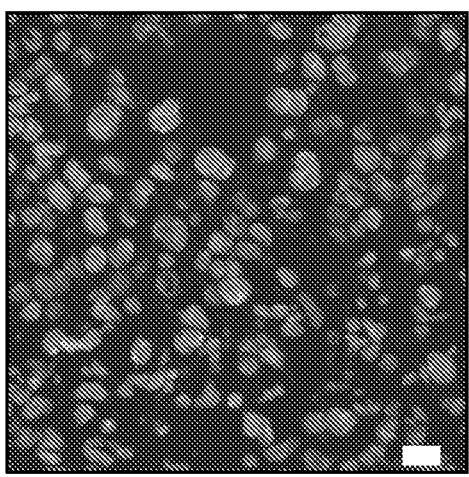
Figure 28G:
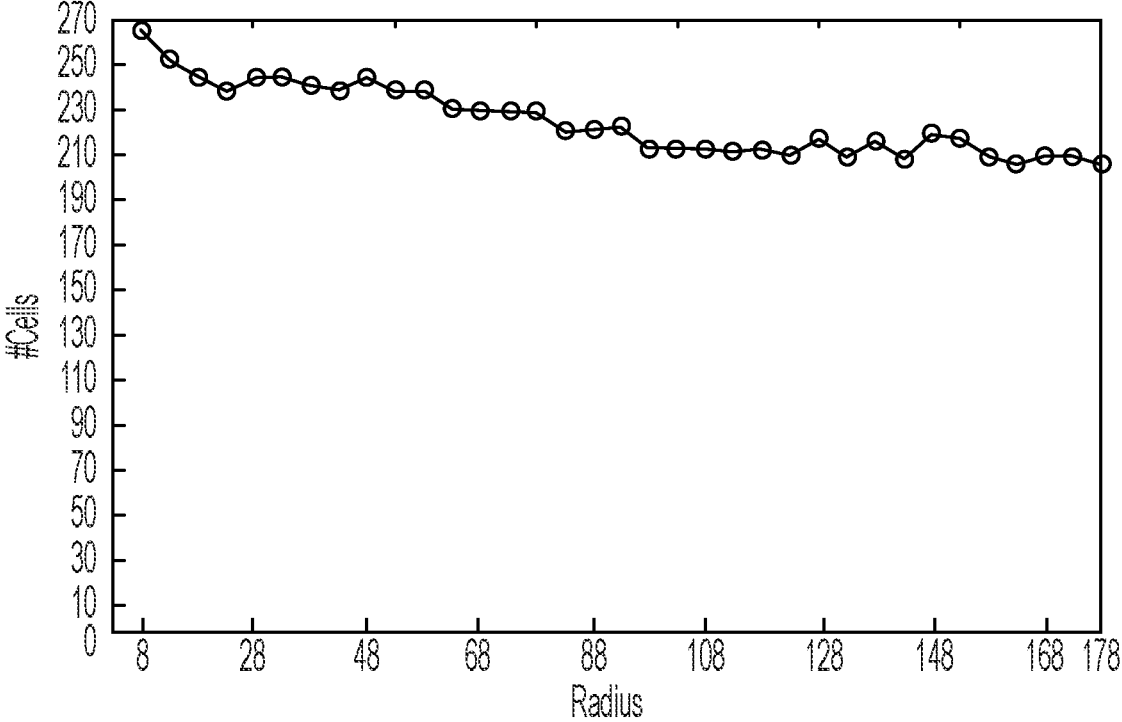
Figure 28H:
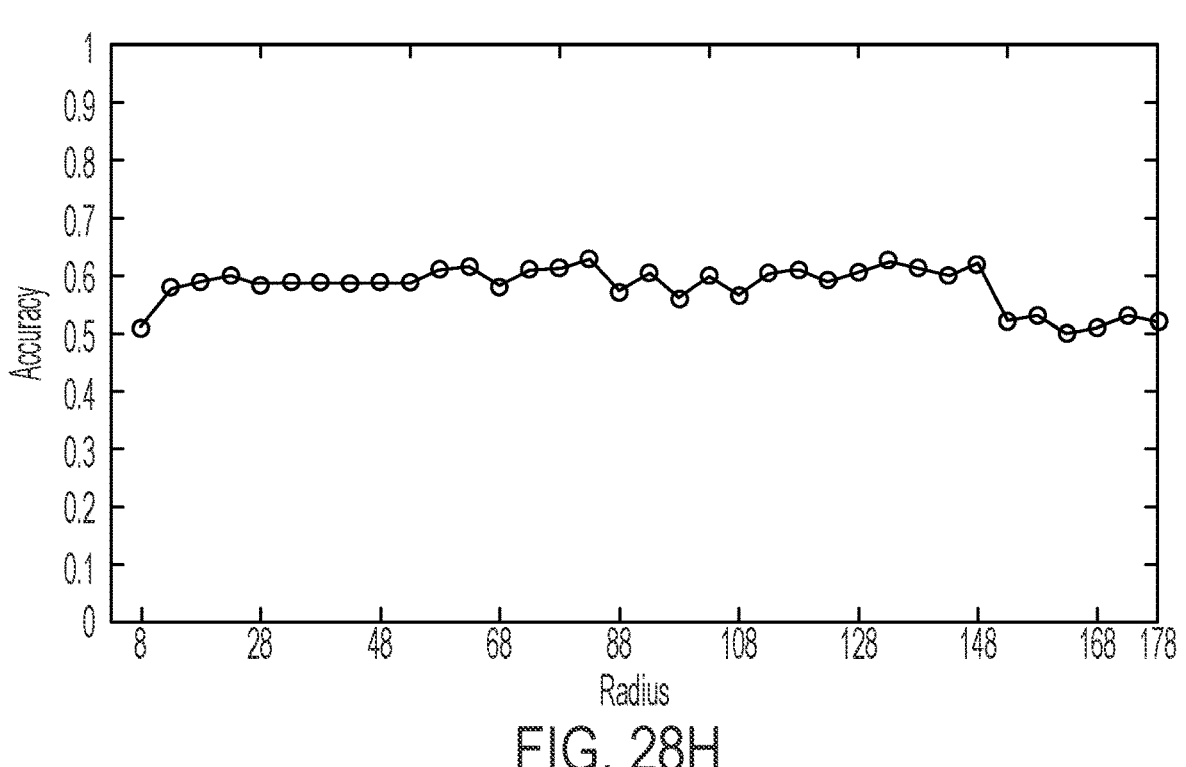
Figure 28I:
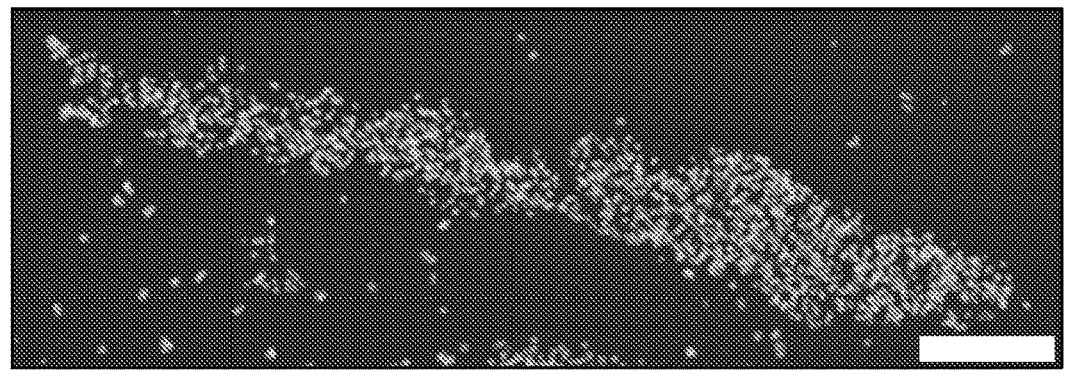
Figure 28J:
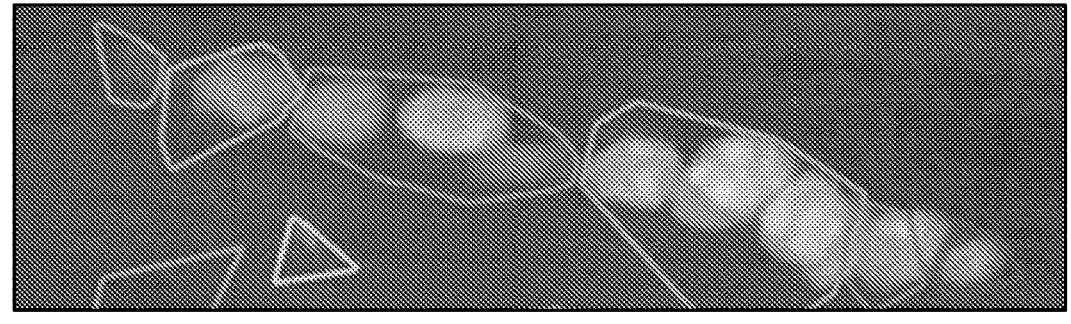
Figure 28K:
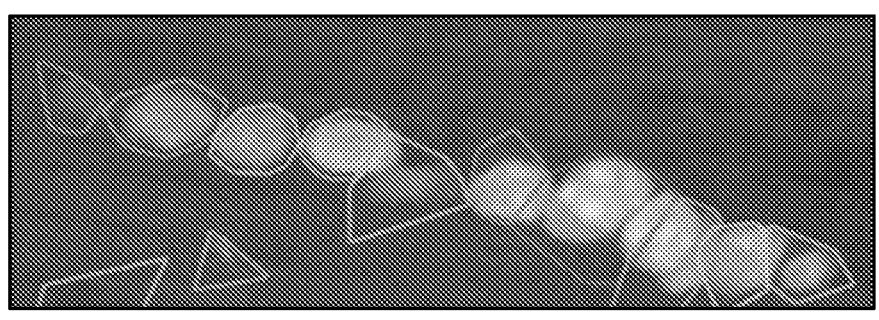

FIGS. 28A-28P show a performance comparison of ClusterMap using physical density, gene distance, and joint information. FIG. 28A shows examples of cell segmentation using only physical density information (left), gene (NGC) distance information (middle), and joint information (right). FIGS. 28B-28C show bar plots demonstrating the percentage of over-/under-segmented cells in ground truth cells (FIG. 28B) and overall accuracy (FIG. 28C) in using physical distances information, gene (NGC) distance information, and joint information. FIGS. 28D-28E show bar plots demonstrating the percentage of over-/under-segmented cells in ground truth cells (left) and overall accuracy (right) in using physical distances information, random (FIG. 28D) or identical (FIG. 28E) gene (NGC) distance information, and joint information. FIG. 28F shows a raw DAPI image of the targeted mouse placenta tissue. Scale bar: 20 μm. FIGS. 28G-28H provide line plots showing the number of cells and overall accuracy to the radius. FIGS. 28I-28M show two examples of the hippocampus regions in STARmap mouse V1 1020-gene datasets showing raw spatial transcriptomics data (FIG. 28I, FIG. 28L), ClusterMap results without DAPI (FIG. 28J, FIG. 28M), and ClusterMap results with DAPI (FIG. 28K, FIG. 28N). Scale bar: 20 μm. FIGS. 28O-28P provide bar plots showing the percentage of over-/under-segmented cells (FIG. 28O) and overall accuracy (FIG. 28P) from ClusterMap without and with DAPI.

Figure 29A:
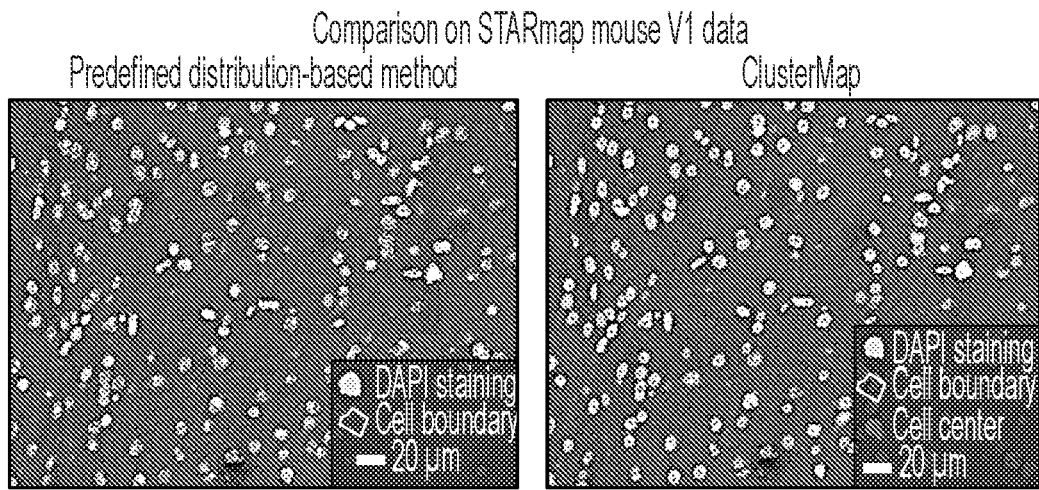
Figure 29B:
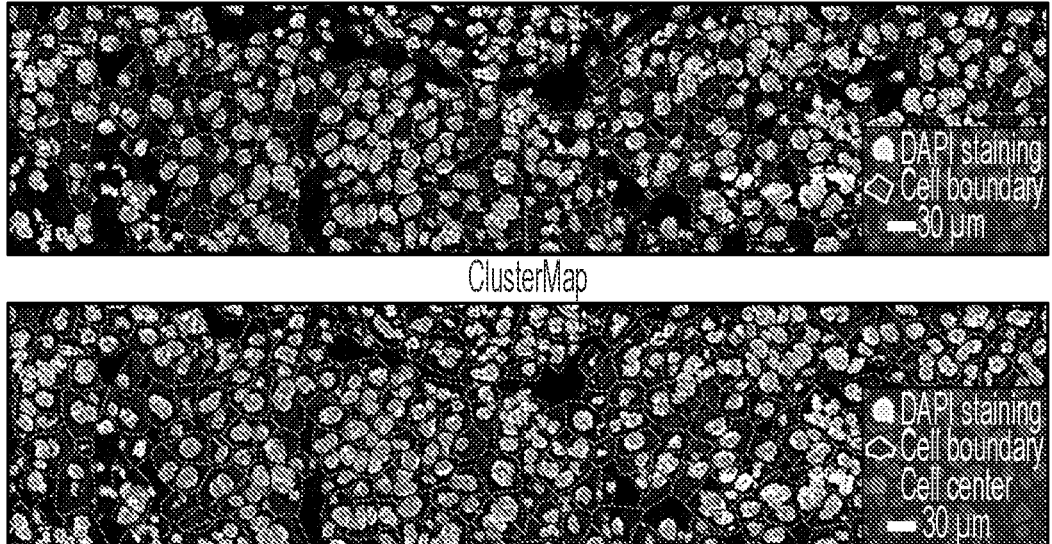
Figure 29C:
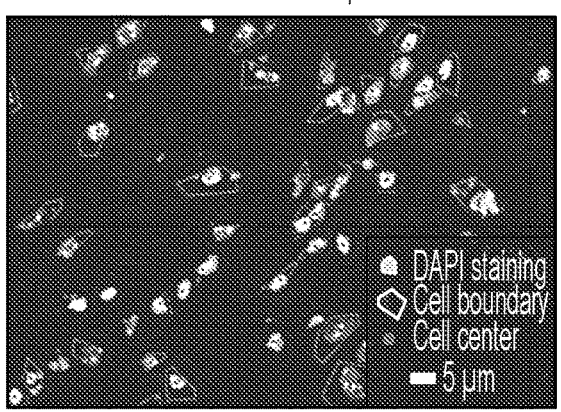

FIGS. 29A-29D show a performance comparison of ClusterMap and other methods across different types of in situ transcriptomic data. FIG. 29A provides an example of a region in the STARmap[6] mouse V1 1020-gene dataset with DAPI signals showing ground truth cell nuclei. Outlining is used to show cell boundaries identified by a predefined distribution-based method[43] (left) and ClusterMap (right), respectively. FIGS. 29B-29C provide examples as in FIG. 29A but using the STARmap[6] mouse placenta 903-gene dataset and published pciSeq[4] dataset. FIG. 29D shows bar plots demonstrating the remaining RNA numbers, cell numbers, and segmentation accuracy for each dataset. In each bar plot, results from a predefined distribution-based method[43], ClusterMap, and published reports are shown from left to right, respectively.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics,* 5th Ed., R. Rieger et al. (eds.), Springer Verlag (1991); and Hale & Marham, *The Harper Collins Dictionary of Biology* (1991). As used herein, the following terms have the meanings ascribed to them unless specified otherwise.

As used herein, the term "gene" refers to a nucleic acid fragment that expresses a protein, including regulatory sequences preceding (5' non-coding sequences) and following (3' non-coding sequences) the coding sequence. "Native gene" refers to a gene as found in nature with its own regulatory sequences.

As used herein, "gene expression" refers to the process by which information from a gene is used in the synthesis of a gene product. Gene products include proteins and RNA transcripts (e.g., messenger RNA, transfer RNA, or small nuclear RNA). Gene expression includes transcription and translation. Transcription is the process by which a segment of DNA is transcribed into RNA by an RNA polymerase. Translation is the process by which an RNA is translated into a peptide or protein by a ribosome. The term "genetic information" as used herein refers to one or more genes and/or one or more RNA transcripts (e.g., any number of genes and/or RNA transcripts).

The terms "polynucleotide", "nucleotide sequence", "nucleic acid", "nucleic acid molecule", "nucleic acid sequence", and "oligonucleotide" refer to a series of nucleotide bases (also called "nucleotides") in DNA and RNA, and mean any chain of two or more nucleotides. The polynucleotides can be chimeric mixtures or derivatives or modified versions thereof, and single-stranded or double-stranded. The oligonucleotide can be modified at the base moiety, sugar moiety, or phosphate backbone, for example, to improve stability of the molecule, its hybridization parameters, etc.

An "RNA transcript" is the product resulting from RNA polymerase-catalyzed transcription of a DNA sequence. When the RNA transcript is a complimentary copy of the DNA sequence, it is referred to as the primary transcript, or it may be an RNA sequence derived from post-transcriptional processing of the primary transcript and is referred to as the mature RNA. "Messenger RNA (mRNA)" refers to the RNA that is without introns and can be translated into polypeptides by the cell. "cRNA" refers to complementary RNA, transcribed from a recombinant cDNA template. "cDNA" refers to DNA that is complementary to and derived from an mRNA template.

A "protein," "peptide," or "polypeptide" comprises a polymer of amino acid residues linked together by peptide bonds. The term refers to proteins, polypeptides, and peptides of any size, structure, or function. Typically, a protein will be at least three amino acids long. A protein may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a protein may be modified, for example, by the addition of a chemical entity such as a carbohydrate group, a hydroxyl group, a phosphate group, a farnesyl group, an isofarnesyl group, a fatty acid group, a linker for conjugation or functionalization, or other modification. A protein may also be a single molecule or may be a multi-molecular complex. A protein may be a fragment of a naturally occurring protein or peptide. A protein may be naturally occurring, recombinant, synthetic, or any combination of these.

A "cell," as used herein, may be present in a population of cells (e.g., in a tissue, an organ, or an organoid). In some embodiments, a population of cells is composed of a plurality of cell types. Cells for use in the methods of the present disclosure can be present within an organism, a single cell type derived from an organism, or a mixture of cell types. Included are naturally occurring cells and cell populations, genetically engineered cell lines, cells derived from transgenic animals, etc. Virtually any cell type and size can be accommodated in the methods and systems described herein. Suitable cells include bacterial, fungal, plant, and animal cells. In some embodiments, the cells are mammalian cells (e.g., complex cell populations such as naturally occurring tissues). In some embodiments, the cells are from a human. In certain embodiments, the cells are collected from a subject (e.g., a human) through a medical procedure such as a biopsy. Alternatively, the cells may be a cultured population (e.g., a culture derived from a complex population or a culture derived from a single cell type where the cells have differentiated into multiple lineages).

Cell types contemplated for use in the methods of the present disclosure include, but are not limited to, stem and progenitor cells (e.g., embryonic stem cells, hematopoietic stem cells, mesenchymal stem cells, neural crest cells, etc.), endothelial cells, muscle cells, myocardial cells, smooth and skeletal muscle cells, mesenchymal cells, epithelial cells, hematopoietic cells, lymphocytes such as T-cells (e.g., Th1 T cells, Th2 T cells, Th0 T cells, cytotoxic T cells) and B cells (e.g., pre-B cells), monocytes, dendritic cells, neutrophils, macrophages, natural killer cells, mast cells, adipocytes, immune cells, neurons, hepatocytes, and cells involved with particular organs (e.g., thymus, endocrine glands, pancreas, brain, neurons, glia, astrocytes, dendrocytes, and genetically modified cells thereof). The cells may also be transformed or neoplastic cells of different types (e.g., carcinomas of different cell origins, lymphomas of different cell types, etc.) or cancerous cells of any kind. Cells of different origins (e.g., ectodermal, mesodermal, and endodermal) are also contemplated for use in the methods of the present disclosure.

As used herein, a "tissue" is a group of cells and their extracellular matrix from the same origin. Together, the cells carry out a specific function. The association of multiple tissue types together forms an organ. The cells may be of different cell types. In some embodiments, a tissue is an epithelial tissue. Epithelial tissues are formed by cells that cover an organ surface (e.g., the surface of the skin, airways, soft organs, reproductive tract, and inner lining of the digestive tract). Epithelial tissues perform protective functions and are also involved in secretion, excretion, and absorption. Examples of epithelial tissues include, but are not limited to, simple squamous epithelium, stratified squamous epithelium, simple cuboidal epithelium, transitional epithelium, pseudostratified epithelium, columnar epithelium, and glandular epithelium. In some embodiments, a tissue is a connective tissue. Connective tissues are fibrous tissues made up of cells separated by non-living material (e.g., an extracellular matrix). Connective tissues provide shape to organs and hold organs in place. Connective tissues include fibrous connective tissue, skeletal connective tissue, and fluid connective tissue. Examples of connective tissues include, but are not limited to, blood, bone, tendon, ligament, adipose, and areolar tissues. In some embodiments, a tissue is a muscular tissue. Muscular tissue is an active contractile tissue formed from muscle cells. Muscle tissue functions to produce force and cause motion. Muscle tissue includes smooth muscle (e.g., as found in the inner linings of organs), skeletal muscle (e.g., as typically attached to bones), and cardiac muscle (e.g., as found in the heart, where it contracts to pump blood throughout an organism). In some embodiments, a tissue is a nervous tissue. Nervous tissue includes cells comprising the central nervous system and peripheral nervous system. Nervous tissue forms the brain, spinal cord, cranial nerves, and spinal nerves (e.g., motor neurons). In certain embodiments, a tissue is brain tissue. In certain embodiments, a tissue is placental tissue. In some embodiments, a tissue is heart tissue.

As used herein, the term "organ" refers to a group of tissues that have similar functions. Organs in human anatomy include, but are not limited to, the lungs, heart, stomach, liver, gallbladder, pancreas, kidneys, bladder, brain, ovaries, and uterus. An "organoid" refers to a miniaturized and simplified version of an organ produced in vitro in three dimensions. Organoids may be derived from one or a few cells from a tissue. For example, organoids can be derived from embryonic stem cells or induced pluripotent stem cells. Organoids include, but are not limited to, cerebral organoids (e.g., organoids resembling the brain), gut organoids (e.g., organoids resembling structures of the gastrointestinal tract), thyroid organoids, thymic organoids, testicular organoids, hepatic organoids, pancreatic organoids, epithelial organoids, lung organoids, kidney organoids, embryonic organoids, cardiac organoids, and retinal organoids.

The term "genetic disease" refers to a disease caused by one or more abnormalities in the genome of a subject, such as a disease that is present from birth of the subject. Genetic diseases may be heritable and may be passed down from the parents' genes. A genetic disease may also be caused by mutations or changes of the DNAs and/or RNAs of the subject. In such cases, the genetic disease will be heritable if it occurs in the germline. Exemplary genetic diseases include, but are not limited to, Aarskog-Scott syndrome, Aase syndrome, achondroplasia, acrodysostosis, addiction, adreno-leukodystrophy, albinism, ablepharon-macrostomia syndrome, alagille syndrome, alkaptonuria, alpha-1 antit-rypsin deficiency, Alport's syndrome, Alzheimer's disease, asthma, autoimmune polyglandular syndrome, androgen insensitivity syndrome, Angelman syndrome, ataxia, ataxia telangiectasia, atherosclerosis, attention deficit hyperactivity disorder (ADHD), autism, baldness, Batten disease, Beck-with-Wiedemann syndrome, Best disease, bipolar disorder, brachydactyl), breast cancer, Burkitt lymphoma, chronic myeloid leukemia, Charcot-Marie-Tooth disease, Crohn's disease, cleft lip, Cockayne syndrome, Coffin Lowry syn-drome, colon cancer, congenital adrenal hyperplasia, Cor-nelia de Lange syndrome, Costello syndrome, Cowden syndrome, craniofrontonasal dysplasia, Crigler-Najjar syn-drome, Creutzfeldt-Jakob disease, cystic fibrosis, deafness, depression, diabetes, diastrophic dysplasia, DiGeorge syn-drome, Down's syndrome, dyslexia, Duchenne muscular dystrophy, Dubowitz syndrome, ectodermal dysplasia Ellis-van Creveld syndrome, Ehlers-Danlos, epidermolysis bullosa, epilepsy, essential tremor, familial hypercholester-olemia, familial Mediterranean fever, fragile X syndrome, Friedreich's ataxia, Gaucher disease, glaucoma, glucose galactose malabsorption, glutaricaciduria, gyrate atrophy, Goldberg Shprintzen syndrome (velocardiofacial syn-drome), Gorlin syndrome, Hailey-Hailey disease, hemihy-pertrophy, hemochromatosis, hemophilia, hereditary motor and sensory neuropathy (HMSN), hereditary non polyposis colorectal cancer (HNPCC), Huntington's disease, immu-nodeficiency with hyper-IgM, juvenile onset diabetes, Klinefelter's syndrome, Kabuki syndrome, Leigh's disease, long QT syndrome, lung cancer, malignant melanoma, manic depression, Marfan syndrome, Menkes syndrome, miscarriage, mucopolysaccharide disease, multiple endo-crine neoplasia, multiple sclerosis, muscular dystrophy, myotrophic lateral sclerosis, myotonic dystrophy, neurofi-bromatosis, Niemann-Pick disease, Noonan syndrome, obe-sity, ovarian cancer, pancreatic cancer, Parkinson's disease, paroxysmal nocturnal hemoglobinuria, Pendred syndrome, peroneal muscular atrophy, phenylketonuria (PKU), polycystic kidney disease, Prader-Willi syndrome, primary biliary cirrhosis, prostate cancer, REAR syndrome, Refsum disease, retinitis pigmentosa, retinoblastoma, Rett syn-drome, Sanfilippo syndrome, schizophrenia, severe com-bined immunodeficiency, sickle cell anemia, spina bifida, spinal muscular atrophy, spinocerebellar atrophy, sudden adult death syndrome, Tangier disease, Tay-Sachs disease, thrombocytopenia absent radius syndrome, Townes-Brocks syndrome, tuberous sclerosis, Turner syndrome, Usher syn-drome, von Hippel-Lindau syndrome, Waardenburg syn-drome, Weaver syndrome, Werner syndrome, Williams syn-drome, Wilson's disease, xeroderma piginentosum, and Zellweger syndrome.

A "proliferative disease" refers to a disease that occurs due to abnormal growth or extension by the multiplication of cells (Walker, *Cambridge Dictionary of Biology*; Cambridge University Press: Cambridge, UK, 1990). A proliferative disease may be associated with: 1) the pathological prolif-eration of normally quiescent cells; 2) the pathological migration of cells from their normal location (e.g., metastasis of neoplastic cells); 3) the pathological expression of proteolytic enzymes such as the matrix metalloproteinases (e.g., collagenases, gelatinases, and elastases); or 4) the pathological angiogenesis as in proliferative retinopathy and tumor metastasis. Exemplary proliferative diseases include cancers (i.e., "malignant neoplasms"), benign neoplasms, angiogenesis, inflammatory diseases, and autoimmune dis-eases.

The term "angiogenesis" refers to the physiological pro-cess through which new blood vessels form from pre-existing vessels. Angiogenesis is distinct from vasculogen-esis, which is the de novo formation of endothelial cells from mesoderm cell precursors. The first vessels in a devel-oping embryo form through vasculogenesis, after which angiogenesis is responsible for most blood vessel growth during normal or abnormal development. Angiogenesis is a vital process in growth and development, as well as in wound healing and in the formation of granulation tissue. However, angiogenesis is also a fundamental step in the transition of tumors from a benign state to a malignant one, leading to the use of angiogenesis inhibitors in the treatment of cancer. Angiogenesis may be chemically stimulated by angiogenic proteins, such as growth factors (e.g., VEGF). "Pathological angiogenesis" refers to abnormal (e.g., exces-sive or insufficient) angiogenesis that amounts to and/or is associated with a disease.

The terms "tumor" and "neoplasm" are used herein refers to an abnormal mass of tissue wherein the growth of the mass surpasses and is not coordinated with the growth of a normal tissue. A tumor may be "benign" or "malignant," depending on the following characteristics: degree of cellu-lar differentiation (including morphology and functionality), rate of growth, local invasion, and metastasis. A "benign neoplasm" is generally well differentiated, has characteris-tically slower growth than a malignant neoplasm, and remains localized to the site of origin. In addition, a benign neoplasm does not have the capacity to infiltrate, invade, or metastasize to distant sites. Exemplary benign neoplasms include, but are not limited to, lipoma, chondroma, adenomas, acrochordon, senile angiomas, seborrheic kera-toses, lentigos, and sebaceous hyperplasias. In some cases, certain "benign" tumors may later give rise to malignant neoplasms, which may result from additional genetic changes in a subpopulation of the tumor's neoplastic cells, and these tumors are referred to as "pre-malignant neo-plasms." An exemplary pre-malignant neoplasm is a tera-toma. In contrast, a "malignant neoplasm" is generally poorly differentiated (anaplasia) and has characteristically rapid growth accompanied by progressive infiltration, inva-sion, and destruction of the surrounding tissue. Furthermore, a malignant neoplasm generally has the capacity to metas-tasize to distant sites. The term "metastasis," "metastatic," or "metastasize" refers to the spread or migration of cancerous cells from a primary or original tumor to another organ or tissue and is typically identifiable by the presence of a "secondary tumor" or "secondary cell mass" of the tissue type of the primary or original tumor and not of that of the organ or tissue in which the secondary (metastatic) tumor is located. For example, a prostate cancer that has migrated to bone is said to be metastasized prostate cancer and includes cancerous prostate cancer cells growing in bone tissue.

The term "cancer" refers to a class of diseases character-ized by the development of abnormal cells that proliferate uncontrollably and have the ability to infiltrate and destroy normal body tissues. See e.g., *Stedman's Medical Diction-ary*, 25th ed.; Hensyl ed.; Williams & Wilkins: Philadelphia, 1990. Exemplary cancers include, but are not limited to, acoustic neuroma; adenocarcinoma; adrenal gland cancer; anal cancer; angiosarcoma (e.g., lymphangiosarcoma, lymphangioendotheliosarcoma, hemangiosarcoma); appendix cancer; benign monoclonal gammopathy; biliary cancer (e.g., cholangiocarcinoma); bladder cancer; breast cancer (e.g., adenocarcinoma of the breast, papillary carcinoma of the breast, mammary cancer, medullary carcinoma of the breast); brain cancer (e.g., meningioma, glioblastomas, glioma (e.g., astrocytoma, oligodendroglioma), medulloblastoma); bronchus cancer; carcinoid tumor; cervical cancer (e.g., cervical adenocarcinoma); choriocarcinoma; chordoma; craniopharyngioma; colorectal cancer (e.g., colon cancer, rectal cancer, colorectal adenocarcinoma); connective tissue cancer; epithelial carcinoma; ependymoma; endotheliosarcoma (e.g., Kaposi's sarcoma, multiple idiopathic hemorrhagic sarcoma); endometrial cancer (e.g., uterine cancer, uterine sarcoma); esophageal cancer (e.g., adenocarcinoma of the esophagus, Barrett's adenocarcinoma); Ewing's sarcoma; ocular cancer (e.g., intraocular melanoma, retinoblastoma); familiar hypereosinophilia; gall bladder cancer; gastric cancer (e.g., stomach adenocarcinoma); gastrointestinal stromal tumor (GIST); germ cell cancer; head and neck cancer (e.g., head and neck squamous cell carcinoma, oral cancer (e.g., oral squamous cell carcinoma), throat cancer (e.g., laryngeal cancer, pharyngeal cancer, nasopharyngeal cancer, oropharyngeal cancer)); hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL)); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., Waldenström's macroglobulinemia), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungoides, Sezary syndrome), angioimmunoblastic T-cell lymphoma, extranodal natural killer T-cell lymphoma, enteropathy type T-cell lymphoma, subcutaneous panniculitis-like T-cell lymphoma, and anaplastic large cell lymphoma); a mixture of one or more leukemia/lymphoma as described above; and multiple myeloma (MM)), heavy chain disease (e.g., alpha chain disease, gamma chain disease, mu chain disease); hemangioblastoma; hypopharynx cancer; inflammatory myofibroblastic tumors; immunocytic amyloidosis; kidney cancer (e.g., nephroblastoma a.k.a. Wilms' tumor, renal cell carcinoma); liver cancer (e.g., hepatocellular cancer (HCC), malignant hepatoma); lung cancer (e.g., bronchogenic carcinoma, small cell lung cancer (SCLC), non-small cell lung cancer (NSCLC), adenocarcinoma of the lung); leiomyosarcoma (LMS); mastocytosis (e.g., systemic mastocytosis); muscle cancer; myelodysplastic syndrome (MDS); mesothelioma; myeloproliferative disorder (MPD) (e.g., polycythemia vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)); neuroblastoma; neurofibroma (e.g., neurofibromatosis (NF) type 1 or type 2, schwannomatosis); neuroendocrine cancer (e.g., gastroenteropancreatic neuroendoctrine tumor (GEP-NET), carcinoid tumor); osteosarcoma (e.g., bone cancer); ovarian cancer (e.g., cystadenocarcinoma, ovarian embryonal carcinoma, ovarian adenocarcinoma); papillary adenocarcinoma; pancreatic cancer (e.g., pancreatic adenocarcinoma, intraductal papillary mucinous neoplasm (IPMN), Islet cell tumors); penile cancer (e.g., Paget's disease of the penis and scrotum); pinealoma; primitive neuroectodermal tumor (PNT); plasma cell neoplasia; paraneoplastic syndromes; intraepithelial neoplasms; prostate cancer (e.g., prostate adenocarcinoma); rectal cancer; rhabdomyosarcoma; salivary gland cancer; skin cancer (e.g., squamous cell carcinoma (SCC), keratoacanthoma (KA), melanoma, basal cell carcinoma (BCC)); small bowel cancer (e.g., appendix cancer); soft tissue sarcoma (e.g., malignant fibrous histiocytoma (MFH), liposarcoma, malignant peripheral nerve sheath tumor (MPNST), chondrosarcoma, fibrosarcoma, myosarcoma); sebaceous gland carcinoma; small intestine cancer; sweat gland carcinoma; synovioma; testicular cancer (e.g., seminoma, testicular embryonal carcinoma); thyroid cancer (e.g., papillary carcinoma of the thyroid, papillary thyroid carcinoma (PTC), medullary thyroid cancer); urethral cancer; vaginal cancer; and vulvar cancer (e.g., Paget's disease of the vulva).

Anti-cancer agents encompass biotherapeutic anti-cancer agents as well as chemotherapeutic agents. Exemplary biotherapeutic anti-cancer agents include, but are not limited to, interferons, cytokines (e.g., tumor necrosis factor, interferon $\alpha$, interferon $\gamma$), vaccines, hematopoietic growth factors, monoclonal serotherapy, immunostimulants and/or immunomodulatory agents (e.g., IL-1, 2, 4, 6, or 12), immune cell growth factors (e.g., GM-CSF) and antibodies (e.g. HERCEPTIN (trastuzumab), T-DM1, AVASTIN (bevacizumab), ERBITUX (cetuximab), VECTIBIX (panitumumab), RITUXAN (rituximab), BEXXAR (tositumomab)). Exemplary chemotherapeutic agents include, but are not limited to, anti-estrogens (e.g. tamoxifen, raloxifene, and megestrol), LHRH agonists (e.g. goscrclin and leuprolide), anti-androgens (e.g. flutamide and bicalutamide), photodynamic therapies (e.g. vertoporfin (BPD-MA), phthalocyanine, photosensitizer Pc4, and demethoxy-hypocrellin A (2BA-2-DMHA)), nitrogen mustards (e.g. cyclophosphamide, ifosfamide, trofosfamide, chlorambucil, estramustine, and melphalan), nitrosoureas (e.g. carmustine (BCNU) and lomustine (CCNU)), alkylsulphonates (e.g. busulfan and treosulfan), triazenes (e.g. dacarbazine, temozolomide), platinum containing compounds (e.g. cisplatin, carboplatin, oxaliplatin), vinca alkaloids (e.g. vincristine, vinblastine, vindesine, and vinorelbine), taxoids (e.g. paclitaxel or a paclitaxel equivalent such as nanoparticle albumin-bound paclitaxel (ABRAXANE), docosahexaenoic acid bound-paclitaxel (DHA-paclitaxel, Taxoprexin), polyglutamate bound-paclitaxel (PG-paclitaxel, paclitaxel poliglumex, CT-2103, XYOTAX), the tumor-activated prodrug (TAP) ANG1005 (Angiopep-2 bound to three molecules of paclitaxel), paclitaxel-EC-1 (paclitaxel bound to the erbB2-recognizing peptide EC-1), and glucose-conjugated paclitaxel, e.g., 2'-paclitaxel methyl 2-glucopyranosyl succinate; docetaxel, taxol), epipodophyllins (e.g. etoposide, etoposide phosphate, teniposide, topotecan, 9-aminocamptothecin, camptoirinotecan, irinotecan, crisnatol, mytomycin C), anti-metabolites, DHFR inhibitors (e.g. methotrexate, dichloromethotrexate, trimetr-exate, edatrexate), IMP dehydrogenase inhibitors (e.g. mycophenolic acid, tiazofurin, ribavirin, and EICAR), ribo-nuclotide reductase inhibitors (e.g. hydroxyurea and defer-oxamine), uracil analogs (e.g. 5-fluorouracil (5-FU), floxu-ridine, doxifluridine, ratitrexed, tegafur-uracil, capecitabine), cytosine analogs (e.g. cytarabine (ara C), cytosine arabinoside, and fludarabine), purine analogs (e.g. mercaptopurine and Thioguanine), Vitamin D3 analogs (e.g. EB 1089, CB 1093, and KH 1060), isoprenylation inhibitors (e.g. lovastatin), dopaminergic neurotoxins (e.g. 1-methyl-4-phenylpyridinium ion), cell cycle inhibitors (e.g. stauro-sporine), actinomycin (e.g. actinomycin D, dactinomycin), bleomycin (e.g. bleomycin A2, bleomycin B2, peplomycin), anthracycline (e.g. daunorubicin, doxorubicin, pegylated liposomal doxorubicin, idarubicin, epirubicin, pirarubicin, zorubicin, mitoxantrone), MDR inhibitors (e.g. verapamil), $Ca^{2+}$ ATPase inhibitors (e.g. thapsigargin), imatinib, thalido-mide, lenalidomide, tyrosine kinase inhibitors (e.g., axitinib (AG013736), bosutinib (SKI-606), cediranib (RECEN-TIN™, AZD2171), dasatinib (SPRYCEL®, BMS-354825), erlotinib (TARCEVA®), gefitinib (IRESSAC)), imatinib (Gleevec®, CGP57148B, STI-571), lapatinib (TYKERB®, TYVERB®), lestaurtinib (CEP-701), neratinib (HKI-272), nilotinib (TASIGNA®), semaxanib (semaxinib, SU5416), sunitinib (SUTENT®, SU11248), toceranib (PALLA-DIA®), vandetanib (ZACTIMA®, ZD6474), vatalanib (PTK787, PTK/ZK), trastuzumab (HERCEPTIN®), beva-cizumab (AVASTIN®), rituximab (RITUXAN®), cetux-imab (ERBITUX®), panitumumab (VECTIBIX®), ranibi-zumab (Lucentis®), nilotinib (TASIGNA®), sorafenib (NEXAVAR®), everolimus (AFINITOR®), alemtuzumab (CAMPATH®), gemtuzumab ozogamicin (MY-LOTARG®), temsirolimus (TORISEL®), ENMD-2076, PCI-32765, AC220, dovitinib lactate (TKI258, CHIR-258), BIBW 2992 (TOVOK™), SGX523, PF-04217903, PF-02341066, PF-299804, BMS-777607, ABT-869, MP470, BIBF 1120 (VARGATEF®), AP24534, JNJ-26483327, MGCD265, DCC-2036, BMS-690154, CEP-11981, tivozanib (AV-951), OSI-930, MM-121, XL-184, XL-647, and/or XL228), proteasome inhibitors (e.g., bort-ezomib (VELCADE)), mTOR inhibitors (e.g., rapamycin, temsirolimus (CCI-779), everolimus (RAD-001), ridaforo-limus, AP23573 (Ariad), AZD8055 (AstraZeneca), BEZ235 (Novartis), BGT226 (Norvartis), XL765 (Sanofi Aventis), PF-4691502 (Pfizer), GDC0980 (Genentech), SF1126 (Semafoe) and OSI-027 (OSI)), oblimersen, gemcitabine, carminomycin, leucovorin, pemetrexed, cyclophosphamide, dacarbazine, procarbizine, prednisolone, dexamethasone, campathecin, plicamycin, asparaginase, aminopterin, methopterin, porfiromycin, melphalan, leurosidine, leuro-sine, chlorambucil, trabectedin, procarbazine, discodermo-lide, carminomycin, aminopterin, and hexamethyl mela-mine.

The terms "inflammatory disease" and "inflammatory condition" are used interchangeably herein, and refer to a disease or condition caused by, resulting from, or resulting in inflammation. Inflammatory diseases and conditions include those diseases, disorders or conditions that are characterized by signs of pain (dolor, from the generation of noxious substances and the stimulation of nerves), heat (calor, from vasodilatation), redness (rubor, from vasodila-tation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exuda-tive, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, trau-matic, and/or ulcerative inflammation. The term "inflamma-tory disease" may also refer to a dysregulated inflammatory reaction that causes an exaggerated response by macro-phages, granulocytes, and/or T-lymphocytes leading to abnormal tissue damage and/or cell death. An inflammatory disease can be either an acute or chronic inflammatory condition and can result from infections or non-infectious causes. Inflammatory diseases include, without limitation, atherosclerosis, arteriosclerosis, autoimmune disorders, multiple sclerosis, systemic lupus erythematosus, polymyal-gia rheumatica (PMR), gouty arthritis, degenerative arthritis, tendonitis, bursitis, psoriasis, cystic fibrosis, arthrosteitis, rheumatoid arthritis, inflammatory arthritis, Sjogren's syn-drome, giant cell arteritis, progressive systemic sclerosis (scleroderma), ankylosing spondylitis, polymyositis, derma-tomyositis, pemphigus, pemphigoid, diabetes (e.g., Type I), myasthenia gravis, Hashimoto's thyroiditis, Graves' dis-ease, Goodpasture's disease, mixed connective tissue dis-ease, sclerosing cholangitis, inflammatory bowel disease, Crohn's disease, ulcerative colitis, pernicious anemia, inflammatory dermatoses, usual interstitial pneumonitis (UIP), asbestosis, silicosis, bronchiectasis, berylliosis, tal-cosis, pneumoconiosis, sarcoidosis, desquamative intersti-tial pneumonia, lymphoid interstitial pneumonia, giant cell interstitial pneumonia, cellular interstitial pneumonia, extrinsic allergic alveolitis, Wegener's granulomatosis and related forms of angiitis (temporal arteritis and polyarteritis nodosa), inflammatory dermatoses, hepatitis, delayed-type hypersensitivity reactions (e.g., poison ivy dermatitis), pneumonia, respiratory tract inflammation, Adult Respira-tory Distress Syndrome (ARDS), encephalitis, immediate hypersensitivity reactions, asthma, hayfever, allergies, acute anaphylaxis, rheumatic fever, glomerulonephritis, pyelone-phritis, cellulitis, cystitis, chronic cholecystitis, ischemia (ischemic injury), reperfusion injury, allograft rejection, host-versus-graft rejection, appendicitis, arteritis, blephari-tis, bronchiolitis, bronchitis, cervicitis, cholangitis, chorio-amnionitis, conjunctivitis, dacryoadenitis, dermatomyositis, endocarditis, endometritis, enteritis, enterocolitis, epicondy-litis, epididymitis, fasciitis, fibrositis, gastritis, gastroenteri-tis, gingivitis, ileitis, iritis, laryngitis, myelitis, myocarditis, nephritis, omphalitis, oophoritis, orchitis, osteitis, otitis, pancreatitis, parotitis, pericarditis, pharyngitis, pleuritis, phlebitis, pneumonitis, proctitis, prostatitis, rhinitis, salpin-gitis, sinusitis, stomatitis, synovitis, testitis, tonsillitis, ure-thritis, urocystitis, uveitis, vaginitis, vasculitis, vulvitis, vul-vovaginitis, angitis, chronic bronchitis, osteomyelitis, optic neuritis, temporal arteritis, transverse myelitis, necrotizing fasciitis, and necrotizing enterocolitis. An ocular inflamma-tory disease includes, but is not limited to, post-surgical inflammation.

Additional exemplary inflammatory conditions include, but are not limited to, inflammation associated with acne, anemia (e.g., aplastic anemia, haemolytic autoimmune anae-mia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lat-eral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, Type II diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myeasthenia gravis, myocardial ischemia, nephrotic syndrome, pemphigus vulgaris, pernicious anaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scleredoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis. In certain embodiments, the inflammatory disorder is selected from arthritis (e.g., rheumatoid arthritis), inflammatory bowel disease, inflammatory bowel syndrome, asthma, psoriasis, endometriosis, interstitial cystitis and prostatitis. In certain embodiments, the inflammatory condition is an acute inflammatory condition (e.g., for example, inflammation resulting from infection). In certain embodiments, the inflammatory condition is a chronic inflammatory condition (e.g., conditions resulting from asthma, arthritis and inflammatory bowel disease). The compounds may also be useful in treating inflammation associated with trauma and non-inflammatory myalgia. The compounds disclosed herein may also be useful in treating inflammation associated with cancer.

The term "liver disease" or "hepatic disease" refers to damage to or a disease of the liver. Non-limiting examples of liver disease include intrahepatic cholestasis (e.g., alagille syndrome, biliary liver cirrhosis), fatty liver (e.g., alcoholic fatty liver, Reye's syndrome), hepatic vein thrombosis, hepatolenticular degeneration (i.e., Wilson's disease), hepatomegaly, liver abscess (e.g., amebic liver abscess), liver cirrhosis (e.g., alcoholic, biliary, and experimental liver cirrhosis), alcoholic liver diseases (e.g., fatty liver, hepatitis, cirrhosis), parasitic liver disease (e.g., hepatic echinococcosis, fascioliasis, amebic liver abscess), jaundice (e.g., hemolytic, hepatocellular, cholestatic jaundice), cholestasis, portal hypertension, liver enlargement, ascites, hepatitis (e.g., alcoholic hepatitis, animal hepatitis, chronic hepatitis (e.g., autoimmune, hepatitis B, hepatitis C, hepatitis D, drug induced chronic hepatitis), toxic hepatitis, viral human hepatitis (e.g., hepatitis A, hepatitis B, hepatitis C, hepatitis D, hepatitis E), granulomatous hepatitis, secondary biliary cirrhosis, hepatic encephalopathy, varices, primary biliary cirrhosis, primary sclerosing cholangitis, hepatocellular adenoma, hemangiomas, bile stones, liver failure (e.g., hepatic encephalopathy, acute liver failure), angiomyolipoma, calcified liver metastases, cystic liver metastases, fibrolamellar hepatocarcinoma, hepatic adenoma, hepatoma, hepatic cysts (e.g., Simple cysts, Polycystic liver disease, hepatobiliary cystadenoma, choledochal cyst), mesenchymal tumors (mesenchymal hamartoma, infantile hemangioendothelioma, hemangioma, peliosis hepatis, lipomas, inflammatory pseudotumor), epithelial tumors (e.g., bile duct hamartoma, bile duct adenoma), focal nodular hyperplasia, nodular regenerative hyperplasia, hepatoblastoma, hepatocellular carcinoma, cholangiocarcinoma, cystadenocarcinoma, tumors of blood vessels, angiosarcoma, Karposi's sarcoma, hemangioendothelioma, embryonal sarcoma, fibrosarcoma, leiomyosarcoma, rhabdomyosarcoma, carcinosarcoma, teratoma, carcinoid, squamous carcinoma, primary lymphoma, peliosis hepatis, erythrohepatic porphyria, hepatic porphyria (e.g., acute intermittent porphyria, porphyria cutanea tarda), and Zellweger syndrome.

The term "lung disease" or "pulmonary disease" refers to a disease of the lung. Examples of lung diseases include, but are not limited to, bronchiectasis, bronchitis, bronchopulmonary dysplasia, interstitial lung disease, occupational lung disease, emphysema, cystic fibrosis, acute respiratory distress syndrome (ARDS), severe acute respiratory syndrome (SARS), asthma (e.g., intermittent asthma, mild persistent asthma, moderate persistent asthma, severe persistent asthma), chronic bronchitis, chronic obstructive pulmonary disease (COPD), emphysema, interstitial lung disease, sarcoidosis, asbestosis, aspergilloma, aspergillosis, pneumonia (e.g., lobar pneumonia, multilobar pneumonia, bronchial pneumonia, interstitial pneumonia), pulmonary fibrosis, pulmonary tuberculosis, rheumatoid lung disease, pulmonary embolism, and lung cancer (e.g., non-small-cell lung carcinoma (e.g., adenocarcinoma, squamous-cell lung carcinoma, large-cell lung carcinoma), small-cell lung carcinoma).

A "hematological disease" includes a disease which affects a hematopoietic cell or tissue. Hematological diseases include diseases associated with aberrant hematological content and/or function. Examples of hematological diseases include diseases resulting from bone marrow irradiation or chemotherapy treatments for cancer, diseases such as pernicious anemia, hemorrhagic anemia, hemolytic anemia, aplastic anemia, sickle cell anemia, sideroblastic anemia, anemia associated with chronic infections such as malaria, trypanosomiasis, HTV, hepatitis virus or other viruses, myelophthisic anemias caused by marrow deficiencies, renal failure resulting from anemia, anemia, polycythemia, infectious mononucleosis (EVI), acute non-lymphocytic leukemia (ANLL), acute myeloid leukemia (AML), acute promyelocytic leukemia (APL), acute myelomonocytic leukemia (AMMoL), polycythemia vera, lymphoma, acute lymphocytic leukemia (ALL), chronic lymphocytic leukemia, Wilm's tumor, Ewing's sarcoma, retinoblastoma, hemophilia, disorders associated with an increased risk of thrombosis, herpes, thalassemia, antibody-mediated disorders such as transfusion reactions and erythroblastosis, mechanical trauma to red blood cells such as micro-angiopathic hemolytic anemias, thrombotic thrombocytopenic purpura and disseminated intravascular coagulation, infections by parasites such as *Plasmodium*, chemical injuries from, e.g., lead poisoning, and hypersplenism.

An "autoimmune disease" refers to a disease arising from an inappropriate immune response of the body of a subject against substances and tissues normally present in the body.

In other words, the immune system mistakes some part of the body as a pathogen and attacks its own cells. This may be restricted to certain organs (e.g., in autoimmune thyroiditis) or involve a particular tissue in different places (e.g., Goodpasture's disease which may affect the basement membrane in both the lung and kidney). The treatment of autoimmune diseases is typically with immunosuppression, e.g., medications which decrease the immune response. Exemplary autoimmune diseases include, but are not limited to, glomerulonephritis, Goodpasture's syndrome, necrotizing vasculitis, lymphadenitis, peri-arteritis nodosa, systemic lupus erythematosis, rheumatoid arthritis, psoriatic arthritis, systemic lupus erythematosis, psoriasis, ulcerative colitis, systemic sclerosis, dermatomyositis/polymyositis, anti-phospholipid antibody syndrome, scleroderma, pemphigus vulgaris, ANCA-associated vasculitis (e.g., Wegener's granulomatosis, microscopic polyangiitis), uveitis, Sjogren's syndrome, Crohn's disease, Reiter's syndrome, ankylosing spondylitis, Lyme disease, Guillain-Barré syndrome, Hashimoto's thyroiditis, and cardiomyopathy.

The term "neurological disease" refers to any disease of the nervous system, including diseases that involve the central nervous system (brain, brainstem and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. Examples of neurological diseases include, but are not limited to, headache, stupor and coma, dementia, seizure, sleep disorders, trauma, infections, neoplasms, neuro-ophthalmology, movement disorders, demyelinating diseases, spinal cord disorders, and disorders of peripheral nerves, muscle and neuromuscular junctions. Addiction and mental illness include, but are not limited to, bipolar disorder and schizophrenia, are also included in the definition of neurological diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal; amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile; phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease; macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

"Neurodegenerative diseases" refer to a type of neurological disease marked by the loss of nerve cells, including, but not limited to, Alzheimer's disease, Parkinson's disease, amyotrophic lateral sclerosis, tauopathies (including frontotemporal dementia), and Huntington's disease. In some embodiments, a neurodegenerative disease is Alzheimer's disease. Causes of Alzheimer's disease are poorly understood but in the majority of cases are thought to include a genetic basis. The disease is characterized by loss of neurons and synapses in the cerebral cortex, resulting in atrophy of the affected regions. Biochemically, Alzheimer's is characterized as a protein misfolding disease caused by plaque accumulation of abnormally folded amyloid beta protein and tau protein in the brain. Symptoms of Alzheimer's disease include, but are not limited to, difficulty remembering recent events, problems with language, disorientation, mood swings, loss of motivation, self-neglect, and behavioral issues. Ultimately, bodily functions are gradually lost, and Alzheimer's disease eventually leads to death. Treatment is currently aimed at treating cognitive problems caused by the disease (e.g. with acetylcholinesterase inhibitors or NMDA receptor antagonists), psychosocial interventions (e.g., behavior-oriented or cognition-oriented approaches), and general caregiving. There are no treatments currently available to stop or reverse the progression of the disease completely.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. In some embodiments, the non-human animal is a mammal (e.g., primate (e.g., cynomolgus monkey or rhesus monkey) or mouse). The term "patient" refers to a subject in need of treatment of a disease. In some embodiments, the subject is human. In some embodiments, the patient is human. The human may be a male or female at any stage of development. A subject or patient "in need" of treatment of a disease or disorder (e.g., a cancer or a neurodegenerative disease) includes, without limitation, those who exhibit any risk factors or symptoms of a disease or disorder. Such risk factors or symptoms may be, for example and without limitation, any of those associated with cancer, neurodegenerative diseases (e.g., Alzheimer's disease), or any other disease as discussed herein.

The term "sample" or "biological sample" refers to any sample including tissue samples (such as tissue sections, surgical biopsies, and needle biopsies of a tissue); cell samples (e.g., cytological smears (such as Pap or blood smears) or samples of cells obtained by microdissection); or cell fractions, fragments or organelles (such as obtained by lysing cells and separating the components thereof by centrifugation or otherwise). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample. In some embodiments, a biological sample is a surgical biopsy taken from a subject, for example, a biopsy of any of the tissues described herein. In certain embodiments, a biological sample is a tumor biopsy (e.g., from a subject diagnosed with, suspected of having, or thought to have cancer).

The terms "treatment," "treat," and "treating" refer to reversing, alleviating, delaying the onset of, or inhibiting the progress of a disease described herein (e.g., a cancer or a neurodegenerative disease). In some embodiments, treatment may be administered after one or more signs or symptoms of the disease have developed or have been observed (e.g., prophylactically (as may be further described herein) or upon suspicion or risk of disease). In other embodiments, treatment may be administered in the absence of signs or symptoms of the disease. For example, treatment may be administered to a susceptible subject prior to the onset of symptoms (e.g., in light of a history of symptoms in the subject, or family members of the subject). Treatment may also be continued after symptoms have resolved, for example, to delay or prevent recurrence. In some embodiments, treatment may be administered after determining the presence of cell types in specific quantities in a tissue sample (e.g. a biopsy) associated with a disease (e.g., a cancer tissue) using the methods disclosed herein. In certain embodiments, a treatment may be administered after differential gene expression (e.g., around protein aggregates associated with a neurodegenerative disease, such as Alzheimer's disease) is observed in a sample taken from a subject.

The terms "administer," "administering," and "administration" refer to implanting, absorbing, ingesting, injecting, inhaling, or otherwise introducing a treatment or therapeutic agent, or a composition of treatments or therapeutic agents, in or on a subject.

A "therapeutically effective amount" of a treatment or therapeutic agent is an amount sufficient to provide a therapeutic benefit in the treatment of a condition (e.g., a cancer or a neurodegenerative disease) or to delay or minimize one or more symptoms associated with the condition. A therapeutically effective amount of a treatment or therapeutic agent means an amount of the therapy, alone or in combination with other therapies, that provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

DETAILED DESCRIPTION OF CERTAIN EMBODIMENTS

The aspects described herein are not limited to specific embodiments, systems, compositions, methods, or configurations, and as such can, of course, vary. The terminology used herein is for the purpose of describing particular aspects only and, unless specifically defined herein, is not intended to be limiting.

The present disclosure provides methods for identifying cells in an image. An apparatus for identifying cells in an image is also provided by the present disclosure. Further provided herein is a non-transitory computer-readable storage medium for performing the methods disclosed herein. Methods of diagnosing a disease or disorder and of treating a disease or disorder in a subject using the methods disclosed are also provided herein. The present disclosure also provides kits for performing any of the methods disclosed herein.

Methods of Identifying Cells in an Image, Apparatus for Identifying Cells in an Image, and Non-transitory Computer-Readable Storage Medium for Performing a Method of Identifying Cells in an Image According to various aspects of the disclosure, cells may be identified in an image. In some embodiments, an image may comprise an image that provides spatial location information and genetic information of cells. For example, a raw fluorescent image of cells may be converted into information describing spatial location and genetic location of RNA spots associated with the cells. An image may be obtained by a camera or other imaging device. In some embodiments, a cell may be identified using spots in the image, for example, RNA spots representing genetic information of the spot. A spot may be represented by a set of one or more pixels in the image. A spot may have an associated gene identity. To identify cells, some spots may be identified as cell centers.

According to various embodiments, cell centers may be determined based on a combination of spatial location information and genetic information. In some embodiments, the spatial location information may represent the physical location of a spot in an image. In some embodiments, the genetic information may represent a gene type associated with the spot, for example, a gene identity expressed by an RNA spot. For example, within a radius around a cell, for each of a set of gene types, the number of spots corresponding to each gene type may be counted. For two spots, a genetic correlation between the numbers of spots of each gene type within the radii around the two spots may be calculated. This genetic correlation may be used with the spatial location of the two spots to determine a parameter that represents both the spatial relationship and genetic relationship for the two spots.

According to various embodiments, the parameter representing the spatial relationship and genetic relationship between spots may be used to calculate a local density of each spot and, for each spot, a minimum distance to a spot of higher local density. For a spot having the highest local density, the minimum distance may instead be calculated to the spot having the highest minimum distance.

The inventors have recognized that spots representing cell centers have both high local density and high minimum distance. Accordingly, for each cell, the local density and minimum distance may be multiplied and compared for all cells. When comparing the product of local density and minimum distance for all cells, an elbow point may be readily identified as a cutoff point, with spots above the cutoff point representing cell centers. A cutoff point may be identified manually or by statistics. In descending order of local density, each remaining spot may then be assigned to its nearest neighbor spot, until all spots are clustered to a cell center. Each cluster around a cell center may then be identified as representing a cell.

After cells have been identified, similar methods may be used to segment cells into subcellular components, including organelles such as the nucleus or cytoplasm, or to cluster cells into tissue regions.

FIG. 12 shows a process flow 1200 of one embodiment of a method related to identifying cells in an image. The process flow 1200 may be performed by at least one computer processor. In some embodiments, there may be at least one non-transitory computer-readable storage medium encoded with a plurality of instructions that, when executed by at least one computer processor, perform process flow 1200. Process flow 1200 comprises step 1202, step 1204, step 1206, and step 1208. In step 1202, the at least one computer processor receives, for each of a plurality of spots in an image, a spatial location of the spot in the image and genetic information associated with the spot, wherein each spot corresponds to one or more pixels in the image. In step 1204, the at least one computer processor, based on the spatial location and the genetic information for each of the plurality of spots, determines at least one spot that represents a cell center. In step 1206, the at least one computer processor, based on the spatial location and the genetic information for each of the plurality of spots, for each spot determined to represent a cell center, identifies, as representing a cell in the image, a set of spots from the plurality of spots, wherein the set of spots belong to a same cell as the spot determined to represent the cell center. In step 1208, the at least one computer processor outputs an indication of the set of spots determined for each of the cells identified in the image. In some embodiments, the spots may comprise RNA spots.

FIG. 13 shows a process flow 1300 of one embodiment of a method related to determining, based on spatial location and genetic information for each of a plurality of spots, at least one spot that represents a cell center. The process flow 1300 may be performed by at least one computer processor. In some embodiments, there may be at least one non-transitory computer-readable storage medium encoded with a plurality of instructions that, when executed by at least one computer processor, perform process flow 1300. Process flow 1300 comprises step 1302, step 1304, step 1306, and step 1308. In step 1302, the at least one computer processor, for each of the plurality of spots, calculates, based on the spatial location and the genetic information, a local density of the spot. In step 1304, the at least one computer processor, for each of the plurality of spots, calculates, based on the spatial location and the genetic information, a minimum distance to another spot of the plurality of spots having a higher local density. In step 1306, the at least one computer processor, for a spot having a highest local density among the plurality of spots, calculates, based on the spatial location and the genetic information, a distance to another spot of the plurality of spots having a highest minimum distance. In step 1308, the at least one computer processor determines the at least one spot that represents the cell centers based, at least in part, on the calculated local densities and the minimum distances of the plurality of spots.

FIG. 14 shows a process flow 1400 of one embodiment of a method related to calculating a local density for a spot and a minimum distance for the spot. The process flow 1400 may be performed by at least one computer processor. In some embodiments, there may be at least one non-transitory computer-readable storage medium encoded with a plurality of instructions that, when executed by at least one computer processor, perform process flow 1400. Process flow 1400 comprises step 1402 and step 1404. In step 1402, the at least one computer processor counts, within a region having a first radius around the spot, numbers of spots corresponding to different gene types. In step 1404, the at least one computer processor calculates a first parameter based on a spatial distance and a genetic correlation. In some embodiments, the spatial distance represents a spatial distance between a spatial location of the spot and a spatial location of another spot. In some embodiments, the genetic correlation represents a correlation between numbers of spots corresponding to different gene types within the first region having a first radius around the spot and numbers of spots corresponding to different gene types within a second region having the first radius around the other spot. In some embodiments, the first radius is approximately equal to the average size of the cells. In some embodiments, the first radius may be selected manually or by statistics.

FIG. 15 shows a process flow 1500 of one embodiment of a method related to determining at least one spot that represents a cell center based on local densities and minimum distances. The process flow 1500 may be performed by at least one computer processor. In some embodiments, there may be at least one non-transitory computer-readable storage medium encoded with a plurality of instructions that, when executed by at least one computer processor, perform process flow 1500. Process flow 1500 comprises step 1502 and step 1504. In step 1502, the at least one computer processor calculates a product of the local density of the spot and the minimum distance of the spot. In step 1504, the at least one computer processor determines that the spot represents a cell center if the product has a value greater than a threshold value. In some embodiments, the threshold value may be selected manually or by statistics.

FIG. 16 shows a process flow 1600 of one embodiment of a method related to segmenting cells into subcellular components. The process flow 1600 may be performed by at least one computer processor. In some embodiments, there may be at least one non-transitory computer-readable storage medium encoded with a plurality of instructions that, when executed by at least one computer processor, perform process flow 1600. Process flow 1600 comprises step 1602, step 1604, and step 1606. In step 1602, the at least one computer processor, for each spot included in the set of spots, counts, within a region having a second radius around the spot, numbers of spots corresponding to different gene types. In step 1604, the at least one computer processor, for each spot included in the set of spots, calculates a second parameter based on a spatial location of the spot and the numbers of spots corresponding to the different gene types within the region having the second radius around the spot. In step 1606, the at least one computer processor, for at least one cell identified in the image, based on the second parameter, segments the cell into subcellular components. In some embodiments, the subcellular components may be subcellular organelles. In some embodiments, the subcellular organelles may include a nucleus and a cytoplasm. In some embodiments, the second radius is approximately equal to the average size of the subcellular organelles. In some embodiments, the second radius may be selected manually or by statistics.

FIG. 17 shows a process flow 1700 of one embodiment of a method related to clustering cells into tissue regions. The process flow 1700 may be performed by at least one computer processor. In some embodiments, there may be at least one non-transitory computer-readable storage medium encoded with a plurality of instructions that, when executed by at least one computer processor, perform process flow 1700. Process flow 1700 comprises step 1702, step 1704, step 1706, and step 1708. In step 1702, the at least one computer processor, for each of the identified cells in the image, classifies the cell into a cell type. In step 1704, the at least one computer processor, for each of the identified cells in the image, counts, within a region having a third radius around the cell, numbers of cells corresponding to different cell types. In step 1706, the at least one computer processor, for each of the identified cells in the image, calculates a third parameter based on a spatial location of the cell and the numbers of cells corresponding to the different cell types within the region having the third radius around the cell. In step 1708, the at least one computer processor clusters at least some of the identified cells in the image into tissue regions based on the third parameter.

FIG. 18 shows a process flow 1800 of one embodiment of a method related to identifying cells in an image. The process flow 1800 may be performed by at least one computer processor. In some embodiments, there may be at least one non-transitory computer-readable storage medium encoded with a plurality of instructions that, when executed by at least one computer processor, perform process flow 1800. Process flow 1800 comprises step 1802, step 1804, step 1806, step 1808 step 1810, and step 1812. In step 1802, the at least one computer processor receives, for each of a plurality of spots in an image, a spatial location of the spot in the image and genetic information associated with the spot, wherein each spot corresponds to one or more pixels in the image. In step 1804, the at least one computer processor, for each of the plurality of spots, calculates, based on the spatial location and the genetic information, a local density of the spot. In step 1806, the at least one computer processor, for each of the plurality of spots, calculates, based on the spatial location and the genetic information, a minimum distance to another spot of the plurality of spots having a higher local density. In step 1808, the at least one computer processor determines the at least one spot that represents the cell centers based, at least in part, on the calculated local densities and the minimum distances of the plurality of spots. In step 1810, the at least one computer processor, based on the spatial location and the genetic information for each of the plurality of spots, for each spot determined to represent a cell center, identifies, as representing a cell in the image, a set of spots from the plurality of spots, wherein the set of spots belong to a same cell as the spot determined to represent the cell center. In step 1812, the at least one computer processor outputs an indication of the set of spots determined for each of the cells identified in the image.

FIG. 19 shows a process flow 1900 of one embodiment of a method related to training a statistical model to identify cells in an image. The process flow 1900 may be performed by at least one computer processor. In some embodiments, there may be at least one non-transitory computer-readable storage medium encoded with a plurality of instructions that, when executed by at least one computer processor, perform process flow 1900. Process flow 1900 comprises step 1902, step 1904, step 1906, step 1908, and step 1910. In step 1902, the at least one computer processor receives, for each of a plurality of spots in an image, a spatial location of the spot in the image and genetic information associated with the spot, wherein each spot corresponds to one or more pixels in the image. In step 1904, the at least one computer processor, based on the spatial location and the genetic information for each of the plurality of spots, determines at least one spot that represents a cell center. In step 1906, the at least one computer processor, based on the spatial location and the genetic information for each of the plurality of spots, for each spot determined to represent a cell center, identifies, as representing a cell in the image, a set of spots from the plurality of spots, wherein the set of spots belong to a same cell as the spot determined to represent the cell center. In step 1908, the at least one computer processor outputs an indication of the set of spots determined for each of the cells identified in the image. In step 1910, the at least one computer processor trains a statistical model by providing as input to the statistical model, the spatial location and genetic information for each of the plurality of spots, wherein the output of the trained statistical model represents an identification of sets of spots for at least one cell in the image.

An illustrative implementation of a computer system 2000 that may be used in connection with any of the embodiments of the disclosure provided herein is shown in FIG. 20. The computer system 2000 may include one or more computer processors 2010 and one or more articles of manufacture that comprise non-transitory computer-readable storage media, for example, memory 2020 and one or more non-volatile storage media 2030. The computer processor 2010 may control writing data to and reading data from the memory 2020 and the non-volatile storage device 2030 in any suitable manner. To perform any of the functionality or methods described herein, such as the methods associated with process flows 1200, 1300, 1400, 1500, 1600, 1700, 1800, 1900, or for example, identifying cells in an image, determining cell centers, calculating local density and minimum distance of spots, segmenting cells into subcellular components, clustering cells into tissue regions, training a statistical model to identify cells in an image, etcetera, the processor 2010 may execute one or more computer processor-executable instructions stored in one or more non-transitory computer-readable storage media, for example the memory 2020, which may serve as non-transitory computer-readable storage media storing processor-executable instructions for execution by the processor 2010.

Methods of Diagnosing a Disease or Disorder

In another aspect, the present disclosure relates to methods of diagnosing a disease or disorder in a subject. In some embodiments, the methods comprise (1) performing the methods for identifying cells in an image of a sample from a subject as described herein; (2) classifying each cell identified in the image into a cell type; and (3) determining, based on the cell type of each cell identified in the image, whether the subject has or is at risk of having the disease or disorder.

The subject being diagnosed may be suspected of having a disease or disorder prior to undergoing the methods for diagnosis described herein. The subject may also be at risk of having a disease or disorder prior to diagnosis. For example, the subject may have one or more symptoms of the disease or disorder (e.g., any of the diseases described herein, including, but not limited to, cancer). The subject may also have a family history of or a genetic risk factor (e.g., a mutation in the genome that has been correlated with a disease, for example, cancer or Alzheimer's disease) for the disease or disorder. In certain embodiments, the subject being diagnosed is not suspected of having or thought to be at risk for having the disease or disorder.

Diagnosis of various diseases is contemplated by the present disclosure. In some embodiments, the disease is a genetic disease, a proliferative disease (e.g., any of the cancers disclosed herein), an inflammatory disease, an autoimmune disease, a liver disease, a pulmonary disease, a hematological disease, a psychiatric disease, a cardiovascular disease, a gastrointestinal disease, a musculoskeletal disease, a genitourinary disease, or a neurological disease (including neurodegenerative diseases, e.g., Alzheimer's disease). In certain embodiments, the disease is cancer (e.g., any of the cancers disclosed herein, including but not limited to skin cancer, breast cancer, colon cancer, etc.). In some embodiments, the disease is Alzheimer's disease.

The methods disclosed herein contemplate evaluation of any sample provided from a subject. In some embodiments, the sample is a tissue sample. For example, the sample may be an epithelial tissue sample, a connective tissue sample, a muscular tissue sample, or a nervous tissue sample. Such tissues may make up the liver, bone marrow, gastrointestinal tract, prostate, skin, circulatory system, lymphatic system, reproductive system, nervous system, or any other organs or organ systems as described herein. In certain embodiments, the sample is taken from a subject by a biopsy (e.g., a biopsy of a tumor from a subject who has cancer). The sample may also be a blood sample.

The step of determining whether the subject has or is at risk of having the disease or disorder may be accomplished by various methods, for example, by determining the numbers and ratios of various cell types relative to one another in the sample. The numbers and ratios of various cell types in the sample provided by the subject can then be compared to other standard samples from cancer patients and healthy subjects to determine whether or not the subject is likely to have the disease or disorder.

Methods of Treating a Disease or Disorder in a Subject

In another aspect, the present disclosure relates to methods of treating a disease or disorder in a subject in need thereof. In some embodiments, the methods comprise (1) performing the methods for identifying cells in an image of a sample from a subject as described herein; (2) classifying each cell identified in the image into a cell type; (3) determining, based on the cell type of each cell identified in the image, whether the subject has or is at risk of having the disease or disorder as described elsewhere herein; and (4) administering a therapy capable of treating the disease or disorder to the subject.

Treatment of any subject as already described herein is contemplated by the present disclosure. Treatment of various diseases and disorders as already described herein is also contemplated by the present disclosure (e.g., the disease is a genetic disease, a proliferative disease (e.g., any of the cancers disclosed herein), an inflammatory disease, an autoimmune disease, a liver disease, a pulmonary disease, a hematological disease, a psychiatric disease, a cardiovascular disease, a gastrointestinal disease, a musculoskeletal disease, a genitourinary disease, or a neurological disease (including neurodegenerative diseases, e.g., Alzheimer's disease)). In certain embodiments, the disease is cancer (e.g., any of the cancers disclosed herein, including but not limited to skin cancer, breast cancer, colon cancer, etc.). In some embodiments, the disease is Alzheimer's disease.

Any therapies known in the art for the diseases and disorders described herein are also contemplated by the present disclosure. Such therapies include, but are not limited to, surgeries (e.g., a surgery to remove a tumor after a subject has been diagnosed with cancer using the methods disclosed herein), radiation therapy (e.g., to treat a subject who has been diagnosed with cancer using the methods disclosed herein), lifestyle changes (e.g., changes to diet or exercise routines after a subject has been diagnosed with a disease or disorder as disclosed herein), psychiatric therapy (e.g., any of the cognitive or behavioral therapies disclosed herein to reduce the severity of Alzheimer's disease symptoms after a subject has been diagnosed with Alzheimer's disease using the methods disclosed herein), or treatment with one or more drugs or other therapeutic agents, as described further below.

In some embodiments, a subject may be provided counseling following diagnosis with a disease or disorder using the methods disclosed herein. In certain embodiments, a subject may undergo another test for diagnosing a disease or disorder to confirm a diagnosis obtained using the methods disclosed herein (e.g., any methods known in the art for diagnosing cancer or another disease or disorder described herein).

The methods of treatment described herein encompass the treatment of subjects with various therapies. In some embodiments, the therapy is a therapeutic agent (e.g., a therapeutic agent administered to a subject in need thereof in a therapeutically effective amount). Such agents may include, but are not limited to, small molecules, nucleic acids, and proteins. In some embodiments, the therapeutic agent is capable of providing some benefit to a subject diagnosed with a disease using the methods described herein. The therapeutic agent may treat a disease or disorder by inhibiting the activity of a protein associated with the disease or disorder (e.g., the therapeutic agent may be a small molecule inhibitor of a protein, or an siRNA capable of reducing or eliminating expression of a protein). In certain embodiments, the therapeutic agent is an antibody. The therapeutic agent may also treat a disease or disorder by increasing the activity or expression of a protein. In some embodiments, the therapeutic agent is an anticancer agent as disclosed herein. In certain embodiments, the therapeutic agent is administered to reduce the symptoms of Alzheimer's disease (e.g., the therapeutic agent is an acetylcholinesterase inhibitor or an NMDA receptor antagonist).

Kits

Also encompassed by the disclosure are kits (e.g., pharmaceutical packs). The kits provided may comprise a therapeutic agent described herein and a container (e.g., a vial, ampule, bottle, syringe, and/or dispenser package, or other suitable container). In some embodiments, the provided kits may optionally further include a second container comprising a pharmaceutical excipient for dilution or suspension of a therapeutic agent described herein. In some embodiments, the therapeutic agent described herein provided in the first container and the second container are combined to form one unit dosage form.

Thus, in one aspect, provided are kits including a first container comprising therapeutic agent(s) described herein. In certain embodiments, the kits are useful for treating a disease (e.g., cancer or Alzheimer's disease) in a subject in need thereof. In certain embodiments, the kits are useful for preventing a disease (e.g., cancer or Alzheimer's disease) in a subject in need thereof. In certain embodiments, the kits are useful for reducing the risk of developing a disease (e.g., cancer or Alzheimer's disease) in a subject in need thereof.

In certain embodiments, a kit described herein further includes instructions for using the kit. A kit described herein may also include information as required by a regulatory agency such as the U.S. Food and Drug Administration (FDA). In certain embodiments, the information included in the kits is prescribing information. A kit described herein may include one or more additional pharmaceutical agents described herein as a separate composition.

In one aspect of the disclosure, kits for diagnosing a subject using any of the methods described herein are provided. Such kits comprise reagents for performing any of the methods described herein. Reagents for performing such methods may include, for example, reagents for performing RNA sequencing (e.g., primers, gene chips, DNase, polymerases).

EXAMPLES

Example 1: ClusterMap Integrates Spatial and Gene Expression Analyses

ClusterMap is based on two key biological phenomena. First, the physical density of RNA molecules is higher inside cells than outside cells; second, cellular RNAs of different genes are enriched at different subcellular locations, cell types, and tissue regions[16,17]. Thus, it was reasoned that biologically meaningful patterns and structures could be identified directly from in situ transcriptomic data by joint clustering the physical density and gene identity of RNAs. The spatial clusters can then be interpreted based on the gene identity and spatial scales to represent subcellular localization, cell segmentation, and region identification.

Figures 1A, 1B:
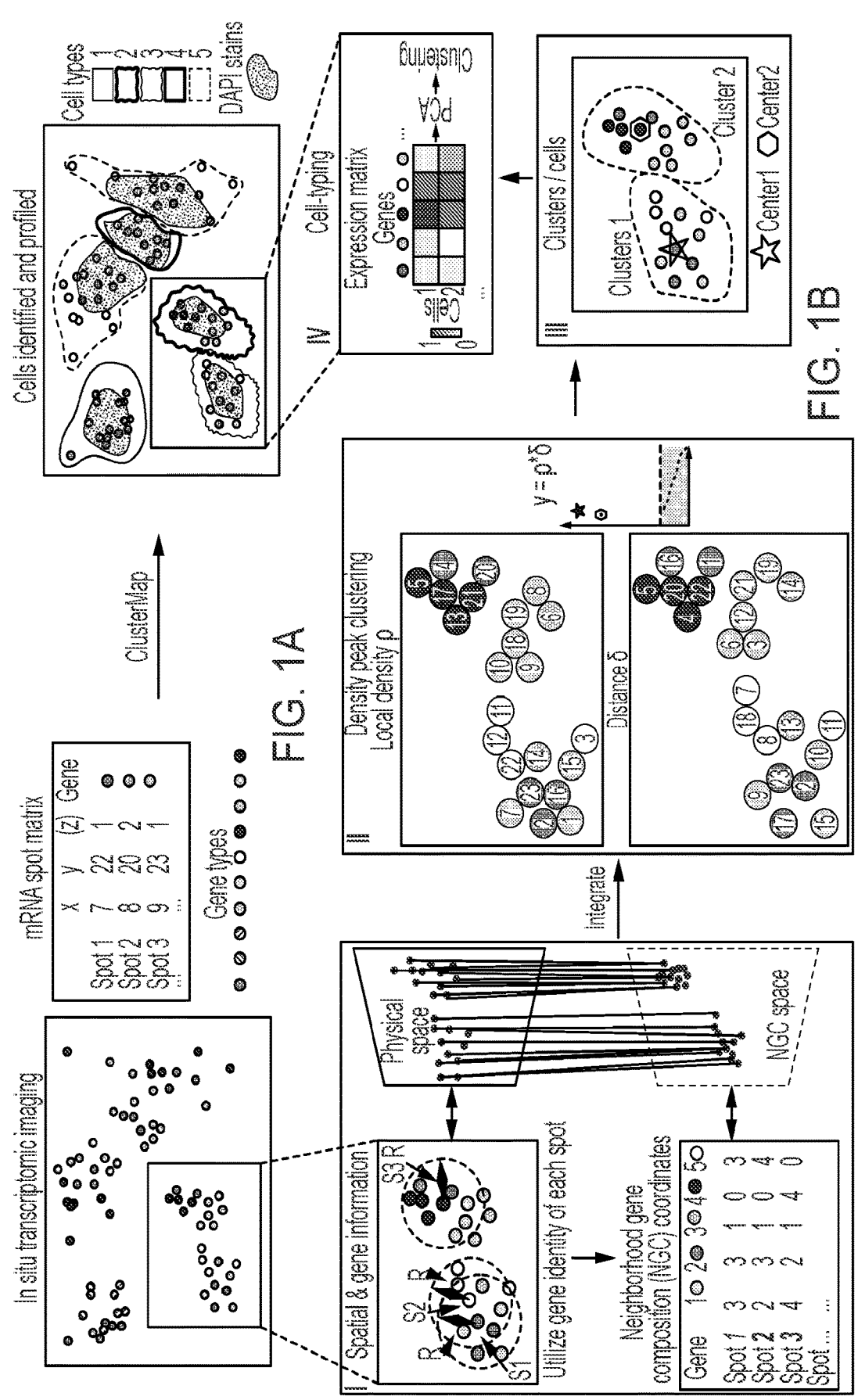
FIGS. 1A-1D provide a schematic of ClusterMap, which enables multiscale spatial clustering analysis of in situ transcriptomic data from sub-cellular to tissue scales.

ClusterMap starts with pre-processed in situ transcriptomic data. First, pre-processing steps convert the raw fluorescent images into discrete RNA spots with physical 3D locations and gene identities (i.e., mRNA spot matrix, FIG. 1A). Second, it was reasoned that spatial clusters can be distinguished based on the gene expression of each RNA spot's local neighborhood. To quantify this, multidimensional coordinates were introduced, termed neighborhood gene composition (NGC) coordinates, which are computed by considering gene expression profiling in a circular window over each spot (FIG. 1B). The size of the window is chosen to match the averaged size of organelles and cells for subcellular and single-cell analysis, respectively. ClusterMap was capable of analysis on different spatial resolutions by changing the radius of the window (FIG. 23). The size of the window was specifically chosen for the same dataset to match the average size of organelles or cells for subcellular or single-cell analysis, respectively (Methods). Third, the NGC coordinates and physical coordinates of each RNA spot are then computationally integrated into joint physical and NGC (P-NGC) coordinates over each spot.

Figure 1C:
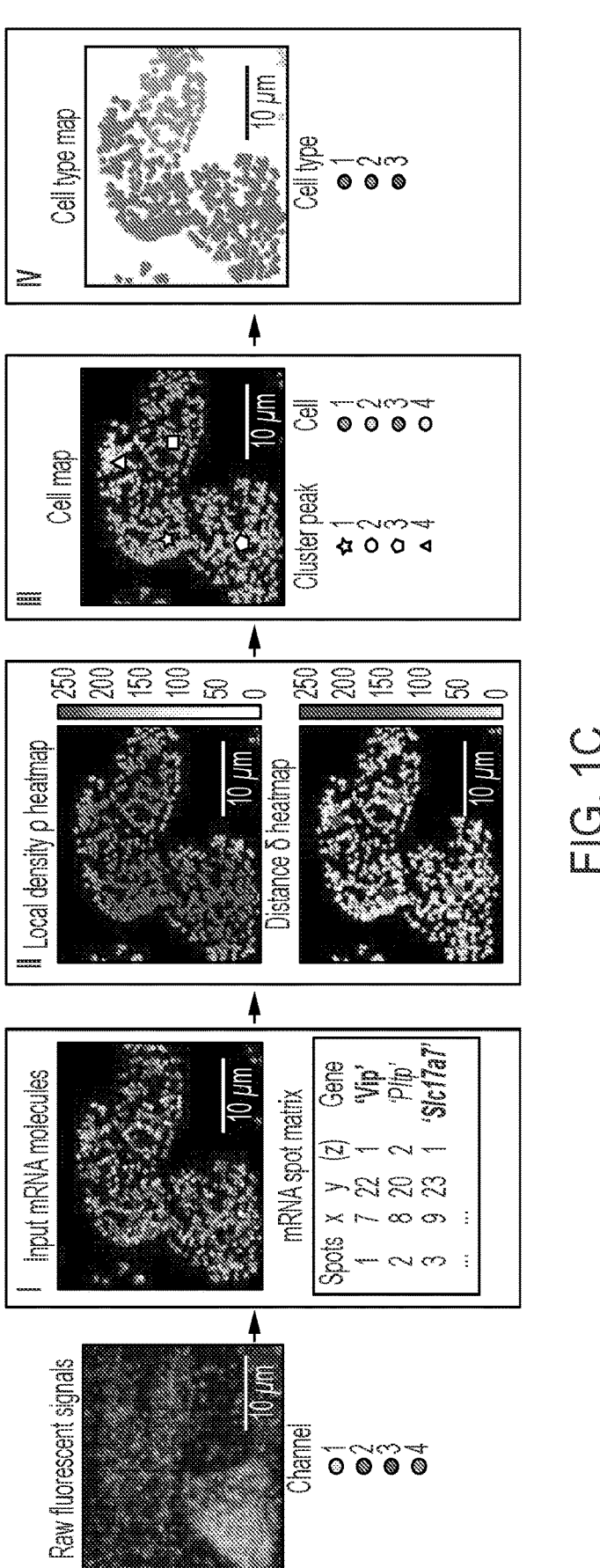

Next, the RNAs in the P-NGC coordinates were clustered for downstream segmentation. Out of numerous clustering algorithms, density peak clustering[18] (DPC), a type of density-based clustering method, was chosen for its versatility in extracting biological features in data and its compatibility with clusters of various shapes and dimensionalities automatically. Applying DPC to the joint P-NGC coordinates results in two variables: local density $\rho$ and distance $\delta$. The product of these two variables, $\gamma$, was then ranked in decreasing order to find the genuine clusters with orders of magnitude higher $\gamma$ values. For example, in FIG. 1B, two spots with the $\gamma$ values that are orders of magnitude higher than other spots are chosen as cell centers (labeled by a star and a hexagon). After selecting the two cluster centers, the remaining spots are assigned to one of the clusters respectively in a descending order of $\rho$ value. Each is assigned to the same cluster as its assigned nearest-neighbor[14], and each cluster of spots is taken to represent an individual, which can be analyzed downstream for purposes such as cell typing, etc. (FIG. 1B). Outliers that were falsely assigned among cells could be filtered out using noise detection in DPC[18]. To illustrate this framework, ClusterMap was applied to in situ transcriptomics data from mouse brain tissue collected by the STARmap method[8] (FIG. 1C). To illustrate this framework, the performance of ClusterMap was tested in five simulated clustering bench-mark datasets (FIG. 22)[44] and one representative in situ transcriptomic data collected by STARmap[6] (FIG. 1C). Compared with previous methods[43], ClusterMap showed consistent performance in all six datasets even when the spot distributions contained irregular boundary, varying physical density, and heterogeneous shapes and sizes.

Figure 1D:
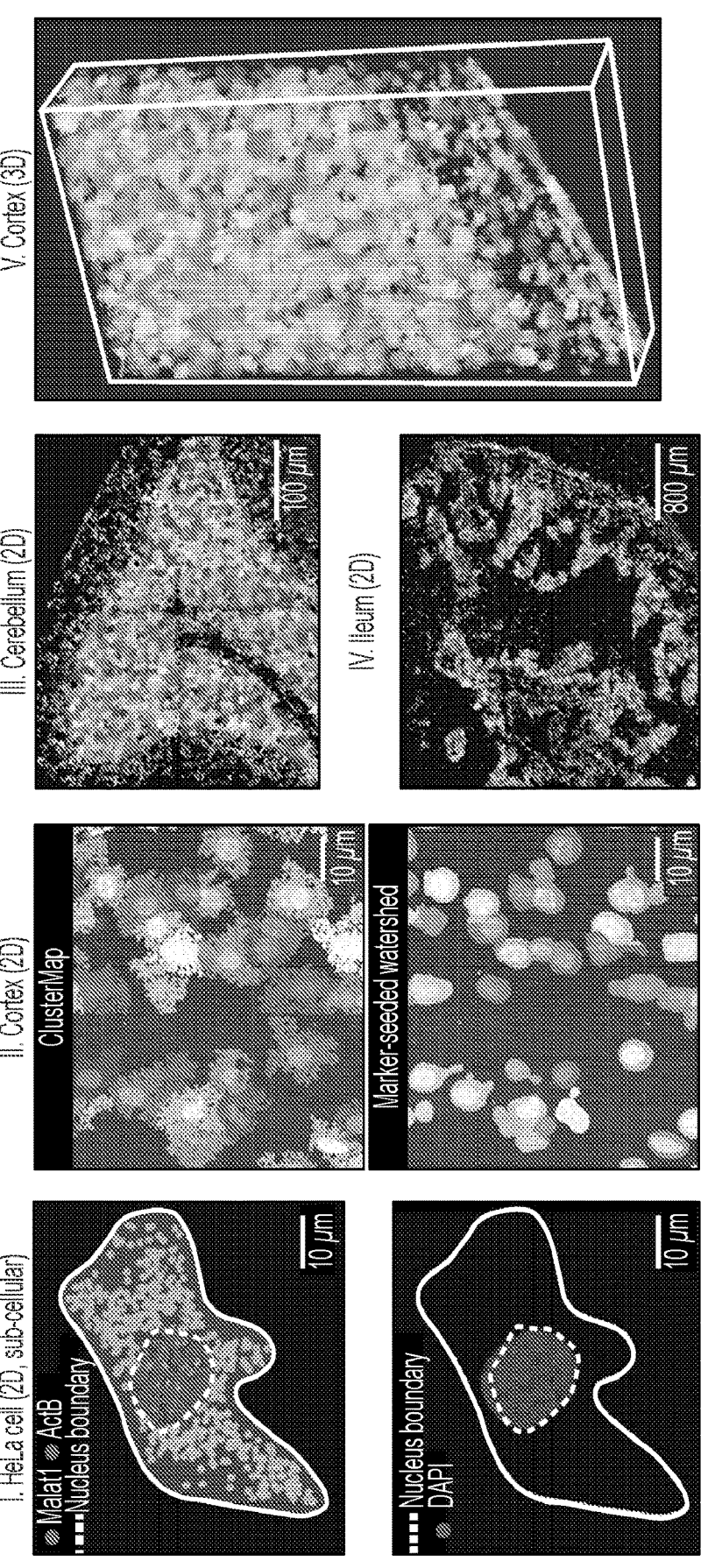

Next, the performance of ClusterMap was examined and validated on diverse biological samples at different spatial scales in both 2D and 3D (FIG. 1D, (I) and (II)). First, based on the assumption that cellular RNAs have a different distribution in the nucleus or cytoplasm[19], ClusterMap was used to cluster mRNAs within one cell to define the nucleus boundary. Here, RNAs with both highly correlated neighboring composition and close spatial distances were merged into a single signature (FIG. 7A). Then, a convex hull was constructed from the nucleus spots, denoting the nucleus boundary. The patterns of ClusterMap-constructed nucleus boundaries were highly correlated with the DAPI stains, confirming the power of ClusterMap for segmentation at subcellular resolution. Second, cell segmentation results by ClusterMap were compared with conventional watershed 13 segmentation on the same mouse cortex cells. Comparing with the conventional watershed method, ClusterMap accurately identified cells, and more precisely outlined cell boundary and illustrated cell morphology. Last, ClusterMap was extended to diverse tissue types at different scales in both 2D and 3D, where dense heterogeneous populations of cells with arbitrary shapes exist. Cell identification results for mouse cerebellum, ileum, and cortex are shown in FIG. 1D (III)-(V).

Example 2: Spatial Clustering Analysis in Mouse Brain

Figure 2A:
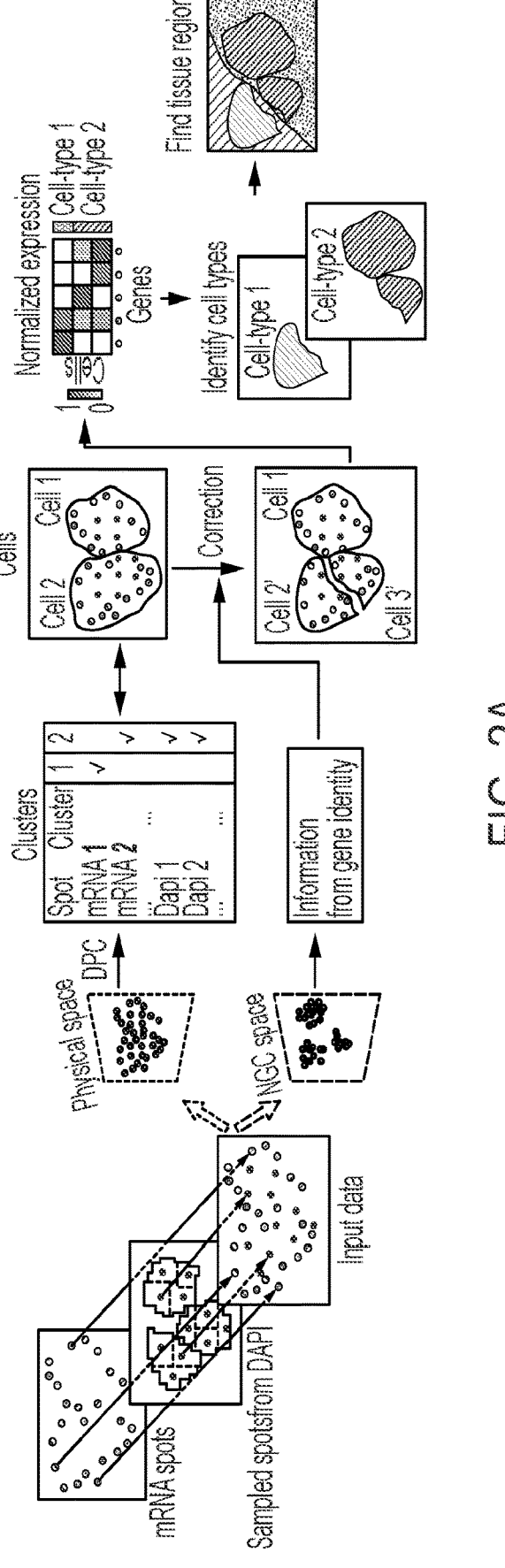
FIGS. 2A-2E show that ClusterMap generates cell-type and tissue-region maps in mouse primary cortex (V1).
Figure 2B:
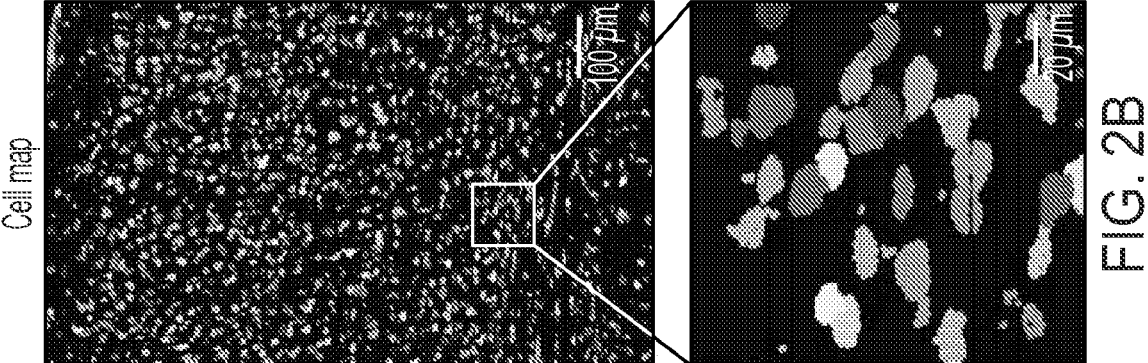
Figure 2C:
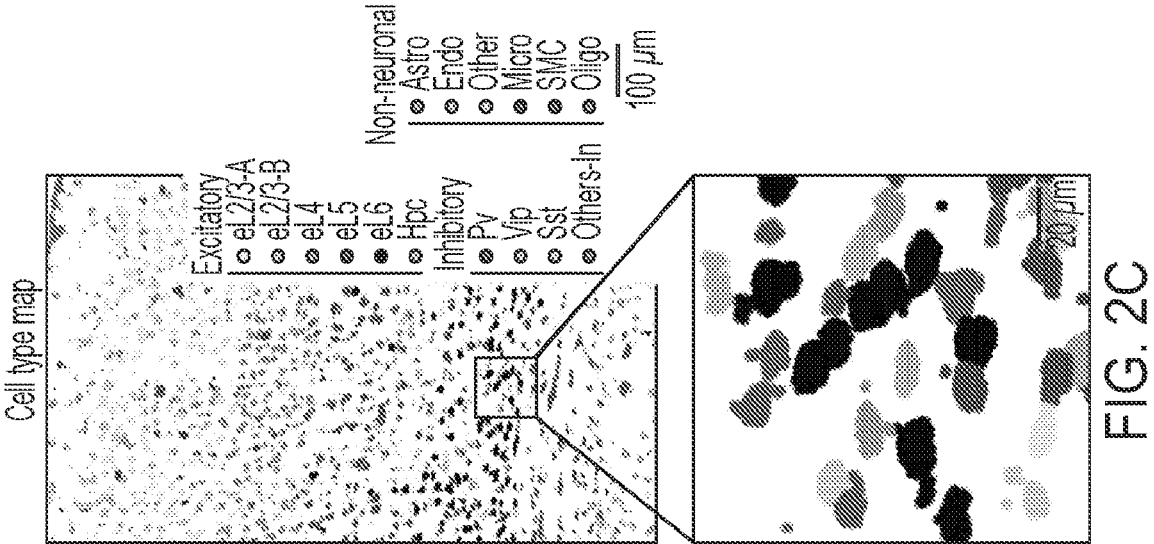
Figure 2D:
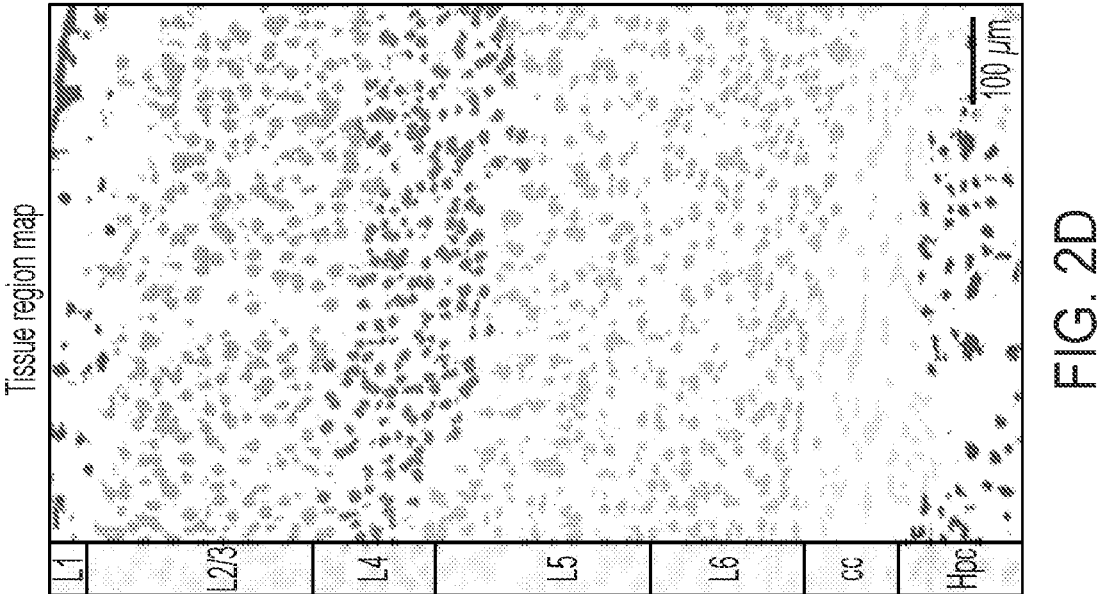

ClusterMap was first demonstrated on the mouse primary visual cortex from the STARmap mouse V1 1020-gene dataset[8] (Table 1). When sequenced mRNA molecules are more likely to populate the cytoplasm, sparsely sampled spots based on DAPI signals were combined with RNAs to compensate for the lack of signals in the centers of cells, and they were together processed with modified ClusterMap procedures (FIG. 2A). The results show clear cell segmentation even in strongly overlapping mouse V1 cortex cells (FIG. 2B).

Additionally, to validate its accuracy, it was evaluated whether ClusterMap-identified cell center coordinates were within corresponding expert-labeled cell regions on eight STARmap mouse V1 datasets (FIGS. 7B-7C). Notably, ClusterMap cell labeling reached accuracy levels of 80-90%. Furthermore, gene expression was integrated in either ClusterMap-identified or expert-labeled cells with scRNA-seq data and their correlation was compared[20,21] (FIG. 8D). Again, ClusterMap exhibited a comparable performance with expert-annotated segmentation. In the mouse V1 cortex dataset, ClusterMap identified cell types[22] that matched both expression signature and tissue localization of the segmentation based on the previous report[8] (FIGS. 8A-8C). Importantly, ClusterMap can consistently identify cell types and their localization across biological replicates and in the mouse brain regions (FIGS. 8E-8H).

The next challenge was applying ClusterMap on the cell-typing map to identify the tissue regions. In this case, ClusterMap further clustered cells based on their physical and cell-type identity, providing similar clustering analyses of physical and high-dimensional cell-type information. ClusterMap computed a neighborhood cell-type composition (NCC) coordinates of each cell[23] and then clustered joint physical and NCC coordinates of cells (FIG. 7D). As a result, cells with both highly correlated neighboring cell-type composition and close spatial distances are clustered into a single tissue region signature. The results showed that ClusterMap accurately detected cortical layering, which allows for the calculation of cell-type composition of each cortical layer (FIG. 2B-2E). The distinct region-specific distribution of excitatory neurons can be observed in the L2/3, L4, L5, and L6 canonical layers respectively, while oligodendrocytes were significantly distributed within the corpus callosum layer. In summary, ClusterMap can effectively, accurately, and automatically conduct cell segmentation, cell typing, and tissue region identification.

Example 3: Spatial Clustering and Cell-Cell Interaction Analyses in Mouse Placenta To further demonstrate the generality of ClusterMap, especially its applicability to tissues with high cell density and variable nuclear/cytosolic distribution of RNAs, ClusterMap was applied to the STARmap mouse placenta 903-gene dataset (FIGS. 3A-3B, Table 1). In analyses performed with the same procedures as FIG. 2A, up to 7,700 cells were identified (FIG. 9A) and then clustered into eleven cell types using Louvain clustering[22], which is consistent with cell types defined from scRNA-seq (FIGS. 3E and 9B-9D). ClusterMap identified seven tissue regions based on the cell-type map (FIGS. 3G-3H). Further analysis shows that Regions IV and VI consisted of similar cell-type compositions, while region I consisted mostly of maternal decidua (MD)-2 cells.

The discovery of the interwovenness of different tissue regions in placenta samples suggests the rich patterns of cell-cell interactions. ClusterMap results were used further to characterize the near-range cell interaction networks by generating a mesh graph via Delaunay triangulation of cells and modeling the cellular relationships based on the i-niche concept[24]. In this way, each cell's nearest neighbors directly contacting each other were identified (FIGS. 4A-4C) and the average number of cells per cell-type among the first-tier neighbors was quantified (FIG. 4E), which could reveal crucial information about the affinity and communication between different cell types.

Through this methodology, cell-type-specific cellular interactions were discovered: MD-1 cells mainly self-aggregate; glandular trophoblast (GT)-2 cells widely connect with four other different types of cells; and ST-1 and ST-2 cells have high affinity to each other. To further explore if cell niche influenced gene expression and further defined cell subtypes, as an example, MD-1 cells were sub-clustered based on either gene expression (Louvain clustering) or the cell niche compositions (K-means clustering). Both sub-clustering results identified two subtypes. The similarity between two sub-clustering results were confirmed by adjusted Rand index (ARI) (ARI=0.62, FIGS. 25A-25D) and suggested that cell adjacency graph analysis could help identify subtypes shaped by cell niche.

Example 4: ClusterMap Across Various In Situ Transcriptomic Methods

Beyond STARmap, ClusterMap was further applied to analyze mouse brain tissue from three other in situ transcriptomics methods. Analyses of the imaged transcripts in the hypothalamic preoptic region by MERFISH[3], the isocortex region by pciSeq[4] and the somatosensory cortex by osmFISH[5] are shown respectively in FIG. 5 (Table 1). RNA spot matrices were used from subsets of the published data and ClusterMap analysis was applied as described in FIG. 1B. Despite the differences in experimental designs and the number of transcript copies, ClusterMap identifies cells successfully compared with the previous cell segmentation results. The identified cell types and their spatial patterns from ClusterMap were consistent with published results analyzed by conventional segmentation methods and scRNA-seq (FIG. 10). Specifically, for ISS data of the mouse hippocampus, further tissue region segmentation was conducted, and this provided detailed statistics of cell type percentage of each region (FIGS. 27A-27D). It was observed that the fine cell classes of the CA1 region displayed distinct laminar locations, and pyramidal cells accounted for 89% of cells in the whole CA1 soma region, which was consistent with results in pciSeq. Notably, ClusterMap can provide more detailed cell morphology and increase the number of identified cells (from 1,420 to 3,113 for MERFISH, and from 893 to 1,962 for osmFISH).

In conclusion, mouse brain data from four representative in situ transcriptomic methods was analyzed, and the utility and universality of ClusterMap was validated under different experimental methods. ClusterMap successfully produced comparable results across different methods with negligible modification applied.

Example 5: 3D ClusterMap Analyses in Thick Tissue Blocks 3D in situ transcriptomics data analysis is considered even more challenging because it is generally infeasible by manual labeling. However, 3D volumetric imaging and analysis are required to understand the structural and functional organization of complex organs. In this regard, exploring ClusterMap's ability to analyze 3D in situ transcriptomics is particularly desired. ClusterMap was applied to two 3D thick-tissue samples: STARmap cardiac organoid 8-gene dataset[25] and STARmap mouse V1 28-gene dataset[8] (Table 1). The 3D data were analyzed following the sample protocol described in FIG. 1B. In the 3D cardiac organoid sample, hierarchical clustering[26] separated cells into three categories with distinct molecular signatures (FIGS. 6A-6C): mesenchymal stem cells (MSCs), induced pluripotent stem cells (iPSCs), and cardiomyocytes were annotated by enrichment of MSCs, CD44, 1; iPSCs, Nanog, 2; and cardiomyocytes, TNNI1, MYH7, MYL7, ATP2A2, 3 (FIGS. 11A-11C). The 100-μm-thick sample of mouse V1 includes all six cortical layers and the corpus callosum, in which up to 24,000 cells were identified and 3D clustered into eleven cell types (FIGS. 6D-6E and 11D-11G). The results showed similar spatial distribution with previously published results, which used conventional fluorescence image segmentation: excitatory neurons exhibited a gradient distribution, with the spatial density of each subtype gradually decaying to adjacent layers across the entire 3D space; inhibitory neurons showed a more dispersed distribution; and non-neuronal cells largely located in the white matter and layer 1 (FIG. 6E). Seven 3D tissue regions were determined based on their corresponding cell-type compositions (FIGS. 6F-6G). The 3D cell-cell interactions in the mouse V1 were further characterized, and the average compositional neighboring cell-types were computed (FIGS. 6H-6K). In the minority inhibitory neurons, a similar self-associative pattern as in the previously published findings was observed: the nearest neighbor of any inhibitory neuron tends to be its own subtype. Three examples of inhibitory neuronal types (Pv, Sst, Vip) interactions are presented in FIGS. 6H-6J, respectively.

Spatial RNA localization intrinsically contains information related to biological structures and cell functions, which are yet to be effectively retrieved. ClusterMap exemplifies a computational framework that combines spatial and high-dimensional transcriptomic information from in situ single-cell transcriptomics to identify subcellular, cellular, and tissue structures in both 2D and 3D space. ClusterMap jointly clusters the physical density and gene identity of RNAs, which provided higher accuracy than clustering only using RNA density or gene identity (FIGS. 28A-28P). Compared with previous methods 43 (FIGS. 22-23, 29A-29D), ClusterMap showed consistently high performance in both simulated and biological datasets. It is widely applicable to various experimental methods including, but not limited to, STARmap, MERFISH, pciSeq, and osmFISH. As a result, ClusterMap accurately created RNA-annotated subcellular and cellular atlases from in situ transcriptomic data across diverse tissue samples with different cell density, morphologies, and connections. ClusterMap also markedly expanded knowledge of cellular organization across all scales from subcellular organelles through cell-type maps to organs and enabled further characterization of the local microenvironment for individual cells. The initial successful demonstration described herein suggests that in situ transcriptomic profiles contained unexplored biological and structural information that could be further extracted by new computational strategies.

Furthermore, ClusterMap is easy to scale up to a large dataset covering large-volume organ-level imaging data. Beyond spatial transcriptomic data, ClusterMap can be generalized and applied to other 2D and 3D mapped high-dimensional discrete signals (e.g., protein or signaling molecule imaging data)[27]. ClusterMap can also be extended by combining with other types of biological features (e.g., subcellular organelles, cell shapes, etc.) to uncover the basic principles of how gene expression shapes cellular architecture and tissue morphology[28].

TABLE 1

| Dataset | Method | Tissue | # Gene | # Cell | # Cell type | FIG. | Notes |
|---------|--------|--------|--------|--------|-------------|------|-------|
| STARmap mouse V1 1020-gene | STARmap | Mouse brain primary visual cortex | 1,020 | 1,447 | 16 | FIG. 1c, FIG. 2, Supplementary FIG. 2 | Source: Wang et al., 2018. 2D analysis. |
| STARmap mouse placenta 903-gene | STARmap | Mouse brain primary visual cortex | 903 | 7224 | 11 | FIG. 3, FIG. 4, Supplementary FIG. 3 | New data, 2D analysis. |
| MERFISH | MERFISH | Mouse brain | 140 | 3,113 | 10 | FIG. 5, | Source: |

TABLE 1-continued

| Dataset | Method | Tissue | # Gene | # Cell | # Cell type | FIG. | Notes |
|---|---|---|---|---|---|---|---|
| mouse POA | | hypothalamic preoptic region | | | | Supplementary FIG. 4 | Codeluppi et al., 2018. 2D analysis. |
| pciSeq mouse isocortex | pciSeq | Mouse brain isocortex region | 98 | 982 | 8 | FIG. 5, Supplementary FIG. 4 | Source: Qian et al., 2020. 2D analysis. |
| osmFISH mouse SSp | osmFISH | Mouse brain somatosensory cortex | 33 | 1,962 | 19 | FIG. 5, Supplementary FIG. 4 | Source: Codeluppi et al., 2018. 2D analysis. |
| STARmap cardiac organoid 8-gene | STARmap | Cardiac organoid | 8 | 1,519 | 3 | FIG. 6, Supplementary FIG. 5 | New data, 3D analysis. |
| STARmap mouse V1 28-gene | STARmap | Mouse brain primary visual cortex | 28 | 24,590 | 11 | FIG. 6, Supplementary FIG. 5 | Source: Wang et al., 2018. 3D analysis. |

Methods

Data Pre-Processing:

1. Thin-Section STARmap Data Processing

All image processing steps were implemented using MATLAB R2019b and related open-source packages in Python 3.6 according to Wang et al., 2018[6].

Image Preprocessing: For better unity of the illuminance and contrast level of the fluorescence raw image, a multi-dimensional histogram matching was performed on each image, which used the image of the first color channel in the first sequencing round as a reference.

Image Registration: Global image registration for aligning spatial position of all amplicons in each round of STARmap imaging was accomplished using a three-dimensional Fast Fourier transform (FFT) to compute the cross-correlation between two image volumes at all translational offsets. The position of the maximal correlation coefficient was identified and used to transform image volumes to compensate for the offset.

Spot Finding: After registration, individual spots were identified separately in each color channel on the first round of sequencing. For this experiment, spots of approximately 6 voxels in diameter were identified by finding local maxima in 3D. After identifying each spot, the dominant color for that spot across all four channels was determined on each round in a 5*5*3 voxel volume surrounding the spot location.

Spots and Barcode Filtering: Spots were first filtered based on fluorescence quality score. Fluorescence quality score is the ratio of targeted single-color channel to all color channels, which quantified the extent to which each spot on each sequencing round came from one color rather than a mixture of colors. Each spot is assigned with a barcode representing a specific kind of gene. The barcode codebook that contains all gene barcodes was converted into color space, based on the expected color sequence following 2-base encoding of the barcode DNA sequence[6]. Spot color sequences that passed the quality threshold and matched sequences in the codebook were kept and identified with the specific gene that that particular barcode represented; all other spots were rejected. The high-quality spots and associated gene identities in the codebook were then saved out for downstream analysis.

2D Cell Manual Segmentation: Two different methods were used to identify cell boundaries. First, the manually labeled segmentation masks from the original reference (Wang et al. 2018[6]) were obtained as baseline. Second, nuclei were automatically identified by the StarDist 2D machine learning model (Schmidt et al. 2018[15]) from a maximum intensity projection of the DAPI channel following the final round of sequencing. Then cell locations were extracted from the segmented DAPI image. Cell bodies were represented by the overlay of DAPI staining and merged amplicon images. Finally, a marker-based watershed transform was then applied to segment the thresholded cell bodies based on the combined thresholded cell body map and identified locations of nuclei. For each segmented cell region, a convex hull was constructed. Points overlapping each convex hull in 2D were then assigned to that cell, to compute a per-cell gene expression matrix.

2. Thick-Tissue STARmap Data Processing

3D Image Registration: The displacement field of each imaging round was first acquired by registering the DAPI channel of each round to first-round globally by 3D FFT. Each sequencing image was applied with the corresponding transform of its round.

Spot Finding: After registration, individual spots were identified separately in each color channel on each round of sequencing. The extended local maxima in 3D were treated as an amplicon location. After identifying each spot, the dominant color for that spot across all four channels was determined on each round in a 3*3*3 voxel volume surrounding the spot location.

Computation of Neighborhood Gene Composition (NGC)

To compute the neighborhood gene expression composition of each spot, a spatially circular (2D) or spherical (3D) window over every spot (5) was considered, and the number of each gene-type in the window was counted. The raw count of each window was normalized to a percentage for downstream analysis. The radius of the window R can be chosen either manually or by statistics to be close to the averaged size of organelles and cells for subcellular and single-cell analysis, respectively.

For a dataset with T kinds of sequenced gene, the definition of an NGC vector to the measured spot i is composed of the number of each gene-type windowed by radius R to the measured spot i.

$$NGC(i) = <Num_{Gene\,1}, Num_{Gene\,2}, \ldots, Num_{Gene\,t}, \ldots,$$

$$Num_{Gene\,T} > Num_{Gene\,t} = \#\left\{S_t^1, S_t^2, \ldots, S_t^j, \ldots, S_t^{Num_{Gene\,t}}\right\}, t \in N^T$$

$$Distance\{S_t^j, i\} < R, t \in N^T, j \in N^{Num_{Gene\,t}}$$

Density Peak Clustering (DPC)

Based on the original DPC algorithm[18], two quantities were first computed: local density $\rho$ and distance $\delta$ of every spot. The density was estimated by a Gaussian kernel with variance $d_c$. The variance $d_c$ is supposed to be close to the averaged radius R of cells for cellular segmentation. R can be used as $d_c$. The definition of local density $\rho$ and distance $\delta$ for spot i is:

$$\rho_i = \sum_j I(d_{ij} - d_{max}) * e^{-(d_{ij}/R)^2}$$

$$\delta_i = \min(d_{ij}), j: \rho_j > \rho_i$$

Note that $I(x)=1$ if $x<0$, else $I(x)=0$, and $d_{ij}$ is the distance between spot i and j. The optional parameter $d_{max}$ is a striction on the maximum radius of the cell. For the point with the highest density, based on principles of DPC[18], its distance value was taken to the highest $\delta$ value. Note that for large data sets, the analysis is insensitive to the choice of $d_c$ and results are robust and consistent.

After computing these two quantities of every spot, a multiplication decision graph was generated by computing $\gamma$, the product of $\rho$ and $\delta$ and plotting every spot's $\gamma$ value in decreasing order. Since the cell centers have both high local density and much higher distance at the same time, the points with distinguishably higher $\gamma$ values were chosen as cluster centers. The 'elbow point' was chosen as the cutoff point in the multiplication decision graph where its $\gamma$ value becomes no longer high and its change tends to be flat. The number of clusters N is equal to the number of points prior to the elbow point.

Next, each remaining point was assigned to one of the N clusters respectively in a descending order of $\rho$ value in a single step manner. Each remaining spot was assigned to the same cluster as its assigned-nearest neighbor. Each cluster was regarded as one cell. Finally, cells were filtered by limiting the minimum number of spots and genes expressed in one cell.

Integration of the Physical and NGC Coordinate

The physical coordinates denote the spatial location of spots and the NGC coordinates denote the gene location of spots in a high-dimensional NGC space. For spot i, its physical and NGC coordinate are:

$$P(i) = \langle x_i, y_i(z_i) \rangle$$

$$NGC(i) = \langle Num_{Gene\,1}, Num_{Gene\,2}, \ldots, Num_{Gene\,t}, \ldots, Num_{Gene\,T} \rangle$$

Inversed Spearman correlation coefficient was used to measure the distance between two NGCs. Integration of these two coordinates can be distance-level, clustering-level, and guided-information based.

Distance-level integration: The NGC and physical coordinates were integrated, and the joint P-NGC coordinate was generated from the normalized NRC and physical coordinates over each spot. Specifically, the physical and NGC distances information between i and its neighboring spots was combined, and the joint distance was used as the metric to measure relationships between spots. Mathematically, the parameter $d_{ij}$ used in the calculation of $\rho$ and $\delta$ in PDC is:

$$d_{ij} = \frac{Distance\{P(i), P(j)\}}{SpearmanCorr\{NGC(i), NGC(j)\}}$$

The DPC algorithm was then performed, and the cells were found. Distance-level integration was used for MER-FISH mouse POA[3], pciSeq mouse isocortex[4], osmFISH mouse SSp[5], STARmap cardiac organoid 8-gene, and STARmap mouse V1 28-gene dataset[6].

Then, the combined distances were used to perform the DPC algorithm for cell segmentation. It was noted that sometimes the inconsistency of spot relationships between physical distance and Spearman correlation may break the physical connectivity of spots within one cell. In this case, a 0.5 lower boundary cutoff may be applied to correlation values. Also, the DPC algorithm implementation was modified by using joint distances to find cell centers and then physical distances to assign other spots to cell centers to preserve the physical connectivity of cells. This integration method was universal to any dataset.

Clustering-level integration: Since data points can be clustered by DPC using physical coordinates and NGC coordinates respectively, integration can then be done on the clustering level. To take these two variables into consideration, joint clustering methods can be explored. To take the correlations between variables into account, a pre-specified objective function can also be optimized.

Guided information-based integration: Spots were first separated into clusters with physical coordinates, and then the clustering was corrected with guided information extracted from the NGC coordinates. To extract the guided information, the neighbors of spot i that were at the distance of R-2R to spot i in the physical space were identified. Then these spots' NGC distances to spot i were computed. If the maximum of the NGC distances from spot k was higher than a threshold, it was evaluated if spot k and spot i belong to the same cluster. If so, as they were both distant from spot i in physical and NGC spaces, this indicated the cell which spot i belongs to may be under-clustered. The overall probability of each cell being missed was counted, and the highly potentially incorrect cells with more than 50% probability to be missed were re-clustered. Guided-information based integration was used for STARmap mouse V1 1020-gene[6] and STARmap mouse placenta 903-gene dataset.

Pre- and Post-Processing for Quality Control.

First, a background identification step to filter input spots was used as pre-processing. Specifically, regions with low-density spots (mRNA or DAPI sampled spots) were considered as noisy background and were removed for the downstream analysis. Second, the noise rejection based on cluster halo (i.e., noise) identification in the original density peak clustering algorithm[18] was used as post-processing. Specifically, instead of introducing a noise-signal cutoff, a border region for each cell was found, then the point of highest density of spots (mRNA or DAPI sampled spots) was identified within its border region as $\rho_b$, and finally points within the cell were considered that showed higher density than $\rho_b$ as the robust assignment for spots in the border region and others as noise. These quality control steps were included in the analysis of three representative in situ transcriptomic datasets[3-5] (FIGS. 21A-21C).

41

Subcellular Segmentation

To perform subcellular segmentation and construct nucleus boundaries, the quantity NGC over each spot in an individual cell was first computed. The difference between NGC for subcellular segmentation and that for cellular segmentation is the radius of the window R. R should be either chosen manually or by statistics to be close to the averaged size of organelles. In addition, when the number of sequenced genes is limited, the NGC can be computed using a mesh graph by Delaunay triangulation of spots that models the relationship between RNA spots in the cell. A ring of spots that are neighbors of the central spot in the mesh graph is considered to locate most closely around the central cell. For a dataset with TR kinds of gene the definition of an NGC vector to the measured spot i is the composition of gene-types in its closest neighbors:

$$NGC(i) = <Num_{Gene\ 1}, Num_{Gene\ 2}, \dots , Num_{Gene\ t}, \dots ,$$

$$Num_{Gene\ TR} > Num_{Gene\ t} = \#\{S_t^1, S_t^2, \dots , S_t^j, \dots , S_t^{Num_{Gene\ t}}\}, t \in N^{TR}$$

$$S_t^j \text{ connects directly with spot } i, \forall\ j \in N^{Num_{Gene\ t}},$$

Then, similar to distance-level integration, a joint P-NGC coordinate from the normalized NGC and physical coordinates over each spot was generated:

$$P–NGC(i) = [NGC(i), \lambda * P(i)]$$

Here the optional parameter $\lambda$ can control the influence of physical coordinates, depending on conditions. K-means clustering was then used to cluster spots into two regions, with one for nucleus and one for cytoplasm. Under a chosen $\lambda$, K-means clustering was performed 100 times with a different seed each time to find the consensus clustering results. Finally, a convex hull was constructed based on the nucleus spots, denoting the nucleus boundary.

Cell-Type Classification

A two-level clustering strategy was applied to identify both major and sub-level cell types in the dataset. Processing steps in this section were implemented using Scanpy v1.6.0 and other customized scripts in Python 3.6 and applied according to Wang et al., 2018[6]. After filtration, normalization, and scaling, principal-components analysis (PCA) was applied to reduce the dimensionality of the cellular expression matrix. Based on the explained variance ratio, the top PCs were used to compute the neighborhood graph of observations. Then the Louvain algorithm[22] was used to identify well-connected cells as clusters in a low dimensional representation of the transcriptomics profile. Clusters enriched for the excitatory neuron marker Slc17a7 (vesicular glutamate transporter), inhibitory neuron marker Gad1, were manually merged to form two neuronal cell clusters, and then other cells represented non-neuronal cell populations. The cells were displayed using the uniform manifold approximation and projection (UMAP) and color-coded according to their cell types. The cells for each top-level cluster were then sub-clustered using PCA decomposition followed by Louvain clustering[22] to determine sub-level cell types. For dataset pciSeq mouse CA1, the probabilistic model in pciSeq[4] was used to assign ClusterMap-identified cells to scRNA seq data and find cell-types. For dataset MERFISH mouse POA and osmFISH mouse SSp, hierarchical clustering was applied to find cell types that matched previous reported cell types. For other datasets, Louvain clustering algorithm was applied to find cell types.

Construct Tissue Regions

1. Neighborhood Cell-Type Composition (NCC)

To construct tissue regions, a global quantity was computed: Neighborhood Cell-type Composition (NCC) over each cell (C). A spatially circular (2D) or spherical (3D) window over every cell was considered, and the composition of cell-types in the window was estimated. The radius of the window RC was chosen manually or by statistics of distances between cells to be as reasonable as possible.

For a dataset with TC kinds of gene, the definition of an NCC vector of the measured cell i was the composition of cell-types in the defined window that had radius RC to the measured cell i.

$$NCC(i) = <Num_{Cell\ type\ 1}, Num_{Cell\ type\ 2}, \dots ,$$

$$Num_{Cell\ type\ t}, \dots , Num_{Cell\ type\ TC} > Num_{Cell\ type\ t} =$$

$$\#\{C_t^1, C_t^2, \dots , C_t^j, \dots , C_t^{Num_{Cell\ type\ t}}\}, t \in N^{TC}$$

$$Distance\{C_t^j, i\} < RC, t \in N^{TC}, j \in N^{Num_{Cell\ type\ t}}$$

2. K-Means Clustering

Tissue region signatures were identified using information from both NCC and physical locations of cells. Then a joint P-NCC coordinate was generated from normalized NCC and physical coordinates over each cell:

$$P–NCC(i) = [NCC(i), \lambda * P(i)]$$

Here, the optional parameter $\lambda$ can control the influence of physical coordinates based on conditions. K-means clustering was then used on these high dimensional P-NCC coordinates to cluster cells into a pre-defined number of regions. Under a chosen $\lambda$, K-means clustering was performed 100 times with a different seed each time, and the most frequent clustering results with interpretable biological meanings was regarded as final clustering. Finally, regions were projected spatially back onto the cell-type map.

Compare with Expert-Annotated Labels

The accuracy of cell identification by ClusterMap was evaluated with corresponding eight expert annotated STARmap[6] datasets (FIG. 7C). Cells defined by ClusterMap consist of spots with physical locations while labels in the expert annotated STARmap datasets are connected components. The accuracy was defined as the percentage of ClusterMap-identified cells of which the center coordinates are correctly located within the labeled cells connected components. Specifically, for each labeled connected component, it was checked if there was only one predicted cell by ClusterMap within the region. More than one cell was counted as over-segmentation and no cell as under-segmentation. In other words, for each labeled connected component, it was assessed whether there was only one cell center (cluster peak defined in DPC[18]) within the region. More than one cell centers were counted as over-clustering and no cell centers as under-clustering. The percentage was calculated by dividing the number of all incorrect cells (including over-clustered and under-clustered ones) by the total number of cells identified by ClusterMap.

The correlation of the single-cell gene expression profiles was also compared between ClusterMap and expert-annotated labels in STARmap[6] mouse V1 1020-gene (FIGS. 24A-24B). For the shared 13 cell types identified in cells from both ClusterMap and manual annotation, the average gene expression values were computed across 1020 genes. Then, the Pearson correlation and p-value was calculated between two cell-type-by-gene-expression matrices and plotted as heatmaps in FIGS. 24A-24F. High correlation values and low p-values were observed in matched cell types in between ClusterMap and expert-annotated labels, which further validated the performance of ClusterMap.

Integration with scRNA-Seq

The cell identification performance was validated by performing a leave-one-out benchmark. Before integration[20,21], the scRNA-seq and in situ sequencing data were pre-processed using the Seurat package.

1. Log-normalization: Divide the gene counts for each cell by the total counts for that cell and multiply by the scale. Factor=10,000. Then perform natural-log transformation using log 1p.
2. Scaling the data: Subtract the average expression for each gene and divide the centered gene expression profiles by their standard deviation.

For a shared gene list of scRNA-seq and in situ sequencing data with n genes, one non-repeating gene was left out in each round, and the rest n−1 genes were used for integration with scRNA-seq data and then the prediction of the left-out gene's expression profile. The integration and prediction steps were performed using FindTransferAnchors and TransferData functions in Seurat, which identified anchors between the reference (scRNA-seq) and query (in situ sequencing) dataset in reduced dimensions (reduction='cca') using mutual nearest neighbors and used these anchors to predict the left-out gene expression.

Next, the Pearson correlation of measured and the predicted profile was calculated as the benchmark metrics. Finally, the correlation between ClusterMap or manual annotation was compared with scRNA-seq, and quantitative analyses were performed using violin plot, which showed the distribution of correlation for different annotation methods, and scatter plot, which represented the correlation values of these two methods for each gene.

Label Transfer

Cell type labels from scRNA-Seq dataset were projected onto spatially resolved cells from STARmap dataset by using the Seurat v3 integration method according to Stuart et al. 2019[20]. First, both datasets were preprocessed (normalization & scaling) and a subset of features (e.g., genes) exhibiting high variability was extracted. For STARmap dataset, all genes profiled were used whereas in scRNA-Seq dataset, the top 2,000 most variable genes identified by "FindVariableFeatures" function were used in downstream integration. Then "FindTransferAnchors" (reduction="cca") and Transfer Data functions were used to map the labels onto spatially resolved cells from the STARmap dataset. After label transferring, 6,672 out of 7,224 cells were observed with high-confidence cell type predictions (prediction score >0.5), 8 out of 10 cell type labels were resolved.

Performance Analysis of Cell Segmentation in ClusterMap

The performance of ClusterMap was further evaluated using the following three conditions: (1) only physical distances, (2) only neighborhood gene composition (NGC) distances, and (3) joint physical and NGC distances from published STARmap V1 1020-gene datasets 6 with ground truth labels in FIGS. 28A-28E. The results showed that solely using physical distance or NGC distance for cell segmentation, ClusterMap was less effective when there was a lack of RNA signals in nuclei or when cells were crowded, as shown in FIG. 28A. ClusterMap with an integrative physical and NGC information can overcome these issues and provide a better cell segmentation, with lower under-/over-segmentation scores and higher accuracy (FIGS. 28A-28C). To further examine and highlight the difference, a toy model was built by assigning random gene identities (FIG. 28D) or identical gene identities (FIG. 28E) to RNA spots, and then the performance of ClusterMap was tested by using the aforementioned three conditions. As shown in FIGS. 28D-28E, the results further supported the conclusion that gene identity was important to generate a more accurate cell segmentation result. In conclusion, ClusterMap incorporated physical and neighborhood gene expression information to improve cell segmentation performance.

Performance analysis of ClusterMap cell segmentation was provided in mouse placenta tissue where the cells were of vastly different sizes and shape, and cell radius dc ranged from 28 to 128 pixels (2.65-12.12 μm) (FIG. 28F). With the radius used in ClusterMap increasing from 8 to 178 pixels, the number of cells decreased from 270 to 220. The accuracy increased first as the radius increased from 8 to 28 pixels, then remained relatively stable, and finally dropped when the radius exceeded 148 pixels (FIGS. 28G-28H). The radius of 83 pixel with the highest accuracy was checked to be a frequent radius for most cells.

Figure 28L:
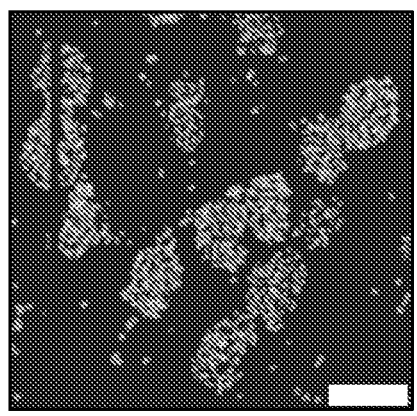
Figure 28M:
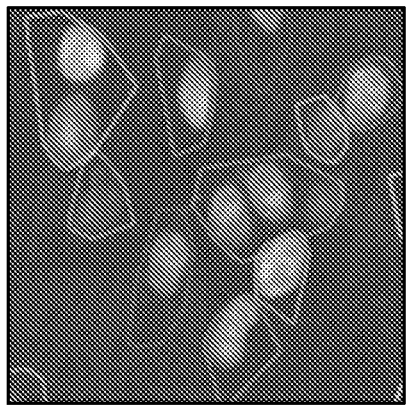

Finally, it was shown that in the cases when RNAs populate nucleus and cytoplasm, incorporation of DAPI signal will improve the performance of ClusterMap. Tests were performed on STARmap mouse V1 1020-gene datasets where thousands of genes have been in situ sequenced and RNA was enriched in the nucleus (FIG. 28I, FIG. 28L). Two examples of the hippocampus regions comparing the performance of ClusterMap with and without DAPI signal input are shown in FIGS. 28I-28N. The results show that the integration of DAPI signals with RNA signals substantially decreased the percentage of over-/under-segmented cells and improved accuracy from 0.75 to 0.81 (FIGS. 28O-28P).

Sub-Clustering by Cell Niche Analysis

Sub-clustering cell types in STARmap mouse placenta 903-gene dataset: First, for 7224 ClusterMap-identified cells, two matrices were constructed: (1) cell by gene matrix, which is 7224×903 dimensions; (2) cell by cell niche composition matrix, which is 7224×12 dimensions. Next, for N cells of a certain cell type T, a N×903 subset matrix and a N×12 subset matrix was arrived at, which provided gene expression and cell niche composition information about the N cells. Then, Louvain clustering was used to cluster the N×903 gene expression matrix into S sub-types, and K-means clustering was used to cluster the N×12 cell niche composition matrix into S sub-types. Finally, N cells were mapped to UMAP based on their gene expression and are shaded based on two data clustering. Adjusted Rand index of two data clustering was computed.

Statistics and Reproducibility

Figure 2E:

In FIG. 2E, the number of cells per cell type in each region are as follows: from L1 to HPC, eL2/3-A: 3, 164, 22, 12, 6, 1, 0; eL2/3-B: 0, 33, 4, 3, 2, 0, 0, 0; eL4: 0, 7, 135, 7, 0, 0, 0; eL5: 0, 1, 9, 62, 39, 2, 5; eL6: 0, 1, 0, 19, 133, 0, 2; Hpc: 0, 0, 0, 1, 0, 0, 9; Pv: 0, 7, 7, 16, 5, 0, 2; Vip: 4, 15, 2, 2, 1, 1, 2; Sst: 0, 6, 6, 13, 3, 0, 12; Others-In: 0, 0, 3, 6, 1, 2, 6; Astro: 7, 24, 12, 24, 14, 19, 21; Endo: 9, 39, 25, 30, 16, 3, 12; Micro: 6, 20, 6, 12, 3, 8, 7; Other: 4, 41, 22, 50, 20, 6, 7; Oligo: 1, 5, 7, 23, 13, 100, 15; and Smc. 10, 0, 0, 1, 0, 0, 1. In FIG. 3H, the number of cells in each region is as follows: I: 1457; II: 1796; III: 2816; IV: 777; and V: 378. In

45

FIG. 6G, the number of cells in each cell type is as follows: Cardiomyocytes, 929; induced pluripotent stem (iPS) cells, 489; and mesenchymal stem cells (MSC), 101. In FIG. 6G, the number of cells per cell type in each region are as follows: from L1 to SC, eL2/3: 31, 1767, 965, 119, 113, 9, 173; eL4: 16, 722, 1596, 168, 89, 4, 136; eL5: 5, 39, 92, 1000, 596, 6, 202; eL6: 11, 74, 191, 541, 2500, 18, 550; Pv: 4, 6, 136, 183, 94, 7, 111; Sst: 97, 72, 101, 196, 81, 11, 136; Vip: 3, 22, 28, 66, 14, 1, 28; Other-In: 30, 78, 74, 83, 112, 39, 68; Astro: 275, 92, 65, 106, 104, 92, 256; and Oligo-A: 28, 33, 33, 80, 95, 1014, 183; Oligo-B: 81, 63, 86, 158, 131, 536, 257. In FIG. 7C, the number of manual annotated cells in each sample are as follows: BZS: 1227; BZ9: 1318; BZ14:1203; BZ19: 1370; BD2: 951; BD6: 788; BY1: 1653; BY3:1008.

Animal Experiment

C57BL/6 (female, 8-12 weeks) mice were purchased from the Jackson Laboratory (JAX). Animals were housed 2-5 per cage and kept on a reversed 12-hour light-dark cycle with ad libitum food and water. For the mouse placenta dataset, snap-frozen tissue sections from C57BL/6 J×CAST/EiJ matings were used, and STARmap was performed to measure expression of 903 genes on the E14.5 mouse placenta tissue slices. Sex: female. Age: E14.5. Strain: C57BL/6 J×CAST/ EiJ matings. Housing conditions: Mice were housed under standard barrier conditions at the Whitehead Institute for Biomedical Research. All procedures involving animals at the Broad Institute were conducted in accordance with the U.S. National Institutes of Health Guide for the Care and Use of Laboratory Animals under protocol number 0255-08-19. Experimental procedures were approved by the Institutional Animal Care and Use Committee of the Broad Institute of MIT and Harvard under protocol number 0255-08-19.

REFERENCES

1. Stark, R., Grzelak, M. & Hadfield, J. RNA sequencing: the teenage years. *Nat. Rev. Genet.* 20, 631-656 (2019).
2. Crosetto, N., Bienko, M. & van Oudenaarden, A. Spatially resolved transcriptomics and beyond. *Nat. Rev. Genet.* 16, 57-66 (2015).
3. Moffitt, J. R. et al. Molecular, spatial, and functional single-cell profiling of the hypothalamic preoptic region. *Science* 362, eaau5324 (2018).
4. Qian, X. et al. Probabilistic cell typing enables fine mapping of closely related cell types in situ. *Nat. Methods* 17, 101-106 (2020).
5. Codeluppi, S. et al. Spatial organization of the somatosensory cortex revealed by osmFISH. *Nat. Methods* 15, 932-935 (2018).
6. Wang, X. et al. Three-dimensional intact-tissue sequencing of single-cell transcriptional states. *Science* 361, eaat 5691 (2018).
7. Eng, C.-H. L. et al. Transcriptome-scale super-resolved imaging in tissues by RNA seqFISH. *Nature* 568, 235 (2019).
8. Lee, J. H. et al. Fluorescent in situ sequencing (FISSEQ) of RNA for gene expression profiling in intact cells and tissues. *Nat. Protoc.* 10, 442-458 (2015).
9. Perkel, J. M. Starfish enterprise: finding RNA patterns in single cells. *Nature* 572, 549-551 (2019).
10. Kishi, J. Y. et al. SABER amplifies FISH: enhanced multiplexed imaging of RNA and DNA in cells and tissues. *Nat. Methods* 16, 533-544 (2019).
11. Thomas, R. M. & John, J. A review on cell detection and segmentation in microscopic images. In 2017 *Interna-*

46

*tional Conference on Circuit, Power and Computing Technologies (ICCPCT)*, 1-5 (2017).
12. Moen, E. et al. Deep learning for cellular image analysis. *Nat. Methods* 16, 1233-1246 (2019).
13. Coelho, LP., Shariff, A. & Murphy, R. F. Nuclear segmentation in microscope cell images: a hand-segmented dataset and comparison of algorithms. In 2009 *IEEE International Symposium on Biomedical Imaging: From Nano to Macro,* 518-521 (2009).
14. Arganda-Carreras, I. et al. Trainable Weka Segmentation: a machine learning tool for microscopy pixel classification. *Bioinformatics* 33, 2424-2426 (2017).
15. Schmidt, U., Weigert, M., Broaddus, C. & Myers, G. Cell detection with star-convex polygons. In *Medical Image Computing and Computer Assisted Intervention— MICCAI 2018* (eds. Frangi, A. F. et al.) 265-273 (Springer International Publishing, 2018).
16. Lein, E., Borm, L. E. & Linnarsson, S. The promise of spatial transcriptomics for neuroscience in the era of molecular cell typing. *Science* 358, 64-69 (2017).
17. Nitzan, M., Karaiskos, N., Friedman, N. & Rajewsky, N. Gene expression cartography. *Nature* 576, 132-137 (2019).
18. Rodriguez, A. & Laio, A. Clustering by fast search and find of density peaks. *Science* 344, 1492-1496 (2014).
19. Wang, G. et al. Spatial organization of the transcriptome in individual neurons. Preprint at biorxiv.org/content/ 10.1101/2020.12.07.414060v1 (2020).
20. Stuart, T. et al. Comprehensive integration of single-cell data. *Cell* 177, 1888-1902 (2019).
21. Abdelaal, T., Mourragui, S., Mahfouz, A. & Reinders, M. J. T. SpaGE: spatial gene enhancement using scRNA-seq. *Nucleic Acids Res.* 48, e107 (2020).
22. Blondel, V. D., Guillaume, J.-L., Lambiotte, R. & Lefebvre, E. Fast unfolding of communities in large networks. *J. Stat. Mech.* 10, P10008 (2008).
23. Park, J. et al. Segmentation-free inference of cell types from in situ transcriptomics data. Preprint at biorxiv.org/ content/10.1101/800748v1 (2019).
24. Goltsev, Y. et al. Deep profiling of mouse splenic architecture with CODEX multiplexed imaging. *Cell* 174, 968-981 (2018).
25. Li, Q. et al. Cyborg organoids: implantation of nano-electronics via organogenesis for tissue-wide electro-physiology. *Nano Lett.* 19, 5781-5789 (2019).
26. Rokach, L., Lior, R. & Oded, M. In *Data Mining and Knowledge Discovery Handbook* 321-352 (2005).
27. McCabe, A., Dolled-Filhart, M., Camp, R. L. & Rimm, D. L. Automated quantitative analysis (AQUA) of in situ protein expression, antibody concentration, and prognosis. *J. Natl. Cancer Inst.* 97, 1808-1815 (2005).
28. He, B. et al. Integrating spatial gene expression and breast tumor morphology via deep learning. *Nat. Biomed. Eng.* 666, 1-8 (2020).
29. Bradski, G. The OpenCV library. *Dr Dobb's J. Software Tools* 25, 120-125 (2000).
30. Goddard, T. D., Huang, C. C. & Ferrin, T. E. Visualizing density maps with UCSF Chimera. *J. Struct. Biol.* 157, 281-287 (2007).
31. Hunter, J. D. Matplotlib: a 2D graphics environment. *Comput. Sci. Eng.* 9, 90-95 (2007).
32. Jones, E., Oliphant, T. & Peterson, P. SciPy: open source scientific tools for Python. scipy.org/(2001).
33. MacQueen, J. B. Some methods for classification and analysis of multivariate observations. In *Proc. of the fifth*

*Berkeley Symposium on Mathematical Statistics and Probability,* 281-297 (University of California Press, Berkeley, 1967).

34. Higham, D. J. & Higham, N. J. *MATLAB Guide,* 150, (Siam, Philadelphia, 2016).

35. McInnes, L., Healy, J., & Melville, J. UMAP: uniform manifold approximation and projection for dimension reduction. Preprint at arxiv.org/abs/1802.03426 (2018).

36. McKinney, W. Data structures for statistical computing in Python. In *Proc. 9th Python in Science Conference* 51-56 (2010).

37. Oliphant, T. E. *Guide to NumPy* 1st edn 1, (Trelgol Publishing USA, 2006).

38. Pedregosa, F. et al. Scikit-learn: machine learning in Python. *J. Machine Learn. Res.* 12, 2825-2830 (2011).

39. Pérez, F., Granger, B. E. & Hunter, J. D. Python: an ecosystem for scientific computing. *Comput. Sci. Eng.* 13, 13-21 (2011).

40. Rueden, C. T. et al. ImageJ2: ImageJ for the next generation of scientific image data. *BMC Bioinformatics* 18, 529 (2017).

41. Heideman, M., Johnson, D., & Burrus, C. Gauss and the history of the fast Fourier transform. *IEEE ASSP Magazine* 1, 14-21 (1984).

42. van derWalt, S. et al. scikit-image: image processing in Python. *Peer J.* 2, e453 (2014).

43. Petukhov, V. et al. Bayesian segmentation of spatially resolved transcriptomics data. doi.org/10.1101/2020.10.05.326777v1 (2020).

44. Franti, P. & Sieranoja, S. K-means properties on six clustering benchmark datasets. *Appl. Intell.* 48, 4743-4759 (2018).

45. Qu, D., McDonald, A., Whiteley, K. J., Bainbridge, S. A. and Adamson, S. L. Layer-Enriched Tissue Dissection Of The Mouse Placenta In Late Gestation. *In The Guide To Investigation Of Mouse Pregnancy,* p. 529-535 (Academic Press, 2014).

46. Chatterjee, S. et al. Nontoxic, double-deletion-mutant rabies viral vectors for retrograde targeting of projection neurons. *Nat. Neurosci.* 21, 638-646 (2018).

47. Yichun, He. et al. ClusterMap for multi-scale clustering analysis of spatial gene expression, ClusterMap: multi-scale clustering analysis of spatial gene expression. doi.org/10.24433/CO.607/CO.6072400.v1 (2021).

INCORPORATION BY REFERENCE

The present application refers to various issued patent, published patent applications, scientific journal articles, and other publications, all of which are incorporated herein by reference. The details of one or more embodiments of the invention are set forth herein. Other features, objects, and advantages of the invention will be apparent from the Detailed Description, the Figures, the Examples, and the Claims.

EQUIVALENTS AND SCOPE

In the articles such as "a," "an," and "the" may mean one or more than one unless indicated to the contrary or otherwise evident from the context. Embodiments or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claims that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the embodiments. Because such embodiments are deemed to be known to one of ordinary skill in the art, they may be excluded even if the exclusion is not set forth explicitly herein. Any particular embodiment of the invention can be excluded from any embodiment, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended embodiments. Those of ordinary skill in the art will appreciate that various changes and modifications to this description may be made without departing from the spirit or scope of the present invention, as defined in the following embodiments.

What is claimed is:

1. A method of identifying cells in an image, the method comprising:

receiving, for each of a plurality of spots in the image, a spatial location of the spot in the image and genetic information associated with the spot, wherein each spot corresponds to one or more pixels in the image;

based on the spatial location and the genetic information for each of the plurality of spots:

determining at least one spot that represents a cell center by, for each of the plurality of spots:

calculating, based on the spatial location and the genetic information, a local density of the spot using at least one computer processor; and calculating, based on the spatial location and the genetic information, a minimum distance to another spot of the plurality of spots having a higher local density using at least one computer processor; and determining the at least one spot that represents the cell centers based, at least in part, on the calculated local densities and the minimum distances of the plurality of spots; and for each spot determined to represent a cell center, identifying, as representing a cell in the image, a set of spots from the plurality of spots, wherein the set of spots belong to a same cell as the spot determined to represent the cell center; and outputting an indication of the set of spots determined for each of the cells identified in the image.

2. The method of claim 1, wherein calculating, based on the spatial location and the genetic information, a minimum distance to another spot of the plurality of spots having a higher local density comprises:

for a spot having a highest local density among the plurality of spots, calculating, based on the spatial location and the genetic information, a distance to another spot of the plurality of spots having a highest minimum distance.

3. The method of claim 1, wherein determining the at least one spot that represents a cell center based on the local densities and the minimum distances comprises, for each spot:

calculating a product of the local density of the spot and the minimum distance of the spot; and determining that the spot represents a cell center if the product has a value greater than a threshold value.

4. The method of claim 1, wherein calculating the local density for the spot and the minimum distance for the spot comprises:

counting, within a region having a first radius around the spot, numbers of spots corresponding to different gene types.

5. The method of claim 4, wherein calculating the local density for the spot and the minimum distance for the spot comprises calculating a first parameter based on a spatial distance and a genetic correlation, wherein:

the spatial distance represents a spatial distance between a spatial location of the spot and a spatial location of another spot; and the genetic correlation represents a correlation between numbers of spots corresponding to different gene types within the first region having a first radius around the spot and numbers of spots corresponding to different gene types within a second region having the first radius around the other spot.

6. The method of claim 4, wherein the first radius is approximately equal to the average size of the cells.

7. The method of claim 1, wherein the spots comprise RNA spots.

8. The method of claim 5, further comprising, for each spot included in the set of spots, counting, within a region having a second radius around the spot, numbers of spots corresponding to different gene types.

9. The method of claim 8, further comprising, for each spot included in the set of spots, calculating a second parameter based on a spatial location of the spot and the numbers of spots corresponding to the different gene types within the region having the second radius around the spot.

10. The method of claim 9, further comprising, for at least one cell identified in the image, based on the second parameter, segmenting the cell into subcellular components.

11. The method of claim 10, wherein the subcellular components are subcellular organelles, wherein the subcellular organelles comprise a nucleus and a cytoplasm.

12. The method of claim 8, further comprising, for each of the identified cells in the image, classifying the cell into a cell type, and for each of the identified cells in the image, counting, within a region having a third radius around the cell, numbers of cells corresponding to different cell types.

13. The method of claim 1, further comprising, after outputting an indication of the set of the spots determined for each of the cells identified in the image:

rejecting noise in the set of the spots determined for each of the cells identified in the image, wherein rejecting noise in the set of the spots determined for each of the cells identified in the image comprises, for each cell:

determining a border region of the cell having disposed therein a subset of spots of the set of spots determined for the cell;

identifying, within the border region, a spot of the subset having a highest border region density of spots;

determining, for each of one or more spots of the set of spots determined for the cell, a point density of spots;

comparing, for each of the one or more spots, the point density and the highest border region density to obtain a density comparison result;

based on each density comparison result:

keeping, in the set of spots determined for the cell, each of the one or more spots having a higher point density than the highest border region density; and discarding, from the set of spots determined for the cell, each of the one or more spots having a lower point density than the highest border region density.

14. An apparatus comprising:

at least one computer processor; and at least one non-transitory computer-readable storage medium encoded with a plurality of instructions that, when executed by at least one computer processor, perform a method of identifying cells in an image, the method comprising:

receiving, for each of a plurality of spots in the image, a spatial location of the spot in the image and genetic information associated with the spot, wherein each spot corresponds to one or more pixels in the image;

based on the spatial location and the genetic information for each of the plurality of spots:

determining at least one spot that represents a cell center by, for each of the plurality of spots:

calculating, based on the spatial location and the genetic information, a local density of the spot using at least one computer processor; and calculating, based on the spatial location and the genetic information, a minimum distance to another spot of the plurality of spots having a higher local density using at least one computer processor; and determining the at least one spot that represents the cell centers based, at least in part, on the calculated local densities and the minimum distances of the plurality of spots; and for each spot determined to represent a cell center, identifying, as representing a cell in the image, a set of spots from the plurality of spots, wherein the set of spots belong to a same cell as the spot determined to represent the cell center; and outputting an indication of the set of spots determined for each of the cells identified in the image.

15. At least one non-transitory computer-readable storage medium encoded with a plurality of instructions that, when executed by at least one computer processor, perform a method of identifying cells in an image, the method comprising:

receiving, for each of a plurality of spots in the image, a spatial location of the spot in the image and genetic information associated with the spot, wherein each spot corresponds to one or more pixels in the image;

based on the spatial location and the genetic information for each of the plurality of spots:

determining at least one spot that represents a cell center by, for each of the plurality of spots:

calculating, based on the spatial location and the genetic information, a local density of the spot using at least one computer processor; and calculating, based on the spatial location and the genetic information, a minimum distance to another spot of the plurality of spots having a higher local density using at least one computer processor; and determining the at least one spot that represents the cell centers based, at least in part, on the calculated local densities and the minimum distances of the plurality of spots; and

for each spot determined to represent a cell center, identifying, as representing a cell in the image, a set of spots from the plurality of spots, wherein the set of spots belong to a same cell as the spot determined to represent the cell center; and outputting an indication of the set of spots determined for each of the cells identified in the image.

16. The method of claim 1, wherein the image is an image of a sample provided by a subject, the method further comprising:

classifying each cell identified in the image into a cell type;

determining, based on the cell type of each cell identified in the image, whether the subject has or is at risk of having a disease or disorder; and administering a therapy capable of treating the disease or disorder to the subject.

17. The method of claim 16, wherein the disease or disorder is selected from the group consisting of genetic diseases, proliferative diseases, inflammatory diseases, autoimmune diseases, liver diseases, pulmonary diseases, hematological diseases, psychiatric diseases, cardiovascular diseases, gastrointestinal diseases, musculoskeletal diseases, genitourinary diseases, and neurological diseases.

18. The method of claim 17, wherein the disease is cancer, and wherein the therapy comprises an anticancer agent.

19. The method of claim 16, wherein the sample is a tissue sample.

* * * * *